US010766902B2

(12) United States Patent
Burkamp et al.

(10) Patent No.: US 10,766,902 B2
(45) Date of Patent: Sep. 8, 2020

(54) WEE-1 INHIBITING PYRAZOLOPYRIMIDINONE COMPOUNDS

(71) Applicant: ALMAC DISCOVERY LIMITED, Craigavon, Armagh (GB)

(72) Inventors: Frank Burkamp, Armagh (GB); James Samuel Shane Rountree, Armagh (GB); Adam Piotr Treder, Armagh (GB)

(73) Assignee: ALMAC DISCOVERY LIMITED, Craigavon, Armagh (GB)

( * ) Notice: Subject to any disclaimer, the term of this patent is extended or adjusted under 35 U.S.C. 154(b) by 0 days.

(21) Appl. No.: 16/317,342

(22) PCT Filed: Jul. 12, 2017

(86) PCT No.: PCT/GB2017/052041

§ 371 (c)(1),
(2) Date: Jan. 11, 2019

(87) PCT Pub. No.: WO2018/011569

PCT Pub. Date: Jan. 18, 2018

(65) Prior Publication Data

US 2019/0248795 A1 Aug. 15, 2019

(30) Foreign Application Priority Data

Jul. 12, 2016 (GB) .................................. 1612092.5

(51) Int. Cl.
*A61K 31/519* (2006.01)
*C07D 487/04* (2006.01)
*C07D 519/00* (2006.01)
*A61P 35/00* (2006.01)

(52) U.S. Cl.
CPC ............ *C07D 487/04* (2013.01); *A61P 35/00* (2018.01); *C07D 519/00* (2013.01)

(58) Field of Classification Search
CPC ............................ A61K 31/519; C07D 487/04
USPC ........................................ 514/262.1; 544/262
See application file for complete search history.

(56) References Cited

U.S. PATENT DOCUMENTS

2007/0254892 A1 11/2007 Sagara et al.

FOREIGN PATENT DOCUMENTS

EP 2213673 A1 8/2010
WO 2008/133866 A1 11/2008

*Primary Examiner* — Jeffrey H Murray
(74) *Attorney, Agent, or Firm* — Brian C. Trinque; Lathrop GPM LLP

(57) ABSTRACT

The present invention relates to pyrazolopyrimidinone derivatives, such as those of Formula (I), that are useful as inhibitors of the activity of Wee-1 kinase. The present invention also relates to pharmaceutical compositions comprising these compounds and to methods of using these compounds in the treatment of cancer and methods of treating cancer (I)

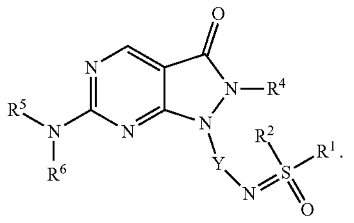

26 Claims, No Drawings

WEE-1 INHIBITING PYRAZOLOPYRIMIDINONE COMPOUNDS

RELATED APPLICATIONS

This application is a 35 U.S.C. § 371 filing of International Application No. PCT/GB2017/052041, filed Jul. 12, 2017, which claims the benefit of Great Britain Patent Application No. 1612092.5, filed Jul. 12, 2016. The entire contents of these applications are incorporated herein by reference in their entireties.

The present invention relates to compounds that are useful as inhibitors of the activity of Wee-1 kinase. The present invention also relates to pharmaceutical compositions comprising these compounds and to methods of using these compounds in the treatment of cancer and methods of treating cancer.

BACKGROUND TO THE INVENTION

Cells are continually challenged on a daily basis, resulting in multiple lesions forming in DNA. The lesions, if not repaired, can lead to mutations or cell death, thus complex signalling networks exist which ensure that lesions are detected and repaired to maintain the integrity of DNA.

Detection of DNA damage initiates a series of events which are key in maintaining the genome. Cell cycle checkpoints are designed to stop the cell cycle and allow repair of the lesion before allowing the cell to continue into mitosis.

Two key checkpoints have been identified, one at the end of the G1 phase and the second at G2, working in tandem to ensure all lesions are identified and repaired. In 50% of human cancers the G1 checkpoint is non-functional due to mutations in the tumour suppressor gene p53. However, the G2 check-point is seldomly mutated and often found to be activated in cancer cells. Cancer cells exploit this to confer resistance to treatment modalities, including DNA damaging agents and radiation.

Three kinases have been identified as key regulators of the G2 checkpoint, namely Chk1, Chk2 and Wee-1. Inhibitors for these kinases are currently being evaluated in clinical trials.

Wee-1 is a nuclear tyrosine kinase which negatively regulates entry into mitosis at the G2/M check-point by catalysing a phosphorylation of the cdc2/cyclin B kinase complex. The phosphorylation occurs on the tyrosine-15 residue and leads to the inactivation of the cdc2/cyclin B complex, ultimately preventing mitosis. Wee-1 function is intimately linked to that of Chk1 and Chk2 due to their phosphorylation and inactivation of cdc25 on serine-216, as well as the reported activation of Wee-1 by Chk 1 & 2 (Ashwell et al., 2012, *DNA Repair in Cancer Therapy*, DOI: 10.1016/B978-0-12-384999-1.10010-1).

Wee-1 is downstream of the Chk family and is a crucial component of the checkpoint signalling cascade as it prevents cells from entering mitosis if lesions are detected (Do et al., Cell Cycle 2013 12 (19) 3159-3164).

Commonly administered anti-cancer compounds induce DNA damage, including antimetabolites, platinum agents, topoisomerase inhibitors and alkylating agents. However, their efficacy is limited due to excessive toxicity, resistance and lack of tumour selectivity. Compounds which work in combination with these agents to prevent DNA repair selectively in tumour cells would be extremely beneficial. As the tumour suppressor gene p53 is commonly mutated in tumour cell lines, the administration of a Wee-1 kinase inhibitor, abrogating the G2 check point, may lead to increased sensitivity to DNA damaging agents. The potential for this has been reported, as silencing of Wee-1 activity was sufficient to sensitize HeLa cells to doxorubicin due to abrogation of G2 arrest. By contrast, in normal breast epithelium due to the fully competent p53 protein, the removal of Wee-1 function had little additional effect compared to doxorubicin alone (Wang et al., 2004, Cancer Biology and Therapy, 3(3), 305-313).

It has been reported that cell lines harbouring mutations in the tumour suppressor gene p53 had increased sensitivity to DNA damaging agents when co-administered with Wee-1 small molecule inhibitors. Synergistic in vitro and in vivo efficacy has been reported when small molecule inhibitors were combined with gemcitabine, 5-fluorouracil, carboplatin, cisplatin (Hirai et al 2010, Cancer Biology & Therapy 9:7, 514-522), cytarabine (Tibes et al., 2012, Blood, 119(12), 2863-2872), for example. Other examples of chemosensitization upon Wee-1 inhibition include but are not limited to combination with irinotecan, topotecan or alkylating agent (temozolomide). Radiosensitization has also been demonstrated in multiple cancer types (Havelek R., et al. 2014 Biochem Biophys Res Commun., 24 (453), 569-75; Caretti V., et al. 2013 Mol Cancer Ther., 12 (2) 141-50; Bridges K A., et al. 2011 Clin Cancer Res., 1(17), 5638-48; PosthumaDeBoer J., et al. 2011 BMC Cancer., 29 (11), 156). Combinations with non-cytotoxic compounds have also been evidenced including for instance with Chk-1 inhibitors (Carrasa et al., 2012 Cell Cycle 1:11(13):2507-2517), (Russell et al., 2013 Cancer Res. 15; 73 (2) 776-784), Src inhibitors (Cozzi et al., 2012, Cell Cycle 11(5), 1-11), PARP inhibitor (Karnak D., et al. 2014 Clin. Cancer Res., 1 (20), 5085-96), HSP90 inhibitor (Lokeshwar V B., 2012 Cell Cycle., 15 (11), 3722-3; Iwai A., et al. 2012 Cell Cycle 1 (11), 3649-55), HDAC inhibitor (Zhou L., et al. 2015 Leukemia, 29(4), 807-18). Interestingly, single agent apoptotic efficacy, independent of p53 status, has also been reported in various cellular models and contexts including sarcoma cell lines and in patient-derived sarcoma samples (Kreahling et al., 2012, Mol. Cancer Ther., 11(1), 174-182) in a panel of cancer cell lines in vivo including lung and melanoma model cell lines (Guertin et al., 2013 Mol Cancer Ther, 12 (2) 141-151) or more recently in H3K36me3-deficient cancer cell lines (Pfister S X., 2015 Cancer Cell., 28(5), 557-568).

Irradiation is known to increase phosphorylation of the Tyr15 and Thr14 residues of cdc2, leading to a radioresistant phenotype. Inhibition of Wee-1 activity by small molecule inhibitors (Wang et al., 2004, Cancer Biology and Therapy 3(3), 305-313), (Caretti et al., 2013 Mol Cancer Ther. 12 (2) 141-150) leads to a reduction in phosphorylation and radiosensitization, with the effect being more pronounced in p53 mutant cell lines.

It has been reported in melanoma that over-expression of Wee-1 is correlated with poor clinical outcome (Magnusson et al., 2012 PLoS One 7; (6)e38254), indicating it may have a significant role as a biomarker and as a targeted therapy.

Compounds having a kinase inhibitory effect, for example a Wee-1 kinase inhibitory effect, are described in WO2007/126122, US2010/0063024, EP 2,213,673, WO2008/133866, US2007/0254892, WO2012/161812, WO2013/126656, US2013/0102590, WO2013/059485 and WO2013/013031.

WO2007/126122 and US2007/0254892 describe various dihydropyrazolopyrimidinone derivatives as having a kinase inhibitory effect.

It is one object of the present invention to overcome at least some of the disadvantages of the prior art or to provide a commercially useful alternative thereto.

It is a further object of the present invention to provide a compound having an enhanced or comparable Wee-1-kinase-inhibitory effect compared to known compounds or compositions.

It is a further object of the present invention to provide compounds having an improved or comparable potency in cells compared to known compounds or compositions.

It is a further object of the present invention to provide compounds with an improved or comparable selectivity towards Wee-1 kinase compared to known compounds or compositions.

It is a further object of the present invention to provide a compound having an improved efficacy and tolerability when administered in combination with other therapies compared to known compounds or compositions.

SUMMARY OF THE INVENTION

In a first aspect the present invention provides a compound of Formula (I):

(I)

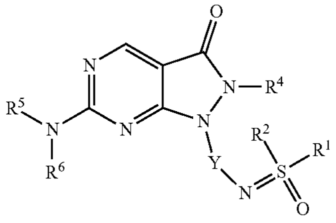

or a pharmaceutically acceptable salt or N-oxide derivative thereof, wherein:

- $R^1$ is an optionally substituted alkyl group, an optionally substituted cycloalkyl group, an optionally substituted aryl group or an optionally substituted heteroaryl group;
- $R^2$ is an optionally substituted alkyl group, an optionally substituted cycloalkyl group, an optionally substituted aryl group or an optionally substituted heteroaryl group,
- or $R^1$, $R^2$ and the sulphur atom to which they are both attached, as taken together, form an optionally substituted heterocyclyl group
- $R^4$ is an optionally substituted alkyl group, an optionally substituted alkenyl group, an optionally substituted alkynyl group or an optionally substituted aryl group;
- $R^5$ is an optionally substituted aryl group, an optionally substituted heteroaryl group, or an optionally substituted cycloalkyl group;
- $R^6$ is a hydrogen atom or an optionally substituted aryl group;
- Y is an optionally substituted aryl group, an optionally substituted heteroaryl group, an optionally substituted aroyl group, an optionally substituted heteroaroyl group, an optionally substituted benzyl group or an optionally substituted methylheteroaryl group.

In a further aspect the present invention provides a compound of Formula (II):

(II)

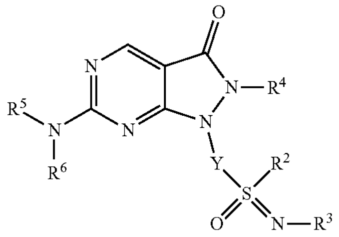

or a pharmaceutically acceptable salt or N-oxide derivative thereof, wherein:

- $R^2$ is an optionally substituted alkyl group, an optionally substituted cycloalkyl group, an optionally substituted aryl group or an optionally substituted heteroaryl group;
- $R^3$ is a hydrogen atom, an optionally substituted alkyl group, an optionally substituted cycloalkyl group, an optionally substituted aryl group, an optionally substituted heteroaryl group, a cyano group, an optionally substituted alkanoyl group, an optionally substituted aroyl group, an optionally substituted heteroaroyl group, an optionally substituted alkoxy-carbonyl group or an optionally substituted alkylamino-carbonyl group;
- $R^4$ is an optionally substituted alkyl group, an optionally substituted alkenyl group, an optionally substituted alkynyl group or an optionally substituted aryl group;
- $R^5$ is an optionally substituted aryl group, an optionally substituted heteroaryl group, or an optionally substituted cycloalkyl group;
- $R^6$ is a hydrogen atom or an optionally substituted aryl group; Y is an optionally substituted aryl group, an optionally substituted heteroaryl group, an optionally substituted aroyl group, an optionally substituted heteroaroyl group, an optionally substituted benzyl group or an optionally substituted methylheteroaryl group.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

In a further aspect the present invention provides the compound of Formula (I) or Formula (II), or a pharmaceutically acceptable salt or N-oxide derivative thereof, and at least one pharmaceutically acceptable excipient.

In a further aspect the present invention provides a pharmaceutical composition comprising the compound of Formula (I) or Formula (II), or a pharmaceutically acceptable salt or N-oxide derivative thereof, and at least one pharmaceutically acceptable excipient.

In a further aspect the present invention provides the compound of Formula (I) or Formula (II), or a pharmaceutically acceptable salt or N-oxide derivative thereof, or the pharmaceutical composition as described herein, for use in therapy.

In a further aspect the present invention provides the compound of Formula (I) or Formula (II), or a pharmaceutically acceptable salt or N-oxide derivative thereof, or the pharmaceutical composition as described herein, for use as a medicament.

In a further aspect the present invention provides the compound of Formula (I) or Formula (II), or a pharmaceutically acceptable salt or N-oxide derivative thereof, or the pharmaceutical composition as described herein, for use in treating or preventing cancer.

In a further aspect the present invention provides the use of the compound of Formula (I) or Formula (II), or a pharmaceutically acceptable salt or N-oxide derivative thereof, or the pharmaceutical composition as described herein, for the manufacture of a medicament for treating or preventing cancer.

In a further aspect the present invention provides a method of treating or preventing cancer in a human or animal patient comprising administering to a patient in need thereof an effective amount of a compound of Formula (I) or Formula (II), or a pharmaceutically acceptable salt or N-oxide derivative thereof, or the pharmaceutical composition as described herein.

Other preferred embodiments of the compounds according to the invention appear throughout the specification and in particular in the examples. Particularly preferred are those named compounds having greater activity as tested. Compounds having higher activity are more preferred over those having lower activity.

The present inventors have surprisingly found that the compounds of the present invention show an improved or similar kinase-inhibitory effect compared to known compounds. In particular, the compounds of the present invention preferably show an improved or comparable Wee-1 kinase-inhibitory effect compared to known compounds or compositions, for example compared to those described in WO2007/126122 and US2007/0254892.

The present inventors have surprisingly found that compounds of the present invention show an improved or comparable selectivity towards Wee-1 kinase compared to known compounds or compositions.

The present inventors have surprisingly found that compounds of the present invention show an improved or similar potency in cells compared to known compounds or compositions.

The present inventors have surprisingly found that compounds of the present invention show an improved selectivity towards Wee-1 kinase compounds whilst also displaying an improved or comparable Wee-1 kinase-inhibitory effect compared to known compounds or compositions.

The present inventors have surprisingly found that compounds of the present invention show an improved selectivity towards Wee-1 kinase compounds whilst also displaying an improved or similar potency in cells compared to known compounds or compositions.

Without wishing to be bound by theory, it is thought that the compounds of the present invention tend to show the advantageous effects discussed above due, at least in part, to the presence of the N-linked or S-linked sulfoximinyl group.

(I)

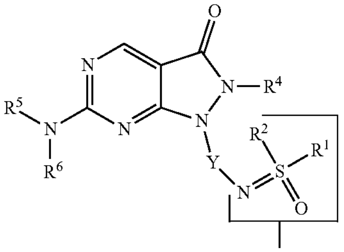

N-linked sulfoximinyl group

-continued (II)

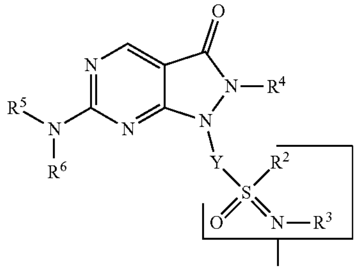

S-linked sulfoximinyl group

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

As used in the specification and the appended claims, unless specified to the contrary, the following terms have the meaning indicated:

The term "alkyl group" (alone or in combination with another term(s)) means a straight- or branched-chain saturated hydrocarbyl substituent typically containing 1 to 15 carbon atoms, such as 1 to 10, 1 to 8, 1 to 6, or 1 to 4 carbon atoms. A "$C_n$ alkyl" group refers to an aliphatic group containing n carbon atoms. For example, a $C_1$-$C_{10}$ alkyl group contains 1, 2, 3, 4, 5, 6, 7, 8, 9 or 10 carbon atoms. Attachment to the alkyl group occurs through a carbon atom. Examples of such substituents include methyl, ethyl, n-propyl, isopropyl, n-butyl, isobutyl, sec-butyl, tert-butyl, pentyl (branched or unbranched), hexyl (branched or unbranched), heptyl (branched or unbranched), octyl (branched or unbranched), nonyl (branched or unbranched), and decyl (branched or unbranched).

The term "alkenyl group" (alone or in combination with another term(s)) means a straight- or branched-chain hydrocarbon substituent containing one or more double bonds and typically 2 to 15 carbon atoms; such as 2 to 10, 2 to 8, 2 to 6 or 2 to 4 carbon atoms. Examples of such substituents include ethenyl (vinyl), 1-propenyl, 3-propenyl, 1,4-pentadienyl, 1,3-butadienyl, 1-butenyl, 2-butenyl, 3-butenyl, pentenyl and hexenyl.

The term "alkynyl group" (alone or in combination with another term(s)) means a straight- or branched-chain hydrocarbon substituent containing one or more triple bonds and typically 2 to 15 carbon atoms; such as 2 to 10, 2 to 8, 2 to 6 or 2 to 4 carbon atoms. Examples of such substituents include ethynyl, 1-propynyl, 3-propynyl, 1-butynyl, 3-butynyl and 4-butynyl.

The term "cycloalkyl group" (alone or in combination with another term(s)) means a saturated cyclic hydrocarbon substituent containing 3 to 14 carbon ring atoms. A cycloalkyl may be a single carbon ring, which typically contains 3 to 8 carbon ring atoms and more typically 3 to 6 ring atoms. It is understood that attachment to a cycloalkyl group is via a ring atom of the cycloalkyl group. Examples of single-ring cycloalkyls include cyclopropyl (cyclopropanyl), cyclobutyl (cyclobutanyl), cyclopentyl (cyclopentanyl), cyclohexyl (cyclohexanyl).

A cycloalkyl may alternatively be partly unsaturated or be polycyclic or contain more than one ring. Examples of polycyclic cycloalkyls include bridged, fused, and spirocyclic cycloalkyls. In a spirocyclic cycloalkyl, one atom is common to two different rings. An example of a spirocyclic cycloalkyl is spiropentanyl. In a bridged cycloalkyl, the rings share at least two common non-adjacent atoms. Examples of bridged cycloalkyls include bicyclo[2.2.1]heptanyl, bicyclo[2.2.1]hept-2-enyl, and adamantanyl. In a fused-ring cycloalkyl system, two or more rings may be fused together, such that two rings share one common bond. Examples of two- or three-fused ring cycloalkyls include tetrahydronaphthalenyl (tetralinyl), indenyl, indanyl (dihydroindenyl) and decalinyl.

The term "aryl group" (alone or in combination with another term(s)) means an aromatic cycloalkyl containing from 6 to 14 carbon ring atoms, or 6 to 12, 6 to 10 or 6 to 8 carbon ring atoms. An aryl may be monocyclic or polycyclic (i.e., may contain more than one ring). In the case of polycyclic aromatic rings, only one ring in the polycyclic system is required to be unsaturated while the remaining ring(s) may be saturated, partially saturated or unsaturated. Attachment to the aryl group occurs through a carbon atom contained in the ring. Examples of aryl groups include phenyl, naphthyl, indenyl, indanyl, and tetrahydronaphthyl.

The term "heterocyclyl group" (alone or in combination with another term(s)) means a saturated (i.e. "heterocycloalkyl"), partially saturated (i.e. "heterocycloalkenyl"), or completely unsaturated (i.e. "heteroaryl") ring structure containing a total of 3 to 14 ring atoms, wherein at least one of the ring atoms is a heteroatom (i.e. oxygen, nitrogen, or sulfur), with the remaining ring atoms being carbon atoms. A heterocyclyl group may, for example, contain one, two, three, four or five heteroatoms. One or more attachments to the heterocyclyl group may occur either through a carbon atom and/or one or more heteroatoms that are contained in the ring. A heterocyclyl may be a single-ring (monocyclic) or polycyclic ring structure.

A heterocyclyl group may be a single ring, which typically contains from 3 to 7 ring atoms, more typically from 3 to 6 ring atoms, and even more typically 5 to 6 ring atoms. Examples of single-ring heterocyclyles include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, isothiazolinyl-toxo, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl) or 1,3,4-oxadiazolyl), pyranyl, dihydropyranyl, thiopyranyl, tetrahydrothiopyranyl, 1-iminotetrahydrothiopyranyl-1-oxo, pyridinyl (azinyl), piperidinyl, diazinyl (including pyridazinyl (1,2-diazinyl), pyrimidinyl (1,3-diazinyl) or pyrazinyl (1,4-diazinyl)), piperazinyl, triazinyl (including 1,3,5-triazinyl, 1.2.4-triazinyl and 1,2,3-triazinyl), oxazinyl (1,4-oxazinyl), morpholinyl, thiomorpholinyl, 1-iminothiomorpholinyl-1-oxo, azepinyl, oxepinyl, thiepinyl, and diazepinyl.

A heterocyclyl group may alternatively be polycyclic (i.e., may contain more than one ring). Examples of polycyclic heterocyclyl groups include bridged, fused, and spirocyclic heterocyclyl groups. In a spirocyclic heterocyclyl group, one atom is common to two different rings. In a bridged heterocyclyl group, the rings share at least two common non-adjacent atoms. In a fused-ring heterocyclyl group, two or more rings may be fused together, such that two rings share one common bond. Examples of fused ring heterocyclyl groups containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyl groups include benzo-fused heterocyclyl groups, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, benzodiazinyl (including cinnolinyl (1,2-benzodiazinyl) or quinazolinyl (1,3-benzodiazinyl)), benzopyranyl (including chromanyl or isochromanyl), benzoxazinyl, and benzisoxazinyl (including 1,2-benzisoxazinyl or 1,4-benzisoxazinyl).

The term "heterocycloalkyl group" (alone or in combination with another term(s)) means a saturated heterocyclyl group.

The term "heteroaryl group" (alone or in combination with another term(s)) means an aromatic heterocyclyl containing from 5 to 14 ring atoms. A heteroaryl may be a single ring or 2 or 3 fused rings. Examples of heteroaryl groups include 6-membered rings such as pyridyl, pyrazinyl, pyrimidinyl, pyridazinyl, and 1,3,5-, 1,2,4- or 1,2,3-triazinyl; 5-membered rings such as imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused rings such as benzothiofuranyl, benzisoxazolyl, benzoxazolyl, purinyl; and 6/6-membered fused rings such as benzopyranyl, quinolinyl, isoquinolinyl, cinnolinyl, quinazolinyl, and benzoxazinyl.

The term "nitrogen-containing heterocyclyl group" refers to a monocyclic or bicyclic heterocyclyl group containing at least one nitrogen atom, in which each ring comprises from 3 to 7 ring atoms and optionally contains, in addition to the nitrogen atom, zero or one or two or more, the same or different hetero atoms, but preferably zero or one hetero atom selected from the group consisting of an oxygen atom, a nitrogen atom and a sulfur atom; and the heterocyclyl group may be saturated (i.e. "heterocycloalkyl"), partially saturated (i.e. "heterocycloalkenyl"), or completely unsaturated (i.e. "heteroaryl"). The bicyclic heterocyclyl group may have a spiro structure of which the two rings share one and the same ring atom, or may have a bicyclo structure of which the rings share two or more ring atoms. Examples of the nitrogen-containing heterocyclyl group include, for example, a pyrrolyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, a pyrido[3,2-b]pyridyl group, an azetidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a piperidinyl group, a piperazinyl group, a dihydropyridyl group, a morpholinyl group, a thiomorpholinyl group, a 2,6-diazaspiro

[3.5]nonyl group, a 2,7-diazaspiro[3.5]nonyl group, a 2,7-diazaspiro[4.5]decyl group, or a 2,7-diazabicyclo[3.3.0]octyl group, a 3,6-diazabicyclo[3.3.0]octyl group.

The nitrogen-containing heterocyclyl group can be optionally substituted (a "substituted nitrogen-containing heterocyclyl group") with one or more substituents, which can be the same or different.

The term "amino group" refers to the $NH_2$ group. The amino group can be optionally substituted (a "substituted amino") with one or more substituents, which can be the same or different. Amino group substituents may be, but are not limited to, an alkyl, alkanoyl, aryl and/or a heterocyclyl group.

The term "amido group" refers to the C(═O)—NR— group. Attachment may be through the carbon and/or nitrogen atom. For example, the amido group may be attached as a substituent via the carbon atom only, in which case the nitrogen atom has two R groups attached (—C(═O)—$NR_2$). The amido group may be attached by the nitrogen atom only, in which case the carbon atom has an R group attached (—NR—C(═O)R).

The term "iminyl" group refers to the C(═NR)— group. Attachment may be through the carbon atom.

The group "═N—R" refers to a substituent nitrogen-R group connected to another atom by a double bond. For example, an iminyl group (C(═NR)— group) is a nitrogen atom connected by a double bond to a carbon atom, the nitrogen atom also being connected to an R group by a single bond.

The term "alkoxy group" refers to an —O-alkyl group. The alkoxy group can refer to linear, branched, or cyclic, saturated or unsaturated hydrocarbon chains, including, for example, methoxy, ethoxy, propoxy, isopropoxy, butoxy, t-butoxy and pentoxy. The alkoxy group can be optionally substituted (a "substituted alkoxy") with one or more substituents.

The term "hydroxy" refers to an OH group.

The term "alkanoyl group" (i.e. acyl group) refers to an organic acid group wherein the —OH of the carboxyl group has been replaced with another substituent. Thus, the alkanoyl group can be represented by the formula RC(═O)—, wherein R includes but is not limited to an alkyl, aralkyl, an aryl group (an "aroyl group"), a heteroaryl group (a "heteroaroyl group") which in turn may be optionally substituted by one or more substituents. Examples of alkanoyl groups include an acetyl group, a propionyl group, a butyryl group, an isobutyryl group, a valeryl group, an isovaleryl group, a pivaloyl group and a benzoyl group.

The term "sulfonyl group" refers to a sulfonic acid group wherein the wherein the OH of the sulfonyl group has been replaced with another substituent. For example, the substituent may be an alkyl group ("an alkylsulfonyl group"). An alkylsulfonyl group can be represented by the formula $RS(═O)_2$—, wherein R is an alkyl group, optionally substituted by one or more substituent. Examples of alkylsulfonyl groups include a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group and an isohexylsulfonyl group.

The term "sulfanyl group" refers to the R—S— group.

The term "sulfinyl group" refers to the RS(═O)— group.

The term "sulfoximinyl group" refers to a "—S(═O)(═NR)(R')" or a "—N═S(═O)(R)(R')" group. Attachment may be through the sulphur atom (S-linked sulfoximinyl) or the nitrogen atom (N-linked sulfoximinyl).

The term "oxo group" refers to the (═O) group, i.e. a substituent oxygen atom connected to another atom by a double bond. For example, a carbonyl group (—C(═O)— is a carbon atom connected by a double bond to an oxygen atom, i.e. an oxo group attached to a carbon atom.

The term "halo group" refers to a group selected from chlorine, fluorine, bromine and iodine. Preferably, the halo group is selected from chlorine and fluorine.

An alkyl, alkenyl, alkynyl, amino, amido, iminyl, alkoxy, clyoalkyl, aryl, heterocyclyl (including heterocycloalkyl, heterocyloalkenyl and heteroaryl), sulfonyl, sulfinyl, sulfoximinyl and nitrogen-containing heterocyclyl group can be optionally substituted with one or more substituents, which can be the same or different. A substituent can be attached through a carbon atom and/or a heteroatom in the alkyl, alkenyl, alkynyl, amino, amido, iminyl, alkoxy, clyloalkyl, aryl, heterocyclyl (including heterocycloalkyl, heterocyloalkenyl and heteroaryl), sulfonyl, sulfinyl, sulfoximinyl and nitrogen-containing heterocyclyl group. The term "substituent" (or "radical") includes but is not limited to alkyl, substituted alkyl, aralkyl, substituted aralkyl, alkenyl, substituted alkenyl, alkynyl, substituted alkynyl, halo, cyano, amino, amido, alkylamino, arylamino, carbocyclyl, cycloalkyl, substituted cycloalkyl, cycloalkenyl, substituted cycloalkenyl, aryl, substituted aryl, nitro, thio, alkanoyl, hydroxyl, aryloxyl, alkoxy, alkylthio, arylthio, aralkyloxyl, aralkylthio, carboxyl, alkoxycarbonyl, oxo, alkylsulfonyl and arylsulfonyl.

If a group (for example an alkyl group) is "optionally substituted", it is understood that the group has one or more substituents attached (substituted) or does not have any substituents attached (unsubstituted).

For completeness, it is also noted that certain chemical formulae used herein define delocalized systems. This definition is known in the art as a definition of aromaticity and may indicate the presence of, for example, a mono-, di- or tri-cyclic system that contains (4n+2) electrons where n is an integer. In other words, these systems may display Hückel aromaticity.

In whatever aspect, the compounds of the present invention may possess some aspect of stereochemistry. For example, the compounds may possess chiral centres and/or planes and/or axes of symmetry. As such, the compounds may be provided as single stereoisomers, single diastereomers, mixtures of stereoisomers or as racemic mixtures. Stereoisomers are known in the art to be molecules that have the same molecular formula and sequence of bonded atoms, but which differ in their spatial orientations of their atoms and/or groups.

In addition, the compounds of the present invention may possess tautomerism. Each tautomeric form is intended to fall within the scope of the invention.

In addition, the compounds of the present invention may be provided as a prodrug. Pro-drugs are transformed, generally in vivo, from one form to the active forms of the drugs described herein. For example, a prodrug may be formed by protecting any —N—H groups with a hydrolysable group that gives NH on hydrolysis. Any —NH group within the compound may be protected as a physiological hydrolyzable amide.

In addition, it will be understood that the elements described herein may be the common isotope or an isotope other than the common isotope. For example, a hydrogen atom may be $^1H$, $^2H$ (deuterium) or $^3H$ (tritium).

In addition, the compounds of the present invention may be provided in the form of their pharmaceutically acceptable salts or as co-crystals. For example, the compounds may be provided having protonated amine groups.

The term "pharmaceutically acceptable salt" refers to ionic compounds formed by the addition of an acid to a base. The term refers to such salts that are considered in the art as being suitable for use in contact with a patient, for example in vivo and pharmaceutically acceptable salts are generally chosen for their non-toxic, non-irritant characteristics.

The term "co-crystal" refers to a multi-component molecular crystal, which may comprise non-ionic interactions.

Pharmaceutically acceptable salts and co-crystals may be prepared by ion exchange chromatography or by reacting the free base or acidic form of a compound with stoichiometric amounts or with an excess of the desired salt-forming inorganic or organic acid or base in one or more suitable solvents, or by mixing the compound with another pharmaceutically acceptable compound capable of forming a co-crystal.

Salts known in the art to be generally suitable for use in contact with a patient include salts derived from inorganic and/or organic acids, including the hydrobromide, hydrochloride, sulfate, bisulfate, nitrate, acetate, oxalate, oleate, palmitate, stearate, laurate, benzoate, lactate, phosphate, tosylate, citrate, maleate, fumarate, succinate and tartrate. These may include cations based on the alkali and alkaline earth metals, such as sodium, potassium, calcium and magnesium, as well as ammonium, tetramethylammonium, tetraethylammonium. Further reference is made to the number of literature sources that survey suitable pharmaceutically acceptable salts, for example the Handbook of pharmaceutical salts published by IUPAC.

In addition, the compounds of the present invention may sometimes exist as zwitterions, which are considered as part of the invention.

The present inventors have discovered that the compounds of the present invention are useful in the treatment of medical conditions associated with disordered cell growth, including, but not restricted to, cancer, in particular (but not restricted to) cancers associated with inactivation in the tumour suppressor gene p53. The compound may have utility and activity as a single agent exploiting synthetic or contextual lethality relationships as well as in diseases including cancers with enhanced susceptibility to increased replicative stress and impaired cell cycle progression. Weel inhibitors according to the invention may also be used in combination modalities including combinations with genotoxic agents, radiotherapy, targeted agents and immune-modulators including but not restricted to immune checkpoint inhibitors.

For example, cancers include cardiac cancers, lung cancers, gastrointestinal cancers, genitourinary tract cancers, liver cancers, bone cancers, nervous system cancers, gynecological cancers, hematologic cancers, skin cancers and adrenal gland cancers, and cancers such as adrenal tumors, bile duct, bladder, blood, bone and connective tissue, brain and central nervous system, breast, cervical, colon and rectal (colorectal), endometrial, esophageal, gallbladder, head and neck, Hodgkin's Lymphoma, hypopharyngeal, kidney, laryngeal, leukemias, liver, lung, lymphoma, mediastinal tumors, melanoma (malignant melanoma), mesothelioma, multiple myeloma, nasal cavity, nasopharyngeal, neuroendocrine tumors, non-Hodgkin's lymphoma, oral, oesophagus, oropharyngeal, ovarian, pancreas, paranasal sinus, parathyroid, penis, pituitary tumors, prostate, salivary gland, sarcoma, skin, spine, stomach, testicular, thyroid, urethra, uterine, vaginal and vulvar. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

The compounds of the present invention are also useful in preparing a medicament that is useful in treating the diseases described above, in particular cancer.

The present invention is further directed to a method of inhibiting Wee-1 activity which comprises administering to a mammal, preferably a human, in need thereof a pharmaceutically effective amount of the compound of the present invention.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The present invention also includes within its scope the use of the compounds of the present invention in combination with a second or further drug in the treatment of cancer. The second or further drug may be a drug that is already known in the art in the treatment of cancer.

The present invention also includes the use of the compounds of the invention in a regime including the step of radiotherapy. The radiotherapy may be an ordinary method of treatment by x-ray, γ-ray, neutron, α-particle, proton or electron beam irradiation. The co-administration of compounds contained in this invention may lead to the potentiation of the radiation therapy, thus classifying them as radio-sensitizers.

In particular, cancers often become resistant to therapy. The development of resistance may be delayed or overcome by the administration of a combination of drugs that includes the compounds of the present invention for example in cancers which are known to be resistant to DNA damaging agents, radiotherapy or any other form of treatment agents and modalities.

For example, drugs that may be used in combination with the compounds of the present invention may target the same or a similar biological pathway to that targeted by the compounds of the present invention or may act on a different or unrelated pathway.

Depending on the disease to be treated, a variety of combination partners may be co-administered with the compounds of the present invention, for example genotoxic agents, targeted agents and immune-modulators. The second active ingredient may include, but is not restricted to: alkylating agents, including cyclophosphamide, ifosfamide, thiotepa, melphalan, chloroethylnitrosourea and bendamustine; platinum derivatives, including cisplatin, oxaliplatin, carboplatin and satraplatin; antimitotic agents, including vinca alkaloids (vincristine, vinorelbine and vinblastine), taxanes (paclitaxel, docetaxel), epothilones and inhibitors of mitotic kinases including aurora and polo kinases; topoisomerase inhibitors, including anthracyclines, epipodophyllotoxins, camptothecin and analogues of camptothecin; antimetabolites, including 5-fluorouracil, capecitabine, cytarabine, gemcitabine, 6-mercaptopurine, 6-thioguanine, fludarabine, methotrexate and premetrexed; targeted therapies, for example protein kinase inhibitors, including imatinib, gefitinib, sorafenib, sunitinib, erlotinib, dasatinib, and lapatinib; proteasome inhibitors, including bortezomib; histone deacetylase inhibitors, including valproate and SAHA; cell cycle and checkpoint inhibitors, including CHK1 and CHK2; antiangiogenic drugs, including bevacizumab; monoclonal antibodies, including trastuzumab, rituximab, alemtuzumab, tositumomab, cetuximab, panitumumab; conjugates of myoclonal antibodies, including Gemtuzumab ozogamicin, Ibritumomab tiuxetan; hormonal therapies, including antiestrogens (tamoxifen, raloxifen, anastrazole, letrozole, examestane) antiandrogens (flutamide, bicalutamide) and Luteinising Hormone analogues or antagonists.

With regard to combination therapy the compounds of the present invention may be administered separately, sequentially, simultaneously, concurrently or may be chronologically staggered with one or more standard therapeutics such as any of those mentioned above.

Preferably, the present invention provides a compound of Formula (I):

(I)

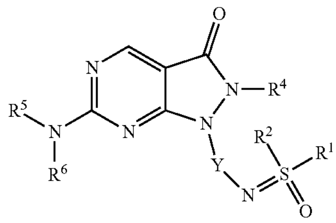

or a pharmaceutically acceptable salt or N-oxide derivative thereof, wherein:

$R^1$ is an optionally substituted alkyl group, an optionally substituted cycloalkyl group, an optionally substituted aryl group or an optionally substituted heteroaryl group;

$R^2$ is an optionally substituted alkyl group, an optionally substituted cycloalkyl group, an optionally substituted aryl group or an optionally substituted heteroaryl group, or $R^1$, $R^2$ and the sulphur atom to which they are both attached, as taken together, form an optionally substituted heterocyclyl group $R^4$ is an optionally substituted alkyl group, an optionally substituted alkenyl group, an optionally substituted alkynyl group or an optionally substituted aryl group;

$R^5$ is an optionally substituted aryl group, an optionally substituted heteroaryl group, or an optionally substituted cycloalkyl group;

$R^6$ is a hydrogen atom or an optionally substituted aryl group;

Y is an optionally substituted aryl group, an optionally substituted heteroaryl group, an optionally substituted aroyl group, an optionally substituted heteroaroyl group, an optionally substituted benzyl group or an optionally substituted methylheteroaryl group.

Preferably, $R^1$ is an optionally substituted alkyl group or an optionally substituted cycloalkyl group. More preferably, $R^1$ is an optionally substituted $C_1$-$C_6$ alkyl group or an optionally substituted $C_3$-$C_6$ cycloalkyl group. More preferably, $R^1$ is an optionally substituted $C_1$-$C_6$ alkyl group. More preferably, $R^1$ is an optionally substituted $C_1$-$C_3$ alkyl group, or an optionally substituted $C_1$-$C_2$ alkyl group. More preferably, $R^1$ is a $C_1$-$C_3$ alkyl group, or a $C_1$-$C_2$ alkyl group. Most preferably, $R^1$ is a methyl group.

Alternatively, preferably, $R^1$ and/or $R^2$ are optionally substituted $C_1$-$C_6$ alkyl groups, or $R^1$, $R^2$ and the sulphur atom to which they are both attached, as taken together, form an optionally substituted heterocyclyl group. More preferably, $R^1$ and/or $R^2$ are optionally substituted $C_1$-$C_3$ alkyl groups, or $R^1$, $R^2$ and the sulphur atom to which they are both attached, as taken together, form an optionally substituted heterocyclyl group. Most preferably, $R^1$ and/or $R^2$ are methyl groups, or $R^1$, $R^2$ and the sulphur atom to which they are both attached, as taken together, form an optionally substituted tetrahydrothiophenyl group Alternatively, preferably, $R^1$ and/or $R^2$ are optionally substituted $C_1$-$C_6$ alkyl groups. More preferably, $R^1$ and/or $R^2$ are optionally substituted $C_1$-$C_6$ alkyl groups. More preferably, $R^1$ and/or $R^2$ are $C_1$-$C_3$ alkyl groups, or $C_1$-$C_2$ alkyl groups. More preferably still, $R^1$ and $R^2$ are $C_1$-$C_3$ alkyl groups, or $C_1$-$C_2$ alkyl groups. Most preferably, $R^1$ and $R^2$ are methyl groups.

Alternatively, preferably, $R^1$, $R^2$ and the sulphur atom to which they are both attached, as taken together, form an optionally substituted heterocyclyl group. Preferably, $R^1$, $R^2$ and the sulphur atom to which they are both attached, as taken together, form an optionally substituted five to seven-membered, or five to six-membered heterocyclyl group. More preferably, $R^1$, $R^2$ and the sulphur atom to which they are both attached, as taken together, form an optionally substituted five-membered, heterocyclyl group. Most preferably, $R^1$, $R^2$ and the sulphur atom to which they are both attached, as taken together, form an optionally substituted tetrahydrothiophenyl group.

Preferably, the present invention provides a compound of Formula (II):

(II)

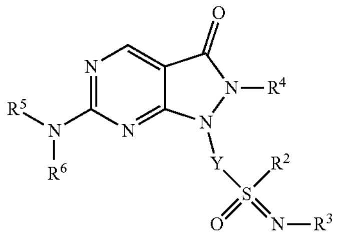

or a pharmaceutically acceptable salt or N-oxide derivative thereof, wherein:

$R^2$ is an optionally substituted alkyl group, an optionally substituted cycloalkyl group, an optionally substituted aryl group or an optionally substituted heteroaryl group;

$R^3$ is a hydrogen atom, an optionally substituted alkyl group, an optionally substituted cycloalkyl group, an optionally substituted aryl group, an optionally substituted heteroaryl group, a cyano group, an optionally substituted alkanoyl group, an optionally substituted aroyl group, an optionally substituted heteroaroyl group, an optionally substituted alkoxy-carbonyl group or an optionally substituted alkylamino-carbonyl group;

$R^4$ is an optionally substituted alkyl group, an optionally substituted alkenyl group, an optionally substituted alkynyl group or an optionally substituted aryl group;

$R^5$ is an optionally substituted aryl group, an optionally substituted heteroaryl group, or an optionally substituted cycloalkyl group;

$R^6$ is a hydrogen atom or an optionally substituted aryl group;

Y is an optionally substituted aryl group, an optionally substituted heteroaryl group, an optionally substituted aroyl group, an optionally substituted heteroaroyl group, an optionally substituted benzyl group or an optionally substituted methylheteroaryl group.

Preferably, $R^3$ is a hydrogen atom, an optionally substituted $C_1$-$C_6$ alkyl group, an optionally substituted $C_3$-$C_6$ cycloalkyl group, an optionally substituted five to seven-membered, or five to six-membered aryl group, an optionally substituted five to seven-membered, or five to six-membered heteroaryl group, a cyano group, an optionally substituted $C_1$-$C_6$ alkanoyl group, an optionally substituted aryl-carbonyl group, an optionally substituted heteroaroyl group, an optionally substituted $C_1$-$C_6$ alkoxy-carbonyl group or an optionally substituted $C_1$-$C_6$ alkylamino-carbonyl group.

More preferably, $R^3$ is a hydrogen atom, an optionally substituted alkyl group, a cyano group or an optionally substituted alkoxy-carbonyl group. More preferably, $R^3$ is a hydrogen atom, an optionally substituted $C_1$-$C_6$ alkyl group, a cyano group or an optionally substituted $C_1$-$C_6$ alkoxy-carbonyl group. More preferably, $R^3$ is a hydrogen atom, an optionally substituted $C_1$-$C_6$ alkyl group, a cyano group or an optionally substituted $C_1$-$C_6$ alkoxy-carbonyl group. More preferably still, $R^3$ is a hydrogen atom, a $C_1$-$C_2$ alkyl group, a cyano group or a $C_1$-$C_3$ alkoxy-carbonyl group. Most preferably, $R^3$ is a hydrogen atom, a methyl group, a cyano group or an ethoxy-carbonyl group. Alternatively, preferably, $R^3$ is a hydrogen atom.

Alternatively, preferably, $R^3$ is a hydrogen atom, an optionally substituted $C_1$-$C_3$ alkyl group, a cyano group or an optionally substituted $C_1$-$C_3$ alkoxy-carbonyl group; and $R^2$ is an optionally substituted $C_1$-$C_3$ alkyl group or an optionally substituted $C_3$-$C_6$ cycloalkyl group. More preferably, $R^3$ is a hydrogen atom, a $C_1$-$C_2$ alkyl group, a cyano group or a $C_1$-$C_3$ alkoxy-carbonyl group; and $R^2$ is a $C_1$-$C_2$ alkyl group or a $C_3$-$C_5$ cycloalkyl group. More preferably, $R^2$ is a hydrogen atom, a methyl group, a cyano group or an ethoxy-carbonyl group; and $R^2$ is a methyl group or a cyclopropyl group.

Unless specifically stated to the contrary, the following preferable features apply to both the compound of Formula (I) and compound of Formula (II) described above.

Preferably, $R^2$ is an optionally substituted alkyl group or an optionally substituted cycloalkyl group. More preferably, $R^2$ is an optionally substituted $C_1$-$C_6$ alkyl group or an optionally substituted $C_3$-$C_6$ cycloalkyl group. More preferably, $R^2$ is an optionally substituted $C_1$-$C_3$ alkyl group or an optionally substituted $C_3$-$C_5$ cycloalkyl group. More preferably, $R^2$ is a $C_1$-$C_2$ alkyl group or a $C_3$-$C_5$ cycloalkyl group. More preferably still, $R^2$ is a methyl group or a cyclopropyl group. Most preferably, $R^2$ is a methyl group.

Preferably, $R^4$ is an optionally substituted alkyl group or an optionally substituted alkenyl group. More preferably, $R^4$ is an optionally substituted $C_1$-$C_6$ alkyl group or an optionally substituted $C_1$-$C_6$ alkenyl group. More preferably, $R^4$ is an optionally substituted $C_1$-$C_4$ alkyl group or an optionally substituted $C_1$-$C_4$ alkenyl group. More preferably, $R^4$ is an optionally substituted $C_2$-$C_4$ alkyl group or an optionally substituted $C_2$-$C_4$ alkenyl group. More preferably, $R^4$ is a $C_2$-$C_4$ alkyl group or a $C_2$-$C_4$ alkenyl group. More preferably, $R^4$ is a propyl group or an allyl group. More preferably, $R^4$ is a 2-propyl group or an allyl group. Most preferably, $R^4$ is an allyl group. Alternatively, preferably, $R^4$ is a 2-propyl group.

Preferably, $R^5$ is an optionally substituted six-membered aryl group, an optionally substituted five- to seven-membered heteroaryl group, or an optionally substituted four- to six-membered cycloalkyl group. More preferably still, $R^5$ is an optionally substituted six-membered aryl group, an optionally substituted five- or six-membered heteroaryl group, or an optionally substituted four- to five-membered cycloalkyl group. More preferably still, $R^5$ is a substituted phenyl group, a substituted pyrazolyl group, or an unsubstituted four- to five-membered cycloalkyl group.

Alternatively, more preferably, $R^5$ is an optionally substituted aryl group or an optionally substituted heteroaryl group. More preferably, $R^5$ is an optionally substituted six-membered aryl group or an optionally substituted five- to seven-membered heteroaryl group. More preferably, $R^5$ is an optionally substituted six-membered aryl group or an optionally substituted five- or six-membered heteroaryl group. More preferably, $R^5$ is a substituted phenyl group or a substituted pyrazolyl group.

In one preferable embodiment, $R^5$ is a substituted pyrazolyl group.

Alternatively, more preferably, $R^5$ is a substituted phenyl group.

Preferably, $R^5$ is a group represented by the formula (d):

(d)

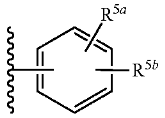

$R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl or cycloalkyl group, an oxo group, a hydroxyl group, an optionally substituted amino group and a group of $=N-R^{5c}$;

or, in formula (d), $R^{5a}$ and $R^{5b}$ exist on adjacent ring atoms and $R^{5a}$ and $R^{5b}$ and the ring atoms to which they are attached may form, as taken together, a three- to seven-membered cycloalkyl group or three- to seven-membered heterocyclyl group, wherein one or two of the ring atoms constituting the three- to seven-membered heterocyclyl group is independently an oxygen atom, a nitrogen atom, a group of $-N(R^{5d})-$, a sulfinyl group, a sulfonyl group or a sulfoximinyl group, wherein the three- to seven-membered cycloalkyl or three- to seven-membered heterocyclyl group may be substituted with one or more substituents selected from the group consisting of a halo group and a $C_1$-$C_6$ alkyl or cycloalkyl group;

or $R^{5a}$ and $R^{5b}$ and the ring atoms to which they are attached may form, as taken together, a spirocyclic group or a bicyclic group formed of a five- to seven-membered aliphatic ring and any other three- to seven-membered aliphatic ring, in which one or two or more methylene groups constituting the spirocyclic group or the bicyclic group may be each independently replaced by an oxygen atom, a sulphur atom, a sulfinyl group, a sulfonyl, a sulfoximinyl group, an oxo group or a group of —N($R^{5e}$)—, and the spirocyclic group or the bicyclic group may be each independently substituted with a substituent selected from the group consisting of a halo group, a hydroxyl group or a $C_1$-$C_6$ alkyl group; wherein $R^{5c}$, $R^{5d}$ and $R^{5e}$ are each independently a hydrogen atom or a $C_1$-$C_6$ alkyl or a cycloalkyl group optionally substituted with a substituent selected from the group consisting of a halo group, a hydroxyl group, a cyano group, an oxo group, a $C_1$-$C_6$ alkyl group, a $C_1$-$C_6$ alkoxy group, an amino group, a substituted amino group and a nitrogen-containing heterocyclyl group.

More preferably, $R^5$ is a group represented by the formula (e) or (n):

(e)

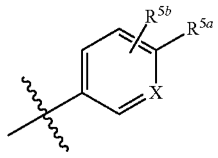

(n)

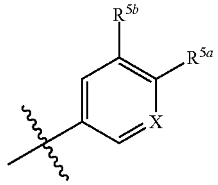

wherein X is a CH-group or a nitrogen atom; and $R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl group, an oxo group, a hydroxyl group, a group of =N—$R^{5f}$ and a group of A-N($R^{5g}$)$R^{5h}$;

$R^{5f}$, $R^{5g}$ and $R^{5h}$ each independently is a hydrogen atom or a $C_1$-$C_6$ alkyl group, or, $R^{5g}$ and $R^{5h}$ and the nitrogen atom to which they are attached, as taken together, may form an optionally substituted six-membered heterocyclyl group; and A is a single bond or a $C_1$-$C_3$ alkyl group.

Preferably X is a CH-group.

Preferably, $R^{5a}$ is selected from the group consisting of a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group; $R^{5b}$ is selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl group, an oxo group, a hydroxyl group, a group of =N—$R^{5f}$ and a group of A-N($R^{5g}$)$R^{5h}$;

$R^{5f}$, $R^{5g}$ and $R^{5h}$ each independently is a hydrogen atom or a $C_1$-$C_6$ alkyl group, or, $R^{5g}$ and $R^{5h}$ and the nitrogen atom to which they are attached, as taken together, may form an optionally substituted six-membered heterocyclyl group; and A is a single bond or a $C_1$-$C_6$ alkyl group.

Preferably, the four- to seven-membered nitrogen-containing heterocyclyl group is a four- to seven-membered nitrogen-containing heterocycloalkyl group. More preferably, the four- to seven-membered nitrogen-containing heterocyclyl group is selected from the group consisting of an azetidinyl group, a pyrrolidinyl group, a piperidinyl group, a piperazine group, a morpholinyl group, a thiomorpholinyl group, a thiomorpholine sulfoximinyl group and a homopiperazinyl group, each of which can be optionally substituted.

Preferably, X is a CH-group, $R^{5a}$ is a $C_1$-$C_3$ alkoxy group substituted with an amino group, or $R^{5a}$ is an optionally substituted amino group, or $R^{5a}$ is a $C_1$-$C_3$ alkyl group substituted by an optionally substituted five- to seven-membered heterocyclyl group, or $R^{5a}$ is a five- to seven-membered nitrogen-containing heterocyclyl group optionally substituted with one or more substituents selected from the group consisting of a $C_1$-$C_3$ alkyl group, a $C_3$-$C_6$ cycloalkyl group, a $C_1$-$C_3$ alkoxy group, a halo group, an oxo group, and a $C_1$-$C_3$ alkyl group substituted with one or more substituents selected from the group consisting of a hydroxyl group, a halo group, a carboxyl group, an oxo group and an amino group, or $R^{5a}$ is a halo group; and $R^{5b}$ is a hydrogen atom, a halo group, a $C_1$-$C_3$ nitrile group, a $C_1$-$C_3$ alkoxy group or a $C_1$-$C_3$ alkyl group optionally substituted with a substituent selected from the group consisting of an amino group and a hydroxyl group.

Alternatively, preferably, X is a CH-group, $R^{5a}$ is a nitrogen-containing heterocyclyl group optionally substituted with a methyl group; and $R^{5b}$ is a hydrogen atom, a methyl group or a methoxy group.

Alternatively, preferably, X is a CH-group, $R^{5a}$ is a unsubstituted nitrogen-containing heterocyclyl group; and $R^{5b}$ is a hydrogen atom, a methyl group or a methoxy group.

Alternatively, preferably, $R^5$ is a group represented by the formula (f):

(f)

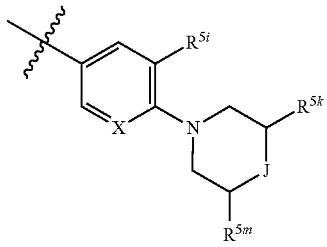

wherein $R^{5i}$ is a hydrogen atom, a halo group, an optionally substituted $C_1$-$C_4$ or $C_r$ $C_3$ alkyl or alkoxy group; $R^{5k}$ and $R^{5m}$ are independently selected from the group consisting of a hydrogen atom, an optionally substituted $C_1$-$C_4$ alkyl group and a $C_1$-$C_4$ alkoxy group, or, $R^{5k}$ and $R^{5m}$, and the carbon atoms to which they are attached, as taken together, form a five membered heterocyclyl group; J is an oxygen atom, $CF_2$ or $NR^{5l}$, wherein $R^{5l}$ is selected from the group consisting of a hydrogen atom and an optionally substituted $C_1$-$C_4$ or $C_1$-$C_3$ alkyl or cycloalkyl group; and X can either be CH or N.

More preferably, $R^{5i}$ is a hydrogen atom, a halo group, a $C_1$-$C_3$ alkyl or alkoxy group; $R^{5k}$ and $R^{5m}$ are independently selected from the group consisting of a hydrogen atom, a $C_1$-$C_3$ alkyl group, a $C_1$-$C_3$ alkoxy group, a $CF_3$ group or a methoxymethyl group, or, $R^{5k}$ and $R^{5m}$, and the carbon atoms to which they are attached, as taken together, form a five membered heterocyclyl group; J is an oxygen atom or $NR^{5l}$, wherein $R^{5l}$ is selected from the group consisting of a hydrogen atom and $C_1$-$C_3$ alkyl or cycloalkyl group; and X can either be CH or N.

More preferably, $R^{5i}$ is a hydrogen atom, a halo group, a $C_1$-$C_3$ alkyl or alkoxy group; $R^{5k}$ is a hydrogen atom or a methyl group, $R^{5m}$ is selected from the group consisting of a hydrogen atom, a $C_1$-$C_3$ alkyl group, a $C_1$-$C_3$ alkoxy group, a $CF_3$ group or a methoxymethyl group; J is an oxygen atom or $NR^{5l}$, wherein $R^{5l}$ is selected from the group consisting of a hydrogen atom and a $C_1$-$C_2$ alkyl group; and X is a CH-group.

More preferably, $R^{5i}$ is a hydrogen atom, a $C_1$-$C_3$ alkyl or alkoxy group; $R^{5k}$ is a hydrogen atom or a methyl group, $R^{5m}$ is selected from the group consisting of a hydrogen atom, a methyl group, a methoxy group, a $CF_3$ group or a methoxymethyl group; J is an oxygen atom or $NR^{5l}$, wherein $R^{5l}$ is selected from the group consisting of a hydrogen atom and a methyl group; and X is a CH-group.

Alternatively, preferably, $R^{5i}$ is a hydrogen atom, a methyl group or a methoxy group; $R^{5k}$ and $R^{5m}$ are each independently an optionally substituted $C_1$-$C_4$ alkyl group; J is an NH-group; and X is a CH-group.

Alternatively, preferably, $R^{5i}$ is a halo group, a $C_1$-$C_3$ alkyl or alkoxy group; $R^{5k}$ is a hydrogen atom, $R^{5m}$ is a hydrogen atom; J is an oxygen atom or $NR^{5l}$, wherein $R^{5l}$ is selected from the group consisting of a hydrogen atom and a $C_1$-$C_3$ alkyl group; and X is a CH-group. More preferably, $R^{5i}$ is a methyl group or a methoxy group; $R^{5k}$ is a hydrogen atom, $R^{5m}$ is a hydrogen atom; J is an oxygen atom, an NH-group or an NMe group; and X is a CH-group. More preferably, $R^{5i}$ is a methyl group or a methoxy group; $R^{5k}$ is a hydrogen atom, $R^{5m}$ is a hydrogen atom; J is an NH-group or an NMe group; and X is a CH-group. More preferably still, $R^{5l}$ is a methyl group or a methoxy group; $R^{5k}$ is a hydrogen atom, $R^{5m}$ is a hydrogen atom; J is an NH-group; and X is a CH-group.

Alternatively, preferably, $R^5$ is a group represented by the formula (g):

(g)

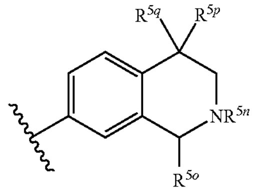

wherein $R^{5n}$ is a hydrogen atom or an optionally substituted $C_1$-$C_3$ alkyl group, $R^{5o}$ is a hydrogen atom or an optionally substituted $C_1$-$C_3$ alkyl group and $R^{5p}$ and $R^{5q}$ are each independently an optionally substituted $C_1$-$C_3$ alkyl group, or $R^{5p}$ and $R^{5q}$ and the carbon atom to which they are attached form a $C_3$-$C_6$ cycloalkyl group. More preferably, $R^{5n}$ is a hydrogen atom or a methyl group, $R^{5o}$ is an optionally substituted $C_1$-$C_3$ alkyl group and $R^{5p}$ and $R^{5q}$ are each independently an optionally substituted $C_1$-$C_3$ alkyl group, or $R^{5p}$ and $R^{5q}$ and the carbon atom to which they are attached form a cyclopropyl group. More preferably, $R^{5n}$ is a hydrogen atom or a methyl group, $R^{5o}$ is a methyl group, a $CF_3$ group, a $CF_2H$ or a $CFH_2$ group, and $R^{5p}$ and $R^{5q}$ are each independently a methyl group, or $R^{5p}$ and $R^{5q}$ and the carbon atom to which they are attached form a cyclopropyl group.

Alternatively, preferably, $R^5$ is an optionally substituted pyrazolyl group. More preferably, $R^5$ is a substituted pyrazolyl group. More preferably, $R^5$ is a pyrazolyl group substituted with an optionally substituted $C_1$-$C_3$ alkyl group. More preferably, $R^5$ is a pyrazolyl group substituted with a $C_1$-$C_3$ alkyl group optionally substituted by one, two or three halo groups. More preferably, $R^5$ is a pyrazolyl group substituted with a $C_1$-$C_3$ alkyl group or a $CH_2$—$CF_3$ group. More preferably, $R^5$ is a pyrazolyl group substituted with a propyl group or a $CH_2$—$CF_3$ group.

More preferably, $R^5$ is a group represented by the formula (p):

(p)

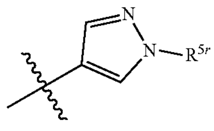

wherein $R^{5r}$ is an optionally substituted $C_1$-$C_3$ alkyl group. More preferably, $R^{5r}$ is a $C_1$-$C_3$ alkyl group optionally substituted by one, two or three halo groups. More preferably, $R^{5r}$ is a $C_1$-$C_3$ alkyl group or a $CH_2$—$CF_3$ group. More preferably, $R^{5r}$ is a propyl group or a $CH_2$—$CF_3$ group.

In an alternative embodiment, $R^5$ an optionally substituted cycloalkyl group. Preferably, the cycloalkyl group is a four- to six-membered cycloalykyl group, more preferably a four- to five-membered cycloalykyl group. Preferably, the cycloalkyl group is bridged or unbridged. Preferably, the cycloalkyl group is a cyclobutyl group or a bridged cyclobutyl group. More preferably, the cycloalkyl group is a cyclobutyl group.

Alternatively, in one embodiment, $R^5$ is not a bridged cycloalkyl group.

In one embodiment, $R^5$ is not an unsubstituted pyridyl group.

In one embodiment, $R^5$ is not a bridged cycloalkyl group or an unsubstituted pyridyl group.

In one embodiment, $R^6$ is not a cyano-substituted phenyl group.

In one embodiment, $R^5$ is not a bridged cycloalkyl group or an unsubstituted pyridyl group and $R^6$ is not a cyano-substituted phenyl group.

Preferably, $R^5$ is a group represented by formula (d) or (p), as defined above. More preferably, $R^5$ is a group represented by formula (e) or (p), as defined above. More preferably, $R^5$ is a group represented by formula (n) or (p), as defined above. More preferably, $R^5$ is a group represented by formula (f) or (p), as defined above.

Preferably $R^6$ is a hydrogen atom.

Preferably, Y is an optionally substituted aryl group or an optionally substituted heteroaryl group. More preferably, Y is an optionally substituted five- to seven-membered aryl group or an optionally substituted five- to seven-membered heteroaryl group. More preferably, Y is an optionally substituted six-membered aryl group or an optionally substituted five- or six-membered heteroaryl group.

More preferably, Y is an optionally substituted phenyl group, an optionally substituted pyridyl group, an optionally substituted pyrazinyl group or an optionally substituted pyrimidinyl group. More preferably, Y is a phenyl group, a pyridyl group, a pyrazinyl group or a pyrimidinyl group.

More preferably, Y is a group represented by any of formulae (j), (k), (l), and (m):

(j)

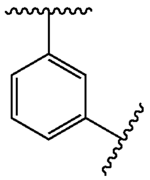

(k)

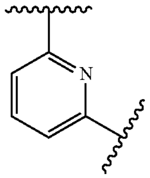

(l)

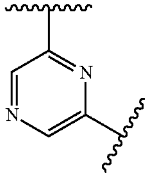

(m)

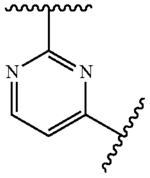

More preferably, Y is a group represented by any of formulae (j), (k), and (l) as defined above. More preferably, Y is a group represented by formula (j) or formula (k) as defined above. Most preferably, Y is a group represented by formula (k) as defined above.

Preferably, in the compound of Formula (I), $R^1$ is a $C_1$-$C_3$ alkyl group; $R^2$ is a $C_1$-$C_3$ alkyl group; $R^4$ is a $C_1$-$C_4$ alkyl group or a $C_2$-$C_4$ alkenyl group; $R^5$ is a group represented by formula (d) or formula (p) as defined above; $R^6$ is a hydrogen atom; and Y is a group represented by any of formulae (j), (k) or (l). More preferably, in the compound of Formula (I), $R^1$ is a $C_1$-$C_3$ alkyl group; $R^2$ is a $C_1$-$C_3$ alkyl group; $R^4$ is a $C_1$-$C_4$ alkyl group or a $C_2$-$C_4$ alkenyl group; $R^5$ is a group represented by formula (e) or formula (p) as defined above; $R^6$ is a hydrogen atom; and Y is a group represented by any of formulae (j), (k) or (l). More preferably, in the compound of Formula (I), $R^1$ is a $C_1$-$C_3$ alkyl group; $R^2$ is a $C_1$-$C_3$ alkyl group; $R^4$ is a $C_1$-$C_4$ alkyl group or a $C_2$-$C_4$ alkenyl group; $R^5$ is a group represented by formula (n) or formula (p) as defined above; $R^6$ is a hydrogen atom; and Y is a group represented by any of formulae (j), (k) or (l). More preferably, in the compound of Formula (I), $R^1$ is a $C_1$-$C_2$ alkyl group; $R^2$ is a $C_1$-$C_2$ alkyl group; $R^4$ is a $C_2$-$C_3$ alkyl group or a $C_2$-$C_3$ alkenyl group; $R^5$ is a group represented by formula (f) or formula (p) as defined above; $R^6$ is a hydrogen atom; and Y is a group represented by any of formulae (j), (k) or (l). More preferably, in the compound of Formula (I), $R^1$ is a methyl group; $R^2$ is a methyl group; $R^4$ is a propyl group or an allyl group; $R^5$ is a group represented by formula (f) as defined above; $R^6$ is a hydrogen atom; and Y is a group represented by formula (k).

Alternatively, preferably, in the compound of Formula (I), $R^1$ is a methyl group; and $R^2$ is a methyl group; and $R^4$ is an allyl group; and/or $R^5$ is a group represented by the formula (d) as defined above; and Y is a pyridyl, phenyl or pyrazinyl group. More preferably, in the compound of Formula (I), $R^1$ is a methyl group; $R^2$ is a methyl group; $R^4$ is an allyl group; $R^5$ is a group represented by the formula (f) as defined above; $R^6$ is a hydrogen atom; and Y is a group represented by formula (k) as defined above.

Alternatively, preferably, in the compound of Formula (I), $R^1$ is a methyl group; $R^2$ is a methyl group; $R^4$ is an allyl group; $R^5$ is a 4-linked N-1-substituted pyrazolyl group; $R^6$ is a hydrogen atom Y is a group represented by formula (j) or formula (k). More preferably, in the compound of Formula (I), $R^1$ is a methyl group; $R^2$ is a methyl group; $R^4$ is an allyl group; $R^5$ is a 4-linked N-1-substituted pyrazolyl group; $R^6$ is a hydrogen atom; and Y is a pyridyl group. More preferably still, in the compound of Formula (I), $R^1$ is a methyl group; $R^2$ is a methyl group; $R^4$ is an allyl group; $R^5$ is a 4-linked N-1-substituted pyrazolyl group; $R^6$ is a hydrogen atom; and Y is a group represented by formula (k) as defined above.

Preferably, in the compound of Formula (II), $R^2$ is a methyl group or a cyclopropyl group; $R^3$ is a hydrogen atom, a methyl group, a cyano group or an alkoxy-carbonyl group; $R^4$ is an allyl group; $R^5$ is a group represented by formula (d) as defined above; $R^6$ is a hydrogen atom; and Y is a pyridyl or phenyl group. More preferably, in the compound of Formula (II), $R^2$ is a methyl group or a cyclopropyl group; $R^3$ is a hydrogen atom, a methyl group, a cyano group or an alkoxy-carbonyl group; $R^4$ is an allyl group; $R^5$ is a group represented by the formula (e) as defined above; $R^6$ is a hydrogen atom; and Y is a group represented by formula (j) or formula (k). More preferably, in the compound of Formula (II), $R^2$ is a methyl group or a cyclopropyl group; $R^3$ is a hydrogen atom, a methyl group, a cyano group or an alkoxy-carbonyl group; $R^4$ is an allyl group; $R^5$ is a group represented by the formula (n) as defined above; $R^6$ is a hydrogen atom; and Y is a group represented by formula (j) or formula (k). More preferably still, in the compound of Formula (II), $R^2$ is a methyl group or a cyclopropyl group; $R^3$ is a hydrogen atom, a methyl group, a cyano group or an alkoxy-carbonyl group; $R^4$ is an allyl group; $R^5$ is a group represented by the formula (f) as defined above; $R^6$ is a hydrogen atom; and Y is a group represented by formula (k) as defined above.

Preferably, the compound of Formula (I) is selected from the following:

(5) 1-(6-{[Dimethyl(oxo)-$\lambda^6$-sulfanylidene]amino}pyridine-2-yl)-6-{[4-(4-methylpiperazin-1-yl)phenyl]amino}-2-(prop-2-en-1-yl)-1H,2H,3H-pyrazolo[3,4-d]pyrimidin-3-one;

(6) 1-(6-{[Dimethyl(oxo)-$\lambda^6$-sulfanylidene]amino}pyridine-2-yl)-6-{[4-(piperazin-1-yl)phenyl]amino}-2-(prop-2-en-1-yl)-1H,2H,3H-pyrazolo[3,4-d]pyrimidin-3-one;

(7: 1-(6-{[Dimethyl(oxo)-$\lambda^6$-sulfanylidene]amino}pyridine-2-yl)-2-(prop-2-en-1-yl)-6-({4-[4-(propan-2-yl)piperazin-1-yl]phenyl}amino)-1H,2H,3H-pyrazolo[3,4-d]pyrimidin-3-one;

(8) 6-{[4-(4-Cyclopropylpiperazin-1-yl)phenyl]amino}-1-(6-{[dimethyl(oxo)-$\lambda^6$-sulfanylidene]amino}pyridine-2-yl)-2-(prop-2-en-1-yl)-1H,2H,3H-pyrazolo[3,4-d]pyrimidin-3-one;

(9) 1-(6-{[Dimethyl(oxo)-$\lambda^6$-sulfanylidene]amino}pyridine-2-yl)-6-({4-[(3R)-3-methylpiperazin-1-yl]phenyl}amino)-2-(prop-2-en-1-yl)-1H,2H,3H-pyrazolo[3,4-d]pyrimidin-3-one;

(10) 1-(6-{[Dimethyl(oxo)-$\lambda^6$-sulfanylidene]amino}pyridine-2-yl)-6-{[4-(4-ethylpiperazin-1-yl)phenyl]amino}-2-(prop-2-en-1-yl)-1H,2H,3H-pyrazolo[3,4-d]pyrimidin-3-one;

(11) 1-(6-{[Dimethyl(oxo)-$\lambda^6$-sulfanylidene]amino}pyridine-2-yl)-6-{[4-(4-methylpiperazin-1-yl)phenyl]amino}-2-propyl-1H,2H,3H-pyrazolo[3,4-d]pyrimidin-3-one;

(12) 1-(6-{[Dimethyl(oxo)-$\lambda^6$-sulfanylidene]amino}pyridine-2-yl)-6-{[4-(morpholin-4-yl)phenyl]amino}-2-(prop-2-en-1-yl)-1H,2H,3H-pyrazolo[3,4-d]pyrimidin-3-one;

(13) 1-(6-{[Dimethyl(oxo)-$\lambda^6$-sulfanylidene]amino}pyridine-2-yl)-6-{[4-(piperidin-4-yl)phenyl]amino}-2-(prop-2-en-1-yl)-1H,2H,3H-pyrazolo[3,4-d]pyrimidin-3-one;

(14) 6-{[3-Chloro-4-(piperazin-1-yl)phenyl]amino}-1-(6-{[dimethyl(oxo)-$\lambda^6$-sulfanylidene]amino}pyridine-2-yl)-2-(prop-2-en-1-yl)-1H,2H,3H-pyrazolo[3,4-d]pyrimidin-3-one;

(15) 1-(6-{[Dimethyl(oxo)-$\lambda^6$-sulfanylidene]amino}pyridine-2-yl)-6-({2'-methyl-2',3'-dihydro-1'H-spiro[cyclopropane-1,4'-isoquinoline]-7'-yl}amino)-2-(prop-2-en-1-yl)-1H,2H,3H-pyrazolo[3,4-d]pyrimidin-3-one;

(16) 1-(3-{[Dimethyl(oxo)-$\lambda^6$-sulfanylidene]amino}phenyl)-6-{[4-(4-methylpiperazin-1-yl)phenyl]amino}-2-(prop-2-en-1-yl)-1H,2H,3H-pyrazolo[3,4-d]pyrimidin-3-one;

(17) 1-(6-{[Dimethyl(oxo)-$\lambda^6$-sulfanylidene]amino}pyridin-2-yl)-6-({4-[(3R,5S)-3,5-dimethylpiperazin-1-yl]phenyl}amino)-2-(prop-2-en-1-yl)-1H,2H,3H-pyrazolo[3,4-d]pyrimidin-3-one;

(18) 1-(3-{[Dimethyl(oxo)-$\lambda^6$-sulfanylidene]amino}phenyl)-6-{[4-(piperazin-1-yl)phenyl]amino}-2-(prop-2-en-1-yl)-1H,2H,3H-pyrazolo[3,4-d]pyrimidin-3-one;

(19) 1-(6-{[Dimethyl(oxo)-$\lambda^6$-sulfanylidene]amino}pyridin-2-yl)-6-(phenylamino)-2-(prop-2-en-1-yl)-1H,2H,3H-pyrazolo[3,4-d]pyrimidin-3-one;

(20) 1-(6-{[Dimethyl(oxo)-$\lambda^6$-sulfanylidene]amino}pyridin-2-yl)-6-{[4-(4-methylpiperazin-1-yl)phenyl]amino}-2-(propan-2-yl)-1H,2H,3H-pyrazolo[3,4-d]pyrimidin-3-one;

(21) 1-(6-{[Dimethyl(oxo)-$\lambda^6$-sulfanylidene]amino}pyridin-2-yl)-6-{[3-methyl-4-(morpholin-4-yl)phenyl]amino}-2-(prop-2-en-1-yl)-1H,2H,3H-pyrazolo[3,4-d]pyrimidin-3-one;

(22) 1-(3-{[Dimethyl(oxo)-$\lambda^6$-sulfanylidene]amino}phenyl)-6-({3-[(methylamino)methyl]-4-(morpholin-4-yl)phenyl}amino)-2-(prop-2-en-1-yl)-1H,2H,3H-pyrazolo[3,4-d]pyrimidin-3-one;

(23) 2-Allyl-6-((4-(4-methylpiperazin-1-yl)phenyl)amino)-1-(6-((1-oxidotetrahydrothiophen-1-ylidene)amino)pyridin-2-yl)-1H-pyrazolo[3,4-d]pyrimidin-3(2H)-one;

(24) 1-(6-{[Dimethyl(oxo)-$\lambda^6$-sulfanylidene]amino}pyridin-2-yl)-6-{[3-methoxy-4-(4-methylpiperazin-1-yl)phenyl]amino}-2-(prop-2-en-1-yl)-1H,2H,3H-pyrazolo[3,4-d]pyrimidin-3-one

(25) 1-(6-{[Dimethyl(oxo)-$\lambda^6$-sulfanylidene]amino}pyridin-2-yl)-6-{[3-methoxy-4-(morpholin-4-yl)phenyl]amino}-2-(prop-2-en-1-yl)-1H,2H,3H-pyrazolo[3,4-d]pyrimidin-3-one;

(26) 1-(6-{[Dimethyl(oxo)-$\lambda^6$-sulfanylidene]amino}pyridin-2-yl)-6-{[3-methyl-4-(piperazin-1-yl)phenyl]amino}-2-(prop-2-en-1-yl)-1H,2H,3H-pyrazolo[3,4-d]pyrimidin-3-one;

(27): 1-(3-{[Dimethyl(oxo)-$\lambda^6$-sulfanylidene]amino}phenyl)-6-({4-[2-(methylamino)ethoxy]phenyl}amino)-2-(prop-2-en-1-yl)-1H,2H,3H-pyrazolo[3,4-d]pyrimidin-3-one;

(28) 1-(6-{[Dimethyl(oxo)-$\lambda^6$-sulfanylidene]amino}pyridin-2-yl)-6-{[3-methyl-4-(4-methylpiperazin-1-yl)phenyl]amino}-2-(prop-2-en-1-yl)-1H,2H,3H-pyrazolo[3,4-d]pyrimidin-3-one;

(29) 1-(3-{[Dimethyl(oxo)-$\lambda^6$-sulfanylidene]amino}phenyl)-6-{[3-(hydroxymethyl)-4-(piperazin-1-yl)phenyl]amino}-2-(prop-2-en-1-yl)-1H,2H,3H-pyrazolo[3,4-d]pyrimidin-3-one;

(30) 1-(3-{[Dimethyl(oxo)-$\lambda^6$-sulfanylidene]amino}phenyl)-6-{[3-(hydroxymethyl)-4-(4-methylpiperazin-1-yl)phenyl]amino}-2-(prop-2-en-1-yl)-1H,2H,3H-pyrazolo[3,4-d]pyrimidin-3-one;

(31) 1-(3-{[Dimethyl(oxo)-$\lambda^6$-sulfanylidene]amino}phenyl)-6-{[4-(morpholin-4-yl)phenyl]amino}-2-(prop-2-en-1-yl)-1H,2H,3H-pyrazolo[3,4-d]pyrimidin-3-one;

(32) 1-(6-{[Dimethyl(oxo)-$\lambda^6$-sulfanylidene]amino}pyridin-2-yl)-6-{4-([(2S,6R)-2,6-dimethylmorpholin-4-yl]phenyl)amino}-2-(prop-2-en-1-yl)-1H,2H,3H-pyrazolo[3,4-d]pyrimidin-3-one

(33) 1-(6-{[Dimethyl(oxo)-$\lambda^6$-sulfanylidene]amino}pyridin-2-yl)-6-{[5-(morpholin-4-yl)pyridin-3-yl]amino}-2-(prop-2-en-1-yl)-1H,2H,3H-pyrazolo[3,4-d]pyrimidin-3-one;

(34) 1-(6-{[Dimethyl(oxo)-$\lambda^6$-sulfanylidene]amino}pyridin-2-yl)-6-{[4-(4,4-difluoropiperidin-1-yl)phenyl]amino}-2-(prop-2-en-1-yl)-1H,2H,3H-pyrazolo[3,4-d]pyrimidin-3-one;

(35) 1-(6-{[Dimethyl(oxo)-$\lambda^6$-sulfanylidene]amino}pyridin-2-yl)-6-{[3-(morpholin-4-yl)phenyl]amino}-2-(prop-2-en-1-yl)-1H,2H,3H-pyrazolo[3,4-d]pyrimidin-3-one;

(36) 1-(6-{[Dimethyl(oxo)-$\lambda^6$-sulfanylidene]amino}pyridin-2-yl)-6-{[4-(8-oxa-3-azabicyclo[3.2.1]octan-3-yl)phenyl]amino}-2-(prop-2-en-1-yl)-1H,2H,3H-pyrazolo[3,4-d]pyrimidin-3-one;

(37) 1-(6-{[Dimethyl(oxo)-$\lambda^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one;

(38) 1-(6-{[Dimethyl(oxo)-$\lambda^6$-sulfanylidene]amino}pyridin-2-yl)-6-{[4-(morpholin-4-yl)phenyl]amino}-2-propyl-1H,2H,3H-pyrazolo[3,4-d]pyrimidin-3-one;

(39) 1-(6-{[Dimethyl(oxo)-λ$^6$-sulfanylidene]amino}pyridin-2-yl)-6-{[6-(morpholin-4-yl)pyridin-3-yl]amino}-2-propyl-1H,2H,3H-pyrazolo[3,4-d]pyrimidin-3-one;

(40) 1-(6-{[Dimethyl(oxo)-λ$^6$-sulfanylidene]amino}pyridin-2-yl)-6-[(4-fluorophenyl)amino]-2-(prop-2-en-1-yl)-1H,2H,3H-pyrazolo[3,4-d]pyrimidin-3-one;

(41) 1-(6-{[Dimethyl(oxo)-λ$^6$-sulfanylidene]amino}pyridin-2-yl)-6-[(4-fluorophenyl)amino]-2-(propan-2-yl)-1H,2H,3H-pyrazolo[3,4-d]pyrimidin-3-one;

(42) 1-(6-{[Dimethyl(oxo)-λ$^6$-sulfanylidene]amino}pyridin-2-yl)-6-[(4-methoxyphenyl)amino]-2-(propan-2-yl)-1H,2H,3H-pyrazolo[3,4-d]pyrimidin-3-one;

(43) 1-(6-{[Dimethyl(oxo)-λ$^6$-sulfanylidene]amino}pyridin-2-yl)-6-{[4-(morpholin-4-yl)phenyl]amino}-2-(propan-2-yl)-1H,2H,3H-pyrazolo[3,4-d]pyrimidin-3-one;

(44) 1-(5-{[Dimethyl(oxo)-λ$^6$-sulfanylidene]amino}pyridin-3-yl)-6-{[4-(morpholin-4-yl)phenyl]amino}-2-(prop-2-en-1-yl)-1H,2H,3H-pyrazolo[3,4-d]pyrimidin-3-one;

(45) rac-1-(6-{[Dimethyl(oxo)-λ$^6$-sulfanylidene]amino}pyridin-2-yl)-2-(propan-2-yl)-6-({4-[3-(trifluoromethyl)piperazin-1-yl]phenyl}amino)-1H,2H,3H-pyrazolo[3,4-d]pyrimidin-3-one;

(46) 6-{[4-(1,4-Diazepan-1-yl)phenyl]amino}-1-(6-{[dimethyl(oxo)-λ$^6$-sulfanylidene]amino}pyridin-2-yl)-2-(propan-2-yl)-1H,2H,3H-pyrazolo[3,4-d]pyrimidin-3-one;

(47) 6-(Cyclobutylamino)-1-(6-{[dimethyl(oxo)-λ$^6$-sulfanylidene]amino}pyridin-2-yl)-2-(propan-2-yl)-1H,2H,3H-pyrazolo[3,4-d]pyrimidin-3-one;

(48) 4-(4-{[1-(6-{[Dimethyl(oxo)-λ$^6$-sulfanylidene]amino}pyridin-2-yl)-3-oxo-2-(propan-2-yl)-1H,2H,3H-pyrazolo[3,4-d]pyrimidin-6-yl]amino}phenyl)piperazin-2-one;

(49) 4-(4-{[1-(6-{[Dimethyl(oxo)-λ$^6$-sulfanylidene]amino}pyridin-2-yl)-3-oxo-2-(propan-2-yl)-1H,2H,3H-pyrazolo[3,4-d]pyrimidin-6-yl]amino}phenyl)morpholin-3-one;

(50) 1-(6-{[Dimethyl(oxo)-λ$^6$-sulfanylidene]amino}pyridin-2-yl)-2-(propan-2-yl)-6-({4-[4-(2,2,2-trifluoroethyl)piperazin-1-yl]phenyl}amino)-1H,2H,3H-pyrazolo[3,4-d]pyrimidin-3-one;

(51) 1-(6-{[Dimethyl(oxo)-λ$^6$-sulfanylidene]amino}pyrazin-2-yl)-6-{[4-(morpholin-4-yl)phenyl]amino}-2-(prop-2-en-1-yl)-1H,2H,3H-pyrazolo[3,4-d]pyrimidin-3-one;

(52) 1-(4-{[Dimethyl(oxo)-λ$^6$-sulfanylidene]amino}pyrimidin-2-yl)-6-{[4-(morpholin-4-yl)phenyl]amino}-2-(prop-2-en-1-yl)-1H,2H,3H-pyrazolo[3,4-d]pyrimidin-3-one;

(53) 1-(6-{[Dimethyl(oxo)-λ$^6$-sulfanylidene]amino}pyridin-2-yl)-6-({4-[(2S)-2-(methoxymethyl)morpholin-4-yl]phenyl}amino)-2-(propan-2-yl)-1H,2H,3H-pyrazolo[3,4-d]pyrimidin-3-one;

(54) 1-(6-{[Dimethyl(oxo)-λ$^6$-sulfanylidene]amino}pyridin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one;

(55) 6-[(4-Fluorophenyl)amino]-1-{6-[(1-oxo-1λ$^6$-thiolan-1-ylidene)amino]pyridin-2-yl}-2-(propan-2-yl)-1H,2H,3H-pyrazolo[3,4-d]pyrimidin-3-one;

(56) 6-[(1-Methyl-1H-pyrazol-4-yl)amino]-1-{6-[(1-oxo-1λ$^6$-thiolan-1-ylidene)amino]pyridin-2-yl}-2-(propan-2-yl)-1H,2H,3H-pyrazolo[3,4-d]pyrimidin-3-one;

(57) 1-(6-{[Dimethyl(oxo)-λ$^6$-sulfanylidene]amino}pyridin-2-yl)-6-{[4-(dimethylamino)phenyl]amino}-2-(prop-2-en-1-yl)-1H,2H,3H-pyrazolo[3,4-d]pyrimidin-3-one;

(58) 1-(6-{[Dimethyl(oxo)-λ$^6$-sulfanylidene]amino}pyridin-2-yl)-6-{[4-(dimethylamino)phenyl]amino}-2-(propan-2-yl)-1H,2H,3H-pyrazolo[3,4-d]pyrimidin-3-one;

(59) 1-{6-[(1-Oxo-1λ$^6$-thiolan-1-ylidene)amino]pyridin-2-yl}-6-{[4-(piperazin-1-yl)phenyl]amino}-2-(propan-2-yl)-1H,2H,3H-pyrazolo[3,4-d]pyrimidin-3-one;

(60) 4-[(4-Cyanophenyl)[1-(6-{[dimethyl(oxo)-λ$^6$-sulfanylidene]amino}pyridin-2-yl)-3-oxo-2-(propan-2-yl)-1H,2H,3H-pyrazolo[3,4-d]pyrimidin-6-yl]amino]benzonitrile;

(61) 6-[(4-Chlorophenyl)amino]-1-(6-{[dimethyl(oxo)-λ$^6$-sulfanylidene]amino}pyridin-2-yl)-2-(propan-2-yl)-1H,2H,3H-pyrazolo[3,4-d]pyrimidin-3-one;

(62) 6-[(4-Chlorophenyl)amino]-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(63) 6-({Bicyclo[1.1.1]pentan-1-yl}amino)-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(64) 6-[(4-tert-Butylphenyl)amino]-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(65) 6-[(2,4-Difluorophenyl)amino]-1-(6-{[dimethyl(oxo)-λ$^6$-sulfanylidene]amino}pyridin-2-yl)-2-(propan-2-yl)-1H,2H,3H-pyrazolo[3,4-d]pyrimidin-3-one;

(66) 6-[(3,4-Difluorophenyl)amino]-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(67) 6-({4-[(3aR,6aS)-Hexahydro-1H-furo[3,4-c]pyrrol-5-yl]phenyl}amino)-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(68) 1-(6-{[Dimethyl(oxo)-λ$^6$-sulfanylidene]amino}pyridin-2-yl)-6-({4-[(1S,4S)-2-oxa-5-azabicyclo[2.2.1]heptan-5-yl]phenyl}amino)-2-(prop-2-en-1-yl)-1H,2H,3H-pyrazolo[3,4-d]pyrimidin-3-one;

(69) rac-1-(6-{[Dimethyl(oxo)-λ$^6$-sulfanylidene]amino}pyridin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one;

(70) 1-(6-{[Dimethyl(oxo)-λ$^6$-sulfanylidene]amino}pyridin-2-yl)-6-[(6-fluoropyridin-3-yl)amino]-2-(prop-2-en-1-yl)-1H,2H,3H-pyrazolo[3,4-d]pyrimidin-3-one;

(71) 4-{[1-(6-{[Dimethyl(oxo)-λ$^6$-sulfanylidene]amino}pyridin-2-yl)-3-oxo-2-(propan-2-yl)-1H,2H,3H-pyrazolo[3,4-d]pyrimidin-6-yl]amino}benzonitrile;

(72) 1-(6-{[Dimethyl(oxo)-λ$^6$-sulfanylidene]amino}pyridin-2-yl)-2-(propan-2-yl)-6-{[4-(trifluoromethyl)phenyl]amino}-1H,2H,3H-pyrazolo[3,4-d]pyrimidin-3-one;

(73) 1-(6-{[Dimethyl(oxo)-λ$^6$-sulfanylidene]amino}pyridin-2-yl)-2-(propan-2-yl)-6-{[3-(trifluoromethyl)phenyl]amino}-1H,2H,3H-pyrazolo[3,4-d]pyrimidin-3-one;

(74) 1-(6-{[Dimethyl(oxo)-λ$^6$-sulfanylidene]amino}pyrazin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one;

(75) 1-(6-{[Dimethyl(oxo)-λ$^6$-sulfanylidene]amino}pyrazin-2-yl)-6-[(4-fluorophenyl)amino]-2-(prop-2-en-1-yl)-1H,2H,3H-pyrazolo[3,4-d]pyrimidin-3-one;

(76) 1-(6-{[Dimethyl(oxo)-$\lambda^6$-sulfanylidene]amino}pyridin-2-yl)-6-({4-[(3S)-3-(methoxymethyl)piperazin-1-yl]phenyl}amino)-2-(prop-2-en-1-yl)-1H,2H,3H-pyrazolo[3,4-d]pyrimidin-3-one;

(77) 1-(6-{[Dimethyl(oxo)-$\lambda^6$-sulfanylidene]amino}pyridin-2-yl)-2-(prop-2-en-1-yl)-6-[(pyridin-3-yl)amino]-1H,2H,3H-pyrazolo[3,4-d]pyrimidin-3-one;

(78) 6-[(1-Methyl-1H-pyrazol-4-yl)amino]-1-{6-[(1-oxo-1$\lambda^6$-thiolan-1-ylidene)amino]pyridin-2-yl}-2-(prop-2-en-1-yl)-1H,2H,3H-pyrazolo[3,4-d]pyrimidin-3-one;

(79) 1-(6-{[(S)-Methyl(oxo)phenyl-$\lambda^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one;

(80) 1-(6-{[Dimethyl(oxo)-$\lambda^6$-sulfanylidene]amino}pyridin-2-yl)-2-(prop-2-en-1-yl)-6-{[1-(propan-2-yl)-1H-pyrazol-4-yl]amino}-1H,2H,3H-pyrazolo[3,4-d]pyrimidin-3-one;

(81) 1-(6-{[Dimethyl(oxo)-$\lambda^6$-sulfanylidene]amino}pyridin-2-yl)-2-(prop-2-en-1-yl)-6-{[6-(trifluoromethyl)pyridin-3-yl]amino}-1H,2H,3H-pyrazolo[3,4-d]pyrimidin-3-one;

(82) 1-(6-{[Dimethyl(oxo)-$\lambda^6$-sulfanylidene]amino}pyridin-2-yl)-6-[(4-fluoro-3-methoxyphenyl)amino]-2-(prop-2-en-1-yl)-1H,2H,3H-pyrazolo[3,4-d]pyrimidin-3-one;

(83) rac-1-(6-{[Dimethyl(oxo)-$\lambda^6$-sulfanylidene]amino}pyridin-2-yl)-6-{[4-(dimethylamino)-3-(2,2,2-trifluoro-1-hydroxyethyl)phenyl]amino}-2-(prop-2-en-1-yl)-1H,2H,3H-pyrazolo[3,4-d]pyrimidin-3-one;

(84) 6-[(3,5-Difluorophenyl)amino]-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(85) 1-(6-{[Dimethyl(oxo)-$\lambda^6$-sulfanylidene]amino}pyridin-2-yl)-2-(prop-2-en-1-yl)-6-{[1-(2,2,2-trifluoroethyl)-1H-pyrazol-4-yl]amino}-1H,2H,3H-pyrazolo[3,4-d]pyrimidin-3-one;

(86) rac-1-(6-{[Dimethyl(oxo)-$\lambda^6$-sulfanylidene]amino}pyridin-2-yl)-6-({3-methoxy-4-[3-(trifluoromethyl)piperazin-1-yl]phenyl}amino)-2-(prop-2-en-1-yl)-1H,2H,3H-pyrazolo[3,4-d]pyrimidin-3-one;

(87) rac-1-(6-{[Dimethyl(oxo)-$\lambda^6$-sulfanylidene]amino}pyridin-2-yl)-6-({3-methoxy-4-[4-methyl-3-(trifluoromethyl)piperazin-1-yl]phenyl}amino)-2-(prop-2-en-1-yl)-1H,2H,3H-pyrazolo[3,4-d]pyrimidin-3-one;

(88) 6-{[4-(1-Cyclobutylpiperidin-4-yl)-3-methylphenyl]amino}-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(89) 1-(6-{[Dimethyl(oxo)-$\lambda^6$-sulfanylidene]amino}pyridin-2-yl)-6-({4-[(2-methoxyethyl)(methyl)amino]phenyl}amino)-2-(prop-2-en-1-yl)-1H,2H,3H-pyrazolo[3,4-d]pyrimidin-3-one;

(90) 6-{[4-(Azetidin-1-yl)phenyl]amino}-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(91) 1-[6-({[Dimethyl(oxo)-$\lambda^6$-sulfanylidene]amino}methyl)pyridin-2-yl]-6-{[4-(morpholin-4-yl)phenyl]amino}-2-(prop-2-en-1-yl)-1H,2H,3H-pyrazolo[3,4-d]pyrimidin-3-one;

(92) 2-(Cyclopropylmethyl)-1-(6-{[dimethyl(oxo)-$\lambda^6$-sulfanylidene]amino}pyridin-2-yl)-6-{[4-(morpholin-4-yl)phenyl]amino}-1H,2H,3H-pyrazolo[3,4-d]pyrimidin-3-one;

(93) rac-1-(6-{[Dimethyl(oxo)-$\lambda^6$-sulfanylidene]amino}pyrazin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one; and

(94) 1-(6-((Dimethyl(oxo)-λ6-sulfaneylidene)amino)pyridin-2-yl)-6-((1-isopropyl-1H-pyrazol-4-yl)amino)-2-(prop-2-yn-1-yl)-1,2-dihydro-3H-pyrazolo[3,4-d]pyrimidin-3-one.

Preferably, the compound of Formula (I) is selected from the following:

(95) 2-Allyl-6-((1-allyl-1H-pyrazol-4-yl)amino)-1-(6-((dimethyl(oxo)-$\lambda^6$-sulfaneylidene)amino)pyridin-2-yl)-1,2-dihydro-3H-pyrazolo[3,4-d]pyrimidin-3-one;

(96) 2-Allyl-6-((1-cyclohexyl-1H-pyrazol-4-yl)amino)-1-(6-((dimethyl(oxo)-$\lambda^6$-sulfaneylidene)amino)pyridin-2-yl)-1,2-dihydro-3H-pyrazolo[3,4-d]pyrimidin-3-one; and

(97) rac-2-Allyl-6-((1-cyclohexyl-1H-pyrazol-4-yl)amino)-1-(6-((dimethyl(oxo)-$\lambda^6$-sulfaneylidene)amino)pyridin-2-yl)-1,2-dihydro-3H-pyrazolo[3,4-d]pyrimidin-3-one.

Preferably, the compound of Formula (II) is selected from the following:

(1) 1-{6-[(Cyanoimino)(methyl)oxo-$\lambda^6$-sulfanyl]pyridin-2-yl}-6-{[4-(4-methylpiperazin-1-yl)phenyl]amino}-2-(prop-2-en-1-yl)-1H,2H,3H-pyrazolo[3,4-d]pyrimidin-3-one;

(2) rac-Ethyl N-{methyl[6-(6-{[4-(4-methylpiperazin-1-yl)phenyl]amino}-3-oxo-2-(prop-2-en-1-yl)-1H,2H,3H-pyrazolo[3,4-d]pyrimidin-1-yl)pyridine-2-yl]oxo-$\lambda^6$-sulfanylidene}carbamate;

(3) rac-2-Allyl-6-((4-(4-methylpiperazin-1-yl)phenyl)amino)-1-(6-(S-methylsulfonimidoyl)pyridin-2-yl)-1H-pyrazolo[3,4-d]pyrimidin-3(2H)-one; and (4) rac-2-Allyl-1-(6-(N,S-dimethylsulfonimidoyl)pyridin-2-yl)-6-((4-(4-methylpiperazin-1-yl)phenyl)amino)-1H-pyrazolo[3,4-d]pyrimidin-3(2H)-one.

Preferably, there is provided the compound of Formula (I) or Formula (II), or a pharmaceutically acceptable salt or N-oxide derivative thereof, and at least one pharmaceutically acceptable excipient.

Suitable pharmaceutically acceptable excipients would be known by the person skilled in the art, for example, fats, water, physiological saline, alcohol (e.g., ethanol), glycerol, polyols, aqueous glucose solution, extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant, saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

Preferably, there is provided a pharmaceutical composition comprising the compound of Formula (I) or Formula (II), or a pharmaceutically acceptable salt or N-oxide derivative thereof, and at least one pharmaceutically acceptable excipient. In certain embodiments, the pharmaceutical composition further comprises an anti-cancer agent, for example as a combination therapy as described herein. In such embodiments, a suitable anti-cancer agent may be any one or more of a genotoxic agent, a targeted agent and an immune-modulator.

Preferably, there is provided the compound of Formula (I) or Formula (II), or a pharmaceutically acceptable salt or N-oxide derivative thereof, or the pharmaceutical composition as described herein, for use in therapy.

Preferably, there is provided the compound of Formula (I) or Formula (II), or a pharmaceutically acceptable salt or N-oxide derivative thereof, or the pharmaceutical composition as described herein, for use as a medicament.

Preferably, there is provided the compound of Formula (I) or Formula (II), or a pharmaceutically acceptable salt or N-oxide derivative thereof, or the pharmaceutical composition as described herein, for use in treating or preventing cancer. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

Preferably, there is provided the use of the compound of Formula (I) or Formula (II), or a pharmaceutically acceptable salt or N-oxide derivative thereof, or the pharmaceutical composition as described herein, for the manufacture of a medicament for treating or preventing cancer. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

Preferably, there is provided a method of treating or preventing cancer in a human or animal patient comprising administering to a patient in need thereof an effective amount of a compound of Formula (I) or Formula (II), or a pharmaceutically acceptable salt or N-oxide derivative thereof, or the pharmaceutical composition as described herein. Preferably the cancer is selected from colon and rectal (colorectal) cancer, head and neck cancer, lung cancer, oesophagus cancer, ovarian cancer and pancreas cancer. More preferably, the cancer is colon and rectal (colorectal) cancer. Alternatively, preferably, the cancer is lung cancer, more preferably non-small cell lung cancer.

Preferably, the compounds of the present invention have an $IC_{50}$ value for Wee-1 kinase of about 0.1 nM to about 1,000 nM, more preferably from about 0.1 nM to about 500 nM, or from about 0.1 nM to about 300 nM, or from about 0.1 nM to about 100 nM, or from about 0.1 nM to about 50 nM, or from about 0.1 nM to about 30 nM, or from about 0.1 nM to about 15 nM, or from about 0.1 nM to about 10 nM, or from about 0.1 nM to about 5 nM, or from about 0.1 nM to about 2 nM, or from about 0.1 nM to about 1 nM, or, preferably, less than 10 nM, more preferably less than 5 nM, more preferably less than 2 nM, most preferably less than 1 nM. A method for determining the $IC_{50}$ value of a compound for Wee-1 kinase is described below (see examples).

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

The following non-limiting examples further illustrate the present invention. The present invention will now be described in relation to several examples.

Examples 1 to 93 were synthesised according to the methods described subsequently. Wee-1 $IC_{50}$ values and other values were determined as described below and are represented in the following tables.

Method 1: Measurement of Wee-1 Kinase Activity

In the measurement of Wee-1 activity, a commercial peptide Poly(Lys Tyr(4:1)) hydrobromide was purchased from Sigma Aldrich and used as the substrate. Activated Wee-1 kinase was purchased from Invitrogen (PV3817) and an ADP-Glo luminescent kit was purchased from Promega.

All reactions took place in 60 μL volumes in reaction buffer containing 40 mM Tris-HCl and 20 mM magnesium chloride, supplemented with 0.1 mg/mL bovine serum albumin and 2 mM DTT. Compounds were serially diluted in buffer and 5 μL of each concentration pipetted into a white 384 well plate (Sigma Aldrich M6186). A 5 μL aliquot of the Wee-1 enzyme was added to each well and the plate centrifuged for 1 min to ensure mixing of the enzyme and inhibitor.

The plate was incubated at room temperature for 30 minutes before the addition of 2.0 μg/mL of substrate and 30 μM ATP in a 5 μL aliquot. The plate was centrifuged for one minute and incubated for 1 h at RT.

15 μL of ADP-Glo stop reagent was added to each well to quench the reaction and deplete unconverted ATP. The plate was incubated for a further 40 min in the dark at RT.

30 μL of ADP-Glo kinase detection reagent was added to each well, converting ADP to ATP, catalysing the generation of luciferin by luciferase. The plate was shaken for 1 min, and incubated in the dark for an additional hour.

Luminescence from each well was detected using the Biotek Synergy4 HD plate reader and the percentage inhibition of kinase activity calculated for each inhibitor tested. Positive (kinase only) and negative (no kinase) controls were added to each plate to ensure specific interaction of kinase and inhibitor. The $IC_{50}$ concentration for each inhibitor was calculated by plotting the percentage kinase inhibition against concentration of inhibitor and the curve generated by non-linear regression fitting.

TABLE 1

Wee-1 inhibition of exemplified compounds

| Example Number | Wee1 IC50 (nM) |
|---|---|
| 1 | 1.1 |
| 2 | 9.2 |
| 3 | 2.9 |
| 4 | 30.8 |
| 5 | 1.2 |
| 6 | 1.8 |
| 7 | 0.7 |
| 8 | 0.3 |
| 9 | 1.5 |
| 10 | 0.9 |
| 11 | 1.2 |
| 12 | 0.5 |
| 13 | 1.2 |
| 14 | 0.8 |

TABLE 1-continued

Wee-1 inhibition of exemplified compounds

| Example Number | Wee1 IC50 (nM) |
|---|---|
| 15 | 0.9 |
| 16 | 1.0 |
| 17 | 1.1 |
| 18 | 0.8 |
| 19 | 1.0 |
| 20 | 1.4 |
| 21 | 0.1 |
| 22 | 2.6 |
| 23 | 0.9 |
| 24 | 1.4 |
| 25 | 0.7 |
| 26 | 0.4 |
| 27 | 1.7 |
| 28 | 0.7 |
| 29 | 0.9 |
| 30 | 0.5 |
| 31 | 1.4 |
| 32 | 0.5 |
| 33 | 0.8 |
| 34 | 4.6 |
| 35 | 0.6 |
| 36 | 0.1 |
| 37 | 1.3 |
| 38 | 0.8 |
| 39 | 1.7 |
| 40 | 0.2 |
| 41 | 4.9 |
| 42 | 1.1 |
| 43 | 0.4 |
| 44 | 20.3 |
| 45 | 0.5 |
| 46 | 0.9 |
| 47 | 67 |
| 48 | 0.9 |
| 49 | N.D. |
| 50 | 0.4 |
| 51 | 0.6 |
| 52 | 0.8 |
| 53 | 0.5 |
| 54 | 0.3 |
| 55 | 13.3 |
| 56 | 18.5 |
| 57 | 0.2 |
| 58 | 0.4 |
| 59 | 1.2 |
| 60 | 760 |
| 61 | 0.6 |
| 62 | 0.3 |
| 63 | 1000 |
| 64 | 1.6 |
| 65 | 68 |
| 66 | 0.5 |
| 67 | 0.1 |
| 68 | 0.3 |
| 69 | 0.4 |
| 70 | 2.5 |
| 71 | 26 |
| 72 | 19 |
| 73 | 66 |
| 74 | 0.3 |
| 75 | 1.4 |
| 76 | 0.6 |
| 77 | 1000 |
| 78 | 2.5 |
| 79 | 46 |
| 80 | 0.3 |
| 81 | 1.3 |
| 82 | 0.4 |
| 83 | 0.4 |
| 84 | 1.0 |
| 85 | 0.6 |
| 86 | 0.4 |
| 87 | 0.5 |
| 88 | 0.4 |
| 89 | 0.2 |

TABLE 1-continued

Wee-1 inhibition of exemplified compounds

| Example Number | Wee1 IC50 (nM) |
|---|---|
| 90 | 0.2 |
| 91 | 22.1 |
| 92 | 8.8 |
| 93 | 0.4 |
| 94 | 1.2 |
| 95 | 0.8 |
| 96 | 0.4 |
| 97 | 1 |

Method 2: Determining the Effect of Compounds on the Phosphorylation of Cdc2 at Tyr15

The colorectal cancer cell lines HT-29 and HCT-116 were purchased from the ATCC and routinely maintained in McCoy's Medium (Invitrogen) supplemented with 10% Foetal Calf Serum.

The cells were trypsinised from their growing vessel and counted, 100 μL of cell suspension containing 6000 cells was pipetted into black 96 well Co-star plates and incubated overnight to allow adherence to the surface at a temperature of 37° C. and an atmosphere of 5% $CO_2$. Test compounds were formulated in DMSO and diluted in foetal calf serum supplemented medium. Incubating medium was removed by aspiration and diluted drug supplemented medium added to each well.

The plate was returned to the incubator for an additional eight hours at 37° C. and an atmosphere of 5% $CO_2$. Post incubation, the drug supplemented medium was aspirated from each well and the cells were washed once in ice-cold phosphate buffered saline (PBS). 100 μL of cell lysis buffer (Cell Signalling Technologies #9803) containing 20 mM Tris, 150 mM NaCl, 1 mM EDTA, 1 mM EGTA, 1% Triton-X100, 2.5 mM sodium pyrophosphate, 1 mM glycerophosphate, 1 mM $Na_3VO_4$ and 1 μg/mL leupeptin was added to each well of the 96 well plate and incubated at 4° C. for 30 min. The samples on the plate were snap frozen at −80° C. until required. Immediately before the continuation of the assay, the sample plate was thawed and centrifuged at 4° C. for 10 min and the supernatant transferred to secondary tubes or 96 well plate.

Cell supernatant was mixed in a ratio of 1:1 with sample dilutent buffer and vortexed for one minute. 100 μL of diluted sample was pipetted into pre-coated plates containing a rabbit polyclonal antibody for phospho-cdc2 (Tyr15) (Cell Signalling Technologies PathScan kit #7176). The plate was sealed and incubated overnight at 4° C.

The plate seal was removed and the well contents aspirated, followed by 3×5 min washes with 200 μL of diluted wash buffer. Between each wash the plate was tapped firmly onto blotting paper to ensure the removal of all kit solution. 100 μL of kit detection antibody was added to each well and the plate re-sealed and incubated at 37° C. for 1 h. Post incubation the plate was washed and processed in a similar manner to that previously described.

100 μL of horseradish peroxidise-linked secondary antibody was added to each test well, the plate sealed and incubated for thirty minutes at 37° C. Post incubation, the plate was washed as previously stated, followed by the addition of 100 μL of 3,3',5,5' tetramethylbenzidine (TMB reagent). The plate was sealed and incubated at RT for 30 min.

100 μL of stop solution was added to each well and the underside of the plate wiped with a lint-free tissue, prior to spectrophotometric determination. Absorbance from each well was read at 450 nm within 30 min of the addition of the stop solution.

The percentage of phospho-cdc2 was calculated compared to DMSO control and plotted versus the concentration of inhibitor using GraphPad Prism. Data was fitted using non-linear regression analysis and $IC_{50}$ values generated.

As shown in Table 2 the compounds of the current invention exhibit an excellent Cdc2-tyrosine 15 phosphorylation-inhibitory effect in human cancer cells (HT29 and HCT116).

TABLE 2 in vitro inhibition of phosphorylation of CDC2 of select exemplified compounds.

| Example Number | ELISA p-CDC2 $EC_{50}$ (nM) |
|---|---|
| 5 | 12 |
| 7 | 9 |
| 12 | 26 |
| 14 | 5 |
| 20 | 47 |
| 21 | 2 |
| 26 | 4 |
| 54 | 5 |
| 57 | 6 |
| 67 | 7 |
| 76 | 28 |

Experimental Section

Abbreviations aq: aqueous; dba: dibenzylideneacetone; DCM: dichloromethane; DIPEA: diisopropylethylamine; DMF: N,N-dimethylformamide; DMFDMA: N,N-dimethylformamide dimethyl acetal; DMA: N,N-dimethylacetamide; dppf: 1,1'-bis(diphenylphosphino)ferrocene; equiv.: equivalents; ESI: electrospray ionisation; EtOAc: ethyl acetate; EtOH: ethanol; h: hour; HPLC: high pressure liquid chromatography; LC: liquid chromatography; LCMS: liquid chromatography mass spectrometry; M: molar; m/z: mass-to-charge ratio; mCPBA: 3-chloroperbenzoic acid; MeOH: methanol; min: minutes; MS: mass spectrometry; NMR: nuclear magnetic resonance; $R_T$: retention time; RB: round-bottomed; RT: room temperature; SM: starting material; TFA: trifluoroacetic acid; THF: tetrahydrofuran; TLC: thin layer chromatography.

General Experimental Conditions

Solvents and Reagents

Common organic solvents that were used in reactions (e.g. THF, dioxane, DMF, DCM, and methanol) were purchased anhydrous from Sigma-Aldrich® in Sure/Seal™ bottles and were handled appropriately under nitrogen. Water was deionised using an Elga PURELAB Option-Q. All other solvents used (i.e. for work-up procedures and purification) were generally HPLC grade and were used as supplied from various commercial sources. Unless otherwise stated, all starting materials used were purchased from commercial suppliers and used as supplied.

Microwave Synthesis

Unless quoted otherwise, microwave experiments were carried out using a CEM Discover™/Explorer24™ system controlled by Synergy 1.5 software. In other cases a Biotage Initiator™ Eight was used. Both machines give good reproducibility and control at temperature ranges from 60-250° C. and pressures of up to maximum of 20 bar.

Flash Chromatography

Purification of compounds by flash chromatography was achieved using a Biotage Isolera Four system. Unless otherwise stated, Biotage KP-Sil SNAP or Grace Silica Gel cartridge columns (10-340 g) were used along with the stated solvent system and an appropriate solvent gradient depending on compound polarity (determined by TLC analysis). In the case of more polar and basic compounds, Biotage KP-NH SNAP cartridge columns (11 g) were used.

NMR Spectroscopy $^1H$ NMR spectra were recorded at ambient temperature using a Bruker Avance (500 MHz) spectrometer. All chemical shifts (δ) are expressed in ppm. Residual solvent signals were used as an internal standard and the characteristic solvent peaks were corrected to the reference data outlined in *J. Org. Chem.*, 1997, 62, p 7512-7515; in other cases, NMR solvents contained tetramethylsilane, which was used as an internal standard.

High Pressure Liquid Chromatography

Liquid Chromatography Mass Spectrometry (LCMS) experiments to determine retention times (RT) and associated mass ions were performed using one of the following methods:

Method A: The system consists of an Agilent Technologies 6140 single quadrupole mass spectrometer linked to an Agilent Technologies 1290 Infinity LC system with UV diode array detector and autosampler. The spectrometer consists of a multimode ionization source (electrospray and atmospheric pressure chemical ionizations) operating in positive and negative ion mode. LCMS experiments were performed on each sample submitted using the following conditions: LC Column: Zorbax Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 95 | 5 |
| 1.80 | 1.0 | 0 | 100 |
| 2.20 | 1.0 | 0 | 100 |
| 2.21 | 1.0 | 95 | 5 |
| 2.50 | 1.0 | 95 | 5 |

Method B: The system consisted of a ThermoFinnigan LCQ Advantage Mass Spectrometer with Surveyor LC system and 200 position autosampler. The LC system was coupled to an inline Surveyor DAD detector and ESI source operating in positive and negative ion mode. LCMS experiments were performed on each sample submitted using the following conditions: LC Column: Luna 3 micron C18 50×2 mm. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 0.6 | 95 | 5 |
| 7.00 | 0.6 | 5 | 95 |
| 8.00 | 0.6 | 5 | 95 |
| 8.20 | 0.6 | 95 | 5 |
| 11.00 | 0.6 | 95 | 5 |

Method C: The system consists of an Agilent Technologies 6130 quadrupole mass spectrometer linked to an Agilent Technologies 1290 Infinity LC system with UV diode array detector and autosampler. The spectrometer consists of a electrospray ionization source operating in positive and negative ion mode. LCMS experiments were performed on each sample submitted using the following conditions: LC Column: Agilent Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 80 | 20 |
| 1.80 | 1.0 | 0 | 100 |
| 2.20 | 1.0 | 0 | 100 |
| 2.50 | 1.0 | 80 | 20 |
| 3.00 | 1.0 | 80 | 20 |

Method D:

Method: The system consists of an Agilent Technologies 6130 quadrupole mass spectrometer linked to an Agilent Technologies 1290 Infinity LC system with UV diode array detector and autosampler. The spectrometer consists of a electrospray ionization source operating in positive and negative ion mode. LCMS experiments were performed on each sample submitted using the following conditions: LC Column: Agilent Eclipse Plus C18 RRHD 1.8 micron 50×2.1 mm maintained at 40° C. Mobile phases: A) 0.1% (v/v) formic acid in water; B) 0.1% (v/v) formic acid in acetonitrile.

| Gradient Time (min) | Flow (mL/min) | % A | % B |
|---|---|---|---|
| 0.00 | 1.0 | 95 | 5 |
| 1.80 | 1.0 | 0 | 100 |
| 2.20 | 1.0 | 0 | 100 |
| 2.50 | 1.0 | 95 | 5 |
| 3.00 | 1.0 | 95 | 5 |

Preparative High Pressure Liquid Chromatography

The system consisted of an Agilent Technologies 6120 single quadrupole mass spectrometer linked to an Agilent Technologies 1200 Preparative LC system with Multiple Wavelength detector and autosampler. The mass spectrometer used a multimode ionization source (electrospray and atmospheric pressure chemical ionizations) operating in positive and negative ion mode. Fraction collection was mass-triggered (multimode positive and negative ion). Purification experiments, unless otherwise stated, were performed under basic conditions at an appropriate solvent gradient that was typically determined by the retention time found using HPLC. In cases were the basic conditions were unsuccessful, acidic conditions were employed.

Basic conditions: LC Column: Waters XBridge™ Prep C18 5 μm OBD™ 19×50 mm column at RT. Mobile phase: A) 0.1% (v/v) ammonium hydroxide in water; B) 0.1% (v/v) ammonium hydroxide in 95:5, acetonitrile/water. Total experiment time was ca. 10 min and an example method is given:

| Gradient Time (min) | Flow (mL/min) | % A | % B |
|---|---|---|---|
| 0.00 | 20.0 | 50 | 50 |
| 3.00 | 20.0 | 12 | 88 |
| 5.00 | 20.0 | 12 | 88 |
| 7.00 | 20.0 | 0 | 100 |
| 8.0 | 20.0 | 0 | 100 |
| 8.20 | 20.0 | 50 | 50 |

-continued

Acidic conditions: LC Column: Waters XBridge™ Prep C18 5 μm OBD™ 19×50 mm column at RT. Mobile phase: A) Water 0.1% (v/v) formic acid in water; B) 0.1% (v/v) formic acid in 95:5, acetonitrile/water. Total experiment time was ca. 10 min and an example method is given:

| Gradient Time (min) | Flow (mL/min) | % A | % B |
|---|---|---|---|
| 0.00 | 20.0 | 95 | 5 |
| 7.00 | 20.0 | 0 | 100 |
| 9.00 | 20.0 | 0 | 100 |
| 9.20 | 20.0 | 95 | 5 |

The pure fractions were combined and concentrated using a Genevac EZ-2 Elite, unless stated otherwise.

Nomenclature

Unless otherwise indicated, the nomenclature of structures was determined using the 'Convert Structure to Name' function of ChemBioDraw Ultra 12.0.2 (CambridgeSoft/PerkinElmer). In instances where names of chemical structures that are followed by a r'" symbol, ChemBioDraw Ultra 12.0.2 was not able to generate a name and therefore, the 'Structure to Name' function/Preferred IUPAC Name' option of MarvinSketch 6.1.2 (ChemAxon) was used instead.

Intermediate A: rac-2-Bromo-6-(S-methylsulfonimidoyl)pyridine

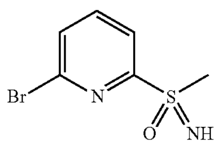

Step 1: rac-N-[(6-Bromopyridin-2-yl)(methyl)-$\lambda^4$-sulfanylidene]-2,2,2-trifluoroacetamide 2-Bromo-6-(methylthio)pyridine (1.00 g, 4.90 mmol) and trifluoroacetamide (0.831 g, 7.35 mmol) in THF (10 mL) was added dropwise to a pre-cooled suspension of sodium hydride (60% in mineral oil) (0.176 g, 4.41 mmol) in THF (5 mL) at 0° C. under nitrogen. After 5 min, a solution of 1,3-dibromo-5,5-dimethylhydantoin (2.10 g, 7.35 mmol) in THF (7.5 mL) was added dropwise. After 1 h, the reaction mixture was partitioned between EtOAc and 25% sodium sulfite (aq) solution, separated, extracted (EtOAc×2), dried (Phase Separator), and the solvents were removed in vacuo to give the title compound as a colourless oil that turned into a white solid on standing. The material was carried through to the next step without further purification.

LCMS (Method A): $R_T$=1.02 min, m/z=315, 317 $[M+H]^+$.

Step 2: rac-2-Bromo-6-(S-methylsulfonimidoyl)pyridine

Oxone (5.12 g, 8.33 mmol) was added portionwise to a solution of rac-N-[(6-bromopyridin-2-yl)(methyl)-$\lambda^4$-sulfanylidene]-2,2,2-trifluoroacetamide (crude, assumed 4.9 mmol) in MeOH (15.0 mL)/sulfolane (2.5 mL, 26.4 mmol)/water (10.0 mL) at RT under nitrogen. After each portion, an aliquot of 50% potassium carbonate (aq) solution was added to adjust to pH 10 [Note: ca. 4.06 g in 4 mL of water were added in total, 6.0 equiv.]. After 20 h, the solvents were removed in vacuo and the residue was partitioned between DCM and 10% sodium sulfite (aq) solution, the layers were separated, the organic phase was washed using water (×3), and dried (Phase Separator). The solvents were removed in vacuo requiring the use of the Genevac EZ-2 at 80° C. to remove the sulfolane to give the title compound (714 mg, 2.91 mmol, 60%) [over 2 steps] as an off white solid.

LCMS (Method A): $R_T$=0.51 min, m/z=235, 237 $[M+H]^+$.

$^1H$ NMR (400 MHz, $CDCl_3$): δ 8.07 (dd, 1H), 7.79 (t, 1H), 7.68 (dd, 1H), 3.29 (s, 3H).

Intermediate B: 1-(6-{[Dimethyl(oxo)-$\lambda^6$-sulfanylidene]amino}pyridine-2-yl)-6-(methylsulfanyl)-2-(prop-2-en-1-yl)-1H,2H,3H-pyrazolo[3,4-d]pyrimidin-3-one*

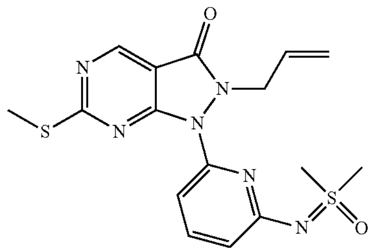 [SMILES: C=CCn1c(=O)c2cnc(SC)nc2n1-c1cccc(N=S(C)(C)=O)n1]

A pre-degassed solution of $Pd_2(dba)_3$ (34.1 mg, 0.037 mmol) and Xantphos (47.4 mg, 0.082 mmol) in 1,4-dioxane (1.0 mL) was added to a pre-degassed solution of 2-allyl-1-(6-bromopyridin-2-yl)-6-(methylthio)-1H-pyrazolo[3,4-d]pyrimidin-3(2H)-one (282 mg, 0.745 mmol) [Prepared according to EP2213673B1 (Example 5, p 55)], (S-methylsulfonimidoyl)methane (69.4 mg, 0.745 mmol) [commercially available] and cesium carbonate (728 mg, 2.24 mmol) in 1,4-dioxane (3.0 mL) in an RB flask under nitrogen. The temperature was increased to 100° C. After 1 h, the reaction mixture was allowed to cool to RT. The solvents were removed in vacuo and the remaining residue was partitioned between DCM and saturated sodium bicarbonate (aq) solution, filtered through Celite®, separated, dried (Phase Separator), the solvents were removed in vacuo and the residue was purified by flash chromatography (0-100%, EtOAc in cyclohexane; then 0-10%, MeOH in EtOAc) to give the title compound (205 mg, 71%) as an off-white solid.

LCMS (Method A): $R_T$=0.97 min, m/z=391 $[M+H]^+$.

$^1H$ NMR (400 MHz, $CDCl_3$): δ 8.92 (s, 1H), 7.68 (t, 1H), 7.31 (dd, 1H), 6.70 (dd, 1H), 5.64 (ddt, 1H), 5.04-4.93 (m, 4H), 3.34 (s, 6H), 2.59 (s, 3H).

Intermediate C: 1-(3-{[Dimethyl(oxo)-$\lambda^6$-sulfanylidene]amino}phenyl)-6-(methylsulfanyl)-2-(prop-2-en-1-yl)-1H,2H,3H-pyrazolo[3,4-d]pyrimidin-3-one*

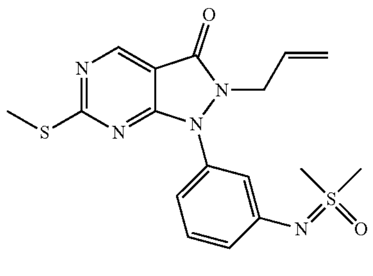 [SMILES: C=CCn1c(=O)c2cnc(SC)nc2n1-c1cccc(N=S(C)(C)=O)c1]

Step 1: Allyl-1-(3-bromophenyl)-6-(methylthio)-1H-pyrazolo[3,4-d]pyrimidin-3(2H)-one Pyridine (1.46 mL, 18.0 mmol) was added to a stirred solution of 2-allyl-6-(methylthio)-1H-pyrazolo[3,4-d]pyrimidin-3(2H)-one (500 mg, 2.25 mmol) [Prepared according to EP2213673B1 (Production Example 1, p 37)], copper (II) acetate (409 mg, 2.25 mmol) and (3-bromophenyl) boronic acid (745 mg, 3.71 mmol) in chloroform (5.0 mL) at RT in an open flask. After 5 days, ammonium hydroxide solution (aq) (30 mL) and brine (30 mL) were added and the resulting mixture was extracted using EtOAc (3×20 mL). The combined organic phase was dried (Phase Separator), the solvents were removed in vacuo and the remaining residue was purified by flash chromatography (0-100%, EtOAc in cyclohexane) to give the title compound (587 mg, 69%) as an orange solid.

LCMS (Method A): $R_T$=1.38 min, m/z=377, 379 $[M+H]^+$.

Step 2: 1-(3-{[Dimethyl(oxo)-$\lambda^6$-sulfanylidene]amino}phenyl)-6-(methylsulfanyl)-2-(prop-2-en-1-yl)-1H,2H,3H-pyrazolo[3,4-d]pyrimidin-3-one*

A pre-degassed solution of $Pd_2(dba)_3$ (70.6 mg, 0.077 mmol) and Xantphos (98.0 mg, 0.17 mmol) in 1,4-dioxane (1.0 mL) was added to a pre-degassed solution of 2-allyl-1-(3-bromophenyl)-6-(methylthio)-1H-pyrazolo[3,4-d]pyrimidin-3(2H)-one (582 mg, 1.54 mmol), (S-methylsulfonimidoyl)methane (144 mg, 1.54 mmol) [commercially available] and cesium carbonate (1.51 g, 4.63 mmol) in 1,4-dioxane (3.0 mL) in an RB flask under nitrogen. The temperature was increased to 100° C. After 1 h, the reaction concentrated in vacuo and the residue was dissolved in DCM and filtered. The resulting solution was washed with saturated sodium bicarbonate (aq) solution, separated, the aqueous layer was extracted (DCM×3), the combined organic phase was dried (Phase Separator), the solvents were removed in vacuo, and the remaining residue was purified by flash chromatography (0-100%, EtOAc in cyclohexane; then 0-10%, MeOH in EtOAc) to give product material as a pink/red solid that was triturated using diethyl ether and the residual solvents were removed in vacuo to give the title compound (321 mg, 53%) as a pale pink solid.

LCMS (Method A): $R_T$=0.94 min, m/z=390 $[M+H]^+$.

$^1H$ NMR (400 MHz, $CDCl_3$): δ 8.90 (s, 1H), 7.35 (t, 1H), 7.12 (t, 1H), 7.10 (ddd, 1H), 6.99 (ddd, 1H), 5.68 (ddt, 1H), 5.11 (dd, 1H), 4.99 (dd, 1H), 4.46 (d, 2H), 3.21 (s, 6H), 2.52 (s, 3H).

Intermediate D: 1-(6-{[Dimethyl(oxo)-$\lambda^6$-sulfanylidene]amino}pyridine-2-yl)-6-(methylsulfanyl)-2-(propan-2-yl)-1H,2H,3H-pyrazolo[3,4-d]pyrimidin-3-one*

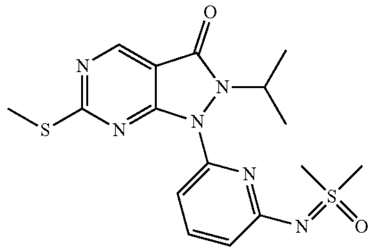 [SMILES: CSc1ncc2c(=O)n(C(C)C)n(-c3cccc(N=S(C)(C)=O)n3)c2n1]

Step 1: 1-(6-Bromopyridin-2-yl)-2-isopropyl-6-(methylthio)-1H-pyrazolo[3,4-c]pyrimidin-3(2H)-one N,N'-Dimethylethane-1,2-diamine (0.020 mL, 0.182 mmol) was added to a pre-degassed stirred suspension of 2-isopropyl-6-(methylthio)-1H-pyrazolo[3,4-d]pyrimidin-3(2H)-one (40.9 mg, 0.182 mmol) [Prepared according to EP2213673B1 (Production Example 2, p 38)], 2,6-dibromopyridine (56.2 mg, 0.237 mmol), potassium carbonate (35.3 mg, 0.255 mmol) and copper(I) iodide (34.7 mg, 0.182 mmol) in 1,4-dioxane (1.0 mL) at RT under nitrogen. The temperature increased to 95° C. After 18 h, the reaction mixture was cooled to RT, $NH_4OH$ (aq) and brine were added and the reaction mixture was extracted using EtOAc (×3), the combined organic phase was dried (Phase Separator), the solvents were removed in vacuo and the remaining residue was purified using flash chromatography (0-100%, EtOAc in cyclohexane) to give the title compound (16.3 mg, 24%) as an off-white solid.

LCMS (Method A): $R_T$=1.34 min, m/z=380, 382 $[M+H]^+$.

Step 2: 1-(6-{[Dimethyl(oxo)-$\lambda^6$-sulfanylidene]amino}pyridine-2-yl)-6-(methylsulfanyl)-2-(propan-2-34)-1H,2H,3H-pyrazolo[3,4-c]pyrimidin-3-one*

A pre-degassed solution of $Pd_2(dba)_3$ (2.0 mg, 2.14 μmol) and Xantphos (2.7 mg, 4.72 μmol) in 1,4-dioxane (1.0 mL) was added to a pre-degassed solution of 1-(6-bromopyridin-2-yl)-2-isopropyl-6-(methylthio)-1H-pyrazolo[3,4-d]pyrimidin-3(2H)-one (16.3 mg, 0.043 mmol), (S-methylsulfonimidoyl)methane (3.99 mg, 0.043 mmol) [commercially available] and cesium carbonate (41.9 mg, 0.129 mmol) in 1,4-dioxane (1.0 mL) in a RB flask under nitrogen. The temperature was increased to 100° C. After 1 h, the reaction mixture was cooled to RT and the solid material was filtered off, washing with DCM. The solvents were removed in vacuo and the remaining residue was partitioned between DCM and saturated sodium bicarbonate (aq) solution, separated, extracted (DCM×2), the combined organic phase was dried (Phase Separator), the solvents were removed in vacuo, and the remaining residue was purified by flash chromatography (0-100%, EtOAc in cyclohexane; then 0-10%, MeOH in EtOAc) to give the title compound (12.9 mg, 77%) as a colourless oil.

LCMS (Method A): $R_T$=0.97 min, m/z=393 $[M+H]^+$.

Intermediate E: 2-Allyl-6-(methylthio)-1-(6-((1-oxidotetrahydrothiophen-1-ylidene)amino)pyridin-2-yl)-1H-pyrazolo[3,4-d]pyrimidin-3(2H)-one

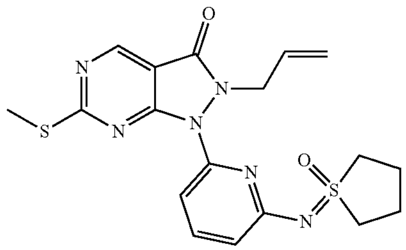 [SMILES: C=CCn1c(=O)c2cnc(SC)nc2n1-c1cccc(N=S2(=O)CCCC2)n1]

A pre-degassed solution of $Pd_2(dba)_3$ (46.5 mg, 0.051 mmol) and Xantphos (64.7 mg, 0.112 mmol) in 1,4-dioxane (1.0 mL) was added to a pre-degassed suspension of 2-allyl-1-(6-bromopyridin-2-yl)-6-(methylthio)-1H-pyrazolo[3,4-d]pyrimidin-3(2H)-one (384 mg, 1.02 mmol) [Prepared according to EP2213673B1 (Example 5, p 55)], 1-iminotetrahydrothiophene 1-oxide (121 mg, 1.02 mmol) [commercially available] and cesium carbonate (993 mg, 3.05 mmol) in 1,4-dioxane (4.0 mL) in an RB flask under nitrogen. The temperature was increased to 100° C. After 1 h, the reaction mixture was cooled to RT and the solvents were removed in vacuo. The residue was dissolved in DCM and was filtered to remove solid material (Phase Separator), washing with further DCM. The combined organic phase was washed using saturated sodium bicarbonate (aq) solution, separated, dried (Phase Separator), the solvents were removed in vacuo, and the residue was purified by flash chromatography (0-100%, EtOAc in cyclohexane; then 0-10%, MeOH in EtOAc) to give the title compound (126 mg, 30%) as a pale yellow solid.

LCMS (Method A): $R_T$=1.05 min, m/z=417 $[M+H]^+$.

Intermediate F: 6-(Methylsulfanyl)-1-{6-[(1-oxo-1$\lambda^6$-thiolan-1-ylidene)amino]pyridin-2-yl}-2-(propan-2-yl)-1H,2H,3H-pyrazolo[3,4-d]pyrimidin-3-one*

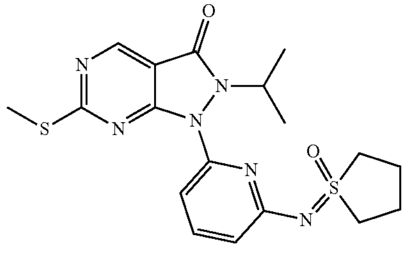 [SMILES: CSc1ncc2c(=O)n(C(C)C)n(-c3cccc(N=S4(=O)CCCC4)n3)c2n1]

Step 1: 1-(6-Bromopyridin-2-yl)iminotetrahydrothiophene-1-oxide

A pre-degassed solution of $Pd_2(dba)_3$ (193 mg, 211 μmol) and Xantphos (269 mg, 464 μmol) in 1,4-dioxane (3.0 mL) was added to a pre-degassed suspension of 2,6-dibromopyridine (1000 mg, 4.22 mmol), 1-iminotetrahydrothiophene-1-oxide (503 mg, 4.22 mmol) [commercially available] and cesium carbonate (4130 mg, 12.7 mmol) in 1,4-dioxane (10 mL) in a RB flask under nitrogen. The temperature was increased to 100° C. After 1 h, the reaction mixture was cooled to RT and the solid material was filtered through Celite and washed with DCM. The solvents were removed in vacuo and the remaining residue was partitioned between DCM and saturated sodium bicarbonate (aq) solution, separated, extracted (DCM×2), the combined organic phase was dried (Phase Separator), the solvents were removed in vacuo, and the remaining residue was purified by flash chromatography (0-100%, EtOAc in cyclohexane; then 0-10%, MeOH in EtOAc) to give the title compound (1064 mg, 92%) as an orange solid.

LCMS (Method A): $R_T$=0.95 min, m/z=275 $[M+H]^+$.

Step 2: 6-(Methylsulfanyl)-1-{6-[(1-oxo-1λ$^6$-thiolan-1-ylidene)amino]pyridin-2-yl}-2-(propan-2-yl)-1H,2H,3H-pyrazolo[3,4-d]pyrimidin-3-one*

N,N'-Dimethylethane-1,2-diamine (0.264 mL, 2.45 mmol) was added to a pre-degassed stirred suspension of 2-isopropyl-6-(methylthio)-1H-pyrazolo[3,4-d]pyrimidin-3(2H)-one (550 mg, 2.45 mmol) [Prepared according to EP2213673B1], 1-[(6-bromopyridin-2-yl)imino]tetrahydrothiophene-1-oxide (877 mg, 3.19 mmol), potassium carbonate (474 mg, 3.43 mmol) and copper(I) iodide (467 mg, 2.45 mmol) in 1,4-dioxane (10 mL) at RT under nitrogen. The temperature was increased to 95° C. After 20 h, the reaction mixture was cooled to RT, $NH_4OH$ (aq) and brine were added and the reaction mixture was extracted using EtOAc (×3), the combined organic phase was dried (Phase Separator), the solvents were removed in vacuo and the remaining residue was purified using flash chromatography (0-100%, EtOAc in cyclohexane) to give the title compound (480 mg, 47%) as an off-white solid.

LCMS (Method A): $R_T$=1.1 min, m/z=419 $[M+H]^+$.

Intermediate G: 1-(6-{[dimethyl(oxo)-λ$^6$-sulfanylidene]amino}pyrazin-2-yl)-6-(methylsulfanyl)-2-(prop-2-en-1-yl)-1H,2H,3H-pyrazolo[3,4-d]pyrimidin-3-one*

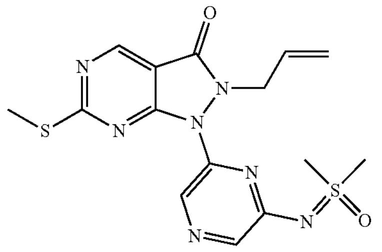 [SMILES: C=CCn1c(=O)c2cnc(SC)nc2n1-c1cncc(N=S(C)(C)=O)n1]

Step 1: [(6-Bromopyrazin-2-yl)imino]dimethyl-λ$^6$-sulfanone*

$Pd_2(dba)_3$ (192 mg, 0.210 mmol) and Xantphos (268 mg, 0.462 mmol) in 1,4-dioxane (17 mL) was added to a suspension of 2,6-dibromopyrazine (1000 mg, 4.20 mmol), (S-methylsulfonimidoyl)methane (392 mg, 4.20 mmol) and $Cs_2CO_3$ (4109 mg, 12.61 mmol) in 1,4-dioxane (17 mL) under nitrogen. The temperature was increased to 100° C. and the reaction mixture was stirred for 6 h. After cooling to RT the reaction mixture was filtered through Celite (washing with EtOAc) and the filtrate was evaporated under reduced pressure. The residue was purified by flash chromatography (15-100% EtOAc in cyclohexane), yielding the title compound as a white solid (521 mg, 50%).

LCMS (Method C): $R_T$=0.78 min, m/z=252 $[M+H]^+$.

$^1$H NMR (300 MHz, $CDCl_3$) δ 8.05 (s, 1H), 7.99 (s, 1H), 3.32 (s, 6H).

Step 2: 1-(6-{[Dimethyl(oxo)-λ$^6$-sulfanylidene]amino}pyrazin-2-yl)-6-(methylsulfanyl)-2-(prop-2-en-1-yl)-1H,2H,3H-pyrazolo[3,4-d]pyrimidin-3-one*

Into a 25 mL microwave vial was added 2-allyl-6-(methylthio)-1H-pyrazolo[3,4-d]pyrimidin-3(2H)-one (355 mg, 1.60 mmol) (obtained according to EP2213673B1, Production Example 1, p 37), [(6-bromopyrazin-2-yl)imino]dimethyl-λ$^6$-sulfanone (520 mg, 2.08 mmol), $K_2CO_3$ (309 mg, 2.24 mmol) and dioxane (7 mL). The resultant suspension was degassed and copper (I) iodide (305 mg, 1.60 mmol) was added followed by $N^1$,$N^2$-dimethylethane-1,2-diamine (0.172 mL, 1.60 mmol). The vial was flushed with nitrogen, capped and the temperature was increased to 95° C. The reaction mixture was stirred vigorously overnight. After cooling to RT the reaction mixture was transferred to a separation funnel and $NH_4OH$ (20 mL) was added. The mixture was extracted with EtOAc (3×30 mL).

The organic extracts were combined, dried ($MgSO_4$) and evaporated under reduced pressure. The residue was purified by flash chromatography (0-15% MeOH in EtOAc). The product containing fractions were concentrated to give the title compound (224 mg, 36%) as a white solid.

LCMS (Method C): $R_T$=1.03 min, m/z=392 $[M+H]^+$.

$^1$H NMR (300 MHz, $CDCl_3$) δ 8.93 (s, 1H), 8.72 (bs, 1H), 8.07 (bs, 1H), 5.78-5.47 (m, 1H), 5.14-4.80 (m, 4H), 3.37 (s, 6H), 2.62 (s, 3H).

Intermediate H: 6-Amino-1-(6-{[dimethyl(oxo)-λ$^6$-sulfanylidene]amino}pyridin-2-yl)-2-(propan-2-yl)-1H,2H,3H-pyrazolo[3,4-d]pyrimidin-3-one*

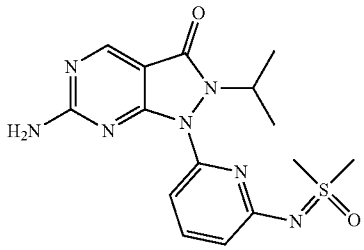 [SMILES: CC(C)n1c(=O)c2cnc(N)nc2n1-c1cccc(N=S(C)(C)=O)n1]

In a 25 mL reaction tube was added Intermediate D (300 mg, 0.764 mmol) followed by dichloromethane (5 mL) to give a white suspension. m-CPBA, 70% purity (188 mg, 0.764 mmol) was added to the reaction mixture. After stirring at room temperature for 30 min. LC-MS analysis showed complete oxidation of the starting material. 7N Ammonia in MeOH (1.1 mL, 7.64 mmol) was added to the reaction mixture and the reaction tube was sealed. The reaction mixture was stirred at 65° C. overnight. The volatiles were evaporated under reduced pressure and the residue was purified by flash chromatography (5-15% MeOH in DCM). The product containing fractions were evaporated under reduced pressure yielding an oily product (271 mg, 98%) that solidified upon storage.

LCMS (Method D): $R_T$=0.99 min, m/z=362 $[M+H]^+$.

$^1$H NMR (300 MHz, DMSO) δ 8.60 (s, 1H), 7.71 (t, J=7.9 Hz, 1H), 7.47 (bs, 2H), 7.04 (d, J=7.5 Hz, 1H), 6.65 (d, J=8.0 Hz, 1H), 4.27-4.04 (m, 1H), 3.36 (s, 6H), 1.24 (d, J=6.8 Hz, 6H).

Intermediate I: 6-Amino-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one*

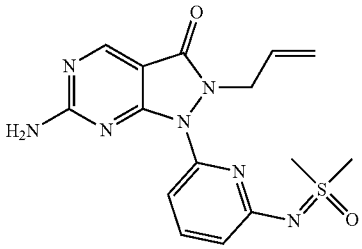 [SMILES: C=CCn1c(=O)c2cnc(N)nc2n1-c1cccc(N=S(C)(C)=O)n1]

In a 25 mL reaction tube was added Intermediate B (500 mg, 1.28 mmol) followed by dichloromethane (5 mL) to give a white suspension. m-CPBA, 70% purity (316 mg, 1.28 mmol) was added to the reaction mixture. After stirring at room temperature for 30 minutes LC-MS analysis showed complete oxidation of starting material. To the reaction mixture was added 1,4-dioxane (10.00 mL) and 7N ammonia in MeOH (1.8 mL, 12.80 mmol). The reaction tube was sealed and heated at 65° C. for 1 h. The volatiles were evaporated under reduced pressure and the residue was purified by flash chromatography (5-15% MeOH in DCM). The product containing fractions were evaporated under reduced pressure yielding an oily product (401 mg, 87%) that solidified upon storage.

LCMS (Method D): $R_T$=0.99 min, m/z=360 $[M+H]^+$.

$^1$H NMR (300 MHz, DMSO) δ 8.67 (s, 1H), 7.70 (t, J=7.9 Hz, 1H), 7.63-7.39 (m, 2H), 7.21 (d, J=7.7 Hz, 1H), 6.57 (d, J=8.0 Hz, 1H), 5.77-5.45 (m, 1H), 5.00 (d, J=9.2 Hz, 1H), 4.88 (d, J=17.0 Hz, 1H), 4.63 (d, J=5.9 Hz, 2H), 3.37 (s, J=5.8 Hz, 6H).

General Procedure A:

mCPBA (<77% pure) (1.35 equiv.) in DCM (0.2 M) [e.g. typically 23.3 mg, 0.104 mmol in 0.5 mL] was added to a stirred solution of Intermediate B, C, D or E (1.0 equiv.) in toluene (0.04 M) [e.g. for Intermediate B, typically 30 mg (0.077 mmol) in 2.0 mL] at RT under nitrogen. After 5 min, the aniline (1.0 equiv.) and DIPEA (3.0 eq) were added. The temperature was increased to 60° C. After 16 h, the reaction mixture was cooled to RT and loaded directly onto a KP-NH column and purified by flash chromatography (0-100%, EtOAc in cyclohexane, followed by 0-10% MeOH in EtOAc, if required). The pure fractions were concentrated to give the desired product (10-70% yield).

General Procedure B:

TFA (2.0 mL, 26.0 mmol) was added to a stirred solution of the N-Boc protected substrate (0.05 mmol-0.50 mmol) in DCM (2.0 mL) at RT under nitrogen. After 1 h, the solvents were removed in vacuo and the remaining residue was partitioned between DCM and saturated sodium bicarbonate (aq) solution, separated, extracted (DCM×3), dried (Phase Separator), the solvents were removed in vacuo, and the remaining residue was purified by flash chromatography using a KP-NH column (0-100% EtOAc in cyclohexane; followed by 0-10% MeOH in EtOAc, if required). The pure fractions were combined to give the desired product (58-83% yield).

General Procedure C:

In a 5 ml microwave reactor vial were added Intermediate B, D, F or G (1.0 equiv., for intermediate B typically 70 mg, 0.179 mmol), 1 ml of DCM and 1 ml of toluene. mCPBA (<77% pure) (1.1 equiv.) [e.g. typically 49 mg, 0.197 mmol] was added and the reaction mixture was stirred for 30 min at RT. The aniline derivative (1.0 equiv.) and DIPEA (3.0 eq) were added, the vial was flushed with nitrogen and capped. The vial was heated at 65° C. while stirring, using a magnetic stirrer hot plate. After 16 h of stirring the reaction mixture was cooled to RT and loaded directly onto a Grace Silica Gel column and purified by flash chromatography (0-100%, EtOAc in cyclohexane, followed by 0-20% MeOH in EtOAc, if required). The pure fractions were concentrated to give the desired product (5-84% yield).

General Procedure D:

TFA (1.0 mL, 26.0 mmol) was added to a stirred solution of the N-Boc protected substrate (0.05 mmol-0.50 mmol) in DCM (2.0 mL) at RT. After 30 min, the solvents were removed in vacuo and the remaining residue was dissolved in DCM was loaded onto a prewashed 5 g SCX-2 cartridge, allowed to bind for 10 minutes, washed with 80:20 dichloromethane:methanol before the product was eluted with 80:20 dichloromethane:7M ammonia in methanol. The product containing fractions were concentrated to dryness under reduced pressure and further lyophilized from ACN/water solution to give the desired product (72-97% yield).

General Procedure E:

mCPBA (<77% pure) (1.35 equiv.) and Intermediate B, C, D or E (1.0 equiv.) were weighed into a reaction tube and suspended in toluene (2 mL)/DCM (1 mL) at RT under nitrogen. After 5 min, the aniline (1.0 equiv.) and DIPEA (3.0 equiv.) were added in DCM (1 mL) via syringe. The temperature was increased to 60° C. After 16 h, the reaction mixture was cooled to RT, the solvent was removed in vacuo and the remainder was purified by preparative HPLC and the pure fractions were concentrated in vacuo to give the desired product.

General Procedure F:

Intermediate H or I (1.0 equiv. typically for Intermediate H 70 mg, 0.194 mmol), aryl bromide (1 equiv., 0.194 mmol) and $Cs_2CO_3$ (3 equiv. typically 189 mg, 0.581 mmol) in 1,4-dioxane (typically 2 mL) were degassed and next $Pd_2(dba)_3$ (0.05 equiv. typically 8.87 mg, 9.68 μmol) and Xantphos (0.11 equiv. typically 12.33 mg, 21 μmol) were added. The temperature was increased to 100° C. and the reaction was stirred intensively for 1 to 16 h. The reaction mixture was cooled to RT and filtered through Celite (washing—EtoAc). The filtrate was evaporated under reduced pressure. The residue was purified by flash chromatography (0-100%, EtOAc in cyclohexane, followed by 0-20% MeOH in EtOAc, if required). The product containing fractions were evaporated under reduced pressure to give the desired product.

Example 1: 1-{6-[(Cyanoimino)(methyl)oxo-λ$^6$-sulfanyl]pyridin-2-yl}-6-{[4-(4-methylpiperazin-1-yl)phenyl]amino}-2-(prop-2-en-1-yl)-1H,2H,3H-pyrazolo[3,4-d]pyrimidin-3-one*

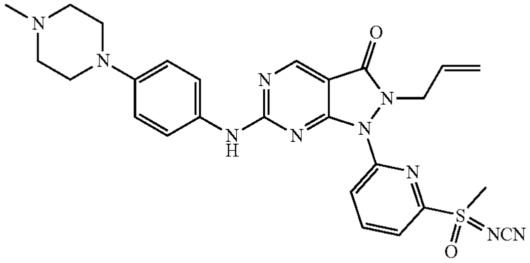

Step 1: rac-[(6-Bromopyridin-2-yl)(methyl)-λ$^4$-sulfanylidene](cyano)amine*

NBS (131 mg, 0.735 mmol) was added to a stirred solution of 2-bromo-6-(methylthio)pyridine (100 mg, 0.490 mmol), cyanamide (26.8 mg, 0.637 mmol) and potassium tert-butoxide (66.0 mg, 0.588 mmol) in methanol (3.0 mL) at RT under nitrogen. After 20 h, the reaction mixture was concentrated in vacuo, partitioned between DCM and satd. sodium thiosulfate (aq) solution, separated, extracted using DCM (×2), dried (Phase Separator), and the solvents were removed in vacuo to give the title compound (crude, 124 mg) as a pale yellow oil that was used directly in the next step without purification.

LCMS (Method A): $R_T$=0.65 min, m/z=244, 246 $[M+H]^+$.

Step 2: rac-[(6-Bromopyridin-2-yl)(methyl)oxo-λ$^6$-sulfanylidene](cyano)amine* mCPBA (<77% pure) (148 mg, 0.66 mmol) in DCM (1.0 mL) was added to a stirred solution of the crude of [(6-bromopyridin-2-yl)(methyl)-λ$^4$-sulfanylidene](cyano)amine* (124 mg, assumed 0.49 mmol) in DCM (2.0 mL) at RT under nitrogen. Potassium carbonate (203 mg, 1.47 mmol) was added. After 1 h, EtOH (2.0 mL) was added to try to dissolve a thick white precipitate and allow better stirring. After a further 16 h, the solvents were removed in vacuo and the remaining residue was partitioned between satd. sodium bicarbonate (aq) solution and DCM, separated, the organic phase was extracted (DCM×2), the combined organic phase was dried (Phase Separator), the solvents were removed in vacuo and the residue was purified by flash chromatography (0-100%, EtOAc in cyclohexane) to give the title compound (74.9 mg, 63%) as a white solid.

LCMS (Method A): $R_T$=0.74 min, m/z=260, 262 $[M+H]^+$.

Step 3: rac-1-{6-[(Cyanoimino)(methyl)oxo-λ$^6$-sulfanyl]pyridin-2-yl}-6-(methylsulfanyl)-2-(prop-2-en-1-yl)-1H,2H,3H-pyrazolo[3,4-d]pyrimidin-3-one*

Copper(I) iodide (42.2 mg, 0.222 mmol) was added to a stirred suspension of 2-allyl-6-(methylthio)-1H-pyrazolo[3,4-d]pyrimidin-3(2H)-one (49.3 mg, 0.222 mmol) [Prepared according to EP2213673B1 (Production Example 1, p 37)], [(6-bromopyridin-2-yl)(methyl)oxo-λ$^6$-sulfanylidene](cyano)amine* (75 mg, 0.288 mmol), N,N'-dimethylethane-1,2-diamine (0.024 mL, 0.222 mmol), potassium carbonate (42.9 mg, 0.311 mmol) in 1,4-dioxane (1.0 mL) at RT. After 1 h, the temperature was increased to 95° C. After 20 h, the reaction mixture was cooled to RT and partitioned between $NH_4OH$ (aq) solution and extracted using EtOAc (×3), the combined organic phase was dried, the solvents were removed in vacuo, and the remaining residue was purified by flash chromatography (0-100%, EtOAc in cyclohexane) to give the title compound (10.1 mg, 11%) as a pale yellow oil.

LCMS (Method A): $R_T$=0.99 min, m/z=402 $[M+H]^+$.

Step 4: rac-1-{6-[(Cyanoimino)(methyl)oxo-λ$^6$-sulfanyl]pyridin-2-yl}-6-{[4-(4-methylpiperazin-1-yl)phenyl]amino}-2-(prop-2-en-1-yl)-1H,2H,3H-pyrazolo[3,4-d]pyrimidin-3-one mCPBA (<77% pure) (7.6 mg, 0.044 mmol) was added to a stirred solution of 1-{6-[(cyanoimino)(methyl)oxo-λ$^6$-sulfanyl]pyridin-2-yl}-6-(methylsulfanyl)-2-(prop-2-en-1-yl)-1H,2H,3H-pyrazolo[3,4-d]pyrimidin-3-one (10.1 mg, 0.025 mmol) in toluene (2.0 mL) at RT under nitrogen. After 5 min, 4-(4-methylpiperazin-1-yl)aniline (4.8 mg, 0.025 mmol) [commercially available] and DIPEA (0.013 mL, 0.075 mmol) were added, successively, and the temperature was increased to 60° C. After 16 h, the reaction mixture was cooled to RT and loaded directly onto a KP-NH column and purified by flash chromatography (0-100%, EtOAc in cyclohexane) to give the title compound (5.1 mg, 32%) as a pale yellow solid.

LCMS (Method A): $R_T$=0.69 min, m/z=545 $[M+H]^+$.

$^1H$ NMR (400 MHz, MeOD): δ 8.82 (s, 1H), 8.47 (br s, 1H), 8.36 (t, 1H), 8.14 (d, 1H), 7.51 (d, 2H), 7.01 (d, 2H), 5.79-5.66 (m, 1H), 5.14-5.02 (m, 2H), 4.92 (apparent dd overlapping solvent peak, 1H), 4.78 (apparent dd overlapping solvent peak, 1H), 3.62 (s, 3H), 3.23 (t, 4H), 2.69 (t, 4H), 2.40 (s, 3H).

Example 2: rac-Ethyl N-{methyl[6-(6-{[4-(4-methylpiperazin-1-yl)phenyl]amino}-3-oxo-2-(prop-2-en-1-yl)-1H,2H,3H-pyrazolo[3,4-d]pyrimidin-1-yl)pyridine-2-yl]oxo-λ$^6$-sulfanylidene}carbamate*

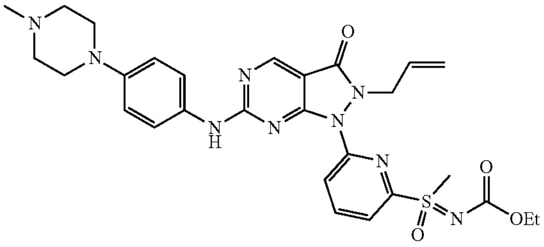 [SMILES: C=CCn1c(=O)c2cnc(Nc3ccc(N4CCN(C)CC4)cc3)nc2n1-c1cccc(S(C)(=O)=NC(=O)OCC)n1]

Step 1: rac-Ethyl N-[(6-bromopyridin-2-yl)(methyl)oxo-λ$^6$-sulfanylidene]carbamate*

Ethyl chloroformate (0.575 mL, 5.99 mmol) was added to a stirred solution of Intermediate A (564 mg, 2.40 mmol) and DIPEA (2.09 mL, 12.0 mmol) in DCM (10 mL) at RT under nitrogen. After 44 h, further ethyl chloroformate (230 uL, 1.0 equiv.) and DIPEA (837 uL, 2.0 equiv.) were added. After a further 6 h, the reaction mixture was partitioned between DCM and 1:1 brine/water, separated, extracted (DCM×2), dried (Phase Separator), the solvents were removed in vacuo, and the remaining residue was purified by flash chromatography (0-100%, EtOAc in cyclohexane) to give the title compound (661 mg, 90%) as a pale yellow oil.

LCMS (Method A): $R_T$=1.36 min, m/z=307, 309 [M+H]$^+$.

Step 2: rac-Ethyl N-[methyl({6-[6-(methylsulfanyl)-3-oxo-2-(prop-2-en-1-yl)-1H,2H,3H-pyrazolo[3,4-d]pyrimidin-1-yl]pyridin-2-yl})oxo-λ6-sulfanylidene]carbamate*

N,N'-Dimethylethane-1,2-diamine (0.232 mL, 2.15 mmol) was added to a stirred solution of 2-allyl-6-(methylthio)-1H-pyrazolo[3,4-d]pyrimidin-3(2H)-one (478 mg, 2.153 mmol) [Prepared according to EP2213673B1 (Production Example 1, p 37)], ethyl N-[(6-bromopyridin-2-yl)(methyl)oxo-λ$^6$-sulfanylidene]carbamate* (661 mg, 2.15 mmol), copper (I) iodide (410 mg, 2.15 mmol), and potassium carbonate (417 mg, 3.01 mmol) in 1,4-dioxane (5.0 mL) at RT. The reaction mixture was heated to 95° C. After 18 h, the reaction mixture was partitioned between saturated ammonium hydroxide (aq) solution and EtOAc, separated, extracted (EtOAc×3), organics combined, washed with brine, dried (Phase Separator), the solvents were removed in vacuo, and the remaining residue was purified by flash chromatography (0-100%, EtOAc in cyclohexane) to give the title compound (607 mg, 63%) as a colourless oil.

LCMS (Method A): $R_T$=1.04 min, m/z=403 [M-OEt]$^+$.

Step 3: rac-Ethyl N-{methyl[6-(6-{[4-(4-methylpiperazin-1-yl)phenyl]amino}-3-oxo-2-(prop-2-en-1-yl)-1H,2H,3H-pyrazolo[3,4-d]pyrimidin-1-yl)pyridine-2-yl]oxo-λ$^6$-sulfanylidene}carbamate* mCPBA (<77% pure) (67.3 mg, ca. 0.30 mmol) in DCM (0.5 mL) was added to a stirred solution of rac-ethyl N-[methyl({6-[6-(methylsulfanyl)-3-oxo-2-(prop-2-en-1-yl)-1H,2H,3H-pyrazolo[3,4-d]pyrimidin-1-yl]pyridin-2-yl})oxo-λ$^6$-sulfanylidene]carbamate* (100 mg, 0.223 mmol) in toluene (2.0 mL) at RT under nitrogen. After 5 min, 4-(4-methylpiperazin-1-yl)aniline (42.6 mg, 0.223 mmol) [commercially available] and DIPEA (0.117 mL, 0.669 mmol) were added, successively, and the temperature was increased to 60° C. After 18 h, the reaction mixture was cooled to RT and loaded directly onto a KP-NH column and purified by flash chromatography (0-100%, EtOAc in cyclohexane) to give the title compound (73.9 mg, 56%) as a pale yellow solid.

LCMS (Method A): $R_T$=0.72 min, m/z=592 [M-OEt]$^+$.

$^1$H NMR (400 MHz, $CDCl_3$): δ 8.84 (s, 1H), 8.29 (dd, 1H), 8.13 (dd, 1H), 8.07 (t, 1H), 7.45-7.39 (m, 2H), 6.97-6.92 (m, 2H), 5.68-5.56 (m, 1H), 5.04-4.88 (m, 3H), 4.66 (dd, 1H), 4.15-3.96 (m, 2H), 3.38 (s, 3H), 3.24 (t, 4H), 2.62 (apparent t, 4H), 2.38 (s, 3H), 1.22 (t, 3H).

Example 3: rac-2-Allyl-6-((4-(4-methylpiperazin-1-yl)phenyl)amino)-1-(6-(S-methylsulfonimidoyl)pyridin-2-yl)-1H-pyrazolo[3,4-d]pyrimidin-3(2H)-one

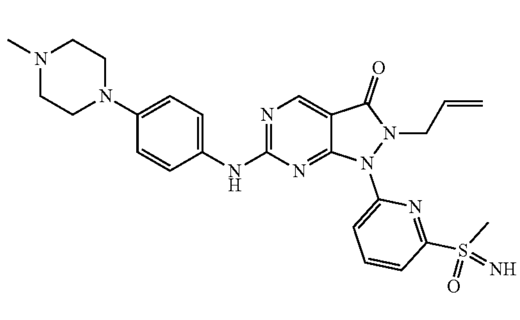 [SMILES: C=CCn1c(=O)c2cnc(Nc3ccc(N4CCN(C)CC4)cc3)nc2n1-c1cccc(S(C)(=N)=O)n1]

Sodium ethoxide (20% in EtOH) (0.036 mL, 0.092 mmol) was added to a solution of rac-ethyl N-{methyl[6-(6-{[4-(4-methylpiperazin-1-yl)phenyl]amino}-3-oxo-2-(prop-2-en-1-yl)-1H,2H,3H-pyrazolo[3,4-d]pyrimidin-1-yl)pyridine-2-yl]oxo-λ$^6$-sulfanylidene}carbamate* (10.9 mg, 0.018 mmol) in EtOH (0.5 mL) in a RB flask. The temperature was increased to 50° C. After 30 min, the reaction mixture was allowed to cool to RT. After 3 days, the solvents were removed in vacuo and the remaining residue was purified by flash chromatography (0-100% EtOAc in cyclohexane; then 0-10% MeOH in EtOAc) to give the title compound (1.6 mg, 16%) as a pale yellow solid.

LCMS (Method A): $R_T$=0.59 min, m/z=520 [M+H]$^+$.

$^1$H NMR (400 MHz, $CDCl_3$): δ 8.85 (s, 1H), 8.24 (d, 1H), 8.02 (t, 1H), 7.96 (dd, 1H), 7.46-7.39 (m, 2H), 6.97-6.91 (m, 2H), 5.67 (ddt, 1H), 5.05-4.86 (m, 4H), 3.28 (s, 3H), 3.23 (t, 4H), 2.62 (t, 4H), 2.38 (s, 3H).

Example 4: rac-2-Allyl-1-(6-(N,S-dimethylsulfonimidoyl)pyridin-2-yl)-6-((4-(4-methylpiperazin-1-yl)phenyl)amino)-1H-pyrazolo[3,4-d]pyrimidin-3(2H)-one

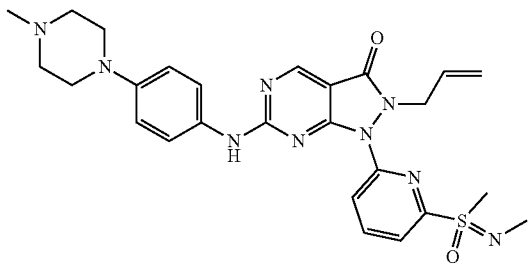

Step 1: [(6-Bromopyridin-2-yl)methyl)oxo-λ$^6$-sulfanylidene](methyl)amine

Paraformaldehyde (63.9 mg, 2.13 mmol) was added to a stirred solution of Intermediate A, (50 mg, 0.213 mmol) in formic acid (2.0 mL, 52.1 mmol) at RT in a 10 mL vial. The vessel was sealed and the temperature was increased to 100° C. After 1 h, the reaction mixture was allowed to cool and added slowly to saturated sodium bicarbonate (aq) solution and extracted using DCM (×3). The organic phase was dried (Phase Separator) and the solvents were removed in vacuo to give the title compound (crude, 54.6 mg) as a yellow oil that was carried through to the next step without further purification.

LCMS (Method A): $R_T$=0.63 min, m/z=249, 251 [M+H]$^+$.

Step 2: 2-Allyl-1-(6-(N,S-dimethylsulfonimidoyl)pyridin-2-yl)-6-(methylthio)-1H-pyrazolo[3,4-d]pyrimidin-3(2H)-one N,N'-dimethylethane-1,2-diamine (0.023 mL, 0.213 mmol) was added to a stirred solution of 2-allyl-6-(methylthio)-1H-pyrazolo[3,4-d]pyrimidin-3(2H)-one (47.3 mg, 0.213 mmol) [Prepared according to EP2213673B1 (Production Example 1, p 37)], [(6-bromopyridin-2-yl)(methyl)oxo-λ$^6$-sulfanylidene](methyl)amine (53.1 mg, 0.213 mmol), copper(I) iodide (40.6 mg, 0.213 mmol), and potassium carbonate (41.2 mg, 0.298 mmol) in 1,4-dioxane (1.0 mL) at RT. The reaction mixture was heated to 95° C. After 20 h, the reaction mixture was partitioned between saturated ammonium hydroxide (aq) solution and EtOAc, separated, extracted (EtOAc×3), organics combined, dried (Phase Separator), the solvents were removed in vacuo, and the remaining residue was purified by flash chromatography (0-100%, EtOAc in cyclohexane) to give the title compound (7.1 mg, 9%) as a pale yellow oil.

LCMS (Method A): $R_T$=0.91 min, m/z=391 [M+H]$^+$.

Step 3: 2-Allyl-1-(6-(N,S-dimethylsulfonimidoyl)pyridin-2-yl)-6-((4-(4-methylpiperazin-1-yl)phenyl)amino)-1H-pyrazolo[3,4-d]pyrimidin-3(2H)-one mCPBA (<77% pure) (5.5 mg, ca. 0.025 mmol) was added to a stirred solution of 2-allyl-1-(6-(N,S-dimethylsulfonimidoyl)pyridin-2-yl)-6-(methylthio)-1H-pyrazolo[3,4-d]pyrimidin-3(2H)-one (7.1 mg, 0.018 mmol) in toluene (2.0 mL) at RT under nitrogen. After 5 min, 4-(4-methylpiperazin-1-yl)aniline (3.5 mg, 0.018 mmol) [commercially available] and DIPEA (9.5 μL, 0.055 mmol) were added, successively, and the temperature was increased to 60° C. After 16 h, the reaction mixture was allowed to cool and loaded directly onto a KP-NH column and purified by flash chromatography to give the title compound (2.4 mg, 23%) as a pale yellow solid.

LCMS (Method A): $R_T$=0.65 min, m/z=534 [M+H]$^+$.

$^1$H NMR (400 MHz, MeOD): δ 8.81 (s, 1H), 8.31 (br s, 1H), 8.26 (t, 1H), 8.01 (d, 1H), 7.53 (d, 2H), 7.01 (d, 2H), 5.81-5.69 (m, 1H), 5.06 (dd, 1H), 4.98 (dd, 1H), 4.92-4.80 (m overlapping solvent peak, 2H), 3.27 (s, 3H), 3.22 (t, 4H), 2.66 (t, 4H), 2.61 (s, 3H), 2.38 (s, 3H).

Example 5: 1-(6-{[Dimethyl(oxo)-λ$^6$-sulfanylidene]amino}pyridine-2-yl)-6-{[4-(4-methylpiperazin-1-yl)phenyl]amino}-2-(prop-2-en-1-yl)-1H,2H,3H-pyrazolo[3,4-d]pyrimidin-3-one*

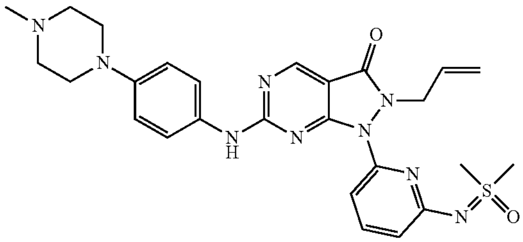 [SMILES: C=CCn1c(=O)c2cnc(Nc3ccc(N4CCN(C)CC4)cc3)nc2n1-c1cccc(N=S(C)(C)=O)n1]

Intermediate B (30.0 mg) was reacted with 4-(4-methylpiperazin-1-yl)aniline (14.7 mg) [commercially available] using General Procedure A to give the title compound (18.8 mg, 44%) as a pale yellow solid.

LCMS (Method A): $R_T$=0.66 min, m/z=534 [M+H]$^+$.

$^1$H NMR (400 MHz, $CDCl_3$): δ 8.81 (s, 1H), 7.66 (t, 1H), 7.48 (d, 2H), 7.35 (d, 1H), 7.31 (br s, 1H, overlapping previous peak), 6.92 (d, 2H), 6.67 (d, 1H), 5.65 (ddt, 1H), 5.04-4.94 (m, 2H), 4.90 (d, 2H), 3.33 (s, 6H), 3.20 (t, 4H), 2.60 (t, 4H), 2.37 (s, 3H).

Example 6: 1-(6-{[Dimethyl(oxo)-λ$^6$-sulfanylidene]amino}pyridine-2-yl)-6-{[4-(piperazin-1-yl)phenyl]amino}-2-(prop-2-en-1-yl)-1H,2H,3H-pyrazolo[3,4-d]pyrimidin-3-one*

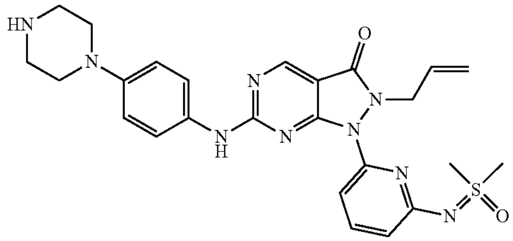 [SMILES: C=CCn1c(=O)c2cnc(Nc3ccc(N4CCNCC4)cc3)nc2n1-c1cccc(N=S(C)(C)=O)n1]

Step 1: tert-Butyl 4-(4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)piperazine-1-carboxylate*

Intermediate B (30.0 mg) was reacted with tert-butyl 4-(4-aminophenyl)piperazine-1-carboxylate (21.3 mg) [commercially available] using General Procedure A to give the title compound (12.4 mg, 26%) as a pale yellow solid.

LCMS (Method A): $R_T$=1.27 min, m/z=620 [M+H]$^+$.

Step 2: 1-(6-{[Dimethyl(oxo)-λ$^6$-sulfanylidene]amino}pyridine-2-yl)-6-{[4-(piperazin-1-yl)phenyl]amino}-2-(prop-2-en-1-yl)-1H,2H,3H-pyrazolo[3,4-d]pyrimidin-3-one* tert-Butyl 4-(4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)piperazine-1-carboxylate* (12.4 mg) was reacted with TFA (2.0 mL) using General Procedure B to give the title compound (8.2 mg, 76% yield) as a yellow solid.

LCMS (Method A): $R_T$=0.65 min, m/z=520 [M+H]$^+$.

$^1$H NMR (400 MHz, MeOD): δ 8.78 (s, 1H), 7.76 (t, 1H), 7.57 (d, 2H), 7.34 (d, 1H), 7.00-6.93 (m, 2H), 6.69 (d, 1H), 5.68 (ddt, 1H), 5.06-4.94 (m, 2H), 4.92-4.88 (m, 2H, overlapping solvent), 3.38 (s, 6H), 3.16-3.09 (m, 4H), 3.04-2.97 (m, 4H).

Example 7: 1-(6-{[Dimethyl(oxo)-λ$^6$-sulfanylidene]amino}pyridine-2-yl)-2-(prop-2-en-1-yl)-6-({4-[4-(propan-2-yl)piperazin-1-yl]phenyl}amino)-1H,2H,3H-pyrazolo[3,4-d]pyrimidin-3-one*

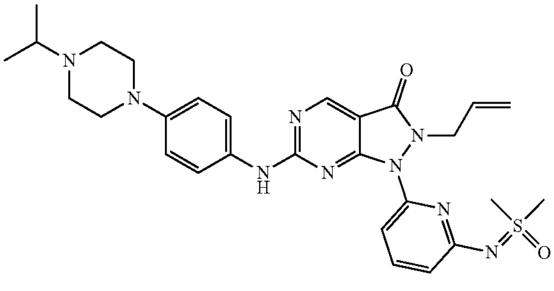 [SMILES: C=CCn1c(=O)c2cnc(Nc3ccc(N4CCN(C(C)C)CC4)cc3)nc2n1-c1cccc(N=S(C)(C)=O)n1]

Intermediate B (30.0 mg) was reacted with 4-(4-isopropylpiperazin-1-yl)aniline (16.9 mg) [commercially available] using General Procedure A to give the title compound (19.0 mg, 43%) as a pale yellow solid.

LCMS (Method A): $R_T$=0.70 min, m/z=562 $[M+H]^+$.

$^1$H NMR (400 MHz, MeOD): δ 8.78 (s, 1H), 7.76 (t, 1H), 7.57 (d, 2H), 7.34 (d, 1H), 7.00-6.94 (m, 2H), 6.69 (d, 1H), 5.68 (ddt, 1H), 5.05-4.93 (m, 2H), 4.91-4.88 (m, 2H, overlapping solvent), 3.38 (s, 6H), 3.20 (t, 4H), 2.83-2.69 (m, 5H), 1.15 (d, 6H).

Example 8: 6-{[4-(4-Cyclopropylpiperazin-1-yl)phenyl]amino}-1-(6-{[dimethyl(oxo)-λ$^6$-sulfanylidene]amino}pyridine-2-yl)-2-(prop-2-en-1-yl)-1H,2H,3H-pyrazolo[3,4-d]pyrimidin-3-one*

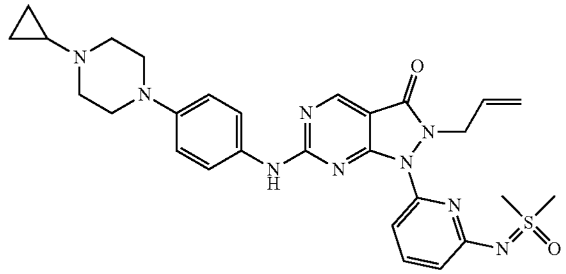 [SMILES: C=CCn1c(=O)c2cnc(Nc3ccc(N4CCN(C5CC5)CC4)cc3)nc2n1-c1cccc(N=S(C)(C)=O)n1]

Intermediate B (30.0 mg) was reacted with 4-(4-cyclopropylpiperazin-1-yl)aniline (16.7 mg) [commercially available] using General Procedure A to give the title compound (17.6 mg, 39%) as a pale yellow solid.

LCMS (Method A): $R_T$=0.72 min, m/z=560 $[M+H]^+$.

$^1$H NMR (400 MHz, MeOD): δ 8.78 (s, 1H), 7.76 (t, 1H), 7.56 (d, 2H), 7.34 (d, 1H), 7.00-6.93 (m, 2H), 6.69 (d, 1H), 5.68 (ddt, 1H), 5.06-4.94 (m, 2H), 4.91-4.88 (m, 2H, overlapping solvent), 3.38 (s, 6H), 3.15 (t, 4H), 2.82 (t, 4H), 1.74 (ddd, 1H), 0.57-0.44 (m, 4H).

Example 9: 1-(6-{[Dimethyl(oxo)-λ$^6$-sulfanylidene]amino}pyridine-2-yl)-6-({4-[(3R)-3-methylpiperazin-1-yl]phenyl}amino)-2-(prop-2-en-1-yl)-1H,2H,3H-pyrazolo[3,4-d]pyrimidin-3-one*

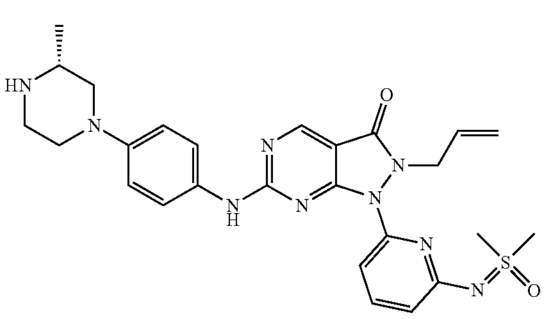 [SMILES: C=CCn1c(=O)c2cnc(Nc3ccc(N4CCN[C@H](C)C4)cc3)nc2n1-c1cccc(N=S(C)(C)=O)n1]

Step 1: (R)-tert-Butyl 2-methyl-4-(4-nitrophenyl)piperazine-1-carboxylate

In a 40 mL reaction tube was added 1-fluoro-4-nitrobenzene (3.25 g, 23.0 mmol), (R)-tert-butyl 2-methylpiperazine-1-carboxylate (4.61 g, 23.02 mmol) [commercially available] and potassium carbonate (4.77 g, 34.5 mmol) in anhydrous DMF (10 mL). The resulting yellow suspension was heated to 50° C. under nitrogen. After 16 h, the reaction mixture was allowed to cool to RT, diluted with water (30 mL) and stirred. After 15 min, the aqueous mixture was extracted using ethyl acetate (50 mL), the organic phase was washed using 1:1, water/brine (3×50 mL), the combined organic phase was dried ($Na_2SO_4$), filtered, and the solvents were removed in vacuo. The resulting residue was purified by flash chromatography (0-50%, EtOAc in cyclohexane) to give the title compound (5.24 g, 71%) as a yellow solid.

LCMS (Method A): $R_T$=1.72 min, m/z=322 $[M+H]^+$.

Step 2: (R)-tert-Butyl 4-(4-aminophenyl)-2-methylpiperazine-1-carboxylate

10% Palladium on carbon (0.497 g, 0.467 mmol) was added to a stirred solution of (R)-tert-butyl 2-methyl-4-(4-nitrophenyl)piperazine-1-carboxylate (3.00 g, 9.33 mmol) and in ethanol (60 mL) under nitrogen in a 100 mL RB flask. The resulting black suspension was heated to 40° C., followed by portion-wise addition of ammonium formate (2.94 g, 46.7 mmol). After 2 h, the reaction mixture was filtered through Celite and the solvents were removed in vacuo. The remaining residue was purified by flash chromatography (0-100%, EtOAc in cyclohexane) to give the title compound (1.42 g, 52%) as a dark brown solid.

LCMS (Method A): $R_T$=0.82 min, m/z=292 $[M+H]^+$.

Step 3: tert-Butyl (2R)-4-(4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)-2-methylpiperazine-1-carboxylate*

Intermediate B (30.0 mg) was reacted with (R)-tert-butyl 4-(4-aminophenyl)-2-methylpiperazine-1-carboxylate (22.4 mg) using General Procedure A to give the title compound (21.3 mg, 44%) as a yellow solid.

LCMS (Method A): $R_T$=1.37 min, m/z=634 $[M+H]^+$.

Step 4: 1-(6-{[Dimethyl(oxo)-λ$^6$-sulfanylidene]amino}pyridine-2-yl)-6-({4-[(3R)-3-methylpiperazin-1-yl]phenyl}amino)-2-(prop-2-en-1-yl)-1H,2H,3H-pyrazolo[3,4-d]pyrimidin-3-one* tert-Butyl (2R)-4-(4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)-2-methylpiperazine-1-carboxylate (21.3 mg) was reacted with TFA (2.0 mL) using General Procedure B to give the title compound (15.2 mg, 83%) as a yellow solid.

LCMS (Method A): $R_T$=0.67 min, m/z=534 $[M+H]^+$.

$^1$H NMR (400 MHz, MeOD): δ 8.78 (s, 1H), 7.76 (t, 1H), 7.57 (d, 2H), 7.34 (d, 1H), 7.00-6.94 (m, 2H), 6.69 (d, 1H), 5.68 (ddt, 1H), 5.06-4.93 (m, 2H), 4.92-4.88 (m, 2H, overlapping solvent), 3.53 (t, 2H), 3.38 (s, 6H), 3.13-3.07 (m, 1H), 3.03-2.93 (m, 2H), 2.68 (dt, 1H), 2.35 (t, 1H), 1.17 (d, 3H).

Example 10: 1-(6-{[Dimethyl(oxo)-λ$^6$-sulfanylidene]amino}pyridine-2-yl)-6-{[4-(4-ethylpiperazin-1-yl)phenyl]amino}-2-(prop-2-en-1-yl)-1H,2H,3H-pyrazolo[3,4-d]pyrimidin-3-one*

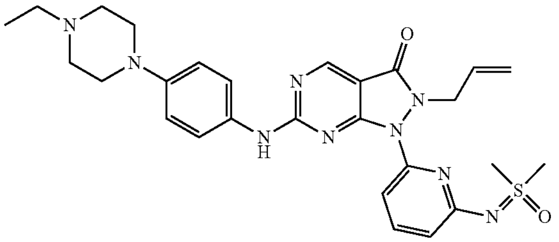 [SMILES: C=CCn1c(=O)c2cnc(Nc3ccc(N4CCN(CC)CC4)cc3)nc2n1-c1cccc(N=S(C)(C)=O)n1]

Intermediate B (30.0 mg) was reacted with 4-(4-ethylpiperazin-1-yl)aniline (15.8 mg) [commercially available] using General Procedure A to give the title compound (24.1 mg, 56%) as a pale yellow solid.

LCMS (Method A): $R_T$=0.69 min, m/z=548 [M+H]$^+$.

$^1$H NMR (400 MHz, $CDCl_3$): δ 8.81 (s, 1H), 7.66 (t, 1H), 7.48 (d, 2H), 7.35 (d, 1H), 7.31 (br s, 1H, overlapping previous peak), 6.96-6.88 (m, 2H), 6.67 (d, 1H), 5.65 (ddt, 1H), 5.04-4.94 (m, 2H), 4.91 (d, 2H), 3.33 (s, 6H), 3.21 (t, 4H), 2.63 (t, 4H), 2.49 (q, 2H), 1.14 (t, 3H).

Example 11: 1-(6-{[Dimethyl(oxo)-λ$^6$-sulfanylidene]amino}pyridine-2-yl)-6-{[4-(4-methylpiperazin-1-yl)phenyl]amino}-2-propyl-1H,2H,3H-pyrazolo[3,4-d]pyrimidin-3-one*

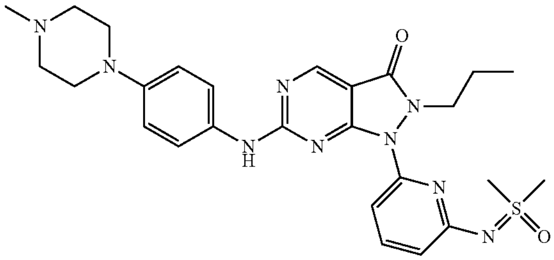

Step 1: 1-(6-{[Dimethyl(oxo)-λ$^6$-sulfanylidene]amino}pyridine-2-yl)-6-(methylsulfanyl)-2-propyl-1H,2H,3H-pyrazolo[3,4-d]pyrimidin-3-one

[Note: Adapted procedure from *Org. Lett.*, 2013, 15, 710-713, Supporting Information] Hydroxylamine (50% in water) (0.039 mL, 0.640 mmol) was added to a solution of 2,2,2-trifluoro-N-(2,2,2-trifluoroacetoxy)acetamide (57.6 mg, 0.256 mmol) and 1-(6-{[dimethyl(oxo)-λ$^6$-sulfanylidene]amino}pyridin-2-yl)-6-(methylsulfanyl)-2-(prop-2-en-1-yl)-1H,2H,3H-pyrazolo[3,4-d]pyrimidin-3-one (50.0 mg, 0.128 mmol) in ethyl acetate (1.0 mL) at RT in a 10 mL vial and the vessel was sealed immediately. The vessel was irradiated at 100° C. for 20 minutes (CEM Discover/Explorer). The reaction mixture was passed through a phase separator, the remaining solid was washed with EtOAc, the combined solvent was removed in vacuo and the remaining residue was purified by flash chromatography using a Grace 12 g column (0-100%, EtOAc in cyclohexane) to give the title compound (29.6 mg, 59%) as a colourless oil that turned into a white solid under vacuum.

LCMS (Method A): $R_T$=1.53 min, m/z=393 [M+H]$^+$.

Step 2: 1-(6-{[Dimethyl(oxo)-λ$^6$-sulfanylidene]amino}pyridine-2-yl)-6-{[4-(4-methylpiperazin-1-yl)phenyl]amino}-2-propyl-1H,2H,3H-pyrazolo[3,4-d]pyrimidin-3-one 1-(6-{[Dimethyl(oxo)-λ$^6$-sulfanylidene]amino}pyridine-2-yl)-6-(methylsulfanyl)-2-propyl-1H,2H,3H-pyrazolo[3,4-d]pyrimidin-3-one (29.6 mg) was reacted with 4-(4-methylpiperazin-1-yl)aniline (14.4 mg) [commercially available] using General Procedure A to give the title compound (23.2 mg, 57%) as a pale yellow solid.

LCMS (Method A): $R_T$=0.68 min, m/z=536 [M+H]$^+$.

$^1$H NMR (400 MHz, $CDCl_3$): δ 8.81 (s, 1H), 7.69 (t, 1H), 7.48 (d, 2H), 7.35 (d, 1H), 7.31 (br s, 1H, overlapping previous peak), 6.96-6.88 (m, 2H), 6.69 (d, 1H), 4.25 (t, 2H), 3.32 (s, 6H), 3.20 (t, 4H), 2.60 (t, 4H), 2.37 (s, 3H), 1.47 (sext, 2H), 0.77 (t, 3H).

Example 12: 1-(6-{[Dimethyl(oxo)-λ$^6$-sulfanylidene]amino}pyridine-2-yl)-6-{[4-(morpholin-4-yl)phenyl]amino}-2-(prop-2-en-1-yl)-1H,2H,3H-pyrazolo[3,4-d]pyrimidin-3-one*

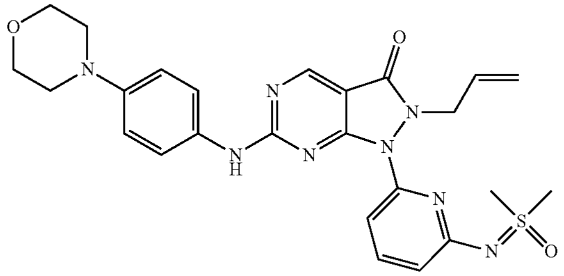

Intermediate B (30.0 mg) was reacted with 4-morpholinoaniline (13.7 mg, 0.077 mmol) [commercially available] using General Procedure A to give the title compound (24.1 mg, 59%) as a pale yellow solid.

LCMS (Method A): $R_T$=0.96 min, m/z=521 [M+H]$^+$.

$^1$H NMR (400 MHz, $CDCl_3$): δ 8.81 (s, 1H), 7.67 (t, 1H), 7.50 (d, 2H), 7.35 (d, 1H), 7.30 (br s, 1H, overlapping previous peak), 6.94-6.87 (m, 2H), 6.67 (d, 1H), 5.65 (ddt, 1H), 5.03-4.95 (m, 2H), 4.91 (d, 2H), 3.88 (t, 4H), 3.33 (s, 6H), 3.15 (t, 4H).

Example 13: 1-(6-{[Dimethyl(oxo)-λ$^6$-sulfanylidene]amino}pyridine-2-yl)-6-{[4-(piperidin-4-yl)phenyl]amino}-2-(prop-2-en-1-yl)-1H,2H,3H-pyrazolo[3,4-d]pyrimidin-3-one

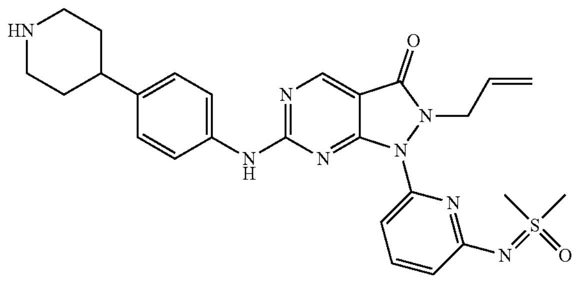 [SMILES: C=CCn1c(=O)c2cnc(Nc3ccc(C4CCNCC4)cc3)nc2n1-c1cccc(N=S(C)(C)=O)n1]

Step 1: tert-Butyl 4-(4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)piperidine-1-carboxylate Intermediate B (34.9 mg) was reacted with tert-butyl 4-(4-aminophenyl)piperidine-1-carboxylate (24.7 mg) [commercially available] using General Procedure A to give the title compound (3.9 mg, 7%) as a colourless oil.

LCMS (Method A): $R_T$=1.39 min, m/z=619 $[M+H]^+$.

Step 2: 1-(6-{[Dimethyl(oxo)-λ$^6$-sulfanylidene]amino}pyridine-2-yl)-6-{[4-(piperidin-4-yl)phenyl]amino}-2-(prop-2-en-1-yl)-1H,2H,3H-pyrazolo[3,4-d]pyrimidin-3-one* tert-Butyl 4-(4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)piperidine-1-carboxylate (3.9 mg) was reacted with TFA (2.0 mL) using General Procedure B to give the title compound (2.6 mg, 76%) as a white solid.

LCMS (Method A): $R_T$=0.86 min, m/z=519 $[M+H]^+$.

$^1$H NMR (400 MHz, $CDCl_3$): δ 8.84 (s, 1H), 7.68 (t, 1H), 7.55 (d, 2H), 7.41 (br s, 1H), 7.36 (d, 1H), 7.21 (d, 2H), 6.69 (d, 1H), 5.66 (ddt, 1H), 5.05-4.95 (m, 2H), 4.92 (d, 2H), 3.33 (s, 6H), 3.22 (apparent br d, 2H), 2.76 (dt, 2H), 2.62 (tt, 1H), 1.85 (br d, 2H) 1.68 (dp, 2H).

Example 14: 6-{[3-Chloro-4-(piperazin-1-yl)phenyl]amino}-1-(6-{[dimethyl(oxo)-λ$^6$-sulfanylidene]amino}pyridine-2-yl)-2-(prop-2-en-1-yl)-1H,2H,3H-pyrazolo[3,4-d]pyrimidin-3-one*

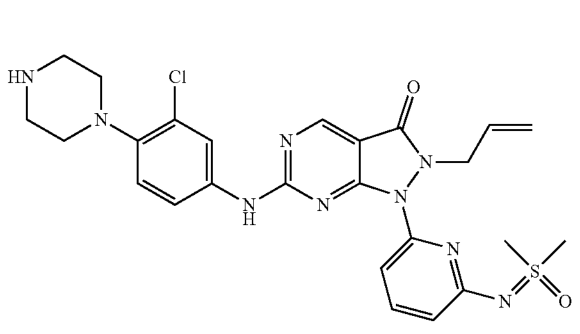 [SMILES: C=CCn1c(=O)c2cnc(Nc3ccc(N4CCNCC4)c(Cl)c3)nc2n1-c1cccc(N=S(C)(C)=O)n1]

Step 1: tert-Butyl 4-(2-chloro-4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)piperazine-1-carboxylate Intermediate B (30.0 mg) was reacted tert-butyl 4-(4-amino-2-chlorophenyl)piperazine-1-carboxylate (24.0 mg) [commercially available] using General Procedure A to give the title compound (17.2 mg, 34%) as an off-white solid.

LCMS (Method A): $R_T$=1.44 min, m/z=654 $[M+H]^+$.

Step 2: 6-{[3-Chloro-4-(piperazin-1-yl)phenyl]amino}-1-(6-{[dimethyl(oxo)-λ$^6$-sulfanylidene]amino}pyridine-2-yl)-2-(prop-2-en-1-yl)-1H,2H,3H-pyrazolo[3,4-d]pyrimidin-3-one* tert-Butyl 4-(2-chloro-4-{[1-(6-{[dimethyl(oxo)-λ$^6$-sulfanylidene]amino}pyridine-2-yl)-3-oxo-2-(prop-2-en-1-yl)-1H,2H,3H-pyrazolo[3,4-d]pyrimidin-6-yl]amino}phenyl)piperazine-1-carboxylate (17.2 mg) was reacted with TFA (2.0 mL) using General Procedure B to give the title compound (8.6 mg, 58%) as a pale yellow solid.

LCMS (Method A): $R_T$=0.72 min, m/z=554 $[M+H]^+$.

$^1$H NMR (400 MHz, $CDCl_3$): δ 8.83 (s, 1H), 8.17 (br s, 1H), 7.78 (t, 1H), 7.45-7.33 (m, 2H), 7.14 (br d, 1H), 7.01 (d, 1H), 6.69 (d, 1H), 5.65 (ddt, 1H), 5.05-4.88 (m, 4H), 3.33 (s, 6H), 3.07 (t, 4H), 3.00 (br t, 4H).

Example 15: 1-(6-{[Dimethyl(oxo)-λ$^6$-sulfanylidene]amino}pyridine-2-yl)-6-({2'-methyl-2',3'-dihydro-1'H-spiro[cyclopropane-1,4'-isoquinoline]-7'-yl}amino)-2-(prop-2-en-1-yl)-1H,2H,3H-pyrazolo[3,4-d]pyrimidin-3-one

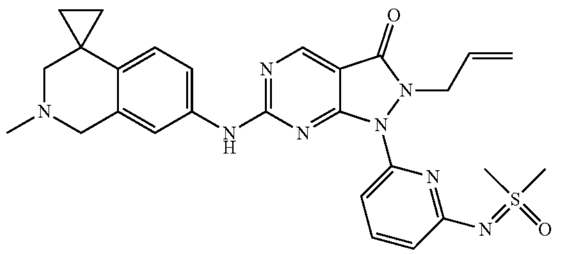

Intermediate B (30.0 mg) was reacted with 2'-methyl-2',3'-dihydro-1'H-spiro[cyclopropane-1,4'-isoquinolin]-7'-amine, 2HCl (20.1 mg, 0.077 mmol) [Prepared according to WO2009151997A1 (Reference Example 1, Page 25)] using General Procedure A except using 2 additional equivalents of triethylamine (total: 5 equivalents, 67 μL) to give the title compound (4.5 mg, 10%) as an off-white solid.

LCMS (Method A): $R_T$=0.72 min, m/z=531 $[M+H]^+$.

$^1$H NMR (400 MHz, $CDCl_3$): δ 8.82 (s, 1H), 7.68 (t, 1H), 7.52 (br s, 1H), 7.35 (d, 2H), 7.20 (br dd, 1H), 6.68 (dd, 1H), 6.64 (d, 1H), 5.65 (ddt, 1H), 5.03-4.95 (m, 2H), 4.92 (d, 2H), 3.70 (s, 2H), 3.33 (s, 6H), 2.54 (s, 2H), 2.47 (s, 3H), 1.01 (apparent t, 2H), 0.92 (apparent t, 2H).

Example 16: 1-(3-{[Dimethyl(oxo)-$\lambda^6$-sulfanylidene]amino}phenyl)-6-{[4-(4-methylpiperazin-1-yl)phenyl]amino}-2-(prop-2-en-1-yl)-1H,2H,3H-pyrazolo[3,4-d]pyrimidin-3-one*

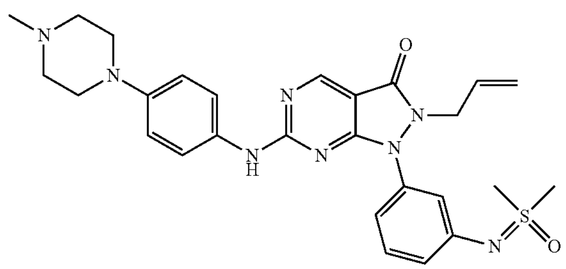

Intermediate C (30.0 mg) was reacted with 4-(4-methylpiperazin-1-yl)aniline (14.7 mg, 0.077 mmol) [commercially available] using General Procedure A to give the title compound (25.9 mg, 62%) as pale yellow solid.

LCMS (Method A): $R_T$=0.66 min, m/z=533 $[M+H]^+$.

$^1$H NMR (400 MHz, $CDCl_3$): δ 8.80 (s, 1H), 7.44 (br d, 2H), 7.35 (t, 1H), 7.13-7.03 (m, 3H), 6.89 (d, 2H), 5.69 (ddt, 1H), 5.10 (dd, 1H), 5.00 (dd, 1H), 4.40 (d, 2H), 3.17 (t, 4H), 3.16 (s, 6H), 2.58 (t, 4H), 2.36 (s, 3H).

Example 17: 1-(6-{[Dimethyl(oxo)-$\lambda^6$-sulfanylidene]amino}pyridin-2-yl)-6-({4-[(3R,5S)-3,5-dimethylpiperazin-1-yl]phenyl}amino)-2-(prop-2-en-1-yl)-1H,2H,3H-pyrazolo[3,4-d]pyrimidin-3-one*

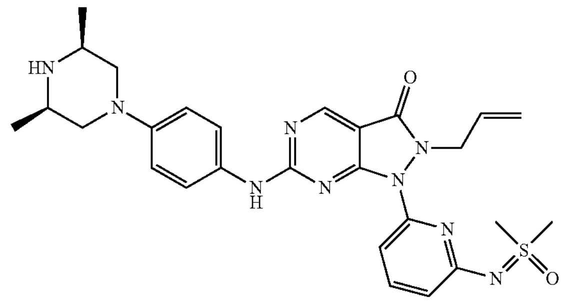

Intermediate B (30.0 mg) was reacted with 4-((3R,5S)-3,5-dimethylpiperazin-1-yl)aniline (15.8 mg, 0.077 mmol) [Prepared according to WO2008090181A1 (Reference Example 8f, Page 65)] using General Procedure A to give the title compound (27.3 mg, 63%) as a yellow solid.

LCMS (Method A): $R_T$=0.68 min, m/z=548 $[M+H]^+$.

$^1$H NMR (400 MHz, $CDCl_3$): δ 8.81 (s, 1H), 7.68 (t, 1H), 7.47 (br d, 2H), 7.35 (d, 1H), 6.94-6.89 (m, 2H), 6.67 (d, 1H), 5.65 (ddt, 1H), 5.04-4.95 (m, 2H), 4.91 (d, 2H), 3.49 (dd, 2H), 3.33 (s, 6H), 3.12-3.00 (m, 2H), 2.29 (t, 2H), 1.16 (d, 6H).

Example 18: 1-(3-{[Dimethyl(oxo)-$\lambda^6$-sulfanylidene]amino}phenyl)-6-{[4-(piperazin-1-yl)phenyl]amino}-2-(prop-2-en-1-yl)-1H,2H,3H-pyrazolo[3,4-d]pyrimidin-3-one

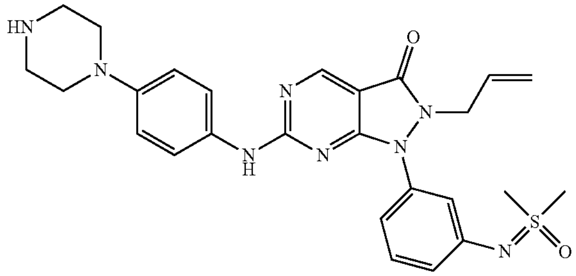 [SMILES: C=CCn1c(=O)c2cnc(Nc3ccc(N4CCNCC4)cc3)nc2n1-c1cccc(N=S(C)(C)=O)c1]

Step 1: tert-Butyl 4-(4-{[1-(3-{[dimethyl(oxo)-$\lambda^6$-sulfanylidene]amino}phenyl)-3-oxo-2-(prop-2-en-1-yl)-1H,2H,3H-pyrazolo[3,4-d]pyrimidin-6-yl]amino}phenyl)piperazine-1-carboxylate Intermediate C (30.0 mg) was reacted with tert-butyl 4-(4-aminophenyl)piperazine-1-carboxylate (21.4 mg, 0.077 mmol) [commercially available] using General Procedure A to give the title compound (35.0 mg, 73%) as pale yellow solid.

LCMS (Method A): $R_T$=0.66 min, m/z=533 $[M+H]^+$.

Step 2: 1-(3-{[Dimethyl(oxo)-$\lambda^6$-sulfanylidene]amino}phenyl)-6-{[4-(piperazin-1-yl)phenyl]amino}-2-(prop-2-en-1-yl)-1H,2H,3H-pyrazolo[3,4-d]pyrimidin-3-one tert-Butyl 4-(4-{[1-(3-{[dimethyl(oxo)-$\lambda^6$-sulfanylidene]amino}phenyl)-3-oxo-2-(prop-2-en-1-yl)-1H,2H,3H-pyrazolo[3,4-d]pyrimidin-6-yl]amino}phenyl)piperazine-1-carboxylate (35.0 mg) was reacted with TFA (2.0 mL) using General Procedure B to give the title compound (25.6 mg, 86%) as a pale yellow solid.

LCMS (Method A): $R_T$=0.65 min, m/z=519 $[M+H]^+$.

$^1$H NMR (400 MHz, $CDCl_3$): δ 8.80 (s, 1H), 7.45 (br d, 2H), 7.35 (t, 1H), 7.14-7.04 (m, 3H), 6.92-6.86 (m, 2H), 5.70 (ddt, 1H), 5.10 (dd, 1H), 5.00 (dd, 1H), 4.40 (d, 2H), 3.16 (s, 6H), 3.14-3.08 (m, 4H), 3.07-3.01 (m, 4H).

Example 19: 1-(6-{[Dimethyl(oxo)-$\lambda^6$-sulfanylidene]amino}pyridin-2-yl)-6-(phenylamino)-2-(prop-2-en-1-yl)-1H,2H,3H-pyrazolo[3,4-d]pyrimidin-3-one*

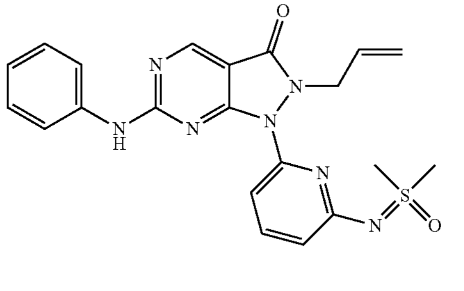 [SMILES: C=CCn1c(=O)c2cnc(Nc3ccccc3)nc2n1-c1cccc(N=S(C)(C)=O)n1]

Intermediate B (30.0 mg) was reacted with aniline (7.15 mg, 0.077 mmol) using General Procedure A to give the title compound (3.0 mg, 9%) as a white solid.

LCMS (Method A): $R_T$=1.08 min, m/z=436 $[M+H]^+$.

$^1H$ NMR (400 MHz, $CDCl_3$): δ 8.85 (s, 1H), 7.69 (t, 1H), 7.63 (d, 2H), 7.43 (br s, 1H), 7.39-7.32 (m, 3H), 7.12 (t, 1H), 6.69 (d, 1H), 5.66 (ddt, 1H), 5.04-4.95 (m, 2H), 4.92 (d, 2H), 3.33 (s, 6H).

Example 20: 1-(6-{[Dimethyl(oxo)-$\lambda^6$-sulfanylidene]amino}pyridin-2-yl)-6-{[4-(4-methylpiperazin-1-yl)phenyl]amino}-2-(propan-2-yl)-1H,2H,3H-pyrazolo[3,4-d]pyrimidin-3-one*

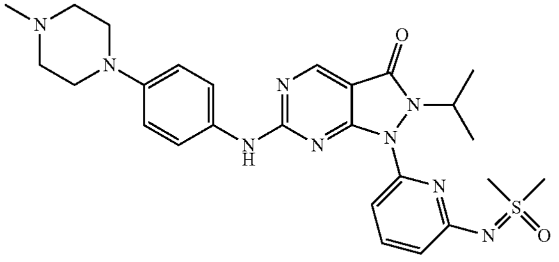

Intermediate D (12.9 mg) was reacted with 4-(4-methylpiperazin-1-yl)aniline (6.29 mg, 0.033 mmol) [commercially available] using General Procedure A to give the title compound (9.1 mg, 50%) as a pale yellow solid.

LCMS (Method A): $R_T$=0.69 min, m/z=536 $[M+H]^+$.

$^1H$ NMR (400 MHz, $CDCl_3$): δ 8.75 (s, 1H), 7.68 (t, 1H), 7.42 (d, 2H), 7.19 (d, 1H), 6.94-6.86 (m, 2H), 6.73 (d, 1H), 4.36 (p, 1H), 3.32 (s, 6H), 3.19 (t, 4H), 2.59 (t, 4H), 2.36 (s, 3H), 1.45 (d, 6H).

Example 21: 1-(6-{[Dimethyl(oxo)-$\lambda^6$-sulfanylidene]amino}pyridin-2-yl)-6-{[3-methyl-4-(morpholin-4-yl)phenyl]amino}-2-(prop-2-en-1-yl)-1H,2H,3H-pyrazolo[3,4-d]pyrimidin-3-one*

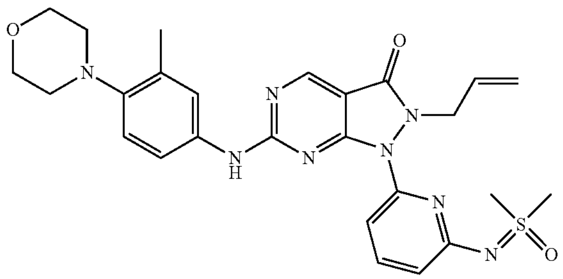

Intermediate B (30.0 mg) was reacted with 3-methyl-4-morpholinoaniline (14.8 mg, 0.077 mmol) [commercially available] using General Procedure A to give the title compound (22.5 mg, 53%) as a very pale yellow solid.

LCMS (Method A): $R_T$=1.10 min, m/z=535 $[M+H]^+$.

$^1H$ NMR (400 MHz, $CDCl_3$): δ 8.83 (s, 1H), 7.69 (t, 1H), 7.59 (br s, 1H), 7.38 (d, 1H), 7.35-7.28 (m, 2H), 7.00 (d, 1H), 6.68 (d, 1H), 5.65 (ddt, 1H), 5.03-4.95 (m, 2H), 4.92 (d, 2H), 3.86 (t, 4H), 3.34 (s, 6H), 2.90 (t, 4H), 2.34 (s, 3H).

Example 22: 1-(3-{[Dimethyl(oxo)-$\lambda^6$-sulfanylidene]amino}phenyl)-6-({3-[(methylamino)methyl]-4-(morpholin-4-yl)phenyl}amino)-2-(prop-2-en-1-yl)-1H,2H,3H-pyrazolo[3,4-d]pyrimidin-3-one

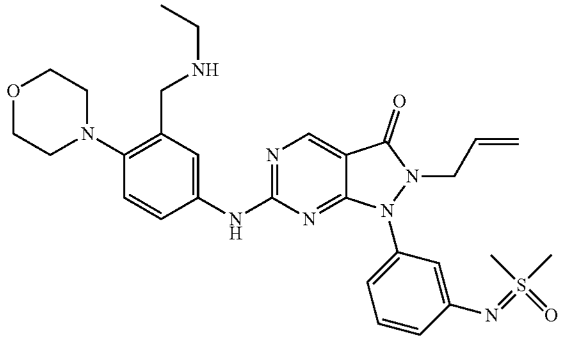 [SMILES: C=CCn1c(=O)c2cnc(Nc3ccc(N4CCOCC4)c(CNCC)c3)nc2n1-c1cccc(N=S(C)(C)=O)c1]

Step 1: tert-Butyl N-[(5-{[1-(3-{[dimethyl(oxo)-$\lambda^6$-sulfanylidene]amino}phenyl)-3-oxo-2-(prop-2-en-1-yl)-1H,2H,3H-pyrazolo[3,4-d]pyrimidin-6-yl]amino}-2-(morpholin-4-yl)phenyl)methyl]-N-methylcarbamate Intermediate C (30.0 mg) was reacted with tert-butyl 5-amino-2-morpholinobenzyl(methyl)carbamate (24.8 mg, 0.077 mmol) [Prepared according to WO2014167347A1 (Example 20, Page 76)] using General Procedure A to give the title compound (29.7 mg, 58%) as a pale yellow oil.

LCMS (Method A): $R_T$=1.22 min, m/z=663 $[M+H]^+$.

Step 2: 1-(3-{[Dimethyl(oxo)-$\lambda^6$-sulfanylidene]amino}phenyl)-6-({3-[(methylamino)methyl]-4-(morpholin-4-yl)phenyl}amino)-2-(prop-2-en-1-yl)-1H,2H,3H-pyrazolo[3,4-d]pyrimidin-3-one tert-butyl N-[(5-{[1-(3-{[dimethyl(oxo)-$\lambda^6$-sulfanylidene]amino}phenyl)-3-oxo-2-(prop-2-en-1-yl)-1H,2H,3H-pyrazolo[3,4-d]pyrimidin-6-yl]amino}-2-(morpholin-4-yl)phenyl)methyl]-N-methylcarbamate (29.7 mg, 0.045 mmol) was reacted with TFA (2.0 mL) using General Procedure B to give the title compound (23.6 mg, 93%) as a pale yellow solid.

LCMS (Method A): $R_T$=0.71 min, m/z=563 $[M+H]^+$.

$^1H$ NMR (400 MHz, $CDCl_3$): δ 8.82 (s, 1H), 7.58 (br s, 1H), 7.74 (dd, 1H), 7.37 (t, 1H), 7.32 (br s, 1H), 7.15-7.09 (m, 2H), 7.09-7.03 (m, 2H), 5.70 (ddt, 1H), 5.10 (dd, 1H), 5.00 (dd, 1H), 4.41 (d, 2H), 3.84 (t, 4H), 3.77 (s, 2H), 3.19 (s, 6H), 2.90 (br t, 4H), 2.41 (s, 3H).

Example 23: 2-Allyl-6-((4-(4-methylpiperazin-1-yl)phenyl)amino)-1-(6-((1-oxidotetrahydrothiophen-1-ylidene)amino)pyridin-2-yl)-1H-pyrazolo[3,4-d]pyrimidin-3(2H)-one

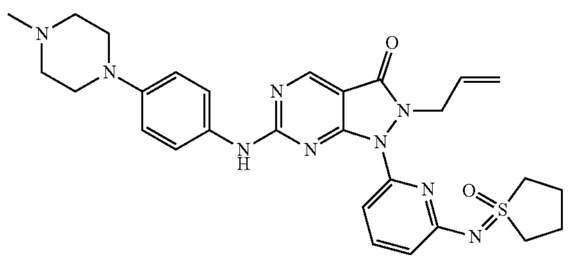 [SMILES: C=CCn1c(=O)c2cnc(Nc3ccc(N4CCN(C)CC4)cc3)nc2n1-c1cccc(N=S2(=O)CCCC2)n1]

Intermediate E (30.0 mg) was reacted with 4-(4-methylpiperazin-1-yl)aniline (13.8 mg, 0.072 mmol) [commercially available] using General Procedure A to give the title compound (16.6 mg, 40%) as a yellow solid.

LCMS (Method A): $R_T$=0.70 min, m/z=560 $[M+H]^+$.

$^1$H NMR (400 MHz, CDCl3): δ 8.81 (s, 1H), 7.67 (t, 1H), 7.48 (br d, 2H), 7.36 (d, 1H), 6.95-6.89 (d, 2H), 6.71 (d, 1H), 5.65 (ddt, 1H), 5.03-4.95 (m, 2H), 4.92 (d, 2H), 3.56 (p, 2H), 3.34 (p, 2H), 3.20 (t, 4H), 2.60 (t, 4H), 2.39-2.26 (m, 5H), 2.23-2.12 (m, 2H).

Example 24: 1-(6-{[Dimethyl(oxo)-λ$^6$-sulfanylidene]amino}pyridin-2-yl)-6-{[3-methoxy-4-(4-methylpiperazin-1-yl)phenyl]amino}-2-(prop-2-en-1-yl)-1H,2H,3H-pyrazolo[3,4-d]pyrimidin-3-one*

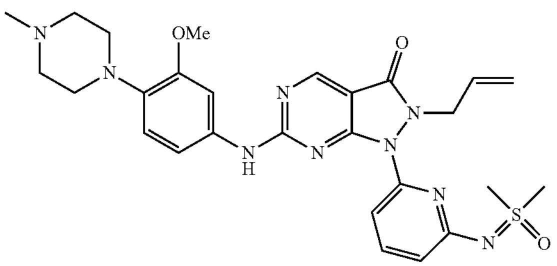

Intermediate B (30.0 mg) was reacted with 3-methoxy-4-(4-methylpiperazin-1-yl)aniline (17.0 mg, 0.077 mmol) [commercially available] using General Procedure A to give the title compound (12.1 mg, 27%) as a pale yellow solid.

LCMS (Method A): $R_T$=0.66 min, m/z=564 $[M+H]^+$.

$^1$H NMR (400 MHz, $CDCl_3$): δ 8.83 (s, 1H), 7.63 (t, 1H), 7.34 (br s, 1H), 7.30 (d, 1H), 7.22 (d, 1H), 7.04 (dd, 1H), 6.90 (d, 1H), 6.68 (dd, 1H), 5.65 (ddt, 1H), 5.03-4.93 (m, 2H), 4.87 (d, 2H), 3.80 (s, 3H), 3.32 (s, 6H), 3.09 (br s, 4H), 2.63 (br s, 4H), 2.37 (s, 3H).

Example 25: 1-(6-{[Dimethyl(oxo)-λ$^6$-sulfanylidene]amino}pyridin-2-yl)-6-{[3-methoxy-4-(morpholin-4-yl)phenyl]amino}-2-(prop-2-en-1-yl)-1H,2H,3H-pyrazolo[3,4-d]pyrimidin-3-one*

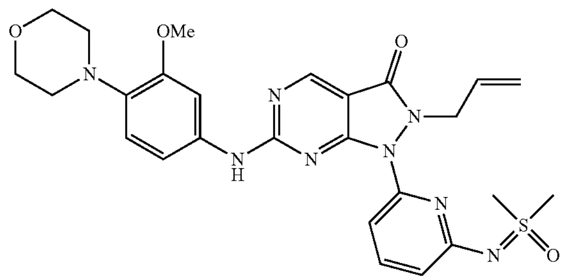 [SMILES: C=CCn1c(=O)c2cnc(Nc3ccc(N4CCOCC4)c(OC)c3)nc2n1-c1cccc(N=S(C)(C)=O)n1]

Intermediate B (19.3 mg) was reacted with 3-methoxy-4-morpholinoaniline (10.3 mg, 0.049 mmol) [commercially available] using General Procedure A to give the title compound (14.7 mg, 53%) as a pale yellow solid.

LCMS (Method A): $R_T$=0.85 min, m/z=551 $[M+H]^+$.

$^1$H NMR (400 MHz, $CDCl_3$): δ 8.83 (s, 1H), 7.64 (t, 1H), 7.35 (br s, 1H), 7.30 (d, 1H), 7.24 (d, 1H), 7.06 (dd, 1H), 6.88 (d, 1H), 6.68 (d, 1H), 5.65 (ddt, 1H), 5.03-4.93 (m, 2H), 4.87 (d, 2H), 3.90 (t, 4H), 3.81 (s, 3H), 3.32 (s, 6H), 3.05 (t, 4H).

Example 26: 1-(6-{[Dimethyl(oxo)-λ$^6$-sulfanylidene]amino}pyridin-2-yl)-6-{[3-methyl-4-(piperazin-1-yl)phenyl]amino}-2-(prop-2-en-1-yl)-1H,2H,3H-pyrazolo[3,4-d]pyrimidin-3-one*

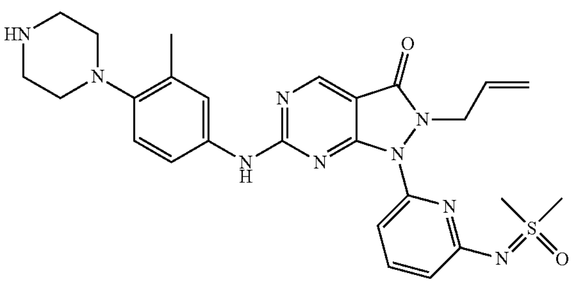 [SMILES: C=CCn1c(=O)c2cnc(Nc3ccc(N4CCNCC4)c(C)c3)nc2n1-c1cccc(N=S(C)(C)=O)n1]

Step 1: tert-Butyl 4-(4-{[1-(6-{[dimethyl(oxo)-λ$^6$-sulfanylidene]amino}pyridin-2-yl)-3-oxo-2-(prop-2-en-1-yl)-1H,2H,3H-pyrazolo[3,4-d]pyrimidin-6-yl]amino}-2-methylphenyl)piperazine-1-carboxylate Intermediate B (50.0 mg) was reacted with tert-butyl 4-(4-amino-2-methylphenyl)piperazine-1-carboxylate (37.3 mg, 0.128 mmol) [commercially available] using General Procedure A to give the title compound (49.9 mg, 62%) as a pale yellow solid.

LCMS (Method A): $R_T$=1.41 min, m/z=634 $[M+H]^+$.

Step 2: 1-(6-{[Dimethyl(oxo)-λ$^6$-sulfanylidene]amino}pyridin-2-yl)-6-{[1-methyl-4-(piperazin-1-yl)phenyl]amino}-2-(prop-2-en-1-yl)-1H,2H,3H-pyrazolo[3,4-d]pyrimidin-3-one tert-Butyl 4-(4-{[1-(6-{[dimethyl(oxo)-λ$^6$-sulfanylidene]amino}pyridin-2-yl)-3-oxo-2-(prop-2-en-1-yl)-1H,2H,3H- pyrazolo[3,4-d]pyrimidin-6-yl]amino}-2-methylphenyl) piperazine-1-carboxylate* (49.9 mg, 0.079 mmol) was reacted with TFA (2.0 mL) using General Procedure B to give the title compound (32.9 mg, 76%) as a pale yellow solid.

LCMS (Method A): $R_T$=0.70 min, m/z=534 $[M+H]^+$.

$^1$H NMR (400 MHz, $CDCl_3$): δ 8.82 (s, 1H), 7.68 (t, 1H), 7.58 (br s, 1H), 7.38 (d, 1H), 7.29 (dd, 1H), 7.00 (d, 1H), 6.68 (d, 1H), 5.65 (ddt, 1H), 5.03-4.95 (m, 2H), 4.92 (d, 2H), 3.33 (s, 6H), 3.03 (t, 4H), 2.86 (t, 4H), 2.34 (s, 3H).

Example 27: 1-(3-{[Dimethyl(oxo)-λ$^6$-sulfanylidene]amino}phenyl)-6-({4-[2-(methylamino)ethoxy]phenyl}amino)-2-(prop-2-en-1-yl)-1H,2H,3H-pyrazolo[3,4-d]pyrimidin-3-one*

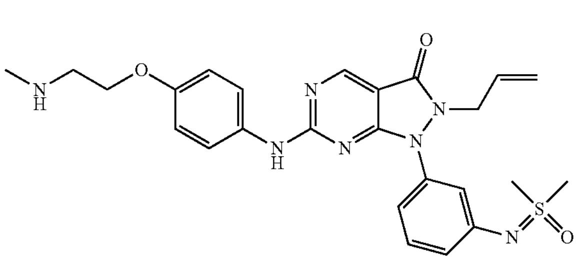 [SMILES: C=CCn1c(=O)c2cnc(Nc3ccc(OCCNC)cc3)nc2n1-c1cccc(N=S(C)(C)=O)c1]

Step 1: tert-Butyl N-[2-(4-{[1-(3-{[dimethyl(oxo)-λ$^6$-sulfanylidene]amino}phenyl)-3-oxo-2-(prop-2-en-1-yl)-1H,2H,3H-pyrazolo[3,4-d]pyrimidin-6-yl]amino}phenoxy)ethyl]-N-methylcarbamate*

Intermediate C (30.0 mg) was reacted with tert-butyl (2-(4-aminophenoxy)ethyl)(methyl)carbamate (20.5 mg, 0.077 mmol) [commercially available] using General Procedure A to give the title compound (16.8 mg, 0.028 mmol, 36%) as a pale yellow solid.

LCMS (Method A): $R_T$=1.25 min, m/z=608 $[M+H]^+$.

Step 2: 1-(3-{[Dimethyl(oxo)-λ$^6$-sulfanylidene]amino}phenyl)-6-({4-[2-(methylamino)ethoxy]phenyl}amino)-2-(prop-2-en-1-yl)-1H,2H,3H-pyrazolo[3,4-d]pyrimidin-3-one* tert-Butyl N-[2-(4-{[1-(3-{[dimethyl(oxo)-λ$^6$-sulfanylidene]amino}phenyl)-3-oxo-2-(prop-2-en-1-yl)-1H,2H,3H-pyrazolo[3,4-d]pyrimidin-6-yl]amino}phenoxy)ethyl]-N-methylcarbamate* (16.8 mg, 0.028 mmol) was reacted with TFA (2.0 mL) using General Procedure B to give the title compound (11.0 mg, 76%) as a very pale yellow solid.

LCMS (Method A): $R_T$=0.67 min, m/z=508 $[M+H]^+$.

$^1$H NMR (400 MHz, $CDCl_3$): δ 8.80 (s, 1H), 7.46 (br d, 2H), 7.35 (t, 1H), 7.13-7.03 (m, 3H), 6.90-6.82 (m, 2H), 5.70 (ddt, 1H), 5.10 (dd, 1H), 5.00 (dd, 1H), 4.41 (d, 2H), 4.06 (t, 2H), 3.16 (s, 6H), 2.98 (t, 2H), 2.52 (s, 3H).

Example 28: 1-(6-{[Dimethyl(oxo)-λ$^6$-sulfanylidene]amino}pyridin-2-yl)-6-{[3-methyl-4-(4-methylpiperazin-1-yl)phenyl]amino}-2-(prop-2-en-1-yl)-1H,2H,3H-pyrazolo[3,4-d]pyrimidin-3-one*

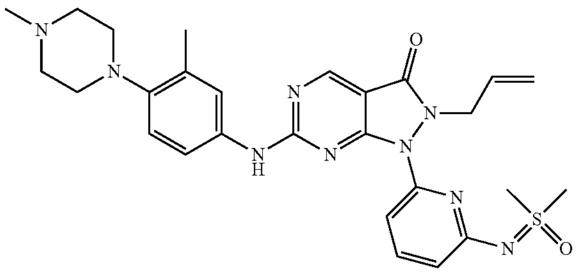 [SMILES: C=CCn1c(=O)c2cnc(Nc3ccc(N4CCN(C)CC4)c(C)c3)nc2n1-c1cccc(N=S(C)(C)=O)n1]

Sodium triacetoxyborohydride (43.5 mg, 0.205 mmol) was added to a stirred solution of 1-(6-{[dimethyl(oxo)-λ$^6$-sulfanylidene]amino}pyridin-2-yl)-6-{[3-methyl-4-(piperazin-1-yl)phenyl]amino}-2-(prop-2-en-1-yl)-1H,2H,3H-pyrazolo[3,4-d]pyrimidin-3-one* (21.9 mg, 0.041 mmol) and formaldehyde, 37% in water solution (6.11 μL, 0.082 mmol) in methanol (1.0 mL) at RT under nitrogen. After 1 h, the reaction mixture was loaded directly onto a pre-washed SCX-2 cartridge. After 15 min, the cartridge was washed using methanol, followed by elution of the compound using 2 M $NH_3$ in methanol solution. The solvents were removed in vacuo and the remaining residue was purified by flash chromatography using a KP-NH column (0-100%, EtOAc in cyclohexane; then 0-10% MeOH in EtOAc) to give the title compound (21.6 mg, 94%) as a very pale yellow solid.

LCMS (Method A): $R_T$=0.72 min, m/z=548 $[M+H]^+$.

$^1$H NMR (400 MHz, $CDCl_3$): δ 8.82 (s, 1H), 7.68 (t, 1H), 7.58 (br s, 1H), 7.38 (d, 1H), 7.32 (br s, 1H), 7.28 (apparent dd, 1H, overlapping solvent), 7.01 (d, 1H), 6.68 (dd, 1H), 5.65 (ddt, 1H), 5.03-4.95 (m, 2H), 4.92 (d, 2H), 3.33 (s, 6H), 2.93 (t, 4H), 2.59 (br s, 4H), 2.37 (s, 3H), 2.33 (s, 3H).

Example 29: 1-(3-{[Dimethyl(oxo)-λ$^6$-sulfanylidene]amino}phenyl)-6-{[3-(hydroxymethyl)-4-(piperazin-1-yl)phenyl]amino}-2-(prop-2-en-1-yl)-1H,2H,3H-pyrazolo[3,4-d]pyrimidin-3-one

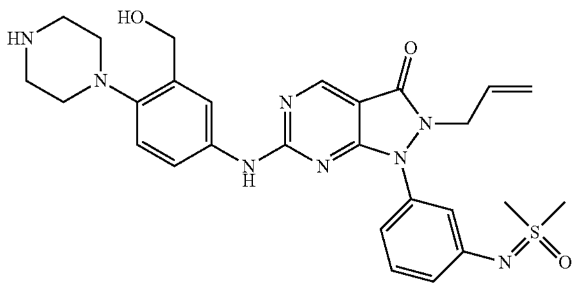 [SMILES: C=CCn1c(=O)c2cnc(Nc3ccc(N4CCNCC4)c(CO)c3)nc2n1-c1cccc(N=S(C)(C)=O)c1]

Step 1: tert-Butyl 4-(4-{[1-(3-{[dimethyl(oxo-λ$^6$-sulfanylidene]amino}phenyl)-3-oxo-2-(prop-2-en-1-yl)-1H,2H,3H-pyrazolo[3,4-d]pyrimidin-6-yl]amino}-2-(hydroxymethyl)phenyl)piperazine-1-carboxylate*

Intermediate C (50.0 mg, 0.128 mmol) was reacted with tert-butyl 4-(4-amino-2-(hydroxymethyl)phenyl)piperazine- 1-carboxylate (39.5 mg, 0.128 mmol) [prepared according to WO2014167347, Example 18, Step 1] using General Procedure A to give the title compound (54.6 mg, 66%) as a pale yellow solid.

LCMS (Method A): $R_T$=1.16 min, m/z=649 $[M+H]^+$.

Step 2: 1-(3-{[Dimethyl(oxo)-λ⁶-sulfanylidene]amino}phenyl)-6-{[1-(hydroxymethyl)-4-(piperazin-1-yl)phenyl]amino}-2-(prop-2-en-1-yl)-1H,2H,3H-pyrazolo[3,4-d]pyrimidin-3-one* tert-Butyl 4-(4-{[1-(3-{[dimethyl(oxo-λ⁶-sulfanylidene]amino}phenyl)-3-oxo-2-(prop-2-en-1-yl)-1H,2H,3H-pyrazolo[3,4-d]pyrimidin-6-yl]amino}-2-(hydroxymethyl)phenyl)piperazine-1-carboxylate* (54.6 mg, 0.084 mmol) was reacted with TFA (2.0 mL) using General Procedure B to give the title compound (38.4 mg, 81%) as a pale yellow solid.

LCMS (Method A): $R_T$=0.63 min, m/z=549 $[M+H]^+$.

$^1$H NMR (400 MHz, $CDCl_3$): δ 8.81 (s, 1H), 7.94 (br s, 1H), 7.41 (br s, 1H), 7.35 (t, 1H), 7.22-7.06 (m, 4H), 6.99 (ddd, 1H), 5.70 (ddt, 1H), 5.10 (dd, 1H), 4.99 (dd, 1H), 4.81 (s, 2H), 4.42 (d, 2H), 3.24 (s, 6H), 3.04 (t, 4H), 2.91 (t, 4H).

Example 30: 1-(3-{[Dimethyl(oxo)-λ⁶-sulfanylidene]amino}phenyl)-6-{[3-(hydroxymethyl)-4-(4-methylpiperazin-1-yl)phenyl]amino}-2-(prop-2-en-1-yl)-1H,2H,3H-pyrazolo[3,4-d]pyrimidin-3-one*

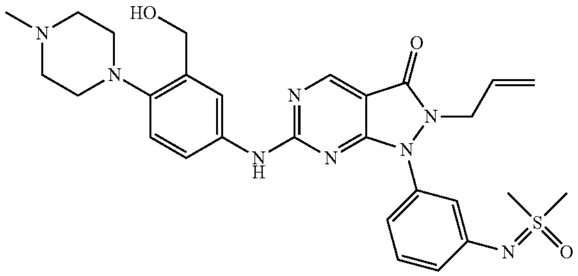 [SMILES: C=CCn1c(=O)c2cnc(Nc3ccc(N4CCN(C)CC4)c(CO)c3)nc2n1-c1cccc(N=S(C)(C)=O)c1]

Sodium triacetoxyborohyride (51.8 mg, 0.244 mmol) was added to a stirred solution of 1-(3-{[dimethyl(oxo)-λ⁶-sulfanylidene]amino}phenyl)-6-{[3-(hydroxymethyl)-4-(piperazin-1-yl)phenyl]amino}-2-(prop-2-en-1-yl)-1H,2H,3H-pyrazolo[3,4-d]pyrimidin-3-one (26.8 mg, 0.049 mmol) and formaldehyde, 37% in water (7.27 μL, 0.098 mmol) in methanol (1.0 mL) at RT under nitrogen. After 1 h, the reaction mixture was loaded directly onto a pre-washed SCX-2 cartridge. After 15 min, the cartridge was washed using methanol, followed by elution of the compound using 2M $NH_3$ in methanol. The solvents were removed in vacuo and the remaining residue was purified by flash chromatography using a KP-NH column (0-100%, EtOAc in cyclohexane; then 0-10% MeOH in EtOAc) to give the title compound (23.4 mg, 84%) as a pale yellow solid.

LCMS (Method A): $R_T$=0.63 min, m/z=563 $[M+H]^+$.

$^1$H NMR (400 MHz, $CDCl_3$): δ 8.81 (s, 1H), 7.93 (br s, 1H), 7.41 (br s, 1H), 7.35 (t, 1H), 7.22-7.05 (m, 4H), 6.99 (ddd, 1H), 5.69 (ddt, 1H), 5.10 (dd, 1H), 4.99 (dd, 1H), 4.80 (s, 2H), 4.42 (d, 2H), 3.24 (s, 6H), 2.97 (t, 4H), 2.60 (br s, 4H), 2.37 (s, 3H).

Example 31: 1-(3-{[Dimethyl(oxo)-λ⁶-sulfanylidene]amino}phenyl)-6-{[4-(morpholin-4-yl)phenyl]amino}-2-(prop-2-en-1-yl)-1H,2H,3H-pyrazolo[3,4-d]pyrimidin-3-one*

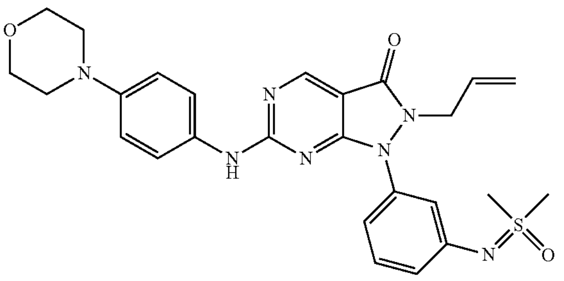 [SMILES: C=CCn1c(=O)c2cnc(Nc3ccc(N4CCOCC4)cc3)nc2n1-c1cccc(N=S(C)(C)=O)c1]

Intermediate C (30.0 mg, 0.077 mmol) was reacted with 4-morpholinoaniline (13.7 mg, 0.077 mmol) [commercially available] using General Procedure A to give the title compound (28.6 mg, 70%) as a pale yellow solid.

LCMS (Method A): $R_T$=0.91 min, m/z=520 $[M+H]^+$.

$^1$H NMR (400 MHz, $CDCl_3$): δ 8.80 (s, 1H), 7.46 (d, 2H), 7.36 (t, 1H), 7.10 (dd, 2H), 7.06 (t, 1H), 6.91-6.84 (m, 2H), 5.69 (ddt, 1H), 5.10 (dd, 1H), 5.00 (dd, 1H), 4.40 (d, 2H), 3.86 (t, 4H), 3.16 (s, 6H), 3.12 (t, 4H).

Example 32: 1-(6-{[Dimethyl(oxo)-λ⁶-sulfanylidene]amino}pyridin-2-yl)-6-{4-([(2S,6R)-2,6-dimethylmorpholin-4-yl]phenyl)amino}-2-(prop-2-en-1-yl)-1H,2H,3H-pyrazolo[3,4-d]pyrimidin-3-one*

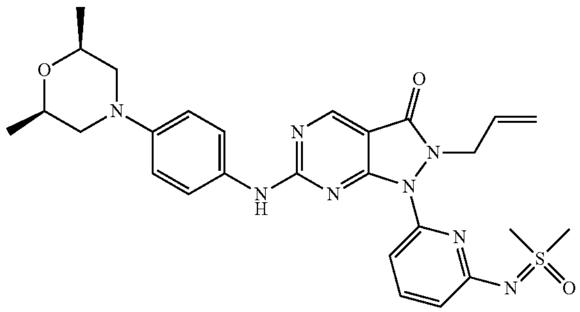 [SMILES: C=CCn1c(=O)c2cnc(Nc3ccc(N4C[C@@H](C)O[C@@H](C)C4)cc3)nc2n1-c1cccc(N=S(C)(C)=O)n1]

Intermediate B (60 mg, 0.15 mmol) was reacted with 4-((2S,6R)-2,6-dimethylmorpholino)aniline (36.5 mg, 0.177 mmol) [commercially available] using General Procedure E to give the title compound (18 mg, 21%) as a yellow solid.

LCMS (Method A): $R_T$=1.14 min, m/z=549 $[M+H]^+$.

$^1$H NMR (400 MHz, $CDCl_3$): δ 8.81 (s, 1H), 7.68 (t, 1H), 7.48-7.50 (m, 2H), 7.35 (d, 1H), 6.90 (m, 2H), 6.67 (d, 1H), 5.65 (m, 1H), 4.90-5.02 (m, 4H), 3.83 (m, 2H), 3.42 (d, 2H), 3.33 (s, 6H), 2.42 (t, 2H), 1.27 (d, 6H).

Example 33: 1-(6-{[Dimethyl(oxo)-$\lambda^6$-sulfanylidene]amino}pyridin-2-yl)-6-{[5-(morpholin-4-yl)pyridin-3-yl]amino}-2-(prop-2-en-1-yl)-1H,2H,3H-pyrazolo[3,4-d]pyrimidin-3-one*

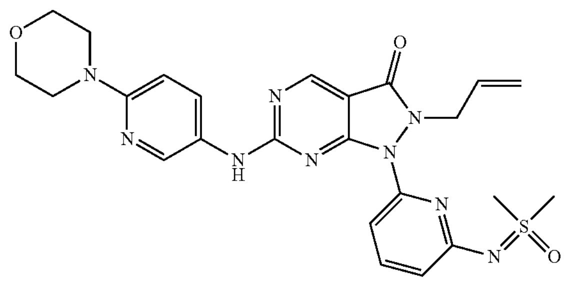 [SMILES: C=CCn1c(=O)c2cnc(Nc3ccc(N4CCOCC4)nc3)nc2n1-c1cccc(N=S(C)(C)=O)n1]

Intermediate B (60 mg, 0.15 mmol) was reacted with 6-morpholinopyridin-3-amine (31.7 mg, 0.177 mmol) [commercially available] using General Procedure E to give the title compound (5.2 mg, 6.5%) as a yellow solid.

LCMS (Method A): $R_T$=0.74 min, m/z=522 $[M+H]^+$.

$^1$H NMR (400 MHz, $CDCl_3$): δ 8.81 (s, 1H), 8.31 (br s, 1H), 7.87 (d, 1H), 7.66 (t, 1H), 7.29 (d, 1H), 6.65-6.68 (m, 2H), 5.64 (m, 1H), 4.89-5.02 (m, 4H), 3.84-3.86 (m, 4H), 3.48-3.50 (m, 4H), 3.33 (s, 6H).

Example 34: 1-(6-{[Dimethyl(oxo)-$\lambda^6$-sulfanylidene]amino}pyridin-2-yl)-6-{[4-(4,4-difluoropiperidin-1-yl)phenyl]amino}-2-(prop-2-en-1-yl)-1H,2H,3H-pyrazolo[3,4-d]pyrimidin-3-one*

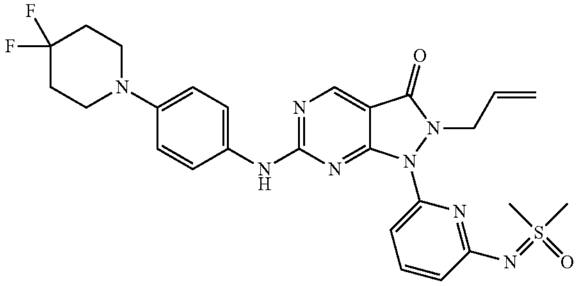 [SMILES: C=CCn1c(=O)c2cnc(Nc3ccc(N4CCC(F)(F)CC4)cc3)nc2n1-c1cccc(N=S(C)(C)=O)n1]

Intermediate B (60 mg, 0.15 mmol) was reacted with 4-(4,4-difluoropiperidin-1-yl)aniline (37.5 mg, 0.177 mmol) [commercially available] using General Procedure E to give the title compound (16.4 mg, 19%) as a yellow solid.

LCMS (Method A): $R_T$=1.2 min, m/z=555 $[M+H]^+$.

$^1$H NMR (400 MHz, $CDCl_3$): δ 8.82 (s, 1H), 7.67 (t, 1H), 7.50 (d, 2H), 7.34 (d, 1H), 6.93 (d, 2H), 6.67 (d, 1H), 5.64 (m, 1H), 4.90-5.02 (m, 4H), 3.31-3.34 (m, 10H), 2.08-2.28 (m, 4H).

Example 35: 1-(6-{[Dimethyl(oxo)-$\lambda^6$-sulfanylidene]amino}pyridin-2-yl)-6-{[3-(morpholin-4-yl)phenyl]amino}-2-(prop-2-en-1-yl)-1H,2H,3H-pyrazolo[3,4-d]pyrimidin-3-one*

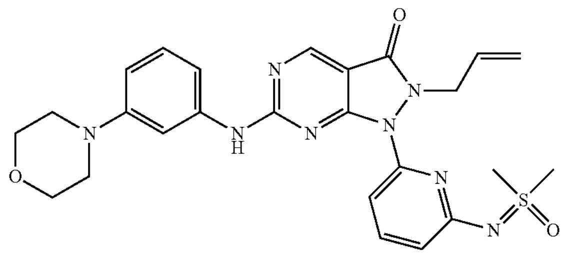 [SMILES: C=CCn1c(=O)c2cnc(Nc3cccc(N4CCOCC4)c3)nc2n1-c1cccc(N=S(C)(C)=O)n1]

Intermediate B (60 mg, 0.15 mmol) was reacted with 3-morpholinoaniline (31.5 mg, 0.177 mmol) [commercially available] using General Procedure E to give the title compound (12 mg, 15%) as a yellow solid.

LCMS (Method A): $R_T$=1.08 min, m/z=521 $[M+H]^+$.

$^1$H NMR (400 MHz, $CDCl_3$): δ 8.86 (s, 1H), 7.66 (t, 2H), 7.21-7.31 (m, 3H), 6.66-6.70 (m, 2H), 5.64 (m, 1H), 4.87-5.04 (m, 4H), 3.84 (m, 4H), 3.22 (s, 6H), 3.11 (m, 4H).

Example 36: 1-(6-{[Dimethyl(oxo)-$\lambda^6$-sulfanylidene]amino}pyridin-2-yl)-6-{[4-(8-oxa-3-azabicyclo[3.2.1]octan-3-yl)phenyl]amino}-2-(prop-2-en-1-yl)-1H,2H,3H-pyrazolo[3,4-d]pyrimidin-3-one*

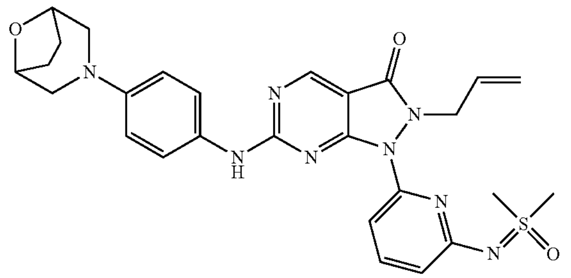 [SMILES: C=CCn1c(=O)c2cnc(Nc3ccc(N4CC5CCC(C4)O5)cc3)nc2n1-c1cccc(N=S(C)(C)=O)n1]

Intermediate B (60 mg, 0.15 mmol) was reacted with 4-(8-oxa-3-azabicyclo[3.2.1]octan-3-yl)aniline (36.1 mg, 0.177 mmol) [commercially available] using General Procedure E to give the title compound (14 mg, 16.7%) as a yellow solid.

LCMS (Method A): $R_T$=1.21 min, m/z=547 $[M+H]^+$.

$^1$H NMR (400 MHz, $CDCl_3$): δ 8.80 (s, 1H), 7.66 (t, 1H), 7.45-7.47 (m, 2H), 7.35 (d, 1H), 6.79 (d, 2H), 6.67 (d, 1H), 5.65 (m, 1H), 4.90-5.02 (m, 4H), 4.50 (br s, 2H), 3.30-3.33 (m, 8H), 3.00-3.03 (m, 2H), 3.32 (s, 6H), 1.97 (br s, 4H).

Example 37: 1-(6-{[Dimethyl(oxo)-$\lambda^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one*

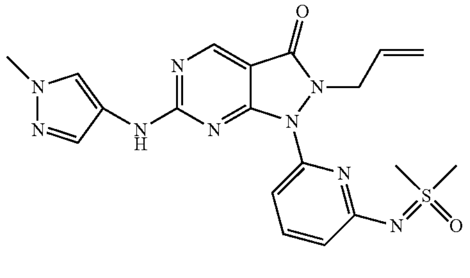 [SMILES: C=CCn1c(=O)c2cnc(Nc3cnn(C)c3)nc2n1-c1cccc(N=S(C)(C)=O)n1]

Intermediate B (100 mg, 0.256 mmol) was reacted with 1-methyl-1H-pyrazol-4-amine (24.9 mg, 0.256 mmol) [commercially available] using General Procedure C to give the title compound (95 mg, 84%) as a white solid.

LCMS (Method C): $R_T$=0.93 min, m/z=440 [M+H]$^+$.

$^1$H NMR (300 MHz, DMSO) δ 10.31 (s, 1H), 8.78 (s, 1H), 7.96-7.64 (m, 2H), 7.64-7.45 (m, 1H), 7.28 (d, J=7.8 Hz, 1H), 6.63 (d, J=7.5 Hz, 1H), 5.79-5.49 (m, 1H), 5.00 (d, J=10.1 Hz, 1H), 4.87 (d, J=17.1 Hz, 1H), 4.81-4.58 (m, 2H), 3.81 (s, 3H), 3.37 (s, 6H).

Example 38: 1-(6-{[Dimethyl(oxo)-$\lambda^6$-sulfanylidene]amino}pyridin-2-yl)-6-{[4-(morpholin-4-yl)phenyl]amino}-2-propyl-1H,2H,3H-pyrazolo[3,4-d]pyrimidin-3-one*

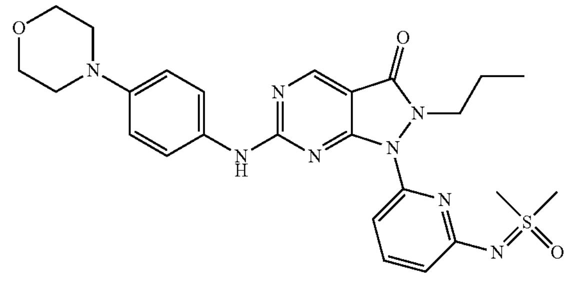 [SMILES: CCCn1c(=O)c2cnc(Nc3ccc(N4CCOCC4)cc3)nc2n1-c1cccc(N=S(C)(C)=O)n1]

Step 1: 1-(6-{[Dimethyl(oxo)-$\lambda^6$-sulfanylidene]amino}pyridin-2-yl)-6-{[4-(morpholin-4-yl)phenyl]amino}-2-(prop-2-en-1-yl)-1H,2H,3H-pyrazolo[3,4-d]pyrimidin-3-one*

Intermediate B (100 mg, 0.256 mmol) was reacted with 4-morpholinoaniline (45.6 mg, 0.256 mmol) using General Procedure C to give the title compound (43 mg, 32%) as yellowish solid.

LCMS (Method C): $R_T$=1.15 min, m/z=521 [M+H]$^+$.

$^1$H NMR (300 MHz, DMSO) δ 10.16 (s, 1H), 8.81 (s, 1H), 7.80 (s, 1H), 7.60 (bs, 2H), 7.30 (d, J=7.8 Hz, 1H), 6.93 (d, J=9.1 Hz, 2H), 6.59 (d, J=8.0 Hz, 1H), 5.79-5.51 (m, 1H), 5.00 (d, J=10.4 Hz, 1H), 4.89 (d, J=17.7 Hz, 1H), 4.75 (s, 2H), 3.84-3.65 (m, 4H), 3.38 (s, 6H), 3.13-3.02 (m, 4H).

Step 2: 1-(6-{[Dimethyl(oxo)-$\lambda^6$-sulfanylidene]amino}pyridin-2-yl)-6-{[4-(morpholin-4-yl)phenyl]amino}-2-propyl-1H,2H,3H-pyrazolo[3,4-d]pyrimidin-3-one*

Hydroxylamine (50% in water) (0.025 mL, 0.413 mmol) was added to a solution of 2,2,2-trifluoro-N-(2,2,2-trifluoroacetoxy)acetamide (37.2 mg, 0.165 mmol) and 1-(6-{[dimethyl(oxo)-$\lambda^6$-sulfanylidene]amino}pyridin-2-yl)-6-{[4-(morpholin-4-yl)phenyl]amino}-2-(prop-2-en-1-yl)-1H,2H,3H-pyrazolo[3,4-d]pyrimidin-3-one (43 mg, 0.083 mmol) in dioxane (1.5 mL) at RT in a 10 mL vial and the vial was sealed immediately and heated at 100° C. for 40 min. LCMS showed that the conversion was not accomplished. An additional batch of 2,2,2-trifluoro-N-(2,2,2-trifluoroacetoxy)acetamide (37.2 mg, 0.165 mmol) and hydroxylamine (50% in water) (0.025 mL, 0.413 mmol) were added, the reaction mixture was heated again for 40 min at 100° C. and subsequently cooled to RT. The volatiles were removed under reduced pressure and the product was purified by flash chromatography (0-20% MeOH in EtOAc) to give the title compound (38 mg, 88%) as a yellow-brown solid.

LCMS (Method C): $R_T$=1.18 min, m/z=523 [M+H]$^+$.

$^1$H NMR (300 MHz, DMSO) δ 10.10 (s, 1H), 8.80 (s, 1H), 7.97-7.76 (m, 1H), 7.60 (bs, 2H), 7.31 (d, J=7.8 Hz, 1H), 6.93 (d, J=8.9 Hz, 2H), 6.62 (d, J=8.0 Hz, 1H), 4.07 (bs, 2H), 3.85-3.66 (m, 4H), 3.38 (s, 6H), 3.07 (s, 4H), 1.44-1.30 (m, 2H), 0.67 (t, J=7.3 Hz, 3H).

Example 39: 1-(6-{[Dimethyl(oxo)-$\lambda^6$-sulfanylidene]amino}pyridin-2-yl)-6-{[6-(morpholin-4-yl)pyridin-3-yl]amino}-2-propyl-1H,2H,3H-pyrazolo[3,4-d]pyrimidin-3-one*

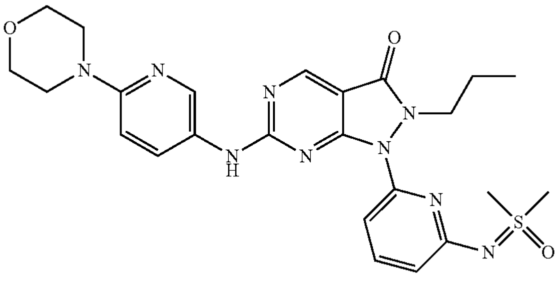 [SMILES: CCCn1c(=O)c2cnc(Nc3ccc(N4CCOCC4)nc3)nc2n1-c1cccc(N=S(C)(C)=O)n1]

Step 1: 1-(6-{[Dimethyl(oxo)-$\lambda^6$-sulfanylidene]amino}pyridin-2-yl)-6-{[6-(morpholin-4-yl)pyridin-3-yl]amino}-2-(prop-2-en-1-yl)-1H,2H,3H-pyrazolo[3,4-d]pyrimidin-3-one*

Intermediate B (100 mg, 0.256 mmol) was reacted with 6-morpholinopyridin-3-amine (46 mg, 0.256 mmol) using General Procedure C to give the title compound (55 mg, 41%) as yellowish solid.

LCMS (Method C): $R_T$=0.83 min, m/z=522 [M+H]$^+$.

$^1$H NMR (300 MHz, DMSO) δ 10.19 (bs, 1H), 8.82 (s, 1H), 8.38 (s, 1H), 8.16-7.84 (m, 1H), 7.75 (t, J=7.9 Hz, 1H), 7.36-7.15 (m, 1H), 6.87 (d, J=9.1 Hz, 1H), 6.60 (d, J=7.9 Hz, 1H), 5.78-5.46 (m, 1H), 5.10-4.78 (m, 2H), 4.84-4.46 (m, 2H), 3.86-3.57 (m, 4H), 3.40 (s, 10H).

Step 2: 1-(6-{[Dimethyl(oxo)-λ$^6$-sulfanylidene]amino}pyridin-2-yl)-6-{[6-(morpholin-4-yl)pyridin-3-yl]amino}-2-propyl-1H,2H,3H-pyrazolo[3,4-d]pyrimidin-3-one*

Hydroxylamine (50% in water) (0.029 mL, 0.479 mmol) was added to a solution of 2,2,2-trifluoro-N-(2,2,2-trifluoroacetoxy)acetamide (43.1 mg, 0.192 mmol) and 1-(6-{[dimethyl(oxo)-λ$^6$-sulfanylidene]amino}pyridin-2-yl)-6-{[6-(morpholin-4-yl)pyridin-3-yl]amino}-2-(prop-2-en-1-yl)-1H,2H,3H-pyrazolo[3,4-d]pyrimidin-3-one (50 mg, 0.096 mmol) in dioxane (1.5 mL) at RT in a 10 mL microwave vial and the vessel was sealed immediately. The vessel was heated for 40 minutes at 100° C. and an additional batch of 2,2,2-trifluoro-N-(2,2,2-trifluoroacetoxy)acetamide (43.1 mg, 0.192 mmol) and hydroxylamine (50% in water) (0.029 mL, 0.479 mmol) was added. The reaction mixture was heated again for 40 min at 100° C. LC-MS confirmed that the reduction was accomplished. The reaction mixture was cooled to RT and the volatiles were removed under reduced pressure. The product was purified by flash chromatography (0-20% MeOH in EtOAc). The product containing fractions were evaporated under reduced pressure and freeze dried (ACN/$H_2O$), yielding the title product (40.1 mg, 80%) as a yellow-brown sticky solid.

LCMS (Method C): $R_T$=0.86 min, m/z=524 $[M+H]^+$.

$^1$H NMR (300 MHz, DMSO) δ 8.88 (s, 1H), 8.50 (s, 1H), 8.29 (s, 1H), 7.81 (s, 1H), 7.44 (d, J=10.1 Hz, 1H), 7.22 (d, J=6.8 Hz, 1H), 6.65 (d, J=8.5 Hz, 1H), 4.18-3.91 (m, 2H), 3.75 (bs, 4H), 3.58 (bs, 4H), 3.32 (s, 6H), 1.50-1.27 (m, 2H), 0.72-0.59 (m, J=6.8 Hz, 3H).

Example 40: 1-(6-{[Dimethyl(oxo)-λ$^6$-sulfanylidene]amino}pyridin-2-yl)-6-[(4-fluorophenyl)amino]-2-(prop-2-en-1-yl)-1H,2H,3H-pyrazolo[3,4-d]pyrimidin-3-one*

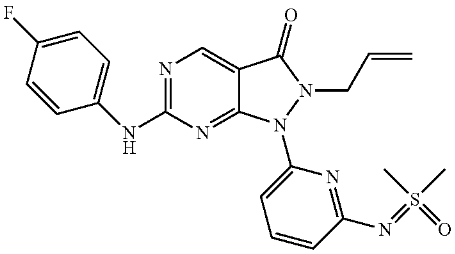 [SMILES: C=CCn1c(=O)c2cnc(Nc3ccc(F)cc3)nc2n1-c1cccc(N=S(C)(C)=O)n1]

Intermediate B (100 mg, 0.256 mmol) was reacted with 4-fluoroaniline (28.5 mg, 0.256 mmol) using General Procedure C, yielding the title compound as a white solid (6 mg, 5%).

LCMS (Method C): $R_T$=1.35 min, m/z=454 $[M+H]^+$.

$^1$H NMR (300 MHz, DMSO) δ 10.31 (s, 1H), 8.88 (s, 1H), 7.90-7.66 (m, 3H), 7.34-7.13 (m, 3H), 6.60 (d, J=8.1 Hz, 1H), 5.74-5.55 (m, 1H), 5.00 (d, J=10.0 Hz, 1H), 4.89 (d, J=16.6 Hz, 1H), 4.75 (s, 2H), 3.37 (s, 6H).

Example 41: 1-(6-{[Dimethyl(oxo)-λ$^6$-sulfanylidene]amino}pyridin-2-yl)-6-[(4-fluorophenyl)amino]-2-(propan-2-yl)-1H,2H,3H-pyrazolo[3,4-d]pyrimidin-3-one

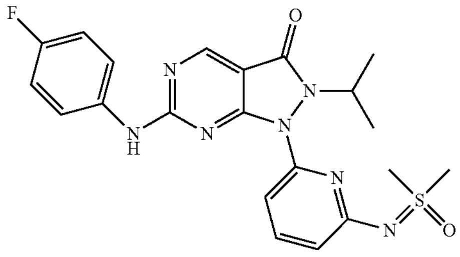 [SMILES: CC(C)n1c(=O)c2cnc(Nc3ccc(F)cc3)nc2n1-c1cccc(N=S(C)(C)=O)n1]

Intermediate D (75 mg, 0.191 mmol) was reacted with 4-fluoroaniline (21.2 mg, 0.191 mmol) using General Procedure C, yielding the title compound as a white solid (25 mg, 29%).

LCMS (Method C): $R_T$=1.47 min, m/z=456 $[M+H]^+$.

$^1$H NMR (300 MHz, DMSO) δ 10.24 (s, 1H), 8.81 (s, 1H), 7.93-7.64 (m, 3H), 7.16 (dd, J=16.6, 7.9 Hz, 3H), 6.67 (d, J=8.0 Hz, 1H), 4.34-4.11 (m, 1H), 3.36 (s, 6H), 1.31 (d, J=6.7 Hz, 6H).

Example 42: 1-(6-{[Dimethyl(oxo)-λ$^6$-sulfanylidene]amino}pyridin-2-yl)-6-[(4-methoxyphenyl)amino]-2-(propan-2-yl)-1H,2H,3H-pyrazolo[3,4-d]pyrimidin-3-one*

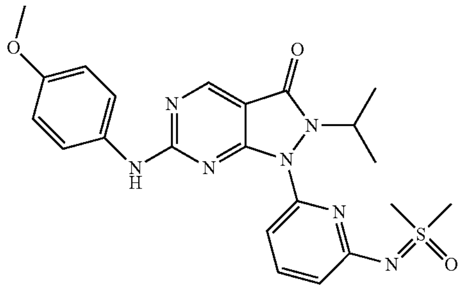 [SMILES: COc1ccc(Nc2ncc3c(=O)n(C(C)C)n(-c4cccc(N=S(C)(C)=O)n4)c3n2)cc1]

Intermediate D (70 mg, 0.178 mmol) was reacted with 4-methoxyaniline (22 mg, 0.178 mmol) using General Procedure C, yielding the title compound as a white solid (54 mg, 65%).

LCMS (Method C): $R_T$=1.32 min, m/z=468 $[M+H]^+$.

$^1$H NMR (300 MHz, $CDCl_3$) δ 8.73 (s, 1H), 7.68 (t, J=7.7 Hz, 1H), 7.45 (d, J=7.9 Hz, 2H), 7.17 (d, J=7.1 Hz, 1H), 6.86 (d, J=8.1 Hz, 2H), 6.74 (d, J=7.7 Hz, 1H), 4.49-4.29 (m, 1H), 3.81 (s, 3H), 3.32 (s, 6H), 1.46 (d, J=6.6 Hz, 6H).

Example 43: 1-(6-{[Dimethyl(oxo)-$\lambda^6$-sulfanylidene]amino}pyridin-2-yl)-6-{[4-(morpholin-4-yl)phenyl]amino}-2-(propan-2-yl)-1H,2H,3H-pyrazolo[3,4-d]pyrimidin-3-one*

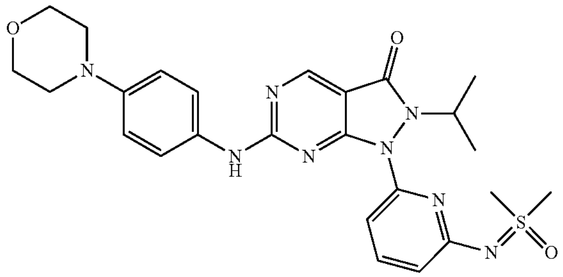 [SMILES: CC(C)n1c(=O)c2cnc(Nc3ccc(N4CCOCC4)cc3)nc2n1-c1cccc(N=S(C)(C)=O)n1]

Intermediate D (70 mg, 0.178 mmol) was reacted with 4-morpholinoaniline (31.8 mg, 0.178 mmol) using General Procedure C, yielding the title compound as a white solid (77 mg, 83%).

LCMS (Method C): $R_T$=1.27 min, m/z=523 $[M+H]^+$.

$^1$H NMR (300 MHz, DMSO) δ 10.11 (bs, 1H), 8.74 (s, 1H), 7.93-7.74 (m, 1H), 7.69-7.42 (m, 2H), 7.19 (d, J=7.5 Hz, 1H), 6.89 (d, J=9.1 Hz, 2H), 6.66 (d, J=8.1 Hz, 1H), 4.33-4.12 (m, 1H), 3.84-3.67 (m, 4H), 3.35 (s, J=5.2 Hz, 6H), 3.13-2.95 (m, 4H), 1.31 (d, J=6.4 Hz, 6H).

Example 44: 1-(5-{[Dimethyl(oxo)-$\lambda^6$-sulfanylidene]amino}pyridin-3-yl)-6-{[4-(morpholin-4-yl)phenyl]amino}-2-(prop-2-en-1-yl)-1H,2H,3H-pyrazolo[3,4-d]pyrimidin-3-one*

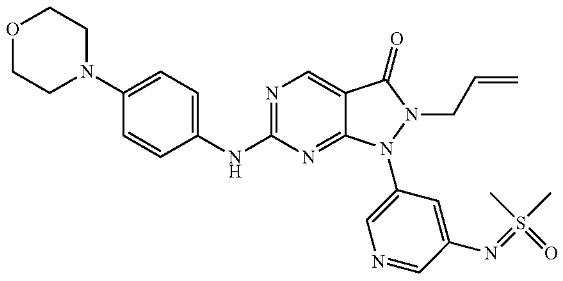 [SMILES: C=CCn1c(=O)c2cnc(Nc3ccc(N4CCOCC4)cc3)nc2n1-c1cncc(N=S(C)(C)=O)c1]

Step 1: [(5-Bromopyridin-3-yl)imino]dimethyl-$\lambda^6$-sulfanon*

A suspension of $Pd_2(dba)_3$ (193 mg, 0.211 mmol) and xantphos (269 mg, 0.464 mmol) in 1,4-dioxane (10 mL) was added to a solution of 3,5-dibromopyridine (1000 mg, 4.22 mmol), (S-methylsulfonimidoyl)methane (393 mg, 4.22 mmol) and cesium carbonate (4126 mg, 12.66 mmol) in 1,4-dioxane (7 mL) under nitrogen. The temperature was increased to 100° C. and the reaction was stirred overnight. After cooling to RT the reaction mixture was filtered through Celite and the filtrate was evaporated under reduced pressure. The residue was purified by flash chromatography (15-100% EtOAc in cyclohexane), yielding the title compound (806 mg, 77% yield) as a brownish oil that crystallized upon storage.

LCMS (Method C): $R_T$=0.70 min, m/z=249 $[M+H]^+$.

$^1$H NMR (300 MHz, DMSO) δ 8.27-8.02 (m, 2H), 7.49 (t, J=2.2 Hz, 1H), 3.39-3.30 (m, 6H).

Step 2: 1-(5-{[Dimethyl(oxo)-$\lambda^6$-sulfanylidene]amino}pyridin-3-yl)-6-(methylsulfanyl)-2-(prop-2-en-1-yl)-1H,2H,3H-pyrazolo[3,4-d]pyrimidin-3-one Into a 25 mL microwave vial was added 2-allyl-6-(methylthio)-1H-pyrazolo[3,4-d]pyrimidin-3(2H)-one (275 mg, 1.235 mmol) (obtained according to EP2213673B1, Production Example 1, p 37), [(5-bromopyridin-3-yl)imino]dimethyl-$\lambda^6$-sulfanon (400 mg, 1.61 mmol), potassium carbonate (239 mg, 1.73 mmol) and dioxane (5 mL). The resultant suspension was degassed (bubbling of $N_2$) and copper (I) iodide (235 mg, 1.235 mmol) was added followed by $N^1$,$N^2$-dimethylethane-1,2-diamine (0.133 mL, 1.24 mmol). The vial was capped and the reaction mixture was stirred at 95° C. overnight. After cooling to RT the reaction mixture was transferred to a separation funnel, $NH_4OH$ (aq, 20 mL) was added and the resulting mixture was extracted with EtOAc (3×30 mL). The organic phases were combined, dried and evaporated under vacuum. The residue was purified using flash chromatography (0-15% MeOH in EtOAc). The product containing fractions were concentrated to give the title compound (60 mg, 12.44% yield) as an yellowish oil that solidified upon storage.

LCMS (Method C): $R_T$=0.99 min, m/z=391 $[M+H]^+$.

$^1$H NMR (300 MHz, $CDCl_3$) δ 9.21 (s, 1H), 8.64 (s, 1H), 8.57 (s, 1H), 8.12 (s, 1H), 5.70-5.41 (m, 1H), 5.17 (t, J=5.1 Hz, 1H), 4.96 (d, J=17.0 Hz, 2H), 4.53 (d, J=6.0 Hz, 2H), 3.31 (s, 6H), 2.53 (s, 3H).

Step 3: 1-(5-{[Dimethyl(oxo)-$\lambda^6$-sulfanylidene]amino}pyridin-3-yl)-6-{[4-(morpholin-4-yl)phenyl]amino}-2-(prop-2-en-1-yl)-1H,2H,3H-pyrazolo[3,4-d]pyrimidin-3-one*

Into a 5 mL microwave vial were added 1-(5-{[dimethyl(oxo)-$\lambda^6$-sulfanylidene]amino}pyridin-3-yl)-6-(methylsulfanyl)-2-(prop-2-en-1-yl)-1H,2H,3H-pyrazolo[3,4-d]pyrimidin-3-one (52 mg, 0.133 mmol) followed by toluene (1 mL) and dichloromethane (1 mL) to give a white suspension. m-CPBA, 70% purity (36 mg, 0.146 mmol) was added to the reaction mixture. After stirring at room temperature for 30 minutes LC-MS analysis showed complete consumption of starting material. 4-Morpholinoaniline (24 mg, 0.133 mmol) and DIPEA (0.070 mL, 0.400 mmol) were added and the reaction mixture was heated at 65° C. overnight. The reaction mixture was loaded directly onto a silica gel column and purified by flash chromatography (0-15% MeOH in EtOAc). The product containing fractions were evaporated under vacuum, yielding the title compound (26 mg, 38%) as a yellowish solid.

LCMS (Method C): $R_T$=1.02 min, m/z=521 $[M+H]^+$.

$^1$H NMR (300 MHz, DMSO) δ 10.14 (bs, 1H), 8.82 (s, 1H), 8.25 (d, J=2.1 Hz, 1H), 8.19 (s, 1H), 7.53 (s, 2H), 7.32 (s, 1H), 6.87 (d, J=9.0 Hz, 2H), 5.93-5.47 (m, 1H), 5.10 (d, J=10.2 Hz, 1H), 4.97 (d, J=18.1 Hz, 1H), 4.27 (s, 2H), 3.88-3.59 (m, 4H), 3.32 (s, 6H), 3.14-2.92 (m, 4H).

Example 45: rac-1-(6-{[Dimethyl(oxo)-$\lambda^6$-sulfanylidene]amino}pyridin-2-yl)-2-(propan-2-yl)-6-({4-[3-(trifluoromethyl)piperazin-1-yl]phenyl}amino)-1H,2H,3H-pyrazolo[3,4-d]pyrimidin-3-one*

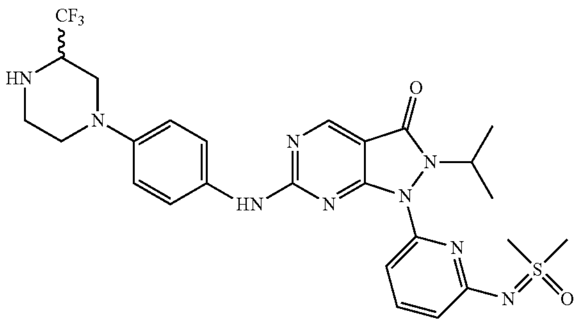 [SMILES: CC(C)n1c(=O)c2cnc(Nc3ccc(N4CCNC(C(F)(F)F)C4)cc3)nc2n1-c1cccc(N=S(C)(C)=O)n1]

Step 1: rac-tert-Butyl 4-(4-{[1-(6-{[dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)-2-(trifluoromethyl)piperazine-1-carboxylate*

Intermediate D (70 mg, 0.178 mmol) was reacted with rac-tert-butyl 4-(4-aminophenyl)-2-(trifluoromethyl)piperazine-1-carboxylate (61.6 mg, 0.178 mmol; prepared as described in WO2015092431A1) using General Procedure C, yielding the title compound as a yellowish oil (77 mg, 63%).

LCMS (Method C): $R_T$=1.90 min, m/z=690 $[M+H]^+$.

$^1$H NMR (300 MHz, $CDCl_3$) δ 8.72 (s, 1H), 7.69 (t, J=7.9 Hz, 1H), 7.46 (d, J=8.9 Hz, 2H), 7.17 (d, J=7.7 Hz, 1H), 6.87 (d, J=9.0 Hz, 2H), 6.75 (d, J=8.0 Hz, 1H), 4.96-4.47 (m, 1H), 4.45-4.27 (m, 1H), 4.22-4.01 (m, 2H), 3.90-3.74 (m, 1H), 3.56-3.43 (m, 1H), 3.32 (s, 6H), 3.05-2.92 (m, 1H), 2.86-2.68 (m, 1H), 1.58-1.37 (m, 15H).

Step 2: rac-1-(6-{[Dimethyl(oxo)-$\lambda^6$-sulfanylidene]amino}pyridin-2-yl)-2-(propan-2-yl)-6-({4-[3-(trifluoromethyl)piperazin-1-yl]phenyl}amino)-1H,2H,3H-pyrazolo[3,4-d]pyrimidin-3-one* rac-tert-Butyl 4-(4-{[1-(6-{[dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)-2-(trifluoromethyl)piperazine-1-carboxylate (77 mg, 0.112 mmol) was reacted according to General Procedure D, yielding the title compound as a yellowish solid (60 mg, 91%).

LCMS (Method C): $R_T$=1.14 min, m/z=590 $[M+H]^+$.

$^1$H NMR (300 MHz, DMSO) δ 10.10 (bs, 1H), 8.75 (s, 1H), 7.83 (s, 1H), 7.57 (s, 2H), 7.20 (d, J=7.1 Hz, 1H), 6.93 (d, J=9.1 Hz, 2H), 6.66 (d, J=8.0 Hz, 1H), 4.33-4.06 (m, 1H), 3.64-3.38 (m, 3H), 3.35 (s, 6H), 3.07-2.77 (m, 3H), 2.71-2.56 (m, 2H), 1.31 (d, J=6.4 Hz, 6H).

Example 46: 6-{[4-(1,4-Diazepan-1-yl)phenyl]amino}-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one*

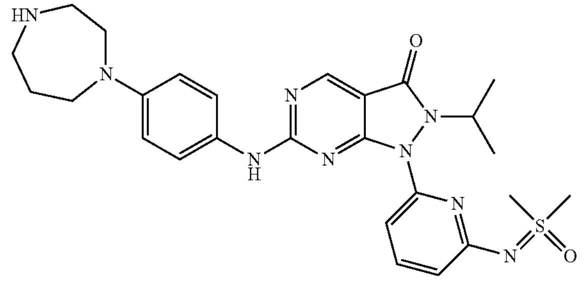 [SMILES: CC(C)n1c(=O)c2cnc(Nc3ccc(N4CCCNCC4)cc3)nc2n1-c1cccc(N=S(C)(C)=O)n1]

Step 1: tert-Butyl 4-(4-{[1-(6-{[dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)-1,4-diazepane-1-carboxylate*

Intermediate D (70 mg, 0.178 mmol) was reacted with tert-butyl 4-(4-aminophenyl)-1,4-diazepane-1-carboxylate (commercially available; 52 mg, 0.178 mmol) using General Procedure C, yielding the title compound as a yellowish oil (55 mg, 48%).

LCMS (Method C): $R_T$=1.72 min, m/z=636 $[M+H]^+$.

$^1$H NMR (300 MHz, $CDCl_3$) δ 8.66 (s, 1H), 7.59 (q, J=7.7 Hz, 1H), 7.30 (d, J=8.0 Hz, 2H), 7.11 (d, J=7.6 Hz, 1H), 6.73-6.44 (m, 3H), 4.43-4.19 (m, 1H), 3.64-3.38 (m, 6H), 3.39-3.02 (m, 8H), 1.93 (bs, 2H), 1.50-1.24 (m, 15H).

Step 2: 6-{[4-(1,4-Diazepan-1-yl)phenyl]amino}-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one tert-Butyl 4-(4-{[1-(6-{[dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)-1,4-diazepane-1-carboxylate (47 mg, 0.074 mmol) was reacted according to General Procedure D, yielding the title compound as a yellow solid (36 mg, 91%).

LCMS (Method C): $R_T$=0.92 min, m/z=536 $[M+H]^+$.

$^1$H NMR (300 MHz, DMSO) δ 9.97 (bs, 1H), 8.70 (s, 1H), 7.78 (t, J=7.9 Hz, 1H), 7.63-7.29 (m, 2H), 7.19 (s, 1H), 6.62 (d, J=9.1 Hz, 3H), 4.31-4.04 (m, 1H), 3.56-3.39 (m, 4H), 3.35 (d, J=2.7 Hz, 6H), 2.91-2.77 (m, 2H), 2.68-2.55 (m, 2H), 1.87-1.67 (m, 2H), 1.30 (bs, 6H).

Example 47: 6-(Cyclobutylamino)-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one*

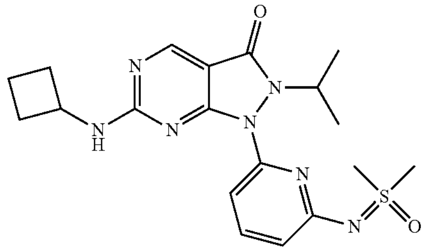 [SMILES: CC(C)n1c(=O)c2cnc(NC3CCC3)nc2n1-c1cccc(N=S(C)(C)=O)n1]

Intermediate D (70 mg, 0.178 mmol) was reacted with cyclobutanamine (12.7 mg, 0.178 mmol) using General Procedure C, yielding the title compound as an off-white solid (41 mg, 55%).

LCMS (Method C): $R_T$=1.37 min, m/z=416 $[M+H]^+$.

$^1$H NMR (300 MHz, DMSO) δ 8.76-8.53 (m, 1H), 8.47-8.05 (m, 1H), 7.85-7.61 (m, 1H), 7.19-7.00 (m, 1H), 6.73-6.51 (m, 1H), 4.53-4.08 (m, 2H), 3.46-3.34 (m, 6H), 2.24-2.07 (m, 2H), 2.06-1.83 (m, J=8.2 Hz, 2H), 1.72-1.50 (m, 2H), 1.36-1.14 (m, 6H).

Example 48: 4-(4-{[1-(6-{[Dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)piperazin-2-one*

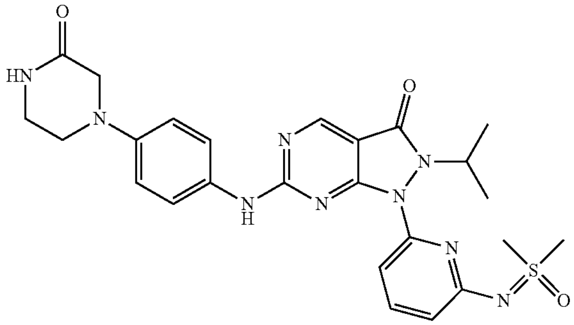 [SMILES: CC(C)n1c(=O)c2cnc(Nc3ccc(N4CCNC(=O)C4)cc3)nc2n1-c1cccc(N=S(C)(C)=O)n1]

Intermediate D (70 mg, 0.178 mmol) was reacted with 4-(4-aminophenyl)piperazin-2-one (34.1 mg, 0.178 mmol) using General Procedure C, yielding the title compound as a yellow solid (60 mg, 63%).

LCMS (Method C): $R_T$=0.90 min, m/z=536 $[M+H]^+$.

$^1$H NMR (300 MHz, $CDCl_3$) δ 8.75 (s, 1H), 7.69 (t, J=7.9 Hz, 1H), 7.49 (d, J=8.9 Hz, 2H), 7.19 (d, J=7.7 Hz, 1H), 6.86 (d, J=9.0 Hz, 2H), 6.74 (d, J=8.0 Hz, 1H), 6.30 (bs, 1H), 4.46-4.28 (m, 1H), 3.87 (s, 2H), 3.61-3.48 (m, 2H), 3.48-3.40 (m, 2H), 1.45 (d, J=6.8 Hz, 6H).

Example 49: 4-(4-{[1-(6-{[Dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)morpholin-3-one*

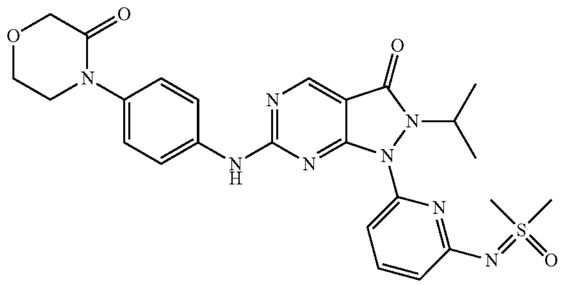 [SMILES: CC(C)n1c(=O)c2cnc(Nc3ccc(N4CCOCC4=O)cc3)nc2n1-c1cccc(N=S(C)(C)=O)n1]

Intermediate D (70 mg, 0.178 mmol) was reacted with 4-(4-aminophenyl)morpholin-3-one (34.3 mg, 0.178 mmol) using General Procedure C, yielding the title compound as a yellow solid (16 mg, 17%).

LCMS (Method C): $R_T$=0.98 min, m/z=537 $[M+H]^+$.

$^1$H NMR (300 MHz, DMSO) δ 10.29 (s, 1H), 8.82 (s, 1H), 7.82 (t, J=7.8 Hz, 1H), 7.74 (d, J=8.9 Hz, 2H), 7.29 (d, J=8.9 Hz, 2H), 7.20 (d, J=7.6 Hz, 1H), 6.68 (d, J=8.1 Hz, 1H), 4.32-4.20 (m, 1H), 4.20 (s, 2H), 4.04-3.89 (m, 2H), 3.76-3.62 (m, 2H), 3.35 (s, 6H), 1.32 (d, J=6.8 Hz, 6H).

Example 50: 1-(6-{[Dimethyl(oxo)-$\lambda^6$-sulfanylidene]amino}pyridin-2-yl)-2-(propan-2-yl)-6-({4-[4-(2,2,2-trifluoroethyl)piperazin-1-yl]phenyl}amino)-1H,2H,3H-pyrazolo[3,4-d]pyrimidin-3-one*

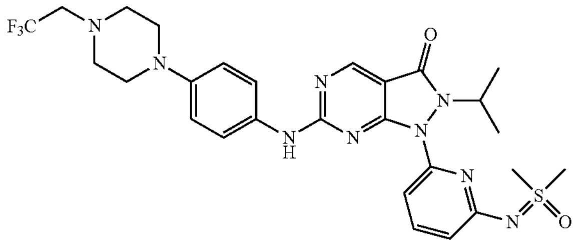 [SMILES: CC(C)n1c(=O)c2cnc(Nc3ccc(N4CCN(CC(F)(F)F)CC4)cc3)nc2n1-c1cccc(N=S(C)(C)=O)n1]

Step 1: 1-(4-Nitrophenyl)-4-(2,2,2-trifluoroethyl)piperazine)

To a stirring suspension of 1-fluoro-4-nitrobenzene (293 mg, 2.074 mmol) and $K_2CO_3$ (1577 mg, 11.41 mmol) in anhydrous DMF (3 mL) was added 1-(2,2,2-trifluoroethyl)piperazine dihydrochloride (500 mg, 2.074 mmol) and the mixture was heated at 50° C. overnight. The reaction mixture was transferred to a separation funnel and 50 mL EtOAc was added. The mixture was washed with 2M $K_2CO_3$ (2×30 mL). The organic layer was dried ($MgSO_4$) and evaporated under reduced pressure. The residue was purified by flash chromatography (15-80% EtOAc in cyclohexane). The product containing fractions were evaporated under vacuum, yielding the title compound as a yellow solid (555 mg, 76% yield).

LCMS (Method C): $R_T$=1.90 min, m/z=290 $[M+H]^+$.

$^1$H NMR (300 MHz, $CDCl_3$) δ 8.20-7.93 (m, 2H), 6.86-6.61 (m, 2H), 3.52-3.24 (m, 4H), 3.13-2.87 (m, 2H), 2.89-2.64 (m, 4H).

Step 2: 4-(4-(2,2,2-Trifluoroethyl)piperazin-1-yl)aniline*

A stirring solution of 1-(4-nitrophenyl)-4-(2,2,2-trifluoroethyl)piperazine (550 mg, 1.901 mmol) in EtOH (25 mL) was heated to 50° C. Pd/C (101 mg, 0.095 mmol) was added followed by portionwise addition of ammonium formate (600 mg, 9.51 mmol) and the suspension was stirred for 10 min. The suspension was filtered through Celite and the solid remainder was washed with ethanol (6 mL). The solvent was removed in vacuo and the resulting residue was purified by flash chromatography (15-100% EtOAc in cyclohexane), yielding the title compound as a white-violet solid (490 mg, 99%).

LCMS (Method C): $R_T$=0.92 min, m/z=260 $[M+H]^+$.

$^1$H NMR (300 MHz, $CDCl_3$) δ 6.77 (d, J=8.7 Hz, 2H), 6.59 (d, J=8.8 Hz, 2H), 3.15-2.86 (m, 6H), 2.88-2.68 (m, 4H).

Step 3: 1-(6-{[Dimethyl(oxo)-$\lambda^6$-sulfanylidene]amino}pyridin-2-yl)-2-(propan-2-yl)-6-({4-[4-(2,2,2-trifluoroethyl)piperazin-1-yl]phenyl}amino)-1H,2H,3H-pyrazolo[3,4-c]pyrimidin-3-one*

Intermediate D (70 mg, 0.178 mmol) was reacted with 4-(4-(2,2,2-trifluoroethyl)piperazin-1-yl)aniline (46.2 mg, 0.178 mmol) using General Procedure C, yielding the title compound as a yellow solid (72 mg, 67%).

LCMS (Method C): $R_T$=1.39 min, m/z=604 $[M+H]^+$.

$^1$H NMR (300 MHz, $CDCl_3$) δ 8.75 (s, 1H), 7.68 (t, J=7.9 Hz, 1H), 7.45 (d, J=8.9 Hz, 2H), 7.42-7.29 (m, 1H), 7.18 (d, J=7.6 Hz, 1H), 6.92 (d, J=8.9 Hz, 2H), 6.73 (d, J=7.9 Hz, 1H), 4.45-4.26 (m, 1H), 3.32 (s, 6H), 3.24-3.15 (m, 4H), 3.05 (q, J=9.5 Hz, 2H), 2.95-2.80 (m, 4H), 1.45 (d, J=6.8 Hz, 6H).

Example 51: 1-(6-{[Dimethyl(oxo)-$\lambda^6$-sulfanylidene]amino}pyrazin-2-yl)-6-{[4-(morpholin-4-yl)phenyl]amino}-2-(prop-2-en-1-yl)-1H,2H,3H-pyrazolo[3,4-d]pyrimidin-3-one*

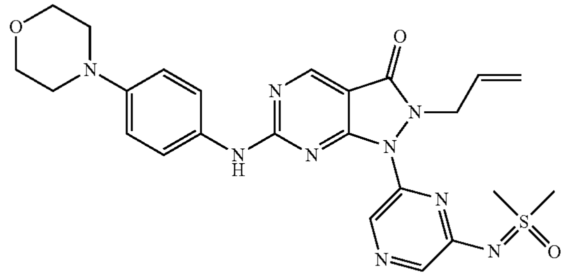 [SMILES: C=CCn1c(=O)c2cnc(Nc3ccc(N4CCOCC4)cc3)nc2n1-c1cncc(N=S(C)(C)=O)n1]

Intermediate G (70 mg, 0.179 mmol) was reacted with 4-morpholinoaniline (31.9 mg, 0.179 mmol) using General Procedure C, yielding the title compound as a yellow sticky solid (58 mg, 62%).

LCMS (Method C): $R_T$=1.00 min, m/z=522 $[M+H]^+$.

$^1$H NMR (300 MHz, $CDCl_3$) δ 8.83 (s, 1H), 8.72 (s, 1H), 8.03 (s, 1H), 7.53 (d, J=7.6 Hz, 3H), 6.99 (d, J=7.5 Hz, 2H), 5.78-5.48 (m, 1H), 5.10-4.94 (m, 2H), 4.87 (d, J=6.3 Hz, 2H), 3.89 (s, 4H), 3.36 (s, 6H), 3.17 (s, 4H).

Example 52: 1-(4-{[Dimethyl(oxo)-$\lambda^6$-sulfanylidene]amino}pyrimidin-2-yl)-6-{[4-(morpholin-4-yl)phenyl]amino}-2-(prop-2-en-1-yl)-1H,2H,3H-pyrazolo[3,4-d]pyrimidin-3-one*

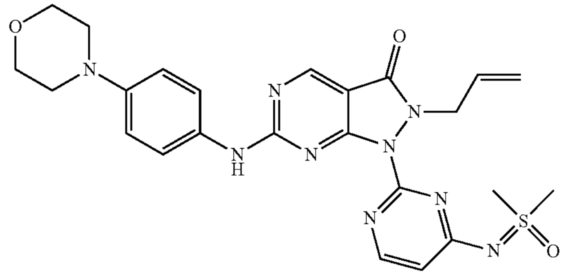 [SMILES: C=CCn1c(=O)c2cnc(Nc3ccc(N4CCOCC4)cc3)nc2n1-c1nccc(N=S(C)(C)=O)n1]

Step 1: [(2-Bromopyrimidin-4-yl)imino]dimethyl-$\lambda^6$-sulfanone*

$Pd_2(dba)_3$ (192 mg, 0.210 mmol) and xantphos (268 mg, 0.462 mmol) were added to a pre-degassed suspension of 2,4-dibromopyrimidine (1000 mg, 4.20 mmol), (5-methylsulfonimidoyl)methane (392 mg, 4.20 mmol) and $Cs_2CO_3$ (4109 mg, 12.61 mmol) in 1,4-dioxane (17 mL). The temperature was increased to 100° C. and the reaction mixture was stirred for 6 h under nitrogen. The reaction mixture was filtered through Celite and the filtrate was evaporated under reduced pressure. The residue was purified by flash chromatography (25-100% EtOAc in cyclohexane), yielding the title compound as a yellowish oil (520 mg, 49.5% yield).

LCMS (Method C): $R_T$=0.59 min, m/z=251 $[M+H]^+$.

$^1$H NMR (300 MHz, $CDCl_3$) δ 8.06 (d, J=5.4 Hz, 1H), 6.57 (d, J=5.5 Hz, 1H), 3.35 (s, 6H).

Step 2: 1-(4-{[Dimethyl(oxo)-$\lambda^6$-sulfanylidene]amino}pyrimidin-2-yl)-6-(methylsulfanyl)-2-(prop-2-en-1-yl)-1H,2H,3H-pyrazolo[3,4-d]pyrimidin-3-one*

Into a 25 mL microwave vial was added 2-allyl-6-(methylthio)-1H-pyrazolo[3,4-d]pyrimidin-3(2H)-one (355 mg, 1.60 mmol)) [Prepared according to EP2213673B1 (Production Example 1, p 37)], [(2-bromopyrimidin-4-yl)imino]dimethyl-$\lambda^6$-sulfanone (520 mg, 2.08 mmol), $K_2CO_3$ (309 mg, 2.24 mmol) and dioxane (7 mL). The resultant suspension was degassed (bubbling of $N_2$) and copper (I) iodide (305 mg, 1.60 mmol) was added followed by $N^1$,$N^2$-dimethylethane-1,2-diamine (0.172 mL, 1.60 mmol). The vial was flushed with nitrogen and capped and the reaction mixture was stirred vigorously at 95° C. overnight. The reaction mixture was transferred to a separation funnel, $NH_4OH$ (aq) was added (20 mL) and the mixture was extracted with EtOAc (3x30 mL). The organic extracts were combined, dried ($MgSO_4$) and evaporated under vacuum. The residue was purified by flash chromatography (0-15% MeOH in EtOAc) and the product containing fractions were concentrated to give the title compound as a white solid (353 mg, 56%).

LCMS (Method C): $R_T$=0.96 min, m/z=392 $[M+H]^+$.

$^1H$ NMR (300 MHz, $CDCl_3$) δ 8.96 (s, 1H), 8.32 (d, J=5.7 Hz, 1H), 6.61 (d, J=5.7 Hz, 1H), 5.75-5.62 (m, 1H), 5.13-4.83 (m, 4H), 3.60 (s, 6H), 2.63 (s, 3H).

Step 3: 1-(4-{[Dimethyl(oxo)-$\lambda^6$-sulfanylidene]amino}pyrimidin-2-yl)-6-{[4-(morpholin-4-yl)phenyl]amino}-2-(prop-2-en-1-yl)-1H,2H,3H-pyrazolo[3,4-d]pyrimidin-3-one*

Into a 5 mL microwave vial was added 1-(4-{[dimethyl(oxo)-$\lambda^6$-sulfanylidene]amino}pyrimidin-2-yl)-6-(methylsulfanyl)-2-(prop-2-en-1-yl)-1H,2H,3H-pyrazolo[3,4-d]pyrimidin-3-one (70 mg, 0.179 mmol) followed by toluene (1 mL) and dichloromethane (1 mL) to give a white suspension. m-CPBA, 70% purity (48.5 mg, 0.197 mmol) was added and the reaction mixture was stirred for 30 min. 4-Morpholinoaniline (31.9 mg, 0.179 mmol) and DIPEA (0.094 mL, 0.536 mmol) were then added and the reaction mixture was heated at 65° C. overnight. The reaction mixture was loaded directly onto a Silica Gel column and purified by flash chromatography (0-10% MeOH in EtOAc). The product containing fractions were evaporated under vacuum yielding the title compound as a yellow solid (47 mg, 50%).

LCMS (Method C): $R_T$=0.94 min, m/z=522 $[M+H]^+$.

$^1H$ NMR (300 MHz, DMSO) δ 10.09 (bs, 1H), 8.83 (s, 1H), 8.52 (s, 1H), 7.84 (s, 2H), 6.93 (d, J=9.1 Hz, 2H), 6.62 (d, J=5.6 Hz, 1H), 5.82-5.51 (m, 1H), 5.02 (d, J=10.3 Hz, 1H), 4.93 (d, J=17.1 Hz, 1H), 4.72 (d, J=4.8 Hz, 2H), 3.84-3.66 (m, 4H), 3.50 (s, 6H), 3.16-2.97 (m, 4H).

Example 53: 1-(6-{[Dimethyl(oxo)-$\lambda^6$-sulfanylidene]amino}pyridin-2-yl)-6-({4-[(2S)-2-(methoxymethyl)morpholin-4-yl]phenyl}amino)-2-(propan-2-yl)-1H,2H,3H-pyrazolo[3,4-d]pyrimidin-3-one*

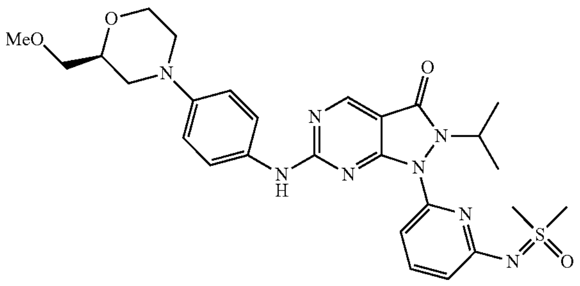 [SMILES: COC[C@@H]1CN(c2ccc(Nc3ncc4c(=O)n(C(C)C)n(-c5cccc(N=S(C)(C)=O)n5)c4n3)cc2)CCO1]

Step 1: (S)-2-(Methoxymethyl)-4-(4-nitrophenyl)morpholine

To a stirring suspension of 1-fluoro-4-nitrobenzene (421 mg, 2.98 mmol) and $K_2CO_3$ (2267 mg, 16.40 mmol) in anhydrous DMF (3 mL) was added (S)-2-(methoxymethyl)morpholine hydrochloride (500 mg, 2.98 mmol) and the mixture heated at 50° C. overnight. The reaction mixture was transferred to a separatory funnel and 100 mL of EtOAc was added. The mixture was washed with 2M $K_2CO_3$ (2×70 mL) and the organic layer was dried ($MgSO_4$) and evaporated, yielding the title compound as a yellow solid (688 mg, 91%).

LCMS (Method C): $R_T$=1.32 min, m/z=253 $[M+H]^+$.

$^1H$ NMR (300 MHz, $CDCl_3$) δ 8.14 (d, J=9.0 Hz, 2H), 6.85 (d, J=9.0 Hz, 2H), 4.17-4.01 (m, 1H), 3.89-3.70 (m, 3H), 3.70-3.60 (m, 1H), 3.60-3.45 (m, 2H), 3.42 (s, 3H), 3.16-3.00 (m, 1H), 2.95-2.79 (m, 1H).

Step 2: (S)-4-(2-(Methoxymethyl)morpholino)aniline

A stirred solution of (S)-2-(methoxymethyl)-4-(4-nitrophenyl)morpholine (680 mg, 2.70 mmol) in EtOH (25 mL) was heated to 50° C. 10% Pd/C (201 mg, 0.189 mmol) was added followed by portionwise addition of ammonium formate (1020 mg, 16.17 mmol) and the suspension was stirred for 10 min. The solid was filtered off and washed with ethanol (25 mL). The solvent was removed in vacuo and the resulting residue was purified by flash chromatography (15-100% EtOAc in cyclohexane) to afford the title compound (525 mg, 88%) as a brownish oil which solidified upon storage.

LCMS (Method C): $R_T$=0.72 min, m/z=223 $[M+H]^+$.

$^1H$ NMR (300 MHz, $CDCl_3$) δ 6.82 (d, J=8.7 Hz, 2H), 6.66 (d, J=8.7 Hz, 2H), 4.03 (dd, J=11.4, 1.8 Hz, 1H), 3.97-3.78 (m, 2H), 3.58-3.43 (m, 2H), 3.40 (s, 3H), 3.36-3.14 (m, 2H), 2.79 (td, J=11.6, 3.3 Hz, 1H), 2.57 (t, J=11.0 Hz, 1H).

Step 3: 1-(6-{[Dimethyl(oxo)-$\lambda^6$-sulfanylidene]amino}pyridin-2-yl)-6-({4-[(2S)-2-(methoxymethyl)morpholin-4-yl]phenyl}amino)-2-(propan-2-34)-1H,2H,3H-pyrazolo[3,4-d]pyrimidin-3-one*

Intermediate D (70 mg, 0.178 mmol) was reacted with (S)-4-(2-(methoxymethyl)morpholino)aniline (39.6 mg, 0.178 mmol) using General Procedure C, yielding the title compound as a yellow solid (45 mg, 44%).

LCMS (Method C): $R_T$=1.18 min, m/z=567 $[M+H]^+$.

$^1H$ NMR (300 MHz, DMSO) δ 10.08 (s, 1H), 8.74 (s, 1H), 7.82 (s, 1H), 7.56 (s, 2H), 7.20 (d, J=7.1 Hz, 1H), 6.89 (d, J=9.1 Hz, 2H), 6.66 (d, J=8.0 Hz, 1H), 4.30-4.15 (m, 1H), 4.01-3.85 (m, 1H), 3.78-3.68 (m, 1H), 3.68-3.57 (m, 1H), 3.55-3.38 (m, 4H), 3.36 (s, 6H), 3.29 (s, 3H), 2.68-2.56 (m, 1H), 2.45-2.32 (m, 1H), 1.31 (d, J=6.6 Hz, 6H).

Example 54: 1-(6-{[Dimethyl(oxo)-$\lambda^6$-sulfanylidene]amino}pyridin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one*

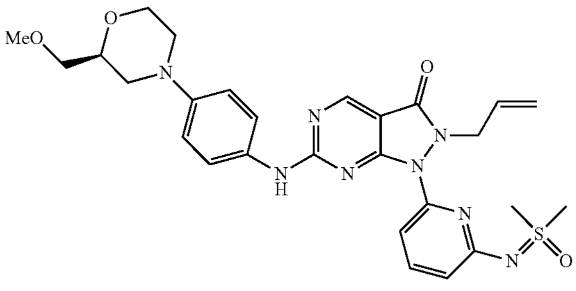 [SMILES: C=CCn1c(=O)c2cnc(Nc3ccc(N4CCO[C@H](COC)C4)cc3)nc2n1-c1cccc(N=S(C)(C)=O)n1]

Step 1: 1-(6-{[Dimethyl(oxo)-λ$^6$-sulfanylidene]amino}pyridin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one*

Intermediate B (70 mg, 0.179 mmol) was reacted with (S)-4-(2-(methoxymethyl)morpholino)aniline (obtained as described above) (39.8 mg, 0.178 mmol) using General Procedure C, yielding the title compound as a yellow solid (38 mg, 38%).

LCMS (Method C): $R_T$=1.16 min, m/z=565 $[M+H]^+$.

$^1$H NMR (300 MHz, DMSO) δ 10.15 (bs, 1H), 8.81 (s, 1H), 7.81 (bs, 1H), 7.60 (bs, 2H), 7.30 (d, J=7.8 Hz, 1H), 6.93 (d, J=9.0 Hz, 2H), 6.60 (d, J=8.0 Hz, 1H), 5.50-5.80 (m, 1H), 5.00 (d, J=10.1 Hz, 1H), 4.89 (d, J=17.0, 1H), 5.00 (d, J=10.1 Hz, 1H), 4.89 (d, J=17.0 Hz, 1H), 4.74 (s, 2H), 4.02-3.85 (m, 1H), 3.81-3.57 (m, 2H), 3.57-3.40 (m, 4H), 3.39 (s, 6H), 3.29 (s, 3H), 2.70-2.57 (m, 1H), 2.46-2.35 (m, 1H).

Example 55: 6-[(4-Fluorophenyl)amino]-1-{6-[(1-oxo-1λ$^6$-thiolan-1-ylidene)amino]pyridin-2-yl}-2-(propan-2-yl)-1H,2H,3H-pyrazolo[3,4-d]pyrimidin-3-one*

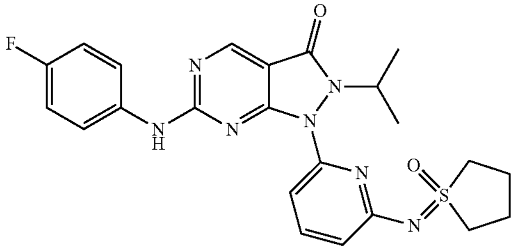 [SMILES: CC(C)n1c(=O)c2cnc(Nc3ccc(F)cc3)nc2n1-c1cccc(N=S2(=O)CCCC2)n1]

Intermediate F (70 mg, 0.167 mmol) was reacted with 4-fluoroaniline (18.6 mg, 0.167 mmol) using General Procedure C, yielding the title compound as a off-white solid (35 mg, 44%).

LCMS (Method C): $R_T$=1.42 min, m/z=482 $[M+H]^+$.

$^1$H NMR (300 MHz, DMSO) δ 10.23 (s, 1H), 8.80 (s, 1H), 7.84 (t, J=7.9 Hz, 1H), 7.72 (dd, J=9.1, 5.0 Hz, 2H), 7.27-7.06 (m, 3H), 6.74 (d, J=8.0 Hz, 1H), 4.42-4.04 (m, 1H), 3.61-3.39 (m, 2H), 3.31-3.14 (m, 2H), 2.25-1.89 (m, 4H), 1.29 (d, J=6.8 Hz, 6H).

Example 56: 6-[(1-Methyl-1H-pyrazol-4-yl)amino]-1-{6-[(1-oxo-1λ$^6$-thiolan-1-ylidene)amino]pyridin-2-yl}-2-(propan-2-yl)-1H,2H,3H-pyrazolo[3,4-d]pyrimidin-3-one*

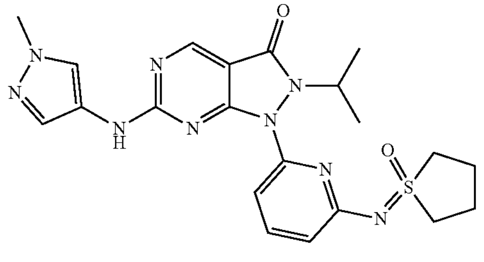 [SMILES: CC(C)n1c(=O)c2cnc(Nc3cnn(C)c3)nc2n1-c1cccc(N=S2(=O)CCCC2)n1]

Intermediate F (70 mg, 0.167 mmol) was reacted with 1-methyl-1H-pyrazol-4-amine (16.2 mg, 0.167 mmol) using General Procedure C, yielding the title compound as a off-white solid (60 mg, 77%).

LCMS (Method C): $R_T$=1.00 min, m/z=468 $[M+H]^+$.

$^1$H NMR (300 MHz, DMSO) δ 10.10 (s, 1H), 8.75 (s, 1H), 7.98-7.68 (m, 2H), 7.46 (s, 1H), 7.32-7.06 (m, 1H), 6.75 (d, J=8.0 Hz, 1H), 4.34-4.06 (m, 1H), 3.80-3.58 (m, 3H), 3.56-3.37 (m, 2H), 3.31-3.08 (m, 2H), 2.23-1.93 (m, 4H), 1.42-1.09 (m, 6H).

Example 57: 1-(6-{[Dimethyl(oxo)-λ$^6$-sulfanylidene]amino}pyridin-2-yl)-6-{[4-(dimethylamino)phenyl]amino}-2-(prop-2-en-1-yl)-1H,2H,3H-pyrazolo[3,4-d]pyrimidin-3-one*

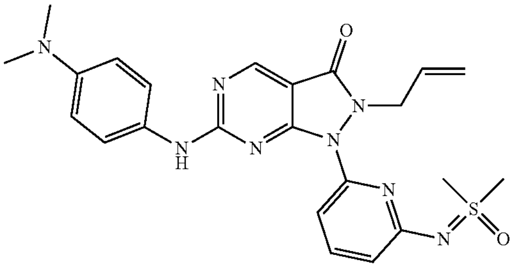 [SMILES: C=CCn1c(=O)c2cnc(Nc3ccc(N(C)C)cc3)nc2n1-c1cccc(N=S(C)(C)=O)n1]

Intermediate B (70 mg, 0.1/9 mmol) was reacted with N',N'-dimethylbenzene-1,4-diamine (24.4 mg, 0.179 mmol) using General Procedure C, yielding the title compound as a yellow solid (62 mg, 72%).

LCMS (Method C): $R_T$=0.83 min, m/z=479 $[M+H]^+$.

$^1$H NMR (300 MHz, DMSO) δ 10.06 (bs, 1H), 8.77 (s, 1H), 7.76 (t, J=7.9 Hz, 1H), 7.63-7.43 (m, 2H), 7.30 (d, J=7.8 Hz, 1H), 6.71 (d, J=9.0 Hz, 2H), 6.57 (d, J=8.0 Hz, 1H), 5.74-5.48 (m, 1H), 5.00 (d, J=10.6 Hz, 1H), 4.89 (d, J=17.2 Hz, 1H), 4.73 (s, 2H), 3.36 (s, 6H), 2.86 (s, 6H).

Example 58: 1-(6-{[Dimethyl(oxo)-λ$^6$-sulfanylidene]amino}pyridin-2-yl)-6-{[4-(dimethylamino)phenyl]amino}-2-(propan-2-yl)-1H,2H,3H-pyrazolo[3,4-d]pyrimidin-3-one*

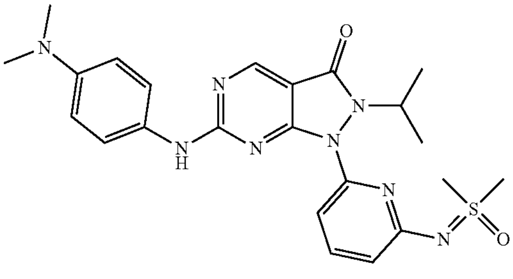 [SMILES: CC(C)n1c(=O)c2cnc(Nc3ccc(N(C)C)cc3)nc2n1-c1cccc(N=S(C)(C)=O)n1]

Intermediate D (70 mg, 0.178 mmol) was reacted with $N^1,N^1$-dimethylbenzene-1,4-diamine (24.3 mg, 0.179 mmol) using General Procedure C, yielding the title compound as a yellow solid (60 mg, 70%).

LCMS (Method C): $R_T$=0.84 min, m/z=481 $[M+H]^+$.

$^1$H NMR (300 MHz, DMSO) δ 10.01 (bs, 1H), 8.71 (s, 1H), 7.99-7.68 (m, 1H), 7.67-7.33 (m, 2H), 7.30-7.05 (m,

1H), 6.83-6.47 (m, 3H), 4.36-4.04 (m, 1H), 3.35 (s, 6H), 2.85 (s, 6H), 1.30 (d, J=5.9 Hz, 6H).

Example 59: 1-{6-[(1-Oxo-1λ$^6$-thiolan-1-ylidene) amino]pyridin-2-yl}-6-{[4-(piperazin-1-yl)phenyl] amino}-2-(propan-2-yl)-1H,2H,3H-pyrazolo[3,4-d] pyrimidin-3-one*

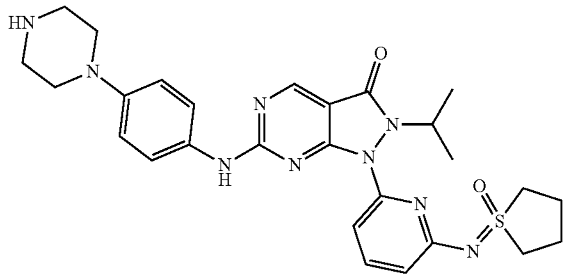 [SMILES: CC(C)n1c(=O)c2cnc(Nc3ccc(N4CCNCC4)cc3)nc2n1-c1cccc(N=S2(=O)CCCC2)n1]

Step 1: tert-Butyl 4-(4-((2-isopropyl-1-(6-(1-oxido-tetrahydrothiophen-1-ylidene)amino)pyridin-2-yl)-3-oxo-2,3-dihydro-1H-pyrazolo[3,4-d]pyrimidin-6-yl) amino)phenyl)piperazine-1-carboxylate Intermediate F (70 mg, 0.167 mmol) was reacted with tert-butyl 4-(4-aminophenyl)piperazine-1-carboxylate (46.4 mg, 0.167 mmol) using General Procedure C, yielding the title compound as a yellow solid (32 mg, 30%).

LCMS (Method C): $R_T$=1.60 min, m/z=646 $[M+H]^+$.

$^1$H NMR (300 MHz, DMSO) δ 10.07 (bs, 1H), 8.75 (s, 1H), 7.83 (t, J=7.8 Hz, 1H), 7.56 (d, J=8.0 Hz, 2H), 7.21 (d, J=7.3 Hz, 1H), 6.90 (d, J=9.1 Hz, 2H), 6.73 (d, J=8.0 Hz, 1H), 4.34-4.09 (m, 1H), 3.66-3.36 (m, 6H), 3.32-3.15 (m, 2H), 3.11-2.91 (m, 4H), 2.26-1.88 (m, 4H), 1.41 (s, 9H), 1.31 (d, J=6.7 Hz, 6H).

Step 2: 2-Isopropyl-1-(6-(1-oxidotetrahydrothio-phen-1-ylidene)amino)pyridin-2-yl)-6-((4-(piper-azin-1-yl)phenyl)amino)-1H-pyrazolo[3,4-d]pyrimi-din-3(2H)-one tert-Butyl 4-(4-((2-isopropyl-1-(6-((1-oxidotetrahydroth-iophen-1-ylidene)amino)pyridin-2-yl)-3-oxo-2,3-dihydro-1H-pyrazolo[3,4-d]pyrimidin-6-yl)amino)phenyl)pipera-zine-1-carboxylate (30 mg, 0.046 mmol) was reacted according to General Procedure D, yielding the title compound as a yellow solid (22 mg, 87%).

LCMS (Method C): $R_T$=0.77 min, m/z=548 $[M+H]^+$.

$^1$H NMR (300 MHz, DMSO) δ 10.04 (s, 1H), 8.74 (s, 1H), 7.84 (s, 1H), 7.66-7.43 (m, 2H), 7.21 (d, J=7.7 Hz, 1H), 6.85 (d, J=9.1 Hz, 2H), 6.73 (d, J=8.1 Hz, 1H), 4.35-4.10 (m, 1H), 3.61-3.43 (m, 2H), 3.31-3.15 (m, 2H), 3.09-2.91 (m, 4H), 2.90-2.76 (m, 4H), 2.25-1.90 (m, 4H), 1.31 (d, J=6.6 Hz, 6H).

Example 60: 4-[(4-Cyanophenyl)[1-(6-{[dimethyl (oxo)-λ$^6$-sulfanylidene]amino}pyridin-2-yl)-3-oxo-2-(propan-2-yl)-1H,2H,3H-pyrazolo[3,4-d]pyrimi-din-6-yl]amino]benzonitrile*

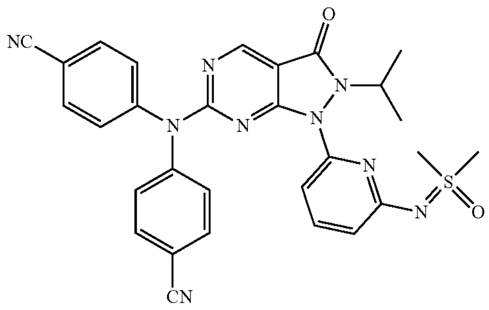 [SMILES: CC(C)n1c(=O)c2cnc(N(c3ccc(C#N)cc3)c3ccc(C#N)cc3)nc2n1-c1cccc(N=S(C)(C)=O)n1]

$Pd_2(dba)_3$ (9.12 mg, 9.96 μmol) and Xantphos (5.8 mg, 9.96 μmol) were added to a degassed suspension of Intermediate H (18 mg, 0.050 mmol), 4-bromobenzonitrile (18.1 mg, 0.100 mmol) and $Cs_2CO_3$ (48.7 mg, 0.149 mmol) in 1,4-dioxane (1 mL). The temperature was increased to 100° C. and the reaction was stirred intensively overnight. The reaction mixture was filtered through Celite. The filtration cake was washed with EtOAc and the combined filtrates were evaporated under reduced pressure. The residue was purified by flash chromatography (15-100% EtOAc in cyclohexane then 0-15% MeOH in EtOAc). The product containing fractions were evaporated under reduced pressure yielding the desired product as a beige solid (10 mg, 36%).

LCMS (Method C): $R_T$=1.36 min, m/z=564 $[M+H]^+$.

$^1$H NMR (300 MHz, DMSO) δ 8.81 (s, 1H), 7.92-7.79 (m, 4H), 7.60-7.42 (m, 5H), 6.87 (t, J=7.7 Hz, 1H), 6.64-6.53 (m, 1H), 4.57-3.98 (m, 1H), 3.34 (s, 6H), 1.39-1.32 (m, 6H).

Example 61: 6-[(4-Chlorophenyl)amino]-1-(6-{[di-methyl(oxo)-λ$^6$-sulfanylidene]amino}pyridin-2-yl)-2-(propan-2-yl)-1H,2H,3H-pyrazolo[3,4-d]pyrimi-din-3-one*

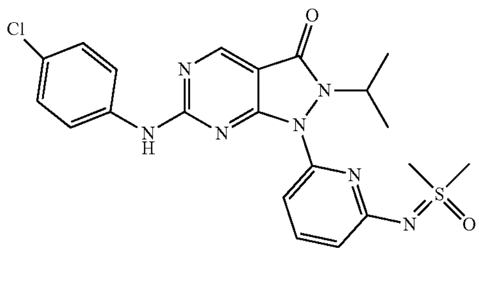 [SMILES: CC(C)n1c(=O)c2cnc(Nc3ccc(Cl)cc3)nc2n1-c1cccc(N=S(C)(C)=O)n1]

Intermediate D (70 mg, 0.178 mmol) was reacted with 4-chloroaniline (22.8 mg, 0.178 mmol) using General Procedure C, yielding the title compound as a beige solid (16 mg, 19%).

LCMS (Method C): $R_T$=1.49 min, m/z=472 $[M+H]^+$.

$^1$H NMR (300 MHz, DMSO) δ 10.34 (s, 1H), 8.84 (s, 1H), 7.85 (t, J=7.9 Hz, 1H), 7.77 (d, J=8.9 Hz, 2H), 7.35 (d, J=8.8 Hz, 2H), 7.19 (d, J=7.6 Hz, 1H), 6.68 (d, J=8.0 Hz, 1H), 4.33-4.14 (m, 1H), 3.36 (s, 6H), 1.32 (d, J=6.8 Hz, 6H).

Example 62: 6-[(4-Chlorophenyl)amino]-1-(6-{[dimethyl(oxo)-λ[6]-sulfanylidene]amino}pyridin-2-yl)-2-(prop-2-en-1-yl)-1H,2H,3H-pyrazolo[3,4-d]pyrimidin-3-one*

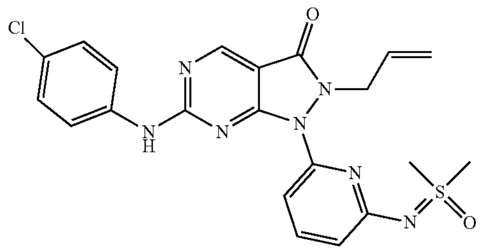 [SMILES: C=CCn1c(=O)c2cnc(Nc3ccc(Cl)cc3)nc2n1-c1cccc(N=S(C)(C)=O)n1]

Intermediate B (70 mg, 0.179 mmol) was reacted with 4-chloroaniline (22.9 mg, 0.179 mmol) using General Procedure C, yielding the title compound as a white solid (12 mg, 14%).

LCMS (Method C): $R_T$=1.37 min, m/z=470 $[M+H]^+$.

$^1$H NMR (300 MHz, DMSO) δ 10.41 (s, 1H), 8.90 (s, 1H), 7.88-7.70 (m, 3H), 7.40 (d, J=8.9 Hz, 2H), 7.27 (d, J=7.8 Hz, 2H), 6.61 (d, J=8.0 Hz, 1H), 5.78-5.53 (m, 1H), 5.00 (d, J=10.3 Hz, 1H), 4.89 (d, J=18.4 Hz, 1H), 4.75 (d, J=5.9 Hz, 2H), 3.37 (s, 6H).

Example 63: 6-({Bicyclo[1.1.1]pentan-1-yl}amino)-1-(6-{[dimethyl(oxo)-λ[6]-sulfanylidene]amino}pyridin-2-yl)-2-(prop-2-en-1-yl)-1H,2H,3H-pyrazolo[3,4-d]pyrimidin-3-one*

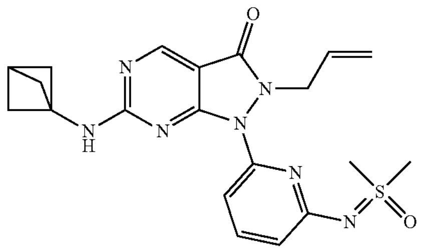 [SMILES: C=CCn1c(=O)c2cnc(NC34CC(C3)C4)nc2n1-c1cccc(N=S(C)(C)=O)n1]

Intermediate B (70 mg, 0.179 mmol) was reacted with bicyclo[1.1.1]pentan-1-amine hydrochloride (21.4 mg, 0.179 mmol) using General Procedure C, yielding the title compound as a white solid (52 mg, 68%).

LCMS (Method C): $R_T$=1.23 min, m/z=426 $[M+H]^+$.

$^1$H NMR (400 MHz, DMSO) δ 8.75 (s, 1H), 8.69 (s, 1H), 7.75 (t, J=8.0 Hz, 1H), 7.28 (d, J=7.9 Hz, 1H), 6.57 (d, J=7.9 Hz, 1H), 5.75-5.50 (m, 1H), 5.00 (dd, J=10.2, 1.4 Hz, 1H), 4.89 (dd, J=17.1, 1.5 Hz, 1H), 4.73 (d, J=5.2 Hz, 2H), 3.38 (s, 6H), 2.48 (s, 1H), 2.08 (s, 6H).

Example 64: 6-[(4-tert-Butylphenyl)amino]-1-(6-{[dimethyl(oxo)-λ[6]-sulfanylidene]amino}pyridin-2-yl)-2-(prop-2-en-1-yl)-1H,2H,3H-pyrazolo[3,4-d]pyrimidin-3-one*

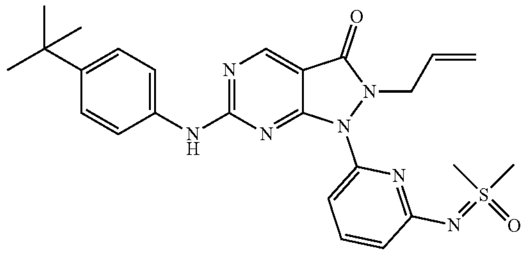 [SMILES: C=CCn1c(=O)c2cnc(Nc3ccc(C(C)(C)C)cc3)nc2n1-c1cccc(N=S(C)(C)=O)n1]

Intermediate B (70 mg, 0.179 mmol) was reacted with 4-(tert-butyl)aniline (26.8 mg, 0.179 mmol) using General Procedure C, yielding the title compound as a white solid (22 mg, 25%).

LCMS (Method C): $R_T$=1.66 min, m/z=492 $[M+H]^+$.

$^1$H NMR (300 MHz, DMSO) δ 10.21 (s, 1H), 8.86 (s, 1H), 7.81 (t, J=8.0 Hz, 1H), 7.67 (d, J=8.4 Hz, 2H), 7.45-7.19 (m, 3H), 6.62 (d, J=8.0 Hz, 1H), 5.78-5.54 (m, 1H), 5.09-4.84 (m, 2H), 4.76 (d, J=5.6 Hz, 2H), 3.38 (s, 6H), 1.29 (s, 9H).

Example 65: 6-[(2,4-Difluorophenyl)amino]-1-(6-{[dimethyl(oxo)-λ[6]-sulfanylidene]amino}pyridin-2-yl)-2-(propan-2-yl)-1H,2H,3H-pyrazolo[3,4-d]pyrimidin-3-one*

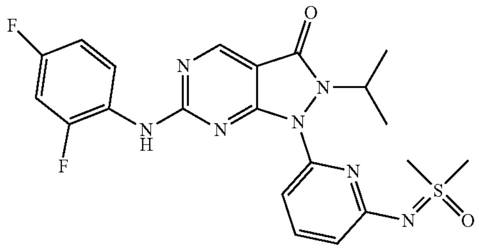 [SMILES: CC(C)n1c(=O)c2cnc(Nc3ccc(F)cc3F)nc2n1-c1cccc(N=S(C)(C)=O)n1]

Intermediate D (70 mg, 0.179 mmol) was reacted with 2,4-difluoroaniline (23 mg, 0.179 mmol) using General Procedure C, yielding the title compound as a beige solid (11 mg, 13%).

LCMS (Method C): $R_T$=1.25 min, m/z=474 $[M+H]^+$.

$^1$H NMR (300 MHz, DMSO) δ 9.76 (s, 1H), 8.74 (s, 1H), 7.71 (t, J=7.4 Hz, 1H), 7.62-7.45 (m, 1H), 7.30 (t, J=10.3 Hz, 1H), 7.08 (d, J=7.9 Hz, 2H), 6.64 (d, J=7.5 Hz, 1H), 4.29-4.13 (m, 1H), 3.34 (s, 6H), 1.30 (d, J=6.4 Hz, 6H).

Example 66: 6-[(3,4-Difluorophenyl)amino]-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one*

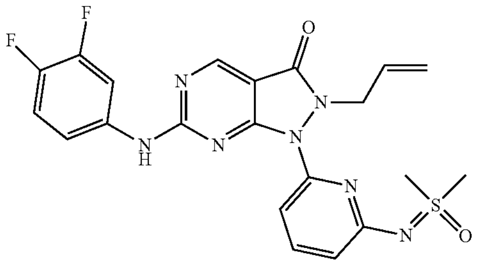 [SMILES: C=CCn1c(=O)c2cnc(Nc3ccc(F)c(F)c3)nc2n1-c1cccc(N=S(C)(C)=O)n1]

Intermediate B (70 mg, 0.179 mmol) was reacted with 3,4-difluoroaniline (46 mg, 0.359 mmol) using General Procedure C, yielding the title compound as a white solid (12 mg, 14%).

LCMS (Method C): $R_T$=1.30 min, m/z=472 $[M+H]^+$.

$^1$H NMR (300 MHz, DMSO) δ 10.47 (s, 1H), 8.92 (s, 1H), 8.05-7.85 (m, 1H), 7.77 (t, J=7.9 Hz, 1H), 7.51-7.33 (m, 2H), 7.27 (d, J=7.8 Hz, 1H), 6.63 (d, J=8.0 Hz, 1H), 5.75-5.54 (m, 1H), 4.94 (d, J=9.2 Hz, 1H), 4.82 (d, J=18.1 Hz, 1H), 4.75 (d, J=6.0 Hz, 2H), 3.37 (s, 6H).

Example 67: 6-({4-[(3aR,6aS)-Hexahydro-1H-furo[3,4-c]pyrrol-5-yl]phenyl}amino)-1-(6-{[dimethyl(oxo)-λ$^6$-sulfanylidene]amino}pyridin-2-yl)-2-(prop-2-en-1-yl)-1H,2H, 3H-pyrazolo[3,4-d]pyrimidin-3-one*

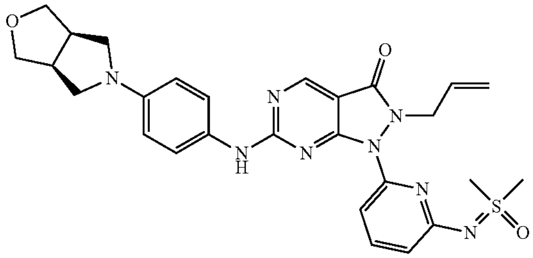 [SMILES: C=CCn1c(=O)c2cnc(Nc3ccc(N4C[C@H]5COC[C@H]5C4)cc3)nc2n1-c1cccc(N=S(C)(C)=O)n1]

Step 1: (3aR,6aS)-5-(4-Nitrophenyl)hexahydro-1H-furo[3,4-c]pyrrole

To a suspension of 1-fluoro-4-nitrobenzene (141 mg, 1.00 mmol) and $K_2CO_3$ (762 mg, 5.51 mmol) in anhydrous DMF (1 mL) was added (3aR,6aS)-hexahydro-1H-furo[3,4-c]pyrrole hydrochloride and the mixture was stirred at 50° C. overnight. The reaction mixture was transferred to a separatory funnel and 100 mL of EtOAc was added. The mixture was washed with 2M $K_2CO_3$ (2×70 ml). The organic layer was dried (anh. $MgSO_4$) and evaporated under reduced pressure. The residue was purified by flash chromatography (15-100% EtOAc in cyclohexane). The product containing fractions were evaporated under reduced pressure yielding a yellow solid product (230 mg, 98% yield).

LCMS (Method C): $R_T$=1.26 min, m/z=235 $[M+H]^+$.

$^1$H NMR (300 MHz, $CDCl_3$) δ 8.23-8.00 (m, 2H), 6.63-6.37 (m, 2H), 3.99 (dd, J=9.0, 6.5 Hz, 2H), 3.85-3.54 (m, 4H), 3.36 (dd, J=10.6, 3.3 Hz, 2H), 3.24-3.04 (m, 2H).

Step 2: 4-((3aR,6aS)-Tetrahydro-1H-furo[3,4-c]pyrrol-5(3H)-yl)aniline

A stirring solution of (3aR,6aS)-5-(4-nitrophenyl)hexahydro-1H-furo[3,4-c]pyrrole (230 mg, 0.982 mmol) in ethanol (10 ml) was heated to 50° C. Pd/C (73.1 mg, 0.069 mmol) was added followed by portionwise addition of ammonium formate (371 mg, 5.89 mmol) and the suspension stirred for about 30 min. The suspension was filtered through Celite washing with fresh ethanol. The ethanol was removed in vacuo. The resulting residue was purified by flash chromatography (15-100% EtOAc in cyclohexane) to afford the title compound (165 mg, 82%) as a brownish solid.

LCMS (Method D): $R_T$=0.72 min, m/z=205 $[M+H]^+$.

$^1$H NMR (300 MHz, $CDCl_3$) δ 6.78-6.33 (m, 2H), 3.92 (dd, J=8.9, 6.9 Hz, 1H), 3.56 (dd, J=8.9, 4.1 Hz, 1H), 3.21 (bs, 1H), 3.07 (bs, 1H), 2.99-2.81 (m, 1H).

Step 3: 6-({4-[(3aR,6aS)-Hexahydro-1H-furo[3,4-c]pyrrol-5-yl]phenyl}amino)-1-(6-{[dimethyl(oxo)-λ$^6$-sulfanylidene]amino}pyridin-2-34)-2-(prop-2-en-1-yl)-1H,2H,3H-pyrazolo[3,4-d]pyrimidin-3-one*

Intermediate B (70 mg, 0.179 mmol) was reacted with 4-((3aR,6aS)-tetrahydro-1H-furo[3,4-c]pyrrol-5(3H)-yl)aniline (37 mg, 0.179 mmol) using General Procedure C, yielding the title compound as a yellow solid (57 mg, 58%).

LCMS (Method C): $R_T$=1.14 min, m/z=547 $[M+H]^+$.

$^1$H NMR (300 MHz, DMSO) δ 10.09 (s, 1H), 8.78 (s, 1H), 7.78 (t, J=7.9 Hz, 1H), 7.54 (bs, 2H), 7.30 (d, J=7.8 Hz, 1H), 6.61 (dd, J=13.0, 8.5 Hz, 3H), 5.77-5.50 (m, 1H), 4.99 (d, J=10.3 Hz, 1H), 4.89 (d, J=18.1 Hz, 1H), 4.75 (s, 2H), 3.85 (dd, J=8.5, 6.7 Hz, 2H), 3.54 (dd, J=8.7, 3.3 Hz, 2H), 3.37 (s, 6H), 3.33-3.22 (m, 2H), 3.15 (d, J=7.7 Hz, 2H), 2.98 (s, 2H).

Example 68: 1-(6-{[Dimethyl(oxo)-λ$^6$-sulfanylidene]amino}pyridin-2-yl)-6-({4-[(1S,4S)-2-oxa-5-azabicyclo[2.2.1]heptan-5-yl]phenyl}amino)-2-(prop-2-en-1-yl)-1H,2H,3H-pyrazolo[3,4-d]pyrimidin-3-one*

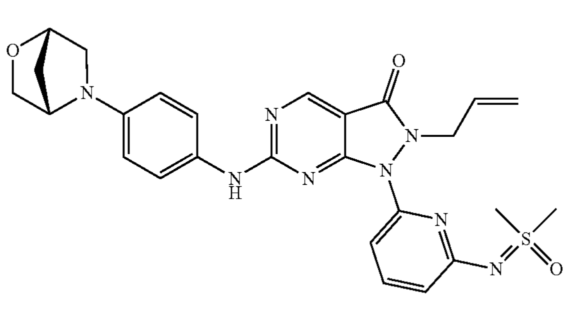 [SMILES: C=CCn1c(=O)c2cnc(Nc3ccc(N4C[C@@H]5C[C@H]4CO5)cc3)nc2n1-c1cccc(N=S(C)(C)=O)n1]

Step 1: (1S,4S)-5-(4-Nitrophenyl)-2-oxa-5-azabicyclo[2.2.1]heptane

To a suspension of 1-fluoro-4-nitrobenzene (520 mg, 3.69 mmol) and $K_2CO_3$ (2800 mg, 20.28 mmol) in anhydrous DMF (3 mL) was added (1S,4S)-2-oxa-5-azabicyclo[2.2.1]heptane hydrochloride (500 mg, 3.69 mmol) and the mixture was stirred at 50° C. overnight. The reaction mixture was transferred to a separatory funnel and 100 mL of EtOAc was added. The mixture was washed with 2M $K_2CO_3$ (2×70 mL). The organic layer was dried (anh. $MgSO_4$) and evaporated under reduced pressure. The residue was purified by flash chromatography (15-100% EtOAc in cyclohexane) to afford the title compound as a yellow solid (756 mg, 3.43 mmol, 93% yield).

LCMS (Method C): $R_T$=1.14 min, m/z=221 $[M+H]^+$.

$^1$H NMR (300 MHz, $CDCl_3$) δ 8.13 (d, J=9.4 Hz, 2H), 6.51 (d, J=9.3 Hz, 2H), 4.75 (s, 1H), 4.56 (d, J=1.4 Hz, 1H), 3.82-3.96 (m, 2H), 3.57 (dd, J=9.7, 1.5 Hz, 1H), 3.33 (d, J=9.7 Hz, 1H), 2.05 (s, 2H).

Step 2: 4-((1S,4S)-2-Oxa-5-azabicyclo[2.2.1]heptan-5-yl)aniline

A stirring solution of (1S,4S)-5-(4-nitrophenyl)-2-oxa-5-azabicyclo[2.2.1]heptane (756 mg, 3.43 mmol) in ethanol (30 mL) was heated to 50° C. 10% Pd/C (256 mg, 0.240 mmol) was added followed by portionwise addition of ammonium formate (1299 mg, 20.60 mmol) and the suspension stirred for 30 min. The suspension was filtered washing with fresh ethanol. The ethanol was removed in vacuo. The resulting residue was purified by flash chromatography (15-100% EtOAc in cyclohexane) to afford the title compound (500 mg, 77%) as brownish solid.

LCMS (Method D): $R_T$=0.57 min, m/z=191 $[M+H]^+$.

$^1$H NMR (300 MHz, $CDCl_3$) δ 6.82-6.17 (m, 4H), 4.52 (s, 1H), 4.22 (bs, 1H), 3.97-3.63 (m, 2H), 3.47 (bs, 1H), 3.00 (bs, 1H), 2.04-1.71 (m, 2H).

Step 3: 1-(6-{[Dimethyl(oxo)-$\lambda^6$-sulfanylidene]amino}pyridin-2-yl)-6-({4-[(1S,4S)-2-oxa-5-azabicyclo[2.2.1]heptan-5-yl]phenyl}amino)-2-(prop-2-en-1-yl)-1H,2H,3H-pyrazolo[3,4-d]pyrimidin-3-one*

Intermediate B (70 mg, 0.179 mmol) was reacted with 4-((1S,4S)-2-oxa-5-azabicyclo[2.2.1]heptan-5-yl)aniline (34 mg, 0.179 mmol) using General Procedure C, yielding the title compound as a yellow solid (75 mg, 79%).

LCMS (Method C): $R_T$=1.08 min, m/z=533 $[M+H]^+$.

$^1$H NMR (300 MHz, DMSO) δ 10.06 (s, 1H), 8.78 (s, 1H), 7.76 (t, J=7.9 Hz, 1H), 7.52 (s, 2H), 7.30 (d, J=7.8 Hz, 1H), 6.59 (t, J=8.4 Hz, 3H), 5.75-5.45 (m, 1H), 4.99 (d, J=10.2 Hz, 1H), 4.89 (d, J=17.5 Hz, 1H), 4.75 (s, 2H), 4.60 s, 1H), 4.43 (s, 1H), 3.74 (d, 7.0 Hz, 1H), 3.66 (d, J=7.3 Hz, 1H), 3.49 (d, J=8.5 Hz, 1H), 3.38 (s, 6H), 2.93 (d, J=9.3 Hz, 1H), 1.92 (d, J=8.0 Hz, 1H), 1.83 (d, J=1.76 Hz, 1H).

Example 69: rac-1-(6-{[Dimethyl(oxo)-$\lambda^6$-sulfanylidene]amino}pyridin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one*

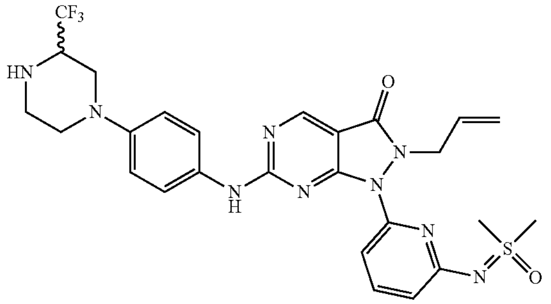 [SMILES: C=CCn1c(=O)c2cnc(Nc3ccc(N4CCNC(C(F)(F)F)C4)cc3)nc2n1-c1cccc(N=S(C)(C)=O)n1]

Step 1: rac-tert-Butyl 4-(4-{[1-(6-{[dimethyl(oxo)-$\lambda^6$-sulfanylidene]amino}pyridin-2-yl)-3-oxo-2-(prop-2-en-1-yl)-1H,2H,3H-pyrazolo[3,4-d]pyrimidin-6-yl]amino}phenyl)-2-(trifluoromethyl)piperazine-1-carboxylate Intermediate B (70 mg, 0.179 mmol) was reacted with tert-butyl 4-(4-aminophenyl)-2-(trifluoromethyl)piperazine-1-carboxylate (62 mg, 0.179 mmol; prepared as described in WO2015092431A1) using General Procedure C, yielding the title compound as a yellow solid (99 mg, 80%).

LCMS (Method C): $R_T$=1.64 min, m/z=688 $[M+H]^+$.

$^1$H NMR (300 MHz, $CDCl_3$) δ 8.75 (s, 1H), 7.70-7.53 (m, 1H), 7.44 (d, J=8.7 Hz, 2H), 7.27 (d, J=7.8 Hz, 1H), 6.84 (d, J=9.0 Hz, 2H), 6.70-6.54 (m, 1H), 5.68-5.47 (m, 1H), 5.01-4.75 (m, 4H), 4.16-3.94 (m, 2H), 3.77 (d, J=13.0 Hz, 1H), 3.42 (d, J=12.2 Hz, 1H), 3.27 (s, 6H), 2.92 (d, J=13.2 Hz, 1H), 2.71 (t, J=10.6 Hz, 1H), 1.43 (s, 9H).

Step 2: rac-1-(6-{[Dimethyl(oxo)-$\lambda^6$-sulfanylidene]amino}pyridin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one* rac-tert-Butyl 4-(4-{[1-(6-{[dimethyl(oxo)-$\lambda^6$-sulfanylidene]amino}pyridin-2-yl)-3-oxo-2-(prop-2-en-1-yl)-1H,2H,3H-pyrazolo[3,4-d]pyrimidin-6-yl]amino}phenyl)-2-(trifluoromethyl)piperazine-1-carboxylate (95 mg, 0.138 mmol) was reacted according to General Procedure D, yielding the title compound as a yellow solid (67 mg, 83%).

LCMS (Method C): $R_T$=0.92 min, m/z=588 $[M+H]^+$.

$^1$H NMR (300 MHz, DMSO) δ 10.17 (s, 1H), 8.82 (s, 1H), 7.82 (s, 1H), 7.69-7.53 (m, 2H), 7.30 (d, J=7.8 Hz, 1H), 6.97 (d, J=9.0 Hz, 2H), 6.60 (d, J=8.0 Hz, 1H), 5.79-5.54 (m, 1H), 5.00 (d, J=9.6 Hz, 1H), 4.89 (d, J=17.1 Hz, 1H), 4.75 (s, 2H), 3.66-3.42 (m, 3H), 3.38 (s, 6H), 3.05-2.77 (m, 3H), 2.71-2.59 (m, 2H).

Example 70: 1-(6-{[Dimethyl(oxo)-λ$^6$-sulfanylidene]amino}pyridin-2-yl)-6-[(6-fluoropyridin-3-yl)amino]-2-(prop-2-en-1-yl)-1H,2H,3H-pyrazolo[3,4-d]pyrimidin-3-one*

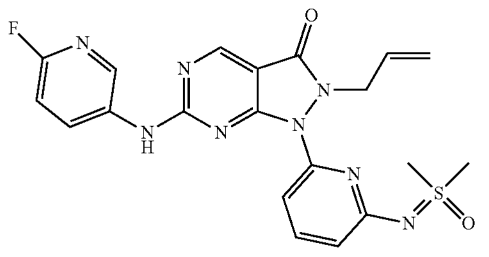 [SMILES: C=CCn1c(=O)c2cnc(Nc3ccc(F)nc3)nc2n1-c1cccc(N=S(C)(C)=O)n1]

Intermediate B (70 mg, 0.179 mmol) was reacted with 6-fluoropyridin-3-amine (20.1 mg, 0.179 mmol) using General Procedure C, yielding the title compound as a beige solid (7 mg, 9%).

LCMS (Method C): $R_T$=1.03 min, m/z=455 $[M+H]^+$.

$^1$H NMR (300 MHz, DMSO) δ 10.42 (s, 1H), 8.90 (s, 1H), 8.50 (s, 1H), 8.42-8.20 (m, 1H), 7.77 (t, J=7.9 Hz, 1H), 7.34-7.09 (m, 2H), 6.61 (d, J=8.0 Hz, 1H), 5.79-5.53 (m, 1H), 4.96 (d, J=10.3 Hz, 1H), 4.82 (d, J=17.1 Hz, 1H), 4.74 (d, J=5.9 Hz, 2H), 3.37 (s, 6H).

Example 71: 4-{[1-(6-{[Dimethyl(oxo)-λ$^6$-sulfanylidene]amino}pyridin-2-yl)-3-oxo-2-(propan-2-yl)-1H,2H,3H-pyrazolo[3,4-d]pyrimidin-6-yl]amino}benzonitrile*

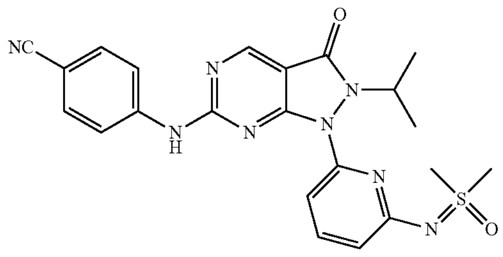 [SMILES: CC(C)n1c(=O)c2cnc(Nc3ccc(C#N)cc3)nc2n1-c1cccc(N=S(C)(C)=O)n1]

Intermediate H (70 mg, 0.194 mmol) was reacted with 4-bromobenzonitrile (35.3 mg, 0.194 mmol) according to General Procedure F, yielding the title compound as a beige solid (64 mg, 71%).

LCMS (Method C): $R_T$=1.18 min, m/z=463 $[M+H]^+$.

1H NMR (300 MHz, DMSO) δ 10.67 (s, 1H), 8.91 (s, 1H), 7.96 (d, J=8.8 Hz, 2H), 7.87 (t, J=7.9 Hz, 1H), 7.76 (d, J=8.8 Hz, 2H), 7.20 (d, J=7.6 Hz, 1H), 6.70 (d, J=8.1 Hz, 1H), 4.34-4.10 (m, 1H), 3.36 (s, 6H), 1.33 (d, J=6.8 Hz, 6H).

Example 72: 1-(6-{[Dimethyl(oxo)-λ$^6$-sulfanylidene]amino}pyridin-2-yl)-2-(propan-2-yl)-6-{[4-(trifluoromethyl)phenyl]amino}-1H,2H,3H-pyrazolo[3,4-d]pyrimidin-3-one*

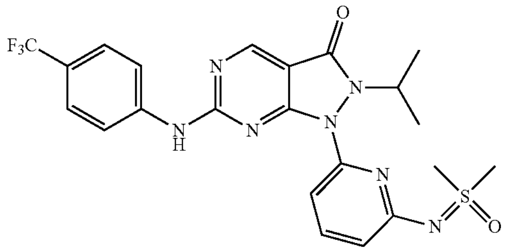 [SMILES: CC(C)n1c(=O)c2cnc(Nc3ccc(C(F)(F)F)cc3)nc2n1-c1cccc(N=S(C)(C)=O)n1]

Intermediate H (40 mg, 0.111 mmol) was reacted with 4-bromobenzonitrile (24.9 mg, 0.111 mmol) according to General Procedure F, yielding the title compound as a beige solid (39 mg, 70%).

LCMS (Method C): $R_T$=1.45 min, m/z=506 $[M+H]^+$.

$^1$H NMR (300 MHz, DMSO) δ 10.58 (s, 1H), 8.89 (s, 1H), 7.97 (d, J=8.6 Hz, 2H), 7.88 (t, J=7.9 Hz, 1H), 7.66 (d, J=8.8 Hz, 2H), 7.22 (d, J=7.6 Hz, 1H), 6.70 (d, J=8.1 Hz, 1H), 4.42-4.04 (m, 1H), 3.36 (s, 6H), 1.33 (d, J=6.8 Hz, 6H).

Example 73: 1-(6-{[Dimethyl(oxo)-λ$^6$-sulfanylidene]amino}pyridin-2-yl)-2-(propan-2-yl)-6-{[3-(trifluoromethyl)phenyl]amino}-1H,2H,3H-pyrazolo[3,4-d]pyrimidin-3-one*

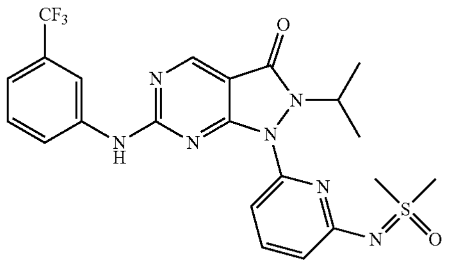 [SMILES: CC(C)n1c(=O)c2cnc(Nc3cccc(C(F)(F)F)c3)nc2n1-c1cccc(N=S(C)(C)=O)n1]

Intermediate H (40 mg, 0.111 mmol) was reacted with 1-bromo-3-(trifluoromethyl)benzene (24.9 mg, 0.111 mmol) according to General Procedure F, yielding the title compound as a beige solid (33 mg, 59%).

LCMS (Method C): $R_T$=1.45 min, m/z=506 $[M+H]^+$.

$^1$H NMR (300 MHz, DMSO) δ 10.55 (s, 1H), 8.88 (s, 1H), 8.33 (s, 1H), 7.85 (d, J=7.4 Hz, 1H), 7.75 (t, J=7.9 Hz, 1H), 7.52 (t, J=8.0 Hz, 1H), 7.34 (d, J=7.9 Hz, 1H), 7.20 (d, J=7.5 Hz, 1H), 6.69 (d, J=8.1 Hz, 1H), 4.36-4.07 (m, 1H), 3.34 (s, 6H), 1.42-1.21 (m, 6H).

Example 74: 1-(6-{[Dimethyl(oxo)-$\lambda^6$-sulfanylidene]amino}pyrazin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one*

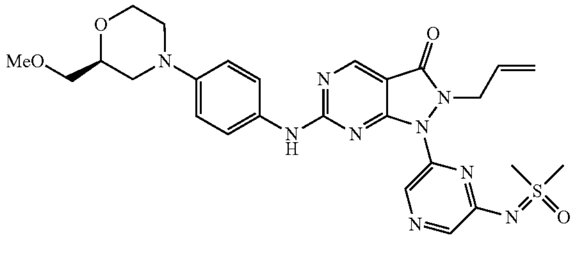 [SMILES: C=CCn1c(=O)c2cnc(Nc3ccc(N4CCO[C@H](COC)C4)cc3)nc2n1-c1cncc(N=S(C)(C)=O)n1]

Step 1: 1-(6-{[Dimethyl(oxo)-$\lambda^6$-sulfanylidene]amino}pyrazin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one*

Intermediate G (50 mg, 0.128 mmol) was reacted with (S)-4-(2-(methoxymethyl)morpholino)aniline (obtained as described above) (28.4 mg, 0.128 mmol) using General Procedure C, yielding the title compound as a yellow solid (39 mg, 54%).

LCMS (Method C): $R_T$=1.02 min, m/z=566 $[M+H]^+$.

$^1$H NMR (300 MHz, DMSO) δ 10.25 (s, 1H), 8.85 (s, 1H), 8.62 (s, 1H), 7.94 (s, 1H), 7.59 (d, J=8.5 Hz, 2H), 6.93 (d, J=9.0 Hz, 2H), 5.78-5.53 (m, 1H), 5.01 (d, J=9.9 Hz, 1H), 4.93 (d, J=16.5 Hz, 1H), 4.73 (d, J=5.9 Hz, 2H), 3.88-4.00 (m, 1H), 3.77-3.60 (m, 4H), 3.58-3.46 (m, 2H), 3.47-3.39 (m, 6H), 3.29 (s, 3H), 2.75-2.64 (m, 1H), 2.46-2.35 (m, 1H).

Example 75: 1-(6-{[Dimethyl(oxo)-$\lambda^6$-sulfanylidene]amino}pyrazin-2-yl)-6-[(4-fluorophenyl)amino]-2-(prop-2-en-1-yl)-1H,2H,3H-pyrazolo[3,4-d]pyrimidin-3-one*

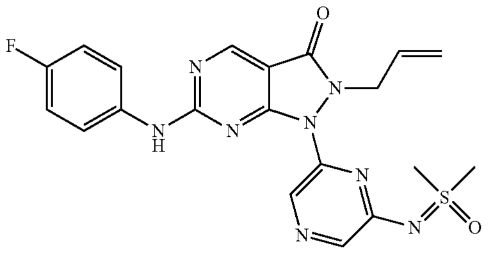 [SMILES: C=CCn1c(=O)c2cnc(Nc3ccc(F)cc3)nc2n1-c1cncc(N=S(C)(C)=O)n1]

Intermediate G (50 mg, 0.128 mmol) was reacted with 4-fluoroaniline (14.2 mg, 0.128 mmol) using General Procedure C, yielding the title compound as a white solid (25 mg, 43%).

LCMS (Method C): $R_T$=1.15 min, m/z=455 $[M+H]^+$.

$^1$H NMR (300 MHz, DMSO) δ 10.36 (s, 1H), 8.91 (s, 1H), 8.60 (s, 1H), 8.04-7.93 (m, 2H), 7.72 (dd, J=9.1, 5.0 Hz, 2H), 7.17 (t, J=8.8 Hz, 2H), 5.78-5.55 (m, 1H), 5.01 (d, J=10.2 Hz, 1H), 4.93 (d, J=17.0 Hz, 1H), 4.74 (d, J=6.0 Hz, 2H), 3.44 (s, 6H).

Example 76: 1-(6-{[Dimethyl(oxo)-$\lambda^6$-sulfanylidene]amino}pyridin-2-yl)-6-({4-[(3S)-3-(methoxymethyl)piperazin-1-yl]phenyl}amino)-2-(prop-2-en-1-yl)-1H,2H, 3H-pyrazolo[3,4-d]pyrimidin-3-one*

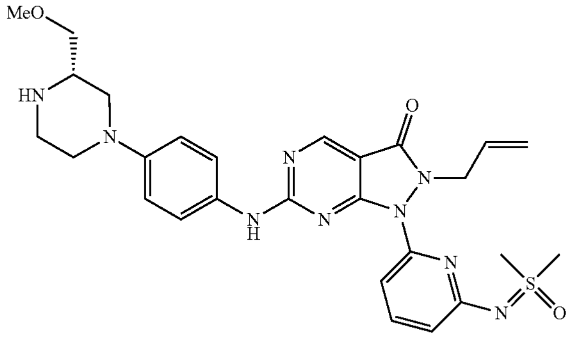 [SMILES: C=CCn1c(=O)c2cnc(Nc3ccc(N4CCN[C@H](COC)C4)cc3)nc2n1-c1cccc(N=S(C)(C)=O)n1]

Step 1: tert-Butyl (2S)-4-(4-{[1-(6-{[dimethyl(oxo)-$\lambda^6$-sulfanylidene]amino}pyridin-2-yl)-3-oxo-2-(prop-2-en-1-yl)-1H,2H,3H-pyrazolo[3,4-d]pyrimidin-6-yl]amino}phenyl)-2-(methoxymethyl)piperazine-1-carboxylate*

Intermediate B (70 mg, 0.179 mmol) was reacted with (S)-tert-butyl 4-(4-aminophenyl)-2-(methoxymethyl)piperazine-1-carboxylate (57.6 mg, 0.179 mmol) using General Procedure C, yielding the title compound as a yellow solid (83 mg, 70%).

LCMS (Method C): $R_T$=1.51 min, m/z=664 $[M+H]^+$.

$^1$H NMR (300 MHz, $CDCl_3$) δ 8.74 (s, 1H), 7.60 (t, J=7.9 Hz, 1H), 7.42 (d, J=8.6 Hz, 2H), 7.28 (d, J=7.8 Hz, 1H), 6.83 (d, J=8.9 Hz, 2H), 6.61 (d, J=8.0 Hz, 1H), 5.71-5.47 (m, 1H), 5.02-4.76 (m, 4H), 4.35-4.12 (m, 1H), 3.99-3.87 (m, 1H), 3.73-3.57 (m, 2H), 3.46-3.35 (m, 2H), 3.32 (d, J=9.3 Hz, 3H), 3.27 (s, 6H), 3.00-3.16 (m, 1H), 2.82-2.62 (m, 2H), 1.43 (s, 9H).

Step 2: 1-(6-{[Dimethyl(oxo)-$\lambda^6$-sulfanylidene]amino}pyridin-2-yl)-6-({4-[(3S)-3-(methoxymethyl)piperazin-1-yl]phenyl}amino)-2-(prop-2-en-1-yl)-1H,2H,3H-pyrazolo[3,4-d]pyrimidin-3-one* tert-Butyl (2S)-4-(4-{[1-(6-{[dimethyl(oxo)-$\lambda^6$-sulfanylidene]amino}pyridin-2-yl)-3-oxo-2-(prop-2-en-1-yl)-1H,2H,3H-pyrazolo[3,4-d]pyrimidin-6-yl]amino}phenyl)-2-(methoxymethyl)piperazine-1-carboxylate (80 mg, 0.121 mmol) was reacted according to General Procedure D, yielding the title compound as a yellow solid (41 mg, 60%).

LCMS (Method C): $R_T$=0.98 min, m/z=564 $[M+H]^+$.

$^1$H NMR (300 MHz, DMSO) δ 10.13 (s, 1H), 8.81 (s, 1H), 7.91-7.70 (m, 1H), 7.68-7.48 (m, 2H), 7.30 (d, J=7.8 Hz, 1H), 6.91 (d, J=9.0 Hz, 2H), 6.60 (d, J=8.0 Hz, 1H), 5.78-5.53 (m, 1H), 5.00 (d, J=10.4 Hz, 1H), 4.89 (d, J=17.2 Hz, 1H), 4.75 (s, 2H), 3.48 (t, J=10.0 Hz, 2H), 3.38 (s, 6H), 3.34-3.30 (m, 2H), 3.29 (s, 3H), 3.03-2.90 (m, 2H), 2.86-2.75 (m, 1H), 2.65-2.54 (m, 1H), 2.37-2.22 (m, 1H).

Example 77: 1-(6-{[Dimethyl(oxo)-λ$^6$-sulfanylidene]amino}pyridin-2-yl)-2-(prop-2-en-1-yl)-6-[(pyridin-3-yl)amino]-1H,2H,3H-pyrazolo[3,4-d]pyrimidin-3-one*

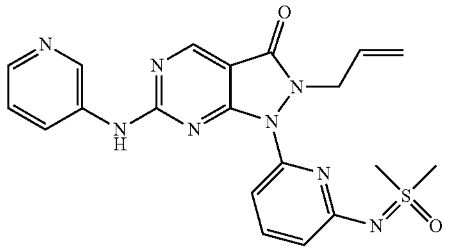 [SMILES: C=CCn1c(=O)c2cnc(Nc3cccnc3)nc2n1-c1cccc(N=S(C)(C)=O)n1]

Intermediate 1 (40 mg, 0.111 mmol) was reacted with 4-bromopyridine (17.6 mg, 0.111 mmol) according to General Procedure F, yielding the title compound as a white solid (11 mg, 23%).

LCMS (Method C): $R_T$=0.80 min, m/z=437 $[M+H]^+$.

$^1$H NMR (300 MHz, DMSO) δ 8.79 (s, 1H), 8.62 (d, J=2.4 Hz, 1H), 8.42 (dd, J=4.7, 1.2 Hz, 1H), 7.83 (d, J=9.0 Hz, 1H), 7.65-7.37 (m, 3H), 6.44 (d, J=7.7 Hz, 1H), 6.11-5.88 (m, 1H), 5.29-5.06 (m, 2H), 4.75 (d, J=5.1 Hz, 2H), 3.44 (s, 6H).

Example 78: 6-[(1-Methyl-1H-pyrazol-4-yl)amino]-1-{6-[(1-oxo-1λ$^6$-thiolan-1-ylidene)amino]pyridin-2-yl}-2-(prop-2-en-1-yl)-1H,2H,3H-pyrazolo[3,4-d]pyrimidin-3-one*

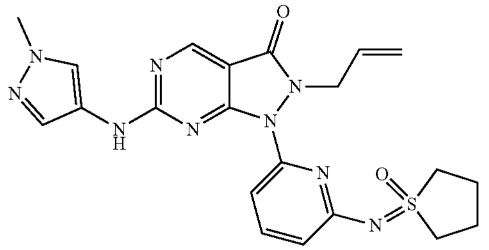 [SMILES: C=CCn1c(=O)c2cnc(Nc3cnn(C)c3)nc2n1-c1cccc(N=S2(=O)CCCC2)n1]

Intermediate E (50 mg, 0.120 mmol) was reacted with 1-methyl-1H-pyrazol-4-amine (11.7 mg, 0.120 mmol) according to General Procedure C, yielding the title compound as a white solid (41 mg, 74%).

LCMS (Method C): $R_T$=0.90 min, m/z=466 $[M+H]^+$.

$^1$H NMR (300 MHz, DMSO) δ 10.30 (s, 1H), 8.78 (s, 1H), 7.96-7.69 (m, 2H), 7.60-7.46 (m, 1H), 7.31 (d, J=7.7 Hz, 1H), 6.70 (d, J=7.9 Hz, 1H), 5.80-5.51 (m, 1H), 5.00 (d, J=10.3 Hz, 1H), 4.88 (d, J=16.2 Hz, 1H), 4.71 (d, J=5.8 Hz, 2H), 3.81 (s, 3H), 3.61-3.45 (m, 2H), 3.33-3.18 (m, 2H), 2.25-1.93 (m, 4H).

Example 79: 1-(6-{[(S)-Methyl(oxo)phenyl-λ$^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one*

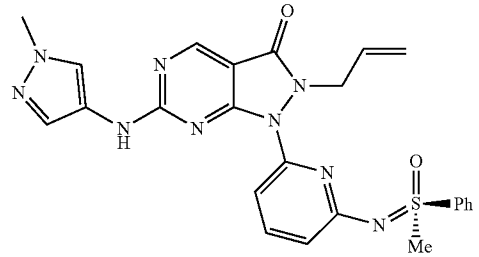 [SMILES: C=CCn1c(=O)c2cnc(Nc3cnn(C)c3)nc2n1-c1cccc(N=[S@@](C)(=O)c2ccccc2)n1]

Step 1: (S)-[(6-Bromopyridin-2-yl)imino]methyl)phenyl-λ$^6$-sulfanone*

$Pd_2(dba)_3$ (58.0 mg, 0.063 mmol) and Xantphos (81 mg, 0.139 mmol) were added to a pre-degassed suspension of 2,6-dibromopyridine (300 mg, 1.27 mmol), $Cs_2CO_3$ (1240 mg, 3.80 mmol), (S)—(S-methylsulfonimidoyl)benzene (197 mg, 1.27 mmol) in 1,4-dioxane (5 mL). The temperature was increased to 100° C. and the reaction was stirred intensively for 6 h. LCMS showed complete conversion to product. The reaction mixture was filtered through Celite and the filtrate was evaporated under reduced pressure. The residue was purified by flash chromatography (15-100% EtOAc in cyclohexane). The product containing fractions were evaporated under reduced pressure yielding the title compound as a beige solid (283 mg, 72% yield).

LCMS (Method C): $R_T$=1.32 min, m/z=311, 313 $[M+H]^+$.

$^1$H NMR (300 MHz, $CDCl_3$) δ 8.00-7.91 (m, 2H), 7.68-7.43 (m, 3H), 7.23 (d, J=7.9 Hz, 1H), 6.84 (d, J=7.6 Hz, 1H), 6.68 (d, J=8.0 Hz, 1H), 3.36 (s, 3H).

Step 2: 1-(6-{[(S)-Methyl(oxo)phenyl-λ$^6$-sulfanylidene]amino}pyridin-2-yl)-6-(methylsulfanyl)-2-(prop-2-en-1-yl)-1H,2H,3H-pyrazolo[3,4-d]pyrimidin-3-one*

To a 25 mL reactor were added 2-allyl-6-(methylthio)-1H-pyrazolo[3,4-d]pyrimidin-3(2H)-one (202 mg, 0.909 mmol) (obtained according to EP2213673B1, Production Example 1, p 37), (S)-[(6-bromopyridin-2-yl)imino](methyl)phenyl-λ$^6$-sulfanone (283 mg, 0.909 mmol), $K_2CO_3$ (277 mg, 2.001 mmol) and dioxane (4 mL). The resultant suspension was flushed with nitrogen and copper (I) iodide (173 mg, 0.909 mmol) was added followed by $N^1$,$N^2$-dimethylethane-1,2-diamine (0.098 mL, 0.909 mmol). The reactor was capped and the temperature was increased to 95° C. After 18 h of intensive stirring, LCMS confirmed accomplished conversion. The reaction mixture was cooled to RT, $NH_4OH$ (aq) was added (5 mL) followed by water (5 mL) and the reaction mixture was extracted using EtOAc (3×50 mL), the organic phases were combined, dried (anh. $MgSO_4$) and evaporated under reduced pressure. The residue was purified using flash chromatography (0-20% MeOH in EtOAc). The product containing fractions were concentrated to give the title compound (269 mg, 65% yield) as a white solid.

LCMS (Method C): $R_T$=1.32 min, m/z=453 $[M+H]^+$.

$^1$H NMR (300 MHz, $CDCl_3$) δ 8.84 (s, 1H), 7.95 (dd, J=7.7, 1.6 Hz, 2H), 7.65 (t, J=7.9 Hz, 1H), 7.60-7.42 (m, 3H), 7.31-7.26 (m, 1H), 6.79 (d, J=8.0 Hz, 1H), 5.63-5.42 (m, 1H), 4.95 (d, J=9.5 Hz, 1H), 4.85 (d, J=18.0 Hz, 1H), 4.74 (dd, J=15.9, 6.3 Hz, 1H), 4.53 (dd, J=15.9, 6.2 Hz, 1H), 3.33 (s, 3H), 2.54 (s, 3H).

Step 3: 1-(6-{[(S)-Methyl(oxo)phenyl-$\lambda^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one*

In a 5 mL microwave reactor vial were added 1-(6-{[(S)-methyl(oxo)phenyl-$\lambda^6$-sulfanylidene]amino}pyridin-2-yl)-6-(methylsulfanyl)-2-(prop-2-en-1-yl)-1H,2H,3H-pyrazolo[3,4-d]pyrimidin-3-one (50 mg, 0.110 mmol), DCM (1 mL) and toluene (1 mL). mCPBA (<70% pure) (30 mg, 0.122 mmol) was added and the reaction mixture was stirred for 30 min. at RT. Next 1-methyl-1H-pyrazol-4-amine (10.7 mg, 0.110 mmol) and DIPEA (0.058 mL, 0.331 mmol) were added and the reaction mixture was heated at 65° C. under a nitrogen atmosphere overnight. The product was purified by flash chromatography (0-5% MeOH in EtOAc). The product containing fractions were evaporated in vacuo yielding the title compound as a white solid (46 mg, 83%).

LCMS (Method C): $R_T$=1.01 min, m/z=502 $[M+H]^+$.

$^1$H NMR (300 MHz, DMSO) δ 10.28 (s, 1H), 8.73 (s, 1H), 8.04-7.70 (m, 4H), 7.70-7.52 (m, 3H), 7.50 (s, 1H), 7.23 (d, J=7.8 Hz, 1H), 6.78 (d, J=8.1 Hz, 1H), 5.61-5.26 (m, 1H), 4.92 (d, J=10.6 Hz, 1H), 4.78-4.60 (m, 1H), 4.33 (dd, J=16.4, 5.4 Hz, 1H), 3.89 (dd, J=16.1, 6.3 Hz, 1H), 3.80 (s, 3H), 3.46 (s, 3H).

Example 80: 1-(6-{[Dimethyl(oxo)-$\lambda^6$-sulfanylidene]amino}pyridin-2-yl)-2-(prop-2-en-1-yl)-6-{[1-(propan-2-yl)-1H-pyrazol-4-yl]amino}-1H,2H,3H-pyrazolo[3,4-d]pyrimidin-3-one*

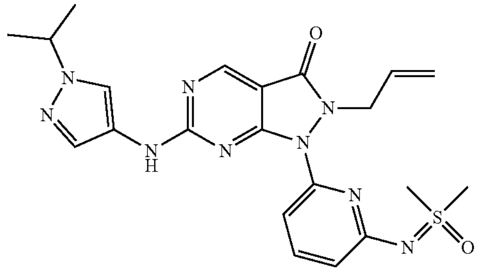 [SMILES: C=CCn1c(=O)c2cnc(Nc3cnn(C(C)C)c3)nc2n1-c1cccc(N=S(C)(C)=O)n1]

Intermediate B (70 mg, 0.179 mmol) was reacted with 1-isopropyl-1H-pyrazol-4-amine (22.4 mg, 0.179 mmol) using General Procedure C, yielding the title compound as a white solid (58 mg, 69%).

LCMS (Method C): $R_T$=0.99 min, m/z=468 $[M+H]^+$.

$^1$H NMR (300 MHz, DMSO) δ 10.38 (s, 1H), 8.79 (s, 1H), 7.97 (s, 1H), 7.79 (t, J=7.9 Hz, 1H), 7.52 (s, 1H), 7.30 (d, J=7.8 Hz, 1H), 6.64 (d, J=8.0 Hz, 1H), 5.77-5.55 (m, 1H), 5.00 (d, J=9.9 Hz, 1H), 4.87 (d, J=17.0 Hz, 1H), 4.70 (d, J=5.6 Hz, 2H), 4.52-4.34 (m, 1H), 3.37 (s, 6H), 1.40 (d, J=6.6 Hz, 6H).

Example 81: 1-(6-{[Dimethyl(oxo)-$\lambda^6$-sulfanylidene]amino}pyridin-2-yl)-2-(prop-2-en-1-yl)-6-{[6-(trifluoromethyl)pyridin-3-yl]amino}-1H,2H,3H-pyrazolo[3,4-d]pyrimidin-3-one*

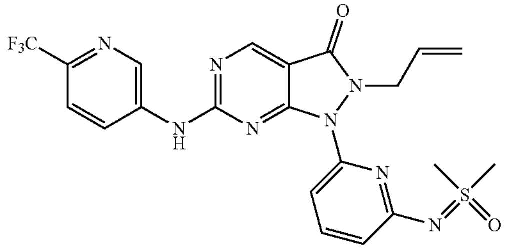 [SMILES: C=CCn1c(=O)c2cnc(Nc3ccc(C(F)(F)F)nc3)nc2n1-c1cccc(N=S(C)(C)=O)n1]

Intermediate 1 (40 mg, 0.111 mmol) was reacted with 5-bromo-2-(trifluoromethyl)pyridine (25.2 mg, 0.111 mmol) according to General Procedure F, yielding the title compound as a white solid (33 mg, 59%).

LCMS (Method C): $R_T$=1.25 min, m/z=505 $[M+H]^+$.

$^1$H NMR (300 MHz, DMSO) δ 10.82 (s, 1H), 9.11-8.92 (m, 2H), 8.59-8.48 (m, 1H), 7.95-7.79 (m, 2H), 7.27 (d, J=7.8 Hz, 1H), 6.65 (d, J=8.0 Hz, 1H), 5.75-5.57 (m, 1H), 5.01 (d, J=10.4 Hz, 1H), 4.89 (d, J=18.3 Hz, 1H), 4.76 (d, J=5.9 Hz, 2H), 3.38 (s, 6H).

Example 82: 1-(6-{[Dimethyl(oxo)-$\lambda^6$-sulfanylidene]amino}pyridin-2-yl)-6-[(4-fluoro-3-methoxyphenyl)amino]-2-(prop-2-en-1-yl)-1H,2H,3H-pyrazolo[3,4-d]pyrimidin-3-one*

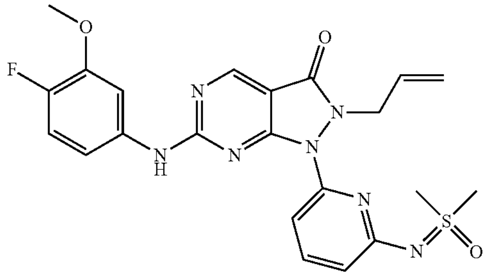 [SMILES: C=CCn1c(=O)c2cnc(Nc3ccc(F)c(OC)c3)nc2n1-c1cccc(N=S(C)(C)=O)n1]

Intermediate 1 (40 mg, 0.111 mmol) was reacted with 4-bromo-1-fluoro-2-methoxybenzene (22.8 mg, 0.111 mmol) according to General Procedure F, yielding the title compound as a white solid (5 mg, 10%).

LCMS (Method C): $R_T$=1.23 min, m/z=484 $[M+H]^+$.

$^1$H NMR (300 MHz, DMSO) δ 10.26 (s, 1H), 8.89 (s, 1H), 7.75 (t, J=7.9 Hz, 1H), 7.64-7.55 (m, 1H), 7.34-7.08 (m, 3H), 6.62 (d, J=7.9 Hz, 1H), 5.74-5.55 (m, 1H), 5.00 (d, J=10.1 Hz, 1H), 4.89 (d, J=17.1 Hz, 1H), 4.70 (d, J=5.8 Hz, 2H), 3.74 (s, 3H), 3.36 (s, 6H).

Example 83: rac-1-(6-{[Dimethyl(oxo)-$\lambda^6$-sulfanylidene]amino}pyridin-2-yl)-6-{[4-(dimethylamino)-3-(2,2,2-trifluoro-1-hydroxyethyl)phenyl]amino}-2-(prop-2-en-1-yl)-1H,2H,3H-pyrazolo[3,4-d]pyrimidin-3-one*

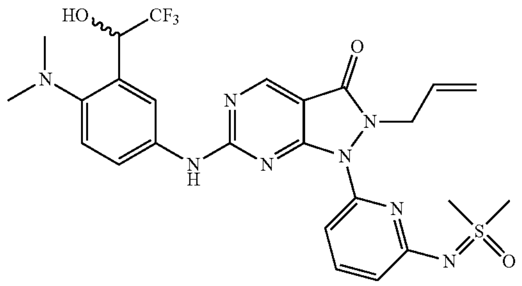 [SMILES: C=CCn1c(=O)c2cnc(Nc3ccc(N(C)C)c(C(O)C(F)(F)F)c3)nc2n1-c1cccc(N=S(C)(C)=O)n1]

Step 1: rac-1-(2-(dimethylamino)-5-nitrophenyl)-2,2,2-trifluoroethanol

A solution of 2-fluoro-5-nitrobenzaldehyde (0.5 g, 2.96 mmol) and trimethyl(trifluoromethyl)silane (0.61 mL, 4.14 mmol) in THF (6 mL) was chilled in an ice bath under $N_2$ atmosphere. Next 1M tetrabutyl ammonium fluoride in THF (0.10 mL, 0.10 mmol) was added dropwise and the reaction mixture was stirred at RT for 1 h. Then 2M dimethylamine in THF (4.40 mL, 8.87 mmol) was added and the reaction mixture was stirred at 40° C. overnight. The volatiles were removed under reduced pressure and the product was purified by flash chromatography (15-100% EtOAc in cyclohexane). The product containing fractions were evaporated under reduced pressure yielding the title compound as a brown oil (144 mg, 18%).

LCMS (Method C): $R_T$=1.41 min, m/z=265 $[M+H]^+$.

$^1H$ NMR (300 MHz, $CDCl_3$) δ 8.22-8.13 (m, 2H), 7.46 (d, J=8.8 Hz, 1H), 5.23 (q, J=7.1 Hz, 1H), 2.72 (s, 6H).

Step 2: rac-1-(5-Amino-2-(dimethylamino)phenyl)-2,2,2-trifluoroethanol

A stirring solution of 1-(2-(dimethylamino)-5-nitrophenyl)-2,2,2-trifluoroethanol (140 mg, 0.530 mmol) in EtOH (5 mL) was heated to 50° C. 10% Pd/C (39.5 mg, 0.037 mmol) was added followed by ammonium formate (200 mg, 3.18 mmol) and the suspension stirred for 10-20 min. The suspension was filtered through Celite washing with fresh ethanol. The solvent was removed in vacuo and the resulting residue was purified by flash chromatography (0-100% EtOAc in DCM) to afford the title compound (79 mg, 64%) as brownish solid.

LCMS (Method D): $R_T$=0.73 min, m/z=235 $[M+H]^+$.

$^1H$ NMR (300 MHz, $CDCl_3$) δ 10.22 (bs, 1H), 7.15 (d, J=8.6 Hz, 1H), 6.73-6.51 (m, 1H), 6.38 (s, 1H), 4.89 (q, J=7.5 Hz, 1H), 2.70-2.48 (m, 6H).

Step 3: rac-1-(6-{[Dimethyl(oxo)-$\lambda^6$-sulfanylidene]amino}pyridin-2-yl)-6-{[4-(dimethylamino)-3-(2,2,2-trifluoro-1-hydroxyethyl)phenyl]amino}-2-(prop-2-en-1-yl)-1H,2H,3H-pyrazolo[3,4-d]pyrimidin-3-one*

Intermediate B (70 mg, 0.179 mmol) was reacted with rac-1-(5-amino-2-(dimethylamino)phenyl)-2,2,2-trifluoroethanol (42 mg, 0.179 mmol) according to General Procedure C, yielding the title compound as a white solid (12 mg, 12%).

LCMS (Method C): $R_T$=0.99 min, m/z=577 $[M+H]^+$.

$^1H$ NMR (300 MHz, DMSO) δ 10.31 (s, 1H), 8.86 (s, 1H), 8.04 (s, 1H), 7.88-7.62 (m, 2H), 7.35 (dd, J=8.2, 6.2 Hz, 2H), 6.94 (s, 1H), 6.59 (d, J=8.0 Hz, 1H), 5.83-5.49 (m, 2H), 5.00 (d, J=10.1 Hz, 1H), 4.88 (d, J=17.2 Hz, 1H), 4.77 (d, J=6.0 Hz, 2H), 3.37 (s, 6H), 2.58 (s, 6H).

Example 84: 6-[(3,5-Difluorophenyl)amino]-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one*

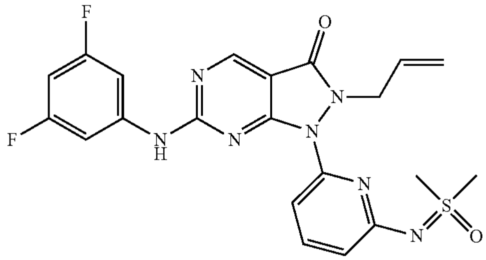 [SMILES: C=CCn1c(=O)c2cnc(Nc3cc(F)cc(F)c3)nc2n1-c1cccc(N=S(C)(C)=O)n1]

Intermediate 1 (40 mg, 0.111 mmol) was reacted with 1-bromo-3,5-difluorobenzene (21.5 mg, 0.111 mmol) according to General Procedure F, yielding the title compound as a white solid (8 mg, 15%).

LCMS (Method C): $R_T$=1.38 min, m/z=472 $[M+H]^+$.

$^1H$ NMR (300 MHz, DMSO) δ 10.63 (s, 1H), 8.97 (s, 1H), 7.74 (t, J=8.0 Hz, 1H), 7.57 (d, J=8.3 Hz, 2H), 7.28 (d, J=8.0 Hz, 1H), 6.86 (t, J=9.0 Hz, 1H), 6.65 (d, J=8.0 Hz, 1H), 5.80-5.50 (m, 1H), 5.01 (d, J=10.8, 1H), 4.89 (d, J=17.0, 1H), 4.76 (d, J=5.3 Hz, 2H), 3.38 (s, 6H).

Example 85: 1-(6-{[Dimethyl(oxo)-$\lambda^6$-sulfanylidene]amino}pyridin-2-yl)-2-(prop-2-en-1-yl)-6-{[1-(2,2,2-trifluoroethyl)-1H-pyrazol-4-yl]amino}-1H,2H,3H-pyrazolo[3,4-d]pyrimidin-3-one*

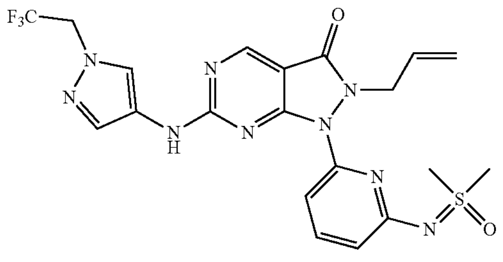 [SMILES: C=CCn1c(=O)c2cnc(Nc3cnn(CC(F)(F)F)c3)nc2n1-c1cccc(N=S(C)(C)=O)n1]

Intermediate B (50 mg, 0.128 mmol) was reacted with 1-(2,2,2-trifluoroethyl)-1H-pyrazol-4-amine (21.1 mg, 0.128 mmol) according to General Procedure C, yielding the title compound as a white solid (29 mg, 45%).

LCMS (Method C): $R_T$=1.06 min, m/z=508 $[M+H]^+$.

$^1H$ NMR (300 MHz, DMSO) δ 10.46 (s, 1H), 8.77 (s, 1H), 8.15 (s, 1H), 7.84 (t, J=7.9 Hz, 1H), 7.72 (s, 1H), 7.31 (d, J=7.7 Hz, 1H), 6.67 (d, J=8.0 Hz, 1H), 5.78-5.59 (m, 1H), 5.30-5.11 (m, 2H), 5.00 (d, J=10.5 Hz, 1H), 4.87 (d, J=17.1 Hz, 1H), 4.86-4.63 (m, 2H), 3.42 (s, 6H).

Example 86: rac-1-(6-{[Dimethyl(oxo)-$\lambda^6$-sulfanylidene]amino}pyridin-2-yl)-6-({3-methoxy-4-[3-(trifluoromethyl)piperazin-1-yl]phenyl}amino)-2-(prop-2-en-1-yl)-1H,2H,3H-pyrazolo[3,4-d]pyrimidin-3-one*

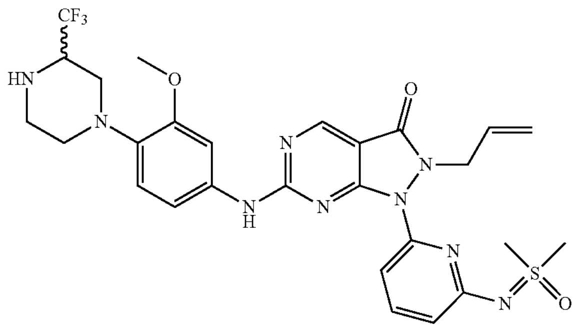 [SMILES: C=CCn1c(=O)c2cnc(Nc3ccc(N4CCNC(C(F)(F)F)C4)c(OC)c3)nc2n1-c1cccc(N=S(C)(C)=O)n1]

Step 1: rac-1-(2-Methoxy-4-nitrophenyl)-3-(trifluoromethyl)piperazine

To a stirring suspension of 1-fluoro-2-methoxy-4-nitrobenzene (1.11 g, 6.49 mmol) and $K_2CO_3$ (4.93 g, 35.7 mmol) in anhydrous DMF (6 mL) was added rac-2-(trifluoromethyl)piperazine (1.00 g, 6.49 mmol) and the mixture heated at 65° C. overnight. LCMS showed accomplished conversion. The reaction mixture was transferred to a separatory funnel and 50 mL of EtOAc was added. The mixture was washed with brine (2×50 mL). The organic layer was dried (anh. $MgSO_4$) and evaporated under reduced pressure. The residue was purified by flash chromatography (15-100% EtOAc in cyclohexane). The product containing fractions were evaporated under reduced pressure yielding the title compound as a yellow solid (1.52 g, 77%).

LCMS (Method C): $R_T$=1.05 min, m/z=306 $[M+H]^+$.

$^1$H NMR (300 MHz, $CDCl_3$) δ 7.88 (dd, J=8.8, 2.5 Hz, 1H), 7.73 (d, J=2.5 Hz, 1H), 6.91 (d, J=8.8 Hz, 1H), 3.96 (s, 3H), 3.85-3.69 (m, 1H), 3.65-3.39 (m, 2H), 3.30-3.03 (m, 2H), 2.97-2.77 (m, 2H).

Step 2: rac-tert-Butyl 4-(2-methoxy-4-nitrophenyl)-2-(trifluoromethyl)piperazine-1-carboxylate In a 100 mL round-bottomed flask was added rac-1-(2-methoxy-4-nitrophenyl)-3-(trifluoromethyl)piperazine (1.52 g, 4.98 mmol) in DCM (30 mL) to give a yellow solution. Next $Boc_2O$ (2.72 g, 12.45 mmol), DIPEA (2.17 mL, 12.45 mmol) and DMAP (0.152 g, 1.24 mmol) were added and the resulting mixture stirred at room temperature overnight. LCMS analysis showed ~50% conversion. An additional batch of $Boc_2O$ (3.80 g, 17.41 mmol), DIPEA (2.17 mL, 12.45 mmol) and of DMAP (50 mg, 0.41 mmol) were added and the reaction was stirred overnight. LCMS showed 80% conversion. $Boc_2O$ (3.8 g, 17.41 mmol), DIPEA (2.17 mL, 12.45 mmol) and DMAP (100 mg, 0.82 mmol) were added again and the reaction mixture was stirred at RT overnight, but no further progress of the reaction was noticed. The volatiles were evaporated under reduced pressure. The residue was dissolved in EtOAc (50 mL) and washed with brine (3×50 mL). The organic layer was dried (anh. $MgSO_4$) and evaporated under reduced pressure. The product was purified by flash chromatography (15% EtOAc in cyclohexane). The product containing fractions were evaporated under reduced pressure, yielding the title compound as a yellow oil (1.46 g, 72%).

LCMS (Method C): $R_T$=1.92 min, m/z=406 $[M+H]^+$.

$^1$H NMR (300 MHz, $CDCl_3$) δ 7.86 (dd, J=8.8, 2.5 Hz, 1H), 7.72 (d, J=2.5 Hz, 1H), 6.85 (d, J=8.8 Hz, 1H), 4.97-4.43 (m, 1H), 4.38-4.05 (m, 2H), 3.94 (s, 3H), 3.62-3.22 (m, 2H), 3.03-2.73 (m, 2H), 1.50 (s, 9H).

Step 3: rac-tert-Butyl 4-(4-amino-2-methoxyphenyl)-2-(trifluoromethyl)piperazine-1-carboxylate A stirring solution of rac-tert-butyl 4-(2-methoxy-4-nitrophenyl)-2-(trifluoromethyl)piperazine-1-carboxylate (1.46 g, 3.60 mmol) in ethanol (60 mL) was heated to 50° C. 10% Pd/C (0.27 g, 0.252 mmol) was added followed by portion-wise addition of ammonium formate (1.36 g, 21.61 mmol) and the suspension stirred for 10-20 min. until intensive gas evolution. The suspension was filtered through Celite washing with fresh ethanol. The ethanol was removed in vacuo. The resulting residue was purified by flash chromatography (20-100% EtOAc in cyclohexane) to afford the title compound as a brownish oil (1.14 g, 84% yield).

LCMS (Method C): $R_T$=1.22 min, m/z=376 $[M+H]^+$.

$^1$H NMR (300 MHz, $CDCl_3$) δ 6.72 (d, J=8.2 Hz, 1H), 6.36-6.15 (m, 2H), 4.92-4.39 (m, 1H), 4.31-4.00 (m, 1H), 3.83 (s, 3H), 3.77 (d, J=12.5 Hz, 1H), 3.60-3.28 (m, 2H), 3.23-3.05 (m, 1H), 2.91-2.72 (m, 1H), 2.74-2.57 (m, 1H), 1.51 (s, 9H).

Step 4: rac-tert-Butyl 4-(4-{[1-(6-{[dimethyl(oxo)-$\lambda^6$-sulfanylidene]amino}pyridin-2-yl)-3-oxo-2-(prop-2-en-1-yl)-1H,2H,3H-pyrazolo[3,4-d]pyrimidin-6-yl]amino}-2-methoxyphenyl)-2-(trifluoromethyl)piperazine-1-carboxylate*

Intermediate B (100 mg, 0.256 mmol) was reacted with rac-tert-butyl 4-(4-amino-2-methoxyphenyl)-2-(trifluoromethyl)piperazine-1-carboxylate (96 mg, 0.256 mmol) according to General Procedure C, yielding the title compound as a yellow solid (76 mg, 41%).

LCMS (Method C): $R_T$=1.72 min, m/z=718 $[M+H]^+$.

$^1$H NMR (300 MHz, $CDCl_3$) δ 8.83 (s, 1H), 7.64 (t, J=7.9 Hz, 1H), 7.44 (s, 1H), 7.29 (d, J=7.8 Hz, 1H), 7.04 (dd, J=8.5, 2.3 Hz, 1H), 6.82 (d, J=8.5 Hz, 1H), 6.69 (d, J=8.0 Hz, 1H), 5.73-5.56 (m, 1H), 5.06-4.79 (m, 4H), 4.65-4.44 (m, 1H), 4.22-4.06 (m, 1H), 3.90 (d, J=13.2 Hz, 1H), 3.80 (s, 3H), 3.54-3.36 (m, 1H), 3.33 (s, 6H), 3.29-3.16 (m, 1H), 2.93-2.75 (m, 1H), 2.74-2.59 (m, 1H), 1.50 (s, 9H).

Step 5: rac-1-(6-{[Dimethyl(oxo)-$\lambda^6$-sulfanylidene]amino}pyridin-2-yl)-6-({3-methoxy-4-[3-(trifluoromethyl)piperazin-1-yl]phenyl}amino)-2-(prop-2-en-1-34)-1H,2H,3H-pyrazolo[3,4-d]pyrimidin-3-one* rac-tert-Butyl 4-(4-{[1-(6-{[dimethyl(oxo)-$\lambda^6$-sulfanylidene]amino}pyridin-2-yl)-3-oxo-2-(prop-2-en-1-yl)-1H,2H,3H-pyrazolo[3,4-d]pyrimidin-6-yl]amino}-2-methoxyphenyl)-2-(trifluoromethyl)piperazine-1-carboxylate (76 mg, 0.106 mmol) was reacted according to General Procedure D, yielding the title compound as a yellow solid (47 mg, 72%).

LCMS (Method C): $R_T$=0.91 min, m/z=618 $[M+H]^+$.

$^1$H NMR (300 MHz, DMSO) δ 10.16 (bs, 1H), 8.85 (s, 1H), 7.76 (t, J=7.9 Hz, 1H), 7.40 (s, 1H), 7.35-7.16 (m, 2H), 6.89 (d, J=8.6 Hz, 1H), 6.62 (d, J=8.0 Hz, 1H), 5.76-5.53 (m,

1H), 5.00 (d, J=10.3 Hz, 1H), 4.89 (d, J=18.1 Hz, 1H), 4.69 (d, J=5.7 Hz, 2H), 3.70 (s, 3H), 3.58-3.45 (m, 1H), 3.36 (s, 6H), 3.32-3.26 (m, 1H), 3.17-3.05 (m, 1H), 3.04-2.94 (m, 1H), 2.92-2.78 (m, 1H), 2.69-2.56 (m, 2H).

Example 87: rac-1-(6-{[Dimethyl(oxo)-λ[6]-sulfanylidene]amino}pyridin-2-yl)-6-({3-methoxy-4-[4-methyl-3-(trifluoromethyl)piperazin-1-yl]phenyl}amino)-2-(prop-2-en-1-yl)-1H,2H,3H-pyrazolo[3,4-d]pyrimidin-3-one*

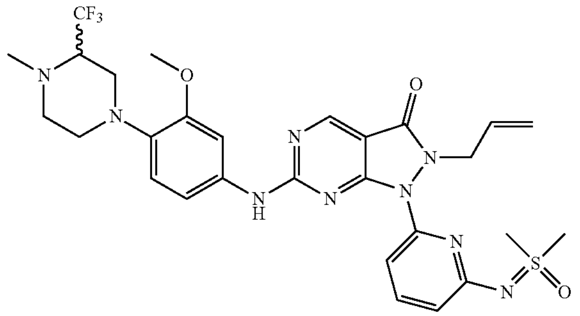 [SMILES: C=CCn1c(=O)c2cnc(Nc3ccc(N4CCN(C)C(C(F)(F)F)C4)c(OC)c3)nc2n1-c1cccc(N=S(C)(C)=O)n1]

In a 5 mL reaction vial was added rac-1-(6-{[dimethyl(oxo)-λ[6]-sulfanylidene]amino}pyridin-2-yl)-6-({3-methoxy-4-[3-(trifluoromethyl)piperazin-1-yl]phenyl}amino)-2-(prop-2-en-1-yl)-1H,2H,3H-pyrazolo[3,4-d]pyrimidin-3-one (obtained as described above) (30 mg, 0.049 mmol) followed by acetonitrile (1 mL) and 37% formaldehyde in water (0.036 mL, 0.486 mmol). Next sodium triacetoxyborohydride (103 mg, 0.486 mmol) was added and the mixture stirred overnight at room temperature. The reaction mixture was quenched with MeOH and evaporated under reduced pressure. The residue was suspended in DCM and transferred to a prewashed SCX-2 (2 g) cartridge. The compound on the resin was washed with 20% MeOH/DCM and next the product was eluted with 20% 7N $NH_3$ in MeOH/DCM.

The product containing fraction was evaporated under reduced pressure and purified by flash chromatography (0-15% of MeOH in DCM) yielding the title compound as a yellow solid (21 mg, 68%).

LCMS (Method C): $R_T$=1.26 min, m/z=632 $[M+H]^+$.

$^1$H NMR (300 MHz, DMSO) δ 10.16 (s, 1H), 8.85 (s, 1H), 7.76 (t, J=7.9 Hz, 1H), 7.40 (s, 1H), 7.33-7.19 (m, 2H), 6.88 (d, J=8.6 Hz, 1H), 6.62 (d, J=8.0 Hz, 1H), 5.76-5.52 (m, 1H), 5.00 (d, J=10.6 Hz, 1H), 4.89 (d, J=18.2 Hz, 1H), 4.69 (d, J=6.0 Hz, 2H), 3.69 (s, 3H), 3.36 (s, 6H), 3.24-3.11 (m, 2H), 3.08-2.81 (m, 4H), 2.62-2.53 (m, 1H), 2.44 (s, 3H).

Example 88: 6-{[4-(1-Cyclobutylpiperidin-4-yl)-3-methylphenyl]amino}-1-(6-{[dimethyl(oxo)-λ[6]-sulfanylidene]amino}pyridin-2-yl)-2-(prop-2-en-1-yl)-1H,2H,3H-pyrazolo[3,4-d]pyrimidin-3-one*

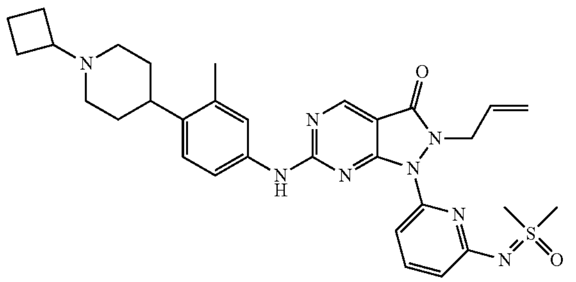 [SMILES: C=CCn1c(=O)c2cnc(Nc3ccc(C4CCN(C5CCC5)CC4)c(C)c3)nc2n1-c1cccc(N=S(C)(C)=O)n1]

Step 1: tert-Butyl 4-(4-{[1-(6-{[dimethyl(oxo)-λ[6]-sulfanylidene]amino}pyridin-2-yl)-3-oxo-2-(prop-2-en-1-yl)-1H,2H,3H-pyrazolo[3,4-d]pyrimidin-6-yl]amino}-2-methylphenyl)piperidine-1-carboxylate*

Intermediate B (70 mg, 0.179 mmol) was reacted with tert-butyl 4-(4-amino-2-methylphenyl)piperidine-1-carboxylate (52.1 mg, 0.179 mmol) according to General Procedure C, yielding the title compound as a clear oil (74 mg, 65%).

LCMS (Method C): $R_T$=1.69 min, m/z=633 $[M+H]^+$.

$^1$H NMR (300 MHz, $CDCl_3$) δ 8.83 (s, 1H), 7.69 (t, J=7.9 Hz, 1H), 7.54 (s, 1H), 7.43 (s, 1H), 7.41-7.30 (m, 2H), 7.13 (d, J=8.5 Hz, 1H), 6.69 (d, J=7.9 Hz, 1H), 5.76-5.53 (m, 1H), 5.06-4.85 (m, 4H), 4.39-4.18 (m, 2H), 3.33 (s, 6H), 2.94-2.69 (m, 3H), 2.37 (s, 3H), 1.83-1.60 (m, 4H), 1.49 (s, 9H).

Step 2: 1-(6-{[Dimethyl(oxo)-λ[6]-sulfanylidene]amino}pyridin-2-yl)-6-{[3-methyl-4-(piperidin-4-yl)phenyl]amino}-2-(prop-2-en-1-yl)-1H,2H,3H-pyrazolo[3,4-d]pyrimidin-3-one* tert-Butyl 4-(4-{[1-(6-{[dimethyl(oxo)-λ[6]-sulfanylidene]amino}pyridin-2-yl)-3-oxo-2-(prop-2-en-1-yl)-1H,2H,3H-pyrazolo[3,4-d]pyrimidin-6-yl]amino}-2-methylphenyl)piperidine-1-carboxylate was reacted according to general procedure D yielding the title compound as a white solid (38 mg, 61%).

LCMS (Method C): $R_T$=0.80 min, m/z=533 $[M+H]^+$.

Step 3: 6-{[4-(1-Cyclobutylpiperidin-4-yl)-3-methylphenyl]amino}-1-(6-{[dimethyl(oxo)-λ[6]-sulfanylidene]amino}pyridin-2-yl)-2-(prop-2-en-1-yl)-1H,2H,3H-pyrazolo[3,4-d]pyrimidin-3-one*

In a 5 mL sample vial were added 1-(6-{[dimethyl(oxo)-λ[6]-sulfanylidene]amino}pyridin-2-yl)-6-{[3-methyl-4-(piperidin-4-yl)phenyl]amino}-2-(prop-2-en-1-yl)-1H,2H,3H-pyrazolo[3,4-d]pyrimidin-3-one (35 mg, 0.066 mmol) and cyclobutanone (0.049 mL, 0.657 mmol) in DCM (1 mL) to give a white suspension. Next sodium triacetoxyborohydride (139 mg, 0.657 mmol) was added and the reaction mixture stirred at room temperature overnight. The reaction mixture was quenched with MeOH (1 mL) and evaporated under reduced pressure. The residue was suspended in DCM and transferred to a prewashed with DCM SCX-2 (2 g) cartridge. The adsorbed compound was washed with 20% MeOH/DCM and finally eluted with 20% 7N $NH_3$ in MeOH/DCM.

The product containing fractions were evaporated under reduced pressure and purified by flash chromatography (0-15% MeOH in DCM), yielding the title compound as a white solid (11 mg, 29%).

LCMS (Method C): $R_T$=0.89 min, m/z=587 $[M+H]^+$.

$^1$H NMR (300 MHz, DMSO) δ 10.19 (s, 1H), 8.86 (s, 1H), 7.77 (t, J=7.9 Hz, 1H), 7.68 (bs, 1H), 7.45 (d, J=9.7 Hz, 1H), 7.32 (d, J=7.8 Hz, 1H), 7.15 (d, J=8.4 Hz, 1H), 6.62 (d, J=8.0 Hz, 1H), 5.75-5.53 (m, 1H), 5.00 (d, J=10.2 Hz, 1H), 4.88 (d, J=17.2 Hz, 1H), 4.75 (d, J=5.1 Hz, 2H), 3.38 (s, 6H), 3.20-2.90 (m, 3H), 2.86-2.73 (m, 2H), 2.29 (s, 3H), 2.20-1.94 (m, 5H), 1.81-1.58 (m, 7H).

Example 89: 1-(6-{[Dimethyl(oxo)-λ$^6$-sulfanylidene]amino}pyridin-2-yl)-6-({4-[(2-methoxyethyl)(methyl)amino]phenyl}amino)-2-(prop-2-en-1-yl)-1H,2H,3H-pyrazolo[3,4-d]pyrimidin-3-one*

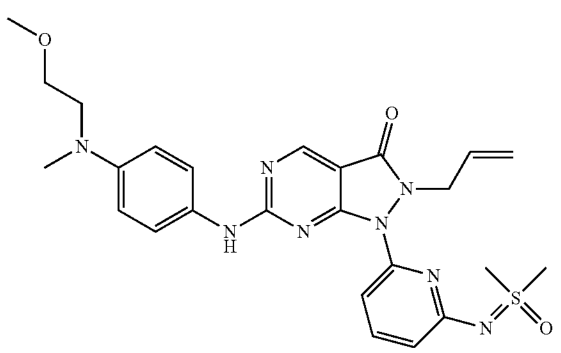 [SMILES: C=CCn1c(=O)c2cnc(Nc3ccc(N(C)CCOC)cc3)nc2n1-c1cccc(N=S(C)(C)=O)n1]

Intermediate B (70 mg, 0.179 mmol) was reacted with $N^1$-(2-methoxyethyl)-$N^1$-methylbenzene-1,4-diamine (48.5 mg, 0.179 mmol) according to General Procedure C, yielding the title compound as a yellow solid (64 mg, 68%).

LCMS (Method C): $R_T$=0.94 min, m/z=523 $[M+H]^+$.

$^1$H NMR (300 MHz, DMSO) δ 10.05 (s, 1H), 8.78 (s, 1H), 7.77 (t, J=7.9 Hz, 1H), 7.51 (s, 2H), 7.31 (d, J=7.8 Hz, 1H), 6.69 (d, J=8.9 Hz, 2H), 6.59 (d, J=8.0 Hz, 1H), 5.77-5.50 (m, 1H), 5.00 (d, J=9.7 Hz, 1H), 4.89 (d, J=17.2 Hz, 1H), 4.75 (s, 2H), 3.48 (s, 4H), 3.38 (s, 6H), 3.25 (s, 3H), 2.90 (s, 3H).

Example 90: 6-{[4-(Azetidin-1-yl)phenyl]amino}-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one*

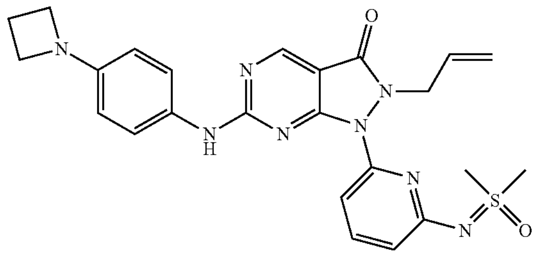 [SMILES: C=CCn1c(=O)c2cnc(Nc3ccc(N4CCC4)cc3)nc2n1-c1cccc(N=S(C)(C)=O)n1]

Intermediate B (70 mg, 0.179 mmol) was reacted with 4-(azetidin-1-yl)aniline (39.9 mg, 0.269 mmol) according to General Procedure C, yielding the title compound as a yellow solid (72 mg, 82%).

LCMS (Method C): $R_T$=1.03 min, m/z=491 $[M+H]^+$.

$^1$H NMR (300 MHz, DMSO) δ 10.07 (s, 1H), 8.79 (s, 1H), 7.76 (t, J=7.9 Hz, 1H), 7.62-7.42 (m, 2H) 7.29 (d, J=7.8 Hz, 1H), 6.59 (d, J=8.0 Hz, 1H), 6.40 (d, J=8.7 Hz, 2H), 5.76-5.50 (m, 1H), 5.00 (d, J=10.2 Hz, 1H), 4.89 (d, J=17.0 Hz, 1H), 4.74 (s, 2H), 3.77 (t, J=7.1 Hz, 4H), 3.38 (s, 6H), 2.37-2.20 (m, 2H).

Example 91: 1-[6-({[Dimethyl(oxo)-λ$^6$-sulfanylidene]amino}methyl)pyridin-2-yl]-6-{[4-(morpholin-4-yl)phenyl]amino}-2-(prop-2-en-1-yl)-1H,2H,3H-pyrazolo[3,4-d]pyrimidin-3-one*

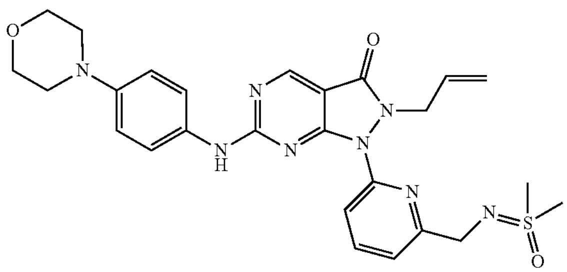 [SMILES: C=CCn1c(=O)c2cnc(Nc3ccc(N4CCOCC4)cc3)nc2n1-c1cccc(CN=S(C)(C)=O)n1]

Step 1: 6-Bromo-N-[dimethyl(oxo)-λ$^6$-sulfanylidene]pyridine-2-carboxamide*

To 6-bromopicolinic acid (500 mg, 2.48 mmol) and (S-methylsulfonimidoyl)methane (231 mg, 2.48 mmol) in DCM (6 mL) were added $N^1$-((ethylimino)methylene)-$N^3$,$N^3$-dimethylpropane-1,3-diamine hydrochloride (949 mg, 4.95 mmol) and DMAP (665 mg, 5.45 mmol). The reaction mixture was stirred overnight at RT. Next the reaction mixture was transferred to a separatory funnel and 30 mL of 1M citric acid solution (aq) was added. The product was extracted with EtOAc (3×30 mL). The combined organic layers were dried (anh. $MgSO_4$) and evaporated under reduced pressure. The product was purified by flash chromatography (50-100% EtOAc in cyclohexane). The product containing fractions were evaporated under reduced pressure yielding the title compound as clear oil that solidified upon storage (510 mg, 74%).

LCMS (Method C): $R_T$=0.24 min, m/z=277, 279 $[M+H]^+$.

$^1$H NMR (300 MHz, $CDCl_3$) δ 8.08 (dd, J=7.2, 1.2 Hz, 1H), 7.67-7.49 (m, 2H), 3.38 (s, 6H).

Step 2: {[(6-Bromopyridin-2-yl)methyl]imino}dimethyl-λ$^6$-sulfanone*

6-Bromo-N-[dimethyl(oxo)-λ$^6$-sulfanylidene]pyridine-2-carboxamide (510 mg, 1.840 mmol) was dissolved in DCM and 1M $BH_3$ in THF (5.52 mL, 5.52 mmol) was added dropwise. The reaction mixture was stirred at RT overnight. LCMS showed appr. 20% conversion. An additional batch of 1M $BH_3$ in THF (12 mL, 12 mmol) was added and the reaction mixture was stirred overnight at RT. The reaction mixture was quenched with MeOH/H2O and extracted with DCM (3×40 mL). The organic layer was dried (anh. $MgSO_4$), evaporated under reduced pressure and purified by flash chromatography (0-10% MeOH in EtOAc). The product containing fractions were evaporated under reduced pressure yielding the title compound as yellowish oil (97 mg, 20%).

LCMS (Method C): $R_T$=0.24 min, m/z=264 $[M+H]^+$.

$^1$H NMR (300 MHz, $CDCl_3$) δ 7.59-7.47 (m, 2H), 7.39-7.29 (m, 1H), 4.39 (s, 2H), 3.11 (d, J=4.1 Hz, 6H).

Step 3: 1-[6-({[Dimethyl(oxo)-λ$^6$-sulfanylidene]amino}methyl)pyridin-2-yl]-6-(methylsulfanyl)-2-(prop-2-en-1-yl)-1H,2H,3H-pyrazolo[3,4-d]pyrimidin-3-one*

In a 25 mL reaction vial were added 2-allyl-6-(methylthio)-1H-pyrazolo[3,4-d]pyrimidin-3(2H)-one) [Prepared according to EP2213673B1 (Production Example 1, p 37)] (80 mg, 0.361 mmol), {[(6-bromopyridin-2-yl)methyl]imino}dimethyl-λ$^6$-sulfanone (95 mg, 0.361 mmol), $K_2CO_3$ (110 mg, 0.794 mmol) and dioxane (2 mL). The resultant suspension was flushed with nitrogen and copper (I) iodide (68.8 mg, 0.361 mmol) was added followed by $N^1$,$N^2$-dimethylethane-1,2-diamine (0.039 mL, 0.361 mmol). The vial was capped and the temperature was increased to 95° C. After 18 h of intensive stirring, LCMS confirmed accomplished conversion. The reaction mixture was cooled to RT. $NH_4OH$ (aq) was added (10 mL) followed by water (10 mL) and the reaction mixture was extracted using EtOAc (3×50 mL). The organic phases were combined, dried (anh. $MgSO_4$) and evaporated under reduced pressure. The residue was purified using flash chromatography (0-20% MeOH in DCM). The product containing fractions were evaporated under reduced pressure yielding the title compound as yellowish oil (74 mg, 51%).

LCMS (Method C): $R_T$=0.90 min, m/z=405 [M+H]$^+$.

$^1$H NMR (300 MHz, $CDCl_3$) δ 8.92 (s, 1H), 7.87 (t, J=7.8 Hz, 1H), 7.71 (d, J=8.0 Hz, 1H), 7.52 (d, J=7.5 Hz, 1H), 5.76-5.59 (m, 1H), 5.02 (d, J=9.6 Hz, 1H), 4.92 (d, J=17.1 Hz, 1H), 4.84 (d, J=6.3 Hz, 2H), 4.41 (s, 2H), 3.11 (s, 6H), 2.56 (s, 3H).

Step 4: 1-[6-({[Dimethyl(oxo)-λ$^6$-sulfanylidene]amino}methyl)pyridin-2-yl]-6-{[4-(morpholin-4-yl)phenyl]amino}-2-(prop-2-en-1-yl)-1H,2H,3H-pyrazolo[3,4-d]pyrimidin-3-one*

1-[6-({[Dimethyl(oxo)-λ$^6$-sulfanylidene]amino}methyl)pyridin-2-yl]-6-(methylsulfanyl)-2-(prop-2-en-1-yl)-1H,2H,3H-pyrazolo[3,4-d]pyrimidin-3-one (70 mg, 0.173 mmol) was reacted with 4-morpholinoaniline (30.8 mg, 0.173 mmol) according to General Procedure C yielding the title compound as a Yellow solid (8 mg, 9%).

LCMS (Method C): $R_T$=0.93 min, m/z=535 [M+H]$^+$.

$^1$H NMR (300 MHz, DMSO) δ 10.18 (s, 1H), 8.83 (s, 1H), 8.02 (t, J=8.0 Hz, 1H), 7.80-7.55 (m, 3H), 7.50 (d, J=7.6 Hz, 1H), 6.93 (d, J=9.0 Hz, 2H), 5.79-5.57 (m, 1H), 5.01 (d, J=9.4 Hz, 1H), 4.89 (d, J=17.1 Hz, 1H), 4.62 (d, J=4.7 Hz, 2H), 4.28 (s, 2H), 3.84-3.62 (m, 4H), 3.09 (s, 6H), 3.08-2.99 (m, 4H).

Example 92: 2-(Cyclopropylmethyl)-1-(6-{[dimethyl(oxo)-λ$^6$-sulfanylidene]amino}pyridin-2-yl)-6-{[4-(morpholin-4-yl)phenyl]amino}-1H,2H,3H-pyrazolo[3,4-d]pyrimidin-3-one*

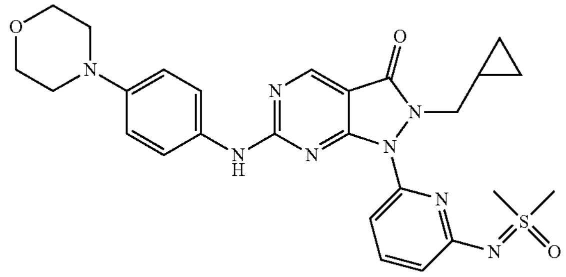 [SMILES: CS(C)(=O)=Nc1cccc(-n2c3nc(Nc4ccc(N5CCOCC5)cc4)ncc3c(=O)n2CC2CC2)n1]

1-(6-{[Dimethyl(oxo)-λ$^6$-sulfanylidene]amino}pyridine-2-yl)-6-{[4-(morpholin-4-yl)phenyl]amino}-2-(prop-2-en-1-yl)-1H,2H,3H-pyrazolo[3,4-d]pyrimidin-3-one (obtained as described above) (50 mg, 0.096 mmol) was dissolved in DCM (1 mL) and bis(benzonitrile)dichloropalladium (II) (1.47 mg, 3.84 μmol) was added. The solution was cooled in an ice bath and 0.6M diazomethane in diethyl ether (0.6 mL, 0.60 mmol) was added. The reaction mixture was stirred in the ice bath for 30 min. and an additional batch of 0.6M diazomethane in diethyl ether (0.6 mL, 0.60 mmol; prepared according to *Organic Syntheses, Coll. Vol.* 2, p. 165 (1943)) was added. The reaction mixture was warmed to RT and stirred overnight. The reaction mixture was loaded directly onto a silica gel cartridge and purified by flash chromatography (0-10% MeOH in DCM). The product containing fractions were evaporated under reduced pressure and repurified by preparative HPLC, using basic conditions. The product containing fractions were freeze dried yielding the title compound as a yellow solid (19 mg, 37%).

LCMS (Method C): $R_T$=1.20 min, m/z=535 [M+H]$^+$.

$^1$H NMR (300 MHz, DMSO) δ 10.15 (bs, 1H), 8.82 (s, 1H), 7.85 (s, 1H), 7.63 (bs, 2H), 7.37 (d, J=7.8 Hz, 1H), 6.95 (d, J=8.9 Hz, 2H), 6.62 (d, J=8.0 Hz, 1H), 4.01 (d, J=5.2 Hz, 2H), 3.85-3.64 (m, 4H), 3.36 (s, 6H), 3.15-2.96 (m, 4H), 0.85-0.69 (m, 1H), 0.38-0.21 (m, 2H), 0.09-(−0.12) (m, 2H).

Example 93: rac-1-(6-{[Dimethyl(oxo)-λ$^6$-sulfanylidene]amino}pyrazin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one*

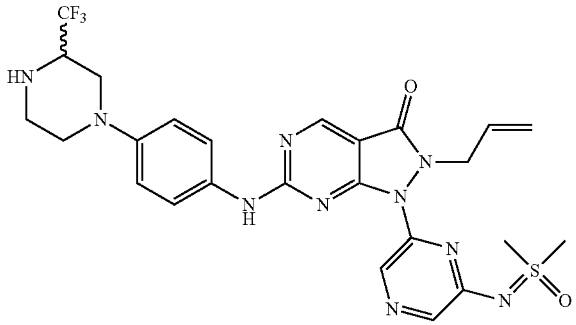 [SMILES: C=CCn1c(=O)c2cnc(Nc3ccc(N4CCNC(C(F)(F)F)C4)cc3)nc2n1-c1cncc(N=S(C)(C)=O)n1]

Step 1: rac-tert-Butyl 4-(4-{[1-(6-{[dimethyl(oxo)-λ$^6$-sulfanylidene]amino}pyrazin-2-yl)-3-oxo-2-(prop-2-en-1-yl)-1H,2H,3H-pyrazolo[3,4-d]pyrimidin-6-yl]amino}phenyl)-2-(trifluoromethyl)piperazine-1-carboxylate*

Intermediate G (30 mg, 0.077 mmol) was reacted with rac-tert-butyl 4-(4-aminophenyl)-2-(trifluoromethyl)piperazine-1-carboxylate (26.5 mg, 0.077 mmol; prepared as described in WO2015092431A1) according to General Procedure C yielding the title compound as a yellow solid (23 mg, 44%).

LCMS (Method C): $R_T$=1.70 min, m/z=689 [M+H]$^+$.

Step 2: rac-1-(6-{[Dimethyl(oxo)-λ$^6$-sulfanylidene]amino}pyrazin-2-yl)-2-(prop-2-en-1-yl)-6-({4-[3-(trifluoromethyl)piperazin-1-yl]phenyl}amino)-1H,2H,3H-pyrazolo[3,4-c]pyrimidin-3-one* rac-tert-Butyl 4-(4-{[1-(6-{[dimethyl(oxo)-λ$^6$-sulfanylidene]amino}pyrazin-2-yl)-3-oxo-2-(prop-2-en-1-yl)-1H,2H,3H-pyrazolo[3,4-d]pyrimidin-6-yl]

amino}phenyl)-2-(trifluoromethyl)piperazine-1-carboxylate was reacted according to General Procedure D yielding the title compound as a yellow solid (19 mg, 97%).

LCMS (Method C): $R_T$=0.94 min, m/z=589 $[M+H]^+$.

$^1H$ NMR (300 MHz, DMSO) δ 10.26 (bs, 1H), 8.85 (s, 1H), 8.64 (bs, 1H), 7.94 (s, 1H), 7.58 (d, J=7.7 Hz, 2H), 6.95 (d, J=9.0 Hz, 2H), 5.76-5.53 (m, 1H), 5.01 (d, J=10.1 Hz, 1H), 4.93 (d, J=17.4 Hz, 1H), 4.73 (d, J=6.2 Hz, 2H), 3.67-3.47 (m, 2H), 3.44 (s, 6H), 3.42-3.36 (m, 1H), 3.13-3.02 (m, 1H), 2.95-2.75 (m, 2H), 2.71-2.59 (m, 2H).

Example 94: 1-(6-((Dimethyl(oxo)-λ$^6$-sulfaneylidene)amino)pyridin-2-yl)-6-((1-isopropyl-1H-pyrazol-4-yl)amino)-2-(prop-2-yn-1-yl)-1,2-dihydro-3H-pyrazolo[3,4-d]pyrimidin-3-one

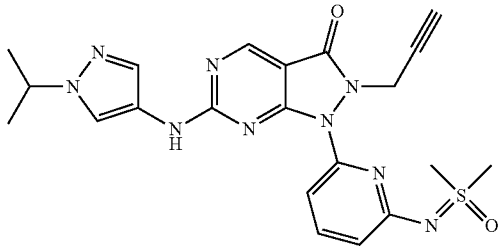 [SMILES: C#CCn1c(=O)c2cnc(Nc3cnn(C(C)C)c3)nc2n1-c1cccc(N=S(C)(C)=O)n1]

Step 1: 1-(6-((Dimethyl(oxo)-λ$^6$-sulfaneylidene)amino)pyridin-2-yl)-6-(methylthio)-2-(prop-2-yn-1-yl)-1,2-dihydro-3H-pyrazolo[3,4-d]pyrimidin-3-one To a mixture of intermediate B (200 mg, 0.512 mmol) and ammonium formate (323 mg, 5.12 mmol) in 1,4-dioxane (6 mL) under nitrogen was added $PdCl_2$(dppf)-DCM adduct (125 mg, 0.154 mmol). The reaction mixture was stirred at 90° C. overnight. The volatiles were evaporated under reduced pressure. 10 ml of brine and 10 ml of DCM were added and the organic layer was separated. The aqueous layer was extracted with DCM (4×20 mL). The organic layers were combined, dried (anh. $MgSO_4$) and evaporated under reduced pressure yielding a dark brown solid of crude 1-(6-((dimethyl(oxo)-λ$^6$-sulfaneylidene)amino)pyridin-2-yl)-6-(methylthio)-1,2-dihydro-3H-pyrazolo[3,4-d]pyrimidin-3-one.

LCMS (Method C): $R_T$=0.97 min, m/z=351 $[M+H]^+$.

The dark residue obtained above was dissolved in DMF (6 mL) and NaH (60% in oil) (44.7 mg, 1.119 mmol) was added. The reaction mixture was stirred for 15 min at RT under nitrogen. Then 3-bromoprop-1-yne (0.072 mL, 0.671 mmol) was added dropwise and the reaction mixture was stirred for 5 h at RT. The reaction mixture was quenched with water and 2M $Na_2CO_3$ (20 mL) was added. The resultant mixture was extracted with EtOAc (3×30 mL). The organic extracts were combined, dried (anh. $MgSO_4$) and evaporated under reduced pressure. The product was purified by flash chromatography (30-100% EtOAc in cyclohexane, then 0-20% MeOH in EtOAc) yielding a yellow-brown oil (40 mg, 20% over two steps).

LCMS (Method C): $R_T$=1.08 min, m/z=389 $[M+H]^+$.

$^1H$ NMR (300 MHz, $CDCl_3$) δ 8.91 (s, 1H), 7.79-7.62 (m, 1H), 7.51 (d, J=7.9 Hz, 1H), 6.69 (d, J=8.0 Hz, 1H), 5.15 (d, J=2.4 Hz, 2H), 3.32 (s, 6H), 2.62 (s, 3H), 2.08 (t, J=2.4 Hz, 1H).

Step 2: 1-(6-((Dimethyl(oxo)-λ$^6$-sulfaneylidene)amino)pyridin-2-yl)-6-((1-isopropyl-1H-pyrazol-4-yl)amino)-2-(prop-2-yn-1-yl)-1,2-dihydro-3H-pyrazolo[3,4-d]pyrimidin-3-one To 1-(6-((dimethyl(oxo)-λ$^6$-sulfaneylidene)amino)pyridin-2-yl)-6-(methylthio)-2-(prop-2-yn-1-yl)-1,2-dihydro-3H-pyrazolo[3,4-d]pyrimidin-3-one (38 mg, 0.098 mmol) in a mixture of toluene (1 mL) and dichloromethane (1 mL) was added m-CPBA, 70% purity (26.5 mg, 0.108 mmol). The reaction mixture was stirred for 30 minutes at RT. LC-MS analysis showed complete oxidation of the starting material. To the reaction mixture were added 1-isopropyl-1H-pyrazol-4-amine (12.2 mg, 0.098 mmol) and DIPEA (0.051 mL, 0.293 mmol). The mixture was heated at 65° C. under a nitrogen atmosphere overnight, then it was loaded directly onto a silica gel cartridge and purified by flash chromatography (0-10% MeOH in EtOAc). The product containing fractions were evaporated under reduced pressure and freeze dried (ACN/water) yielding the title compound as a beige solid.

LCMS (Method C): $R_T$=0.98 min, m/z=466 $[M+H]^+$.

$^1H$ NMR (300 MHz, DMSO) δ 10.42 (s, 1H), 8.96-8.77 (m, 1H), 8.11-7.94 (m, 1H), 7.80 (t, J=8.0 Hz, 1H), 7.57-7.50 (m, 1H), 7.45 (d, J=7.7 Hz, 1H), 6.63 (d, J=7.9 Hz, 1H), 4.88 (s, 2H), 4.55-4.40 (m, 1H), 3.37 (s, 6H), 3.23-3.15 (m, 1H), 1.49-1.34 (m, 6H).

Example 95: 2-Allyl-6-((1-allyl-1H-pyrazol-4-yl)amino)-1-(6-((dimethyl(oxo)-λ$^6$-sulfaneylidene)amino)pyridin-2-yl)-1,2-dihydro-3H-pyrazolo[3,4-d]pyrimidin-3-one

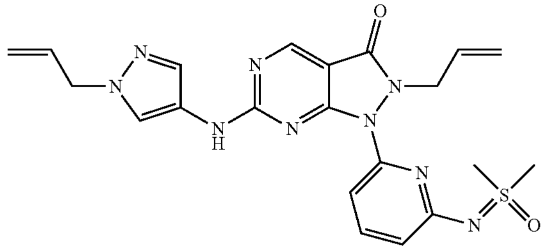 [SMILES: C=CCn1cc(Nc2ncc3c(=O)n(CC=C)n(-c4cccc(N=S(C)(C)=O)n4)c3n2)cn1]

Step 1: 1-Allyl-4-nitro-1H-pyrazole

4-Nitro-1H-pyrazole (500 mg, 4.42 mmol) was dissolved in DMF (2 mL) and NaH (60% in oil) (265 mg, 6.63 mmol) was added. The reaction mixture was stirred for 15 min at RT under nitrogen. Then 3-bromoprop-1-ene (0.459 mL, 5.31 mmol) was added dropwise and the reaction mixture was stirred for 5 h at RT. The reaction mixture was quenched with water and 2M $Na_2CO_3$ (20 ml) was added. The resultant mixture was extracted with EtOAc (3×30 mL). The organic extracts were combined, dried (anh. $MgSO_4$) and evaporated under reduced pressure. The product was purified by flash chromatography (15-50% EtOAc in cyclohexane) yielding a yellow oil of product (230 mg, 34%).

LCMS (Method C): RT=1.73 min, m/z=154 $[M+H]^+$.

$^1H$ NMR (300 MHz, $CDCl_3$) δ 8.15 (s, 1H), 8.09 (s, 1H), 6.13-5.93 (m, 1H), 5.43 (d, J=10.2 Hz, 1H), 5.36 (d, J=17.0 Hz, 1H), 4.83-4.73 (m, 2H).

Step 2: 1-Allyl-4-amino-1H-pyrazole

1-Allyl-4-nitro-1H-pyrazole (90 mg, 0.5900 mmol) was added to a mixture of iron powder (656 mg, 11.75 mmol)

and ammonium chloride (629 mg, 11.75 mmol) in a solution of methanol (5 ml) and water (1 mL) to give a yellow/black suspension. This was heated to reflux under a nitrogen atmosphere for 5 h. The reaction mixture was allowed to cool to room temperature, filtered through celite and the filtrate was concentrated to dryness under reduced pressure. The residue was triturated with EtOAc (4×5-mL). The extract was filtered (0.4 PTFE syringe filter) evaporated under reduced pressure yielding a dark red oil of the crude desired product (63 mg, 87%). The crude was used in the next step without further purification.

$^1$H NMR (300 MHz, $CDCl_3$) δ 7.19 (s, 1H), 7.04 (s, 1H), 6.07-5.86 (m, 1H), 5.33-5.13 (m, 2H), 4.71-4.52 (m, 2H), 2.29-2.11 (m, 3H).

Step 3: 2-Allyl-6-((1-allyl-1H-pyrazol-4-yl)amino)-1-(6-((dimethyl(oxo)-λ$^6$-sulfaneylidene)amino)pyridin-2-yl)-1,2-dihydro-3H-pyrazolo[3,4-d]pyrimidin-3-one Intermediate B (50 mg, 0.128 mmol) was reacted with 1-allyl-1H-pyrazol-4-amine (15.8 mg, 0.128 mmol) according to General Procedure C, yielding the title compound as a white solid (32 mg, 56%).

LCMS (Method C): RT=0.97 min, m/z=466 $[M+H]^+$.

$^1$H NMR (300 MHz, DMSO-$d_6$) δ 10.41-9.99 (m, 1H), 8.95-8.70 (m, 1H), 7.93 (s, 1H), 7.89-7.66 (m, 1H), 7.55 (s, 1H), 7.32-7.11 (m, 1H), 6.63 (d, J=7.9 Hz, 1H), 6.13-5.90 (m, 1H), 5.78-5.52 (m, 1H), 5.29-5.09 (m, 2H), 5.00 (d, J=10.3 Hz, 1H), 4.87 (d, J=17.5 Hz, 1H), 4.81-4.57 (m, 4H), 3.38 (s, 6H).

Example 96: 2-Allyl-6-((1-cyclohexyl-1H-pyrazol-4-yl)amino)-1-(6-((dimethyl(oxo)-λ$^6$-sulfaneylidene)amino)pyridin-2-yl)-1,2-dihydro-3H-pyrazolo[3,4-d]pyrimidin-3-one

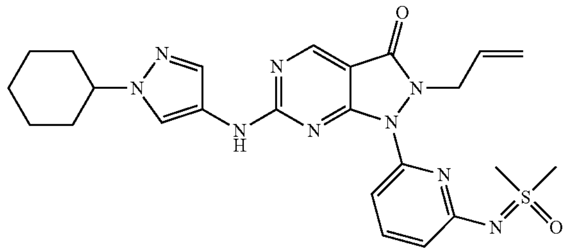 [SMILES: C=CCn1c(=O)c2cnc(Nc3cnn(C4CCCCC4)c3)nc2n1-c1cccc(N=S(C)(C)=O)n1]

Intermediate B (50 mg, 0.128 mmol) was reacted with 1-cyclohexyl-1H-pyrazol-4-amine (21.2 mg, 0.128 mmol) according to General Procedure C, yielding the title compound as a white solid (43 mg, 65%).

LCMS (Method C): RT=1.33 min, m/z=508 $[M+H]^+$.

$^1$H NMR (300 MHz, DMSO-$d_6$) δ 10.38-9.95 (m, 1H), 8.95-8.69 (m, 1H), 7.97 (s, 1H), 7.76 (t, J=7.9 Hz, 1H), 7.50 (s, 1H), 7.28 (d, J=7.7 Hz, 1H), 6.65 (d, J=8.0 Hz, 1H), 5.79-5.51 (m, 1H), 5.00 (d, J=10.3 Hz, 1H), 4.87 (d, J=16.8 Hz, 1H), 4.69 (d, J=5.7 Hz, 2H), 4.18-4.00 (m, 1H), 3.37 (s, 6H), 2.07-1.93 (m, 2H), 1.91-1.75 (m, 2H), 1.75-1.52 (m, 3H), 1.51-1.32 (m, 2H), 1.32-1.18 (m, 1H).

Example 97: rac-2-Allyl-6-((1-cyclohexyl-1H-pyrazol-4-yl)amino)-1-(6-((dimethyl(oxo)-λ$^6$-sulfaneylidene)amino)pyridin-2-yl)-1,2-dihydro-3H-pyrazolo[3,4-d]pyrimidin-3-one

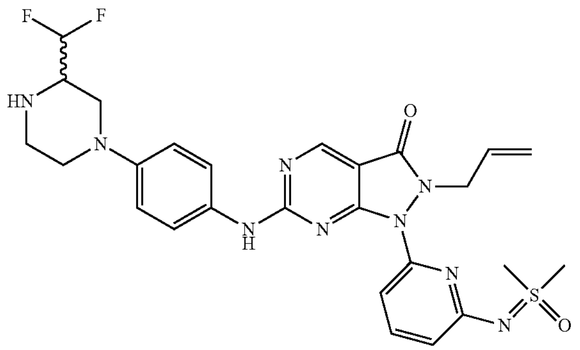 [SMILES: C=CCn1c(=O)c2cnc(Nc3ccc(N4CCNC(C(F)F)C4)cc3)nc2n1-c1cccc(N=S(C)(C)=O)n1]

Step 1: 2-(Difluoromethyl)pyrazine

To triethylamine trihydrofluoride (1.956 mL, 12.00 mmol) in DCM (18 mL) at RT were added successively XtalFluor-E (2.061 g, 9.00 mmol) and pyrazine-2-carbaldehyde (0.649 g, 6 mmol). The reaction mixture was stirred overnight at RT. The reaction mixture was quenched with sat. $NaHCO_3$ solution and next extracted with DCM (3×50 mL), dried ($MgSO_4$) and evaporated under reduced pressure. The product was purified by flash chromatography (100% DCM) yielding the title compound as a clear oil (703 mg, 90%).

LCMS (Method C): RT=0.58 min, m/z=131 $[M+H]^+$.

$^1$H NMR (500 MHz, $CDCl_3$) δ 8.95 (s, 1H), 8.74 (s, 1H), 8.65 (s, 1H), 6.71 (t, J=54.7 Hz, 1H).

Step 2: rac-2-(Difluoromethyl)piperazine diacetate 2-(Difluoromethyl)pyrazine (0.70 g. 5.40 mmol) was dissolved in MeOH (25 mL) and AcOH was added (0.5 mL). The mixture was hydrogenated using the H-CUBE® ($PtO_2$, 50 C deg. 70 bar, 16 h). The volatiles were evaporated under reduced pressure yielding the title compound as a clear oil (0.98 g, 71%).

$^1$H NMR (500 MHz, $CDCl_3$) δ 6.27 (s, 4H), 5.69 (td, J=55.7, 5.3 Hz, 1H), 3.42-2.67 (m, 7H), 2.06 (s, 6H).

Step 3: rac-3-(Difluoromethyl)-1-(4-nitrophenyl)piperazine

To 1-fluoro-4-nitrobenzene (0.540 g, 3.82 mmol) and $K_2CO_3$ (2.91 g, 21.03 mmol) was added a solution of rac-2-(difluoromethyl)piperazine diacetate (0.98 g, 3.82 mmol) in dry DMF (10 mL). The suspension was stirred at 90° C. overnight. The reaction mixture was transferred to a separatory funnel and 50 mL of AcOEt was added. The mixture was washed with brine (2×50 mL). The organic layer was dried (anh. $MgSO_4$) and evaporated. The residue was purified by column chromatography (15 to 80% AcOEt in cyclohexane). The product containing fractions were evaporated under vacuum yielding the title product as a yellow oil (238 mg, 24% yield).

LCMS (Method A): RT=0.51 min, m/z=258 $[M+H]^+$.

$^1$H NMR (500 MHz, $CDCl_3$) δ 8.15 (d, J=8.7 Hz, 2H), 6.87 (d, J=8.9 Hz, 2H), 5.74 (td, J=56.2, 6.3 Hz, 1H), 3.84

(d, J=12.2 Hz, 1H), 3.72 (d, J=12.1 Hz, 1H), 3.20 (d, J=11.9 Hz, 2H), 3.07 (t, J=11.9 Hz, 1H), 2.97 (q, J=10.8 Hz, 2H), 1.90 (s, 1H).

Step 4: rac-tert-Butyl 2-(difluoromethyl)-4-(4-nitrophenyl)piperazine-1-carboxylate rac-3-(Difluoromethyl)-1-(4-nitrophenyl)piperazine (235 mg, 0.914 mmol) was dissolved in DCM (6 mL). $Boc_2O$ (2.72 g, 12.45 mmol), DIPEA (0.319 ml, 1.827 mmol) and DMAP (22.32 mg, 0.183 mmol) were added and the resulting mixture was stirred at room temperature over the weekend. Additional $Boc_2O$ (2.72 g, 12.45 mmol), DIPEA (0.319 ml, 1.827 mmol) and DMAP (22.32 mg, 0.183 mmol) were added and the resulting mixture was stirred at room temperature overnight. The reaction mixture was evaporated under reduced pressure and purified by flash chromatography (10-50% EtOAc in cyclohexane). The title compound was obtained as a yellow oil that solidified upon storage (215 mg, 66%).

LCMS (Method C): RT=1.70 min, m/z=358 $[M+H]^+$.

$^1$H NMR (500 MHz, $CDCl_3$) δ 8.16 (d, J=9.0 Hz, 2H), 6.82 (d, J=9.0 Hz, 2H), 6.00 (td, J=56.2, 5.0 Hz, 1H), 4.54-4.25 (m, 1H), 4.23-3.89 (m, 2H), 3.82-3.65 (m, 1H), 3.56-3.24 (m, 2H), 3.24-3.05 (m, 1H), 1.50 (s, 9H).

Step 5: rac-tert-Butyl 4-(4-aminophenyl)-2-(difluoromethyl)piperazine-1-carboxylate A stirring solution of rac-tert-butyl 2-(difluoromethyl)-4-(4-nitrophenyl)piperazine-1-carboxylate (210 mg, 0.588 mmol) in ethanol (20 mL) was heated to 75° C. Pd/C (43.8 mg, 0.041 mmol) was added followed by addition of ammonium formate (222 mg, 3.53 mmol) and the suspension stirred for 1 h (until gas evolution ceased). The reaction mixture was chilled to RT and evaporated under reduced pressure. The resulting residue was purified by flash chromatography (20-80% EtOAc in cyclohexane. The product containing fractions were evaporated under reduced pressure yielding the title compound as a brownish oil (165 mg, 86%).

LCMS (Method C): RT=0.88 min, m/z=328 $[M+H]^+$.

$^1$H NMR (400 MHz, $CDCl_3$) δ 6.80 (d, J=8.8 Hz, 2H), 6.66 (d, J=8.7 Hz, 2H), 6.24 (ddd, J=58.0, 56.1, 7.0 Hz, 1H), 4.50-4.25 (m, 1H), 4.20-4.01 (m, 1H), 3.60-3.43 (m, 1H), 3.37-3.04 (m, 3H), 2.86-2.76 (m, 1H), 2.69 (td, J=11.9, 3.8 Hz, 1H), 1.49 (s, 9H).

Step 6: rac-tert-Butyl 4-(4-((2-allyl-1-(6-((dimethyl(oxo)-λ$^6$-sulfaneylidene)amino)pyridin-2-yl)-3-oxo-2,3-dihydro-1H-pyrazolo[3,4-d]pyrimidin-6-yl)amino)phenyl)-2-(difluoromethyl)piperazine-1-carboxylate Intermediate B (50 mg, 0.128 mmol) was reacted with rac-tert-butyl 4-(4-aminophenyl)-2-(difluoromethyl)piperazine-1-carboxylate (42 mg, 0.128 mmol) according to General Procedure C, yielding the title compound as a yellowish oil (29 mg, 34%).

LCMS (Method C): RT=1.50 min, m/z=670 $[M+H]^+$.

$^1$H NMR (400 MHz, $CDCl_3$) δ 8.82 (s, 1H), 7.68 (t, J=7.9 Hz, 1H), 7.52 (d, J=8.9 Hz, 2H), 7.46-7.36 (m, 1H), 7.34 (d, J=7.8 Hz, 1H), 6.95-6.88 (m, 2H), 6.68 (d, J=7.9 Hz, 1H), 6.20 (td, J=56.8, 6.8 Hz, 1H), 5.65 (ddt, J=16.6, 10.2, 6.3 Hz, 1H), 5.04-4.95 (m, 2H), 4.91 (d, J=6.3 Hz, 2H), 4.57-4.27 (m, 1H), 4.25-4.02 (m, 1H), 3.78-3.62 (m, 1H), 3.34 (s, 6H), 3.31-3.11 (m, 1H), 2.98-2.88 (m, 1H), 2.84-2.73 (m, 1H), 1.50 (s, 9H).

Step 7: rac-2-Allyl-6-((4-(3-(difluoromethyl)piperazin-1-yl)phenyl)amino)-1-(6-((dimethyl(oxo)-λ$^6$-sulfaneylidene)amino)pyridin-2-yl)-1,2-dihydro-3H-pyrazolo[3,4-c]pyrimidin-3-one rac-tert-Butyl 4-(4-((2-allyl-1-(6-((dimethyl(oxo)-λ$^6$-sulfaneylidene)amino)pyridin-2-yl)-3-oxo-2,3-dihydro-1H-pyrazolo[3,4-d]pyrimidin-6-yl)amino)phenyl)-2-(difluoromethyl)piperazine-1-carboxylate was reacted according to General procedure D yielding the title compound as a yellowish solid (24 mg, 97%).

LCMS (Method C): RT=0.68 min, m/z=570 $[M+H]^+$.

$^1$H NMR (500 MHz, DMSO-$d_6$) δ 10.14 (s, 1H), 8.81 (s, 1H), 7.85-7.76 (m, 1H), 7.67-7.53 (m, 2H), 7.30 (d, J=7.8 Hz, 1H), 6.94 (d, J=8.4 Hz, 2H), 6.60 (d, J=7.9 Hz, 1H), 5.99 (td, J=55.9, 5.9 Hz, 1H), 5.69-5.59 (m, 1H), 5.00 (d, J=10.2 Hz, 1H), 4.89 (d, J=17.1 Hz, 1H), 4.79-4.70 (m, 2H), 3.50-3.44 (m, 1H), 3.43-3.39 (m, 1H), 3.37 (s, 6H), 3.13-3.04 (m, 1H), 3.04-2.98 (m, 1H), 2.84-2.77 (m, 1H), 2.67-2.61 (m, 1H), 2.59-2.53 (m, 1H).

Comparison of Compounds of the Present Invention with Those of the Prior Art:

The table below highlights the increased potency of selected Wee-1 inhibitors of the current invention to inhibit the proliferation of HT29-, A427-, A498- and SK-LU-1-cells relative to Example 53 of US2007/0254892.

TABLE 3

Comparative in vitro data of selected examples from present invention versus Wee-1 inhibitor Example 53 of US2007/0254892

| Example Number | Reference | ELISA p-CDC2 $EC_{50}$ (nM) | HT29 $EC_{50}$ (nM) | A427 $EC_{50}$ (nM) | A498 $EC_{50}$ (nM) | SK-LU-1 $EC_{50}$ (nM) |
|---|---|---|---|---|---|---|
| 53 | US2007/0254892 | 66 | 154 | 101 | 103 | 40 |
| 5 | Present invention | 12 | 33 | 29 | 25 | 12 |
| 12 | Present invention | 26 | 27 | 27 | 27 | 30 |
| 54 | Present invention | 5 | 32 | 17 | 16 | 35 |

Method 3:

All cell lines (HT29, A427, A498, SKLU-1) were obtained from the American Type Culture Collection (ATCC), maintained in the recommended media supplemented with 10% (v/v) FBS, 1% (v/v) Penicillin/streptomycin and kept at 37° C. in a humidified atmosphere with 5% CO2. Cells were seeded in 96 wp format typically at a seeding density of 3500-5000 cells/well and treated after 24 hours with increasing concentration of compound from 0 to 100 μM in ½ log unit increments. Cell viability was assessed after 72 hours (HT29, A427) or after 6 days (SKLU-1, A498) by CellTiter-Glo® as recommended by the manufacturer's instructions (Promega). Analysis and $EC_{50}$ values were derived using GraphPadPrism.

Table 4 below highlights the selectivity of a representative compound of the invention, Example 5, against a panel of 50 kinases (assessed using the Invitrogen SelectScreen® Kinase Profiling Service). Unexpectedly, Example 5 shows greater selectivity against this panel of kinases than compounds of the prior art such as the corresponding compound claimed in WO 2007/126122 and US 2007/0254892.

TABLE 4

| | Selectivity | |
|---|---|---|
| Kinase | 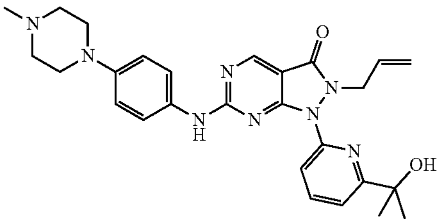<br>Example 53<br>(WO 2007/126122<br>US 2007/0254892) | 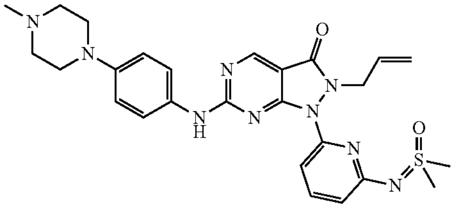<br>Example 5<br>(present<br>invention) |
| ABL1 | + | − |
| ACVR1B (ALK4) | − | − |
| AKT1 (PKB alpha) | − | − |
| AMPK A1/B1/G1 | − | − |
| AURKA (Aurora A) | − | − |
| BTK | − | − |
| CDK1/cyclin B | − | − |
| CHEK1 (CHK1) | − | − |
| CSNK1G2 (CK1 gamma 2) | − | − |
| CSNK2A1 (CK2 alpha 1) | − | − |
| DYRK3 | − | − |
| EGFR (ErbB1) | + | − |
| EPHA2 | − | − |
| ERBB2 (HER2) | − | − |
| FGFR1 | − | − |
| FLT3 | − | − |
| FRAP1 (mTOR) | − | − |
| GSK3B (GSK3 beta) | − | − |
| IGF1R | − | − |
| IKBKB (IKK beta) | − | − |
| INSR | − | − |
| IRAK4 | − | − |
| JAK3 | − | − |
| KDR (VEGFR2) | − | − |
| KIT | − | − |
| LCK | + | − |
| MAP2K1 (MEK1) | − | − |
| MAP4K4 (HGK) | + | − |
| MAPK1 (ERK2) | − | − |
| MAPK14 (p38 alpha) | − | − |
| MAPK8 (JNK1) | − | − |
| MAPKAPK2 | − | − |
| MARK2 | − | − |
| MET (cMet) | − | − |
| NEK1 | − | − |
| NTRK1 (TRKA) | − | − |
| PAK4 | − | − |
| PDGFRB (PDGFR beta) | − | − |
| PHKG2 | − | − |
| PIM1 | − | − |
| PLK1 | − | − |
| PRKACA (PKA) | − | − |
| PRKCB1 (PKC beta I) | − | − |
| RET | − | − |
| ROCK1 | − | − |
| RPS6KA3 (RSK2) | − | − |
| RPS6KB1 (p70S6K) | − | − |
| SRC | + | − |
| SYK | + | − |
| TEK (Tie2) | − | − |

Key: + inhibition over 50% (tested at 300-350 nM)
− inhibition under 50% (tested at 300-350 nM)

Compounds of the present invention have superior binding potency and superior efficacy compared with those known in the prior art. For example, the potency and/or efficacy of Example 5 shown below is comparable or improved compared to corresponding compounds of WO 2007/126122 and US 2007/0254892, as shown in Table 5 below:

TABLE 5

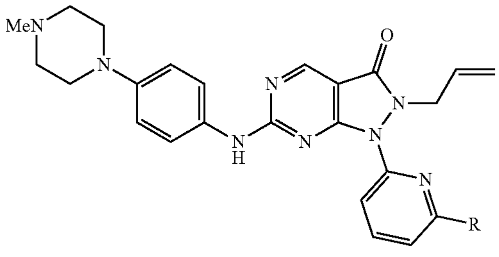

| R: | 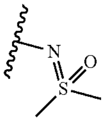 | 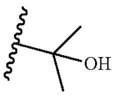 [SMILES: *C(C)(C)O] | 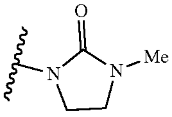 [SMILES: *N1CCN(C)C1=O] | 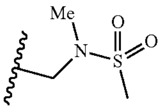 [SMILES: *CN(C)S(C)(=O)=O] |
|---|---|---|---|---|
| Reference | Present Invention | US 2007/ 0254892 | US 2007/0254892 | US 2007/0254892 |
| Example | 5 | 53 | 148 | 99 |
| Wee-1/nM | 1.2 | 11/1.2* | 17 | 8.8 |
| ELISA/nM | 12 | 68/67* | 79 | 86 |

*Data obtained as described in the experimental section of the current invention.

In addition, the potency and/or efficacy of Inventive Example 20 shown below is improved compared to corresponding compounds of WO 2007/126122 and US 2007/0254892, as shown in Table 6 below:

TABLE 6

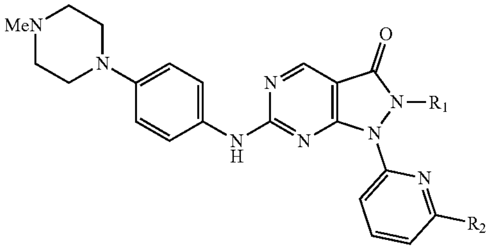

| | R2 | 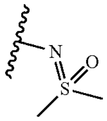 [SMILES: *N=S(C)(C)=O] | 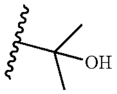 [SMILES: *C(C)(C)O] | 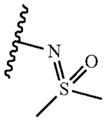 [SMILES: *N=S(C)(C)=O] | 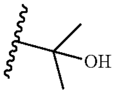 [SMILES: *C(C)(C)O] |
|---|---|---|---|---|---|
| | Reference | Present Invention Wee-1/nM | US 2007/ 0254892 Wee-1/nM | Present Invention ELISA/nM | US 2007/ 0254892 ELISA/nM |
| R1 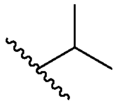 | | 1.4 | 26 | 47 | 107 |
| | Example | 20 | 137 | 20 | 137 |

Furthermore, the potency of Inventive examples 5, 12 and 57 is similar or improved compared to the corresponding compounds of ACS Chem. Biol. 2016, 11, 921, as shown in Table 7 below:

TABLE 7

| 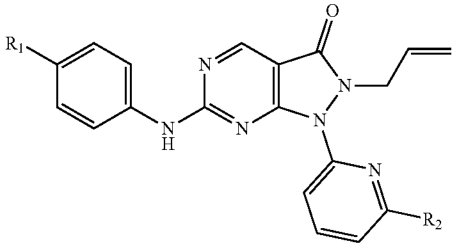 | $R_2$ | 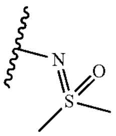 [SMILES: *N=S(C)(C)=O] | 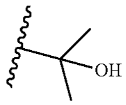 [SMILES: *C(C)(C)O] |
|---|---|---|---|
| Reference | | Present Invention Wee-1/nM | ACS Chem Biol 2016, 11, 921 Wee-1/nM |
| $R_1$ 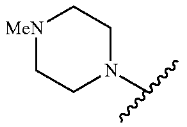 | | 1.2 | 18.7/1.2* |
| | Example | 5 Wee-1/nM | AZD1775 Wee-1/nM |
| $R_1$ 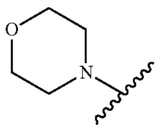 | | 0.5 | 37.8 |
| | Example | 12 Wee-1/nM | 11c Wee-1/nM |
| $R_1$ 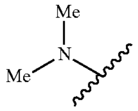 | | 0.2 | 42.8 |
| | Example | 57 | 11a |

*Data obtained as described in the experimental section of the current invention.

The invention claimed is:

1. A compound of Formula (I):

(I)

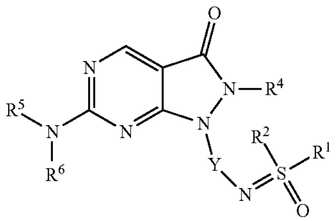

or a pharmaceutically acceptable salt thereof, wherein:

$R^1$ is an optionally substituted alkyl group, an optionally substituted cycloalkyl group, an optionally substituted aryl group, or an optionally substituted heteroaryl group;

$R^2$ is an optionally substituted alkyl group, an optionally substituted cycloalkyl group, an optionally substituted aryl group, or an optionally substituted heteroaryl group, or $R^1$, $R^2$ and the sulphur atom to which they are both attached, as taken together, form an optionally substituted heterocyclyl group;

$R^4$ is an optionally substituted alkyl group, an optionally substituted alkenyl group, an optionally substituted alkynyl group, or an optionally substituted aryl group;

$R^5$ is an optionally substituted aryl group, an optionally substituted heteroaryl group, or an optionally substituted cycloalkyl group;

$R^6$ is a hydrogen atom or an optionally substituted aryl group;

Y is a phenyl group or a five- or six-membered heteroaryl group.

2. A compound of Formula (II):

(II)

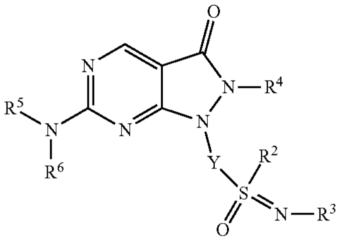

or a pharmaceutically acceptable salt thereof, wherein:

$R^2$ is an optionally substituted alkyl group, an optionally substituted cycloalkyl group, an optionally substituted aryl group, or an optionally substituted heteroaryl group;

$R^3$ is a hydrogen atom, an optionally substituted alkyl group, an optionally substituted cycloalkyl group, an optionally substituted aryl group, an optionally substituted heteroaryl group, a cyano group, an optionally substituted alkanoyl group, an optionally substituted aroyl group, an optionally substituted heteroaroyl group, an optionally substituted alkoxy-carbonyl group, or an optionally substituted alkylamino-carbonyl group;

$R^4$ is an optionally substituted alkyl group, an optionally substituted alkenyl group, an optionally substituted alkynyl group, or an optionally substituted aryl group;

$R^5$ is an optionally substituted aryl group, an optionally substituted heteroaryl group, or an optionally substituted cycloalkyl group;

$R^6$ is a hydrogen atom or an optionally substituted aryl group;

Y is a phenyl group or a five- or six-membered heteroaryl group.

3. The compound of claim 1, or a pharmaceutically acceptable salt thereof, wherein $R^1$ and/or $R^2$ are optionally substituted $C_1$-$C_3$ alkyl groups, or $R^1$, $R^2$ and the sulphur atom to which they are both attached, as taken together, form an optionally substituted heterocyclyl group.

4. The compound of claim 1, or a pharmaceutically acceptable salt thereof, wherein $R^1$ is a methyl group.

5. The compound of claim 2, or a pharmaceutically acceptable salt thereof, wherein $R^3$ is a hydrogen atom, an optionally substituted alkyl group, a cyano group, or an optionally substituted alkoxy-carbonyl group.

6. The compound of claim 1, or a pharmaceutically acceptable salt thereof, wherein $R^2$ is an optionally substituted alkyl group or an optionally substituted cycloalkyl group.

7. The compound of claim 1, or a pharmaceutically acceptable salt thereof, wherein $R^2$ is a methyl group.

8. The compound of claim 1, or a pharmaceutically acceptable salt thereof, wherein $R^4$ is an optionally substituted alkyl group or an optionally substituted alkenyl group.

9. The compound of claim 1, or a pharmaceutically acceptable salt thereof, wherein $R^4$ is a 2-propyl group or an allyl group.

10. The compound of claim 1, or a pharmaceutically acceptable salt thereof, wherein $R^5$ is group or an optionally substituted heteroaryl group.

11. The compound of claim 1, or a pharmaceutically acceptable salt thereof, wherein $R^5$ is not a bridged cycloalkyl group.

12. The compound of claim 1, or a pharmaceutically acceptable salt thereof, wherein $R^5$ is not an unsubstituted pyridyl group.

13. The compound of claim 1, or a pharmaceutically acceptable salt thereof, wherein $R^5$ is an optionally substituted six-membered aryl group or an optionally substituted five- to seven-membered heteroaryl group.

14. The compound of claim 1, or a pharmaceutically acceptable salt thereof, wherein $R^5$ is a group represented by the formula (d):

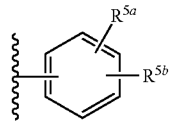

(d)

$R^{5a}$ and $R^{5b}$ are independently selected from the group consisting of a hydrogen atom, a halo group, an optionally substituted $C_1$-$C_6$ alkyl group, an optionally substituted $C_1$-$C_6$ nitrile group, an optionally substituted amino group, an optionally substituted $C_1$-$C_6$ alkoxy group, an optionally substituted sulfanyl group, an optionally substituted sulfonyl group, an optionally substituted sulfoximinyl group, and an optionally substituted four- to seven-membered nitrogen-containing heterocyclyl group;

wherein the optionally substituted four- to seven-membered nitrogen-containing heterocyclyl group is optionally substituted with one or more substituents selected from the group consisting of a halo group, an optionally substituted $C_1$-$C_6$ alkyl or cycloalkyl group, an oxo group, a hydroxyl group, an optionally substituted amino group, and a group of $=N-R^{5c}$;

or, in formula (d), $R^{5a}$ and $R^{5b}$ exist on adjacent ring atoms and $R^{5a}$ and $R^{5b}$ and the ring atoms to which they are attached may form, as taken together, a three- to seven-membered cycloalkyl group, or three- to seven-membered heterocyclyl group, wherein one or two of the ring atoms constituting the three- to seven-membered heterocyclyl group is independently an oxygen atom, a nitrogen atom, a group of $-N(R^{5d})-$, a sulfinyl group, a sulfonyl group, or a sulfoximinyl group, wherein the three- to seven-membered cycloalkyl or three- to seven-membered heterocyclyl group may be substituted with one or more substituents selected from the group consisting of a halo group and a $C_1$-$C_6$ alkyl or cycloalkyl group;

or $R^{5a}$ and $R^{5b}$ and the ring atoms to which they are attached may form, as taken together, a spirocyclic group or a bicyclic group formed of a five- to seven-membered aliphatic ring and any other three- to seven-membered aliphatic ring, in which one or two or more methylene groups constituting the spirocyclic group or the bicyclic group may be each independently replaced by an oxygen atom, a sulphur atom, a sulfinyl group, a sulfonyl, a sulfoximinyl group, an oxo group or a group of $-N(R^{5e})-$, and the spirocyclic group or the bicyclic group may be each independently substituted with a substituent selected from the group consisting of a halo group, a hydroxyl group, or a $C_1$-$C_6$ alkyl group; wherein $R^{5c}$, $R^{5d}$ and $R^{5e}$ are each independently a hydrogen atom or a $C_1$-$C_6$ alkyl or cycloalkyl group optionally substituted with a substituent selected from the group consisting of a halo group, a hydroxyl group, a cyano group, an oxo group, a $C_1$-$C_6$ alkyl group, a $C_1$-$C_6$ alkoxy group, an amino group, a substituted amino group, and a nitrogen-containing heterocyclyl group.

15. The compound of claim 1, or a pharmaceutically acceptable salt thereof, wherein $R^6$ is a hydrogen atom.

16. The compound of claim 1, or a pharmaceutically acceptable salt thereof, wherein $R^1$ is a methyl group; $R^2$ is a methyl group; $R^4$ is an allyl group; $R^5$ is a group represented by the formula (d) as defined above; $R^6$ is a hydrogen atom; and Y is a pyridyl, phenyl or pyrazinyl group.

17. The compound of claim 2, or a pharmaceutically acceptable salt thereof, wherein $R^2$ is a methyl group or a cyclopropyl group; $R^3$ is a hydrogen atom, a methyl group, a cyano group, or an alkoxy-carbonyl group; $R^4$ is an allyl group; and $R^5$ is a group represented by the formula (d) as defined above; $R^6$ is a hydrogen atom; and Y is a pyridyl or phenyl group.

18. The compound of claim 1, or a pharmaceutically acceptable salt thereof, wherein the compound is selected from the following:

(5) 1-(6-{[Dimethyl(oxo)-λ$^6$-sulfanylidene]amino}pyridine-2-yl)-6-{[4-(4-methylpiperazin-1-yl)phenyl]amino}-2-(prop-2-en-1-yl)-1H,2H,3H-pyrazolo[3,4-d]pyrimidin-3-one;

(6) 1-(6-{[Dimethyl(oxo)-λ$^6$-sulfanylidene]amino}pyridine-2-yl)-6-{[4-(piperazin-1-yl)phenyl]amino}-2-(prop-2-en-1-yl)-1H,2H,3H-pyrazolo[3,4-d]pyrimidin-3-one;

(7: 1-(6-{[Dimethyl(oxo)-λ$^6$-sulfanylidene]amino}pyridine-2-yl)-2-(prop-2-en-1-yl)-6-({4-[4-(propan-2-yl)piperazin-1-yl]phenyl}amino)-1H,2H,3H-pyrazolo[3,4-d]pyrimidin-3-one;

(8) 6-{[4-(4-Cyclopropylpiperazin-1-yl)phenyl]amino}-1-(6-{[dimethyl(oxo)-λ$^6$-sulfanylidene]amino}pyridine-2-yl)-2-(prop-2-en-1-yl)-1H,2H,3H-pyrazolo[3,4-d]pyrimidin-3-one;

(9) 1-(6-{[Dimethyl(oxo)-λ$^6$-sulfanylidene]amino}pyridine-2-yl)-6-({4-[(3R)-3-methylpiperazin-1-yl]phenyl}amino)-2-(prop-2-en-1-yl)-1H,2H,3H-pyrazolo[3,4-d]pyrimidin-3-one;

(10) 1-(6-{[Dimethyl(oxo)-λ$^6$-sulfanylidene]amino}pyridine-2-yl)-6-{[4-(4-ethylpiperazin-1-yl)phenyl]amino}-2-(prop-2-en-1-yl)-1H,2H,3H-pyrazolo[3,4-d]pyrimidin-3-one;

(11) 1-(6-{[Dimethyl(oxo)-λ$^6$-sulfanylidene]amino}pyridine-2-yl)-6-{[4-(4-methylpiperazin-1-yl)phenyl]amino}-2-propyl-1H,2H,3H-pyrazolo[3,4-d]pyrimidin-3-one;

(12) 1-(6-{[Dimethyl(oxo)-λ$^6$-sulfanylidene]amino}pyridine-2-yl)-6-{[4-(morpholin-4-yl)phenyl]amino}-2-(prop-2-en-1-yl)-1H,2H,3H-pyrazolo[3,4-d]pyrimidin-3-one;

(13) 1-(6-{[Dimethyl(oxo)-λ$^6$-sulfanylidene]amino}pyridine-2-yl)-6-{[4-(piperidin-4-yl)phenyl]amino}-2-(prop-2-en-1-yl)-1H,2H,3H-pyrazolo[3,4-d]pyrimidin-3-one;

(14) 6-{[3-Chloro-4-(piperazin-1-yl)phenyl]amino}-1-(6-{[dimethyl(oxo)-λ$^6$-sulfanylidene]amino}pyridine-2-yl)-2-(prop-2-en-1-yl)-1H,2H,3H-pyrazolo[3,4-d]pyrimidin-3-one;

(15) 1-(6-{[Dimethyl(oxo)-λ$^6$-sulfanylidene]amino}pyridine-2-yl)-6-({2'-methyl-2',3'-dihydro-1'H-spiro[cyclopropane-1,4'-isoquinoline]-7'-yl}amino)-2-(prop-2-en-1-yl)-1H,2H,3H-pyrazolo[3,4-d]pyrimidin-3-one;

(16) 1-(3-{[Dimethyl(oxo)-λ$^6$-sulfanylidene]amino}phenyl)-6-{[4-(4-methylpiperazin-1-yl)phenyl]amino}-2-(prop-2-en-1-yl)-1H,2H,3H-pyrazolo[3,4-d]pyrimidin-3-one;

(17) 1-(6-{[Dimethyl(oxo)-λ$^6$-sulfanylidene]amino}pyridin-2-yl)-6-({4-[(3R,5S)-3,5-dimethylpiperazin-1-yl]phenyl}amino)-2-(prop-2-en-1-yl)-1H,2H,3H-pyrazolo[3,4-d]pyrimidin-3-one;

(18) 1-(3-{[Dimethyl(oxo)-λ$^6$-sulfanylidene]amino}phenyl)-6-{[4-(piperazin-1-yl)phenyl]amino}-2-(prop-2-en-1-yl)-1H,2H,3H-pyrazolo[3,4-d]pyrimidin-3-one;

(19) 1-(6-{[Dimethyl(oxo)-λ$^6$-sulfanylidene]amino}pyridin-2-yl)-6-(phenylamino)-2-(prop-2-en-1-yl)-1H,2H,3H-pyrazolo[3,4-d]pyrimidin-3-one;

(20) 1-(6-{[Dimethyl(oxo)-λ$^6$-sulfanylidene]amino}pyridin-2-yl)-6-{[4-(4-methylpiperazin-1-yl)phenyl]amino}-2-(propan-2-yl)-1H,2H,3H-pyrazolo[3,4-d]pyrimidin-3-one;

(21) 1-(6-{[Dimethyl(oxo)-λ$^6$-sulfanylidene]amino}pyridin-2-yl)-6-{[3-methyl-4-(morpholin-4-yl)phenyl]amino}-2-(prop-2-en-1-yl)-1H,2H,3H-pyrazolo[3,4-d]pyrimidin-3-one;

(22) 1-(3-{[Dimethyl(oxo)-λ$^6$-sulfanylidene]amino}phenyl)-6-({3-[(methylamino)methyl]-4-(morpholin-4-yl)phenyl}amino)-2-(prop-2-en-1-yl)-1H,2H,3H-pyrazolo[3,4-d]pyrimidin-3-one;

(23) 2-Allyl-6-((4-(4-methylpiperazin-1-yl)phenyl)amino)-1-(6-((1-oxidotetrahydrothiophen-1-ylidene)amino)pyridin-2-yl)-1H-pyrazolo[3,4-d]pyrimidin-3(2H)-one;

(24) 1-(6-{[Dimethyl(oxo)-λ$^6$-sulfanylidene]amino}pyridin-2-yl)-6-{[3-methoxy-4-(4-methylpiperazin-1-yl)phenyl]amino}-2-(prop-2-en-1-yl)-1H,2H,3H-pyrazolo[3,4-d]pyrimidin-3-one (25) 1-(6-{[Dimethyl(oxo)-λ$^6$-sulfanylidene]amino}pyridin-2-yl)-6-{[3-methoxy-4-(morpholin-4-yl)phenyl]amino}-2-(prop-2-en-1-yl)-1H,2H,3H-pyrazolo[3,4-d]pyrimidin-3-one;

(26) 1-(6-{[Dimethyl(oxo)-λ$^6$-sulfanylidene]amino}pyridin-2-yl)-6-{[3-methyl-4-(piperazin-1-yl)phenyl]amino}-2-(prop-2-en-1-yl)-1H,2H,3H-pyrazolo[3,4-d]pyrimidin-3-one;

(27): 1-(3-{[Dimethyl(oxo)-λ$^6$-sulfanylidene]amino}phenyl)-6-({4-[2-(methylamino)ethoxy]phenyl}amino)-2-(prop-2-en-1-yl)-1H,2H,3H-pyrazolo[3,4-d]pyrimidin-3-one;

(28) 1-(6-{[Dimethyl(oxo)-λ$^6$-sulfanylidene]amino}pyridin-2-yl)-6-{[3-methyl-4-(4-methylpiperazin-1-yl)phenyl]amino}-2-(prop-2-en-1-yl)-1H,2H,3H-pyrazolo[3,4-d]pyrimidin-3-one;

(29) 1-(3-{[Dimethyl(oxo)-λ$^6$-sulfanylidene]amino}phenyl)-6-{[3-(hydroxymethyl)-4-(piperazin-1-yl)phenyl]amino}-2-(prop-2-en-1-yl)-1H,2H,3H-pyrazolo[3,4-d]pyrimidin-3-one;

(30) 1-(3-{[Dimethyl(oxo)-λ$^6$-sulfanylidene]amino}phenyl)-6-{[3-(hydroxymethyl)-4-(4-methylpiperazin-1-yl)phenyl]amino}-2-(prop-2-en-1-yl)-1H,2H,3H-pyrazolo[3,4-d]pyrimidin-3-one;

(31) 1-(3-{[Dimethyl(oxo)-λ$^6$-sulfanylidene]amino}phenyl)-6-{[4-(morpholin-4-yl)phenyl]amino}-2-(prop-2-en-1-yl)-1H,2H,3H-pyrazolo[3,4-d]pyrimidin-3-one;

(32) 1-(6-{[Dimethyl(oxo)-λ$^6$-sulfanylidene]amino}pyridin-2-yl)-6-{4-([(2S,6R)-2,6-dimethylmorpholin-4-yl]phenyl)amino}-2-(prop-2-en-1-yl)-1H,2H,3H-pyrazolo[3,4-d]pyrimidin-3-one

(33) 1-(6-{[Dimethyl(oxo)-λ$^6$-sulfanylidene]amino}pyridin-2-yl)-6-{[5-(morpholin-4-yl)pyridin-3-yl]amino}-2-(prop-2-en-1-yl)-1H,2H,3H-pyrazolo[3,4-d]pyrimidin-3-one;

(34) 1-(6-{[Dimethyl(oxo)-λ$^6$-sulfanylidene]amino}pyridin-2-yl)-6-{[4-(4,4-difluoropiperidin-1-yl)phenyl]amino}-2-(prop-2-en-1-yl)-1H,2H,3H-pyrazolo[3,4-d]pyrimidin-3-one;

(35) 1-(6-{[Dimethyl(oxo)-λ$^6$-sulfanylidene]amino}pyridin-2-yl)-6-{[3-(morpholin-4-yl)phenyl]amino}-2-(prop-2-en-1-yl)-1H,2H,3H-pyrazolo[3,4-d]pyrimidin-3-one;

(36) 1-(6-{[Dimethyl(oxo)-$\lambda^6$-sulfanylidene]amino}pyridin-2-yl)-6-{[4-(8-oxa-3-azabicyclo[3.2.1]octan-3-yl)phenyl]amino}-2-(prop-2-en-1-yl)-1H,2H,3H-pyrazolo[3,4-d]pyrimidin-3-one;

(37) 1-(6-{[Dimethyl(oxo)-$\lambda^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one;

(38) 1-(6-{[Dimethyl(oxo)-$\lambda^6$-sulfanylidene]amino}pyridin-2-yl)-6-{[4-(morpholin-4-yl)phenyl]amino}-2-propyl-1H,2H,3H-pyrazolo[3,4-d]pyrimidin-3-one;

(39) 1-(6-{[Dimethyl(oxo)-$\lambda^6$-sulfanylidene]amino}pyridin-2-yl)-6-{[6-(morpholin-4-yl)pyridin-3-yl]amino}-2-propyl-1H,2H,3H-pyrazolo[3,4-d]pyrimidin-3-one;

(40) 1-(6-{[Dimethyl(oxo)-$\lambda^6$-sulfanylidene]amino}pyridin-2-yl)-6-[(4-fluorophenyl)amino]-2-(prop-2-en-1-yl)-1H,2H,3H-pyrazolo[3,4-d]pyrimidin-3-one;

(41) 1-(6-{[Dimethyl(oxo)-$\lambda^6$-sulfanylidene]amino}pyridin-2-yl)-6-[(4-fluorophenyl)amino]-2-(propan-2-yl)-1H,2H,3H-pyrazolo[3,4-d]pyrimidin-3-one;

(42) 1-(6-{[Dimethyl(oxo)-$\lambda^6$-sulfanylidene]amino}pyridin-2-yl)-6-[(4-methoxyphenyl)amino]-2-(propan-2-yl)-1H,2H,3H-pyrazolo[3,4-d]pyrimidin-3-one;

(43) 1-(6-{[Dimethyl(oxo)-$\lambda^6$-sulfanylidene]amino}pyridin-2-yl)-6-{[4-(morpholin-4-yl)phenyl]amino}-2-(propan-2-yl)-1H,2H,3H-pyrazolo[3,4-d]pyrimidin-3-one;

(44) 1-(5-{[Dimethyl(oxo)-$\lambda^6$-sulfanylidene]amino}pyridin-3-yl)-6-{[4-(morpholin-4-yl)phenyl]amino}-2-(prop-2-en-1-yl)-1H,2H,3H-pyrazolo[3,4-d]pyrimidin-3-one;

(45) rac-1-(6-{[Dimethyl(oxo)-$\lambda^6$-sulfanylidene]amino}pyridin-2-yl)-2-(propan-2-yl)-6-({4-[3-(trifluoromethyl)piperazin-1-yl]phenyl}amino)-1H,2H,3H-pyrazolo[3,4-d]pyrimidin-3-one;

(46) 6-{[4-(1,4-Diazepan-1-yl)phenyl]amino}-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one;

(47) 6-(Cyclobutylamino)-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one;

(48) 4-(4-{[1-(6-{[Dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)piperazin-2-one;

(49) 4-(4-{[1-(6-{[Dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino}phenyl)morpholin-3-one;

(50) 1-(6-{[Dimethyl(oxo)-$\lambda^6$-sulfanylidene]amino}pyridin-2-yl)-2-(propan-2-yl)-6-({4-[4-(2,2,2-trifluoroethyl)piperazin-1-yl]phenyl}amino)-1H,2H,3H-pyrazolo[3,4-d]pyrimidin-3-one;

(51) 1-(6-{[Dimethyl(oxo)-$\lambda^6$-sulfanylidene]amino}pyrazin-2-yl)-6-{[4-(morpholin-4-yl)phenyl]amino}-2-(prop-2-en-1-yl)-1H,2H,3H-pyrazolo[3,4-d]pyrimidin-3-one;

(52) 1-(4-{[Dimethyl(oxo)-$\lambda^6$-sulfanylidene]amino}pyrimidin-2-yl)-6-{[4-(morpholin-4-yl)phenyl]amino}-2-(prop-2-en-1-yl)-1H,2H,3H-pyrazolo[3,4-d]pyrimidin-3-one;

(53) 1-(6-{[Dimethyl(oxo)-$\lambda^6$-sulfanylidene]amino}pyridin-2-yl)-6-({4-[(2S)-2-(methoxymethyl)morpholin-4-yl]phenyl}amino)-2-(propan-2-yl)-1H,2H,3H-pyrazolo[3,4-d]pyrimidin-3-one;

(54) 1-(6-{[Dimethyl(oxo)-$\lambda^6$-sulfanylidene]amino}pyridin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one;

(55) 6-[(4-Fluorophenyl)amino]-1-{6-[(1-oxo-1$\lambda^6$-thiolan-1-ylidene)amino]pyridin-2-yl}-2-(propan-2-yl)-1H,2H,3H-pyrazolo[3,4-d]pyrimidin-3-one;

(56) 6-[(1-Methyl-1H-pyrazol-4-yl)amino]-1-{6-[(1-oxo-1$\lambda^6$-thiolan-1-ylidene)amino]pyridin-2-yl}-2-(propan-2-yl)-1H,2H,3H-pyrazolo[3,4-d]pyrimidin-3-one;

(57) 1-(6-{[Dimethyl(oxo)-$\lambda^6$-sulfanylidene]amino}pyridin-2-yl)-6-{[4-(dimethylamino)phenyl]amino}-2-(prop-2-en-1-yl)-1H,2H,3H-pyrazolo[3,4-d]pyrimidin-3-one;

(58) 1-(6-{[Dimethyl(oxo)-$\lambda^6$-sulfanylidene]amino}pyridin-2-yl)-6-{[4-(dimethylamino)phenyl]amino}-2-(propan-2-yl)-1H,2H,3H-pyrazolo[3,4-d]pyrimidin-3-one;

(59) 1-{6-[(1-Oxo-1$\lambda^6$-thiolan-1-ylidene)amino]pyridin-2-yl}-6-{[4-(piperazin-1-yl)phenyl]amino}-2-(propan-2-yl)-1H,2H,3H-pyrazolo[3,4-d]pyrimidin-3-one;

(60) 4-[(4-Cyanophenyl)[1-(6-{[dimethyl(oxo)-$\lambda^6$-sulfanylidene]amino}pyridin-2-yl)-3-oxo-2-(propan-2-yl)-1H,2H,3H-pyrazolo[3,4-d]pyrimidin-6-yl]amino]benzonitrile;

(61) 6-[(4-Chlorophenyl)amino]-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one;

(62) 6-[(4-Chlorophenyl)amino]-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(63) 6-({Bicyclo[1.1.1]pentan-1-yl}amino)-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(64) 6-[(4-tert-Butylphenyl)amino]-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(65) 6-[(2,4-Difluorophenyl)amino]-1-(6-{[dimethyl(oxo)-$\lambda^6$-sulfanylidene]amino}pyridin-2-yl)-2-(propan-2-yl)-1H,2H,3H-pyrazolo[3,4-d]pyrimidin-3-one;

(66) 6-[(3,4-Difluorophenyl)amino]-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(67) 6-({4-[(3aR,6aS)-Hexahydro-1H-furo[3,4-c]pyrrol-5-yl]phenyl}amino)-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one;

(68) 1-(6-{[Dimethyl(oxo)-$\lambda^6$-sulfanylidene]amino}pyridin-2-yl)-6-({4-[(1S,4S)-2-oxa-5-azabicyclo[2.2.1]heptan-5-yl]phenyl}amino)-2-(prop-2-en-1-yl)-1H,2H,3H-pyrazolo[3,4-d]pyrimidin-3-one;

(69) rac-1-(6-{[Dimethyl(oxo)-$\lambda^6$-sulfanylidene]amino}pyridin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one;

(70) 1-(6-{[Dimethyl(oxo)-$\lambda^6$-sulfanylidene]amino}pyridin-2-yl)-6-[(6-fluoropyridin-3-yl)amino]-2-(prop-2-en-1-yl)-1H,2H,3H-pyrazolo[3,4-d]pyrimidin-3-one;

(71) 4-{[1-(6-{[Dimethyl(oxo)-λ$^6$-sulfanylidene]amino}pyridin-2-yl)-3-oxo-2-(propan-2-yl)-1H,2H,3H-pyrazolo[3,4-d]pyrimidin-6-yl]amino}benzonitrile;

(72) 1-(6-{[Dimethyl(oxo)-λ$^6$-sulfanylidene]amino}pyridin-2-yl)-2-(propan-2-yl)-6-{[4-(trifluoromethyl)phenyl]amino}-1H,2H,3H-pyrazolo[3,4-d]pyrimidin-3-one;

(73) 1-(6-{[Dimethyl(oxo)-λ$^6$-sulfanylidene]amino}pyridin-2-yl)-2-(propan-2-yl)-6-{[3-(trifluoromethyl)phenyl]amino}-1H,2H,3H-pyrazolo[3,4-d]pyrimidin-3-one;

(74) 1-(6-{[Dimethyl(oxo)-λ$^6$-sulfanylidene]amino}pyrazin-2-yl)-6-({4-[(2S)-2-(methoxymethyl)morpholin-4-yl]phenyl}amino)-2-(prop-2-en-1-yl)-1H,2H,3H-pyrazolo[3,4-d]pyrimidin-3-one;

(75) 1-(6-{[Dimethyl(oxo)-λ$^6$-sulfanylidene]amino}pyrazin-2-yl)-6-[(4-fluorophenyl)amino]-2-(prop-2-en-1-yl)-1H,2H,3H-pyrazolo[3,4-d]pyrimidin-3-one;

(76) 1-(6-{[Dimethyl(oxo)-λ$^6$-sulfanylidene]amino}pyridin-2-yl)-6-({4-[(3S)-3-(methoxymethyl)piperazin-1-yl]phenyl}amino)-2-(prop-2-en-1-yl)-1H,2H,3H-pyrazolo[3,4-d]pyrimidin-3-one;

(77) 1-(6-{[Dimethyl(oxo)-λ$^6$-sulfanylidene]amino}pyridin-2-yl)-2-(prop-2-en-1-yl)-6-[(pyridin-3-yl)amino]-1H,2H,3H-pyrazolo[3,4-d]pyrimidin-3-one;

(78) 6-[(1-Methyl-1H-pyrazol-4-yl)amino]-1-{6-[(1-oxo-1λ$^6$-thiolan-1-ylidene)amino]pyridin-2-yl}-2-(prop-2-en-1-yl)-1H,2H,3H-pyrazolo[3,4-d]pyrimidin-3-one;

(79) 1-(6-{[(S)-Methyl(oxo)phenyl-λ$^6$-sulfanylidene]amino}pyridin-2-yl)-6-[(1-methyl-1H-pyrazol-4-yl)amino]-2-(prop-2-en-1-yl)-1H,2H,3H-pyrazolo[3,4-d]pyrimidin-3-one;

(80) 1-(6-{[Dimethyl(oxo)-λ$^6$-sulfanylidene]amino}pyridin-2-yl)-2-(prop-2-en-1-yl)-6-{[1-(propan-2-yl)-1H-pyrazol-4-yl]amino}-1H,2H,3H-pyrazolo[3,4-d]pyrimidin-3-one;

(81) 1-(6-{[Dimethyl(oxo)-λ$^6$-sulfanylidene]amino}pyridin-2-yl)-2-(prop-2-en-1-yl)-6-{[6-(trifluoromethyl)pyridin-3-yl]amino}-1H,2H,3H-pyrazolo[3,4-d]pyrimidin-3-one;

(82) 1-(6-{[Dimethyl(oxo)-λ$^6$-sulfanylidene]amino}pyridin-2-yl)-6-[(4-fluoro-3-methoxyphenyl)amino]-2-(prop-2-en-1-yl)-1H,2H,3H-pyrazolo[3,4-d]pyrimidin-3-one;

(83) rac-1-(6-{[Dimethyl(oxo)-λ$^6$-sulfanylidene]amino}pyridin-2-yl)-6-{[4-(dimethylamino)-3-(2,2,2-trifluoro-1-hydroxyethyl)phenyl]amino}-2-(prop-2-en-1-yl)-1H,2H,3H-pyrazolo[3,4-d]pyrimidin-3-one;

(84) 6-[(3,5-Difluorophenyl)amino]-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(85) 1-(6-{[Dimethyl(oxo)-λ$^6$-sulfanylidene]amino}pyridin-2-yl)-2-(prop-2-en-1-yl)-6-{[1-(2,2,2-trifluoroethyl)-1H-pyrazol-4-yl]amino}-1H,2H,3H-pyrazolo[3,4-d]pyrimidin-3-one;

(86) rac-1-(6-{[Dimethyl(oxo)-λ$^6$-sulfanylidene]amino}pyridin-2-yl)-6-({3-methoxy-4-[3-(trifluoromethyl)piperazin-1-yl]phenyl}amino)-2-(prop-2-en-1-yl)-1H,2H,3H-pyrazolo[3,4-d]pyrimidin-3-one;

(87) rac-1-(6-{[Dimethyl(oxo)-λ$^6$-sulfanylidene]amino}pyridin-2-yl)-6-({3-methoxy-4-[4-methyl-3-(trifluoromethyl)piperazin-1-yl]phenyl}amino)-2-(prop-2-en-1-yl)-1H,2H,3H-pyrazolo[3,4-d]pyrimidin-3-one;

(88) 6-{[4-(1-Cyclobutylpiperidin-4-yl)-3-methylphenyl]amino}-1-(6-{[dimethyl(oxo)-λ$^6$-sulfanylidene]amino}pyridin-2-yl)-2-(prop-2-en-1-yl)-1H,2H,3H-pyrazolo[3,4-d]pyrimidin-3-one;

(89) 1-(6-{[Dimethyl(oxo)-λ$^6$-sulfanylidene]amino}pyridin-2-yl)-6-({4-[(2-methoxyethyl)(methyl)amino]phenyl}amino)-2-(prop-2-en-1-yl)-1H,2H,3H-pyrazolo[3,4-d]pyrimidin-3-one;

(91) 1-[6-({[Dimethyl(oxo)-λ$^6$-sulfanylidene]amino}methyl)pyridin-2-yl]-6-{[4-(morpholin-4-yl)phenyl]amino}-2-(prop-2-en-1-yl)-1H,2H,3H-pyrazolo[3,4-d]pyrimidin-3-one;

(92) 2-(Cyclopropylmethyl)-1-(6-{[dimethyl(oxo)-λ$^6$-sulfanylidene]amino}pyridin-2-yl)-6-{[4-(morpholin-4-yl)phenyl]amino}-1H,2H,3H-pyrazolo[3,4-d]pyrimidin-3-one;

(93) rac-1-(6-{[Dimethyl(oxo)-λ$^6$-sulfanylidene]amino}pyrazin-2-yl)-2-(prop-2-en-1-yl)-6-({4-[3-(trifluoromethyl)piperazin-1-yl]phenyl}amino)-1H,2H,3H-pyrazolo[3,4-d]pyrimidin-3-one; and

(94) 1-(6-((Dimethyl(oxo)-λ6-sulfaneylidene)amino)pyridin-2-yl)-6-((1-isopropyl-1H-pyrazol-4-yl)amino)-2-(prop-2-yn-1-yl)-1,2-dihydro-3H-pyrazolo[3,4-d]pyrimidin-3-one.

19. The compound of claim 1, or a pharmaceutically acceptable salt thereof, wherein the compound is selected from the following:

(95) 2-Allyl-6-((1-allyl-1H-pyrazol-4-yl)amino)-1-(6-((dimethyl(oxo)-λ$^6$-sulfaneylidene)amino) pyridin-2-yl)-1,2-dihydro-3H-pyrazolo[3,4-d]pyrimidin-3-one;

(96) 2-Allyl-6-((1-cyclohexyl-1H-pyrazol-4-yl)amino)-1-(6-((dimethyl(oxo)-λ$^6$-sulfaneylidene) amino)pyridin-2-yl)-1,2-dihydro-3H-pyrazolo[3,4-d]pyrimidin-3-one; and

(97) rac-2-Allyl-6-((1-cyclohexyl-1H-pyrazol-4-yl)amino)-1-(6-((dimethyl(oxo)-λ$^6$-sulfaneylidene)amino)pyridin-2-yl)-1,2-dihydro-3H-pyrazolo[3,4-d]pyrimidin-3-one.

20. The compound of claim 2, or a pharmaceutically acceptable salt thereof, wherein the compound is selected from the following:

(1) 1-{6-[(Cyanoimino)(methyl)oxo-λ$^6$-sulfanyl]pyridin-2-yl}-6-{[4-(4-methylpiperazin-1-yl)phenyl]amino}-2-(prop-2-en-1-yl)-1H,2H,3H-pyrazolo[3,4-d]pyrimidin-3-one;

(2) rac-Ethyl N-{methyl[6-(6-{[4-(4-methylpiperazin-1-yl)phenyl]amino}-3-oxo-2-(prop-2-en-1-yl)-1H,2H,3H-pyrazolo[3,4-d]pyrimidin-1-yl)pyridine-2-yl]oxo-λ$^6$-sulfanylidene}carbamate;

(3) rac-2-Allyl-6-((4-(4-methylpiperazin-1-yl)phenyl)amino)-1-(6-(S-methylsulfonimidoyl)pyridin-2-yl)-1H-pyrazolo[3,4-d]pyrimidin-3(2H)-one; and (4) rac-2-Allyl-1-(6-(N,S-dimethylsulfonimidoyl)pyridin-2-yl)-6-((4-(4-methylpiperazin-1-yl)phenyl)amino)-1H-pyrazolo[3,4-d]pyrimidin-3(2H)-one.

21. The compound of claim 1, or a pharmaceutically acceptable salt thereof, and at least one pharmaceutically acceptable excipient.

22. A pharmaceutical composition comprising the compound of claim 1, or a pharmaceutically acceptable salt thereof, and at least one pharmaceutically acceptable excipient.

23. The pharmaceutical composition of claim 22 comprising one or more further pharmaceutically active agents.

24. A method of treating cancer in a human or animal patient comprising administering to a patient in need thereof an effective amount of a compound according to claim 1, or a pharmaceutically acceptable salt thereof, wherein said cancer is selected from the group consisting of lung cancer, gastrointestinal cancer, bone cancer, nervous system cancer, skin cancer, adrenal gland cancer, connective tissue cancer, brain cancer, breast cancer, cervical cancer, colon cancer, rectal cancer, endometrial cancer, kidney cancer, leukemia, lymphoma, melanoma, ovarian cancer, pancreatic cancer, prostate cancer and sarcoma.

25. A method of treating cancer in a human or animal patient comprising administering to a patient in need thereof an effective amount of a compound according to claim 2, or a pharmaceutically acceptable salt thereof, wherein said cancer is selected from the group consisting of lung cancer, gastrointestinal cancer, bone cancer, nervous system cancer, skin cancer, adrenal gland cancer, connective tissue cancer, brain cancer, breast cancer, cervical cancer, colon cancer, rectal cancer, endometrial cancer, kidney cancer, leukemia, lymphoma, melanoma, ovarian cancer, pancreatic cancer, prostate cancer and sarcoma.

26. A compound, or a pharmaceutically acceptable salt thereof, wherein the compound is:

(90) 6-{[4-(Azetidin-1-yl)phenyl]amino}-1-(6-{[dimethyl(oxo)-$\lambda^6$-sulfanylidene]amino}pyridin-2-yl)-2-(prop-2-en-1-yl)-1H,2H,3H-pyrazolo[3,4-d]pyrimidin-3-one.

* * * * *